(12) United States Patent
Endermann et al.

(10) Patent No.: US 7,655,643 B2
(45) Date of Patent: Feb. 2, 2010

(54) ANTIBACTERIAL MACROCYCLES WITH SUBSTITUTED BIPHENYL

(75) Inventors: Rainer Endermann, Wuppertal (DE); Kerstin Ehlert, Velbert (DE); Siegfried Raddatz, Cologne (DE); Yolanda Cancho-Grande, Leverkusen (DE); Martin Michels, Cologne (DE); Stefan Weigand, Penzberg (DE); Isabelle Adelt, Haan (DE); Thomas Lampe, Dusseldorf (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 0 days.

(21) Appl. No.: 11/453,375

(22) Filed: Jun. 15, 2006

(65) Prior Publication Data
US 2007/0099885 A1     May 3, 2007

Related U.S. Application Data

(63) Continuation of application No. PCT/EP2004/013688, filed on Dec. 2, 2004.

(30) Foreign Application Priority Data

Dec. 16, 2003   (DE) ................................ 103 58 824

(51) Int. Cl.
*A01N 43/00*     (2006.01)
*A61K 31/33*    (2006.01)
*C07D 487/00*  (2006.01)

(52) U.S. Cl. ........................................ 514/183; 540/471
(58) Field of Classification Search .................. None
See application file for complete search history.

(56) References Cited

U.S. PATENT DOCUMENTS

| 3,452,136 A | 6/1969 | Martin et al. | |
| 5,840,682 A | 11/1998 | Clerc et al. | |
| 2005/0256037 A1* | 11/2005 | Lampe et al. | 514/9 |
| 2006/0258571 A1* | 11/2006 | Lampe et al. | 514/9 |
| 2007/0099885 A1 | 5/2007 | Endermann et al. | |
| 2007/0129288 A1* | 6/2007 | Lampe et al. | 514/9 |

FOREIGN PATENT DOCUMENTS

| CA | 2 489 454 | 12/2004 |
| CA | 2 549 874 | 6/2005 |
| CA | 2 581 527 | 4/2006 |
| DE | 102 26 921 | 12/2003 |
| EP | 1 515 983 | 12/2003 |
| FR | 2801591 | 1/2001 |
| WO | WO-01/40198 | 6/2001 |
| WO | WO-03/106480 | 12/2003 |
| WO | WO-2004/012816 | 2/2004 |
| WO | WO-2005/033129 | 4/2005 |
| WO | WO-2005/058943 | 6/2005 |
| WO | WO-2005/100380 | 10/2005 |
| WO | WO-2005/118613 | 12/2005 |
| WO | WO-2006/034786 | 4/2006 |
| WO | WO-2006/103009 | 10/2006 |
| WO | WO-2006/103015 | 10/2006 |

OTHER PUBLICATIONS

Schmidt et al. Journal of the Chemical Society, Chemical Communications, 1991, 275-77.*
Ezaka et al. The Journal of Antibiotics, 1985, 38(11), 1453-61.*
Gupta, VK. Agar, In Handbook of Pharmaceutical Excipients, Fifth Edition; Raymond Bowe, Paul Sheskey, Sian owen, EDs. Pharmaceutical Press: Chicago, 2006, 14-15.*
U.S. Appl. No. 10/518,600, filed Dec. 2005, Lampe et al.*
Ezaki et al. Journal of Antibiotics, 1993, 46(1), 135-40.*
Greene and Wuts, Protective Groups in Organic Synthesis, Third Edition, 1999, p. 521, entry No. 8.*
"Prophylaxis definition", http://medterms.com/script/main/art.asp?articlekey=12063, accessed Oct. 31, 2007.*
"Syphilis facts", http://www.dhpe.org/infect/syphilis.html, accessed Oct. 31, 2007.*
LaVoie et al. Chemical Reviews, 1996, 96, 3147-76.*
Chang et al., Journal of Antibiotics (1991) 44:674-677.
International Search Report for PCT/EP2004/013688, mailed on Jan. 21, 2005, 4 pages.
Krenitsky et al., Tetrahedron Letters (2003) 44(21):4019-4022.
Schmidt et al., Synthesis (1992) 10:1025-1030.
Schmidt et al., Synthesis (1992) 12:1248-1254.
Allen and Danishefsky, J Prakt Chem (2000) 342:736-744.
Bajusz et al., Bioorg Med Chem Lett (1998) 8:1477-1482.
Brands et al., Bioorg Med Chem Lett (2003) 13:241-246.
Brands et al., J Med Chem (2002) 45:4246-4253.
Brown et al., J Am Chem Soc (1989)111(19):7328-7333.
Brown et al., J Chem Soc, Perkins Trans (1992) 1:123-130.
Carlstrom et al., J Chem Soc, Chem Commun (1991) 17:1216-1217.
English Translation of the International Preliminary Report on Patentability for PCT/EP2005/009912, mailed May 3, 2007, 6 pages.
Ezaki et al., Applied Environ Microbiol (1992) 58(12):3879-3882.
Ezaki et al., J Antibiot (1993) 46(3):C-2.
Giroux et al., Tetrahedron Lett (1997) 3841-3844.
Hempel et al., J Am Chem Soc (1989) 111(19):7323-7327.
International Search Report for PCT/EP2005/009912, mailed on Oct. 31, 2005, 2 pages.
Ishiyama et al., J Org Chem (1995) 23:7508-7510.
Jorgensen and Gautun, Tetrahedron (1999) 55:10527-10536.
Kannan and Williams, J Org Chem (1987) 52(24):5435-5437.
Lepine and Zhu, Org Lett (2005) 7:2981-2984.
Miyaura et al., Chem Rev (1995) 95:2457-2483.
Muller and Blobel, PNAS USA (1984) 81:7421-7425.

(Continued)

*Primary Examiner*—James O Wilson
*Assistant Examiner*—Noble Jarrell
(74) *Attorney, Agent, or Firm*—Morrison & Foerster LLP

(57) ABSTRACT

The invention relates to antibacterial macrocycles with substituted biphenyl and processes for their preparation, their use for the treatment and/or prophylaxis of diseases, and their use for the production of medicaments for the treatment and/or prophylaxis of diseases, especially of bacterial infections.

11 Claims, No Drawings

OTHER PUBLICATIONS

National Committee for Clinical Laboratory Standards, Fifth Edition, 2000, Document M7-A5, vol. 20, No. 2 [ISBN 1-56238-394-9].
Paintner et al., Synlett (2003) 4:522-526.
Popieniek and Pratt, Anal Biochem (1987) 165(1):108-113.
Rompp Lexikon Chemie—Version 2.0, Stuttgart/New York: Georg Thieme Verlag, 1999 [English translation abstract only].
Rudolph et al., Org Lett (2001) 3(20):3153-3155.
Sandstrom, Chirality (1995) 7(4):181-192.
Schmidt et al., J Chem Soc, Chem Commun (1991) 10:744.
Schmidt et al., J Chem Soc, Chem Commun (1992) 13:951-953.
Schmidt et al., Synthesis (1991) 5:409-413.
Sobirov et al., Russ J Bioorg Chem (1994) 20:397-405.
"Syphilis facts", http://www.dhpe.org/infect/syphilis.html, accessed Jan. 10, 2008.
Thesis of R. U. Meyer, Stuttgart University, Germany, 1991 [English translation abstract included].
Thesis of V. Leitenberger, Stuggart University, Germany, 1991 [English translation abstract included].
Uchida et al., J Antibiot (1985) 38(11):1462-1468.
Uchida et al., J Org Chem (1985) 50(8):1341-1342.
Vippagunta et al., Advanced Drug Delivery Reviews (2001) 48:3-26.
Watanabe et al., Synlett (1992) 3:207-210.
Zhao and Moore, J Org Chem (2002) 67:3548-3554.
U.S. Appl. No. 10/518,600, Internationally filed on Jun. 10, 2003 [Lampe et al.].
Non-Final Office Action for U.S. Appl. No. 10/518,600, mailed on Dec. 26, 2008, 13 pages.
Amendment in Response to Non-Final Office Action for U.S. Appl. No. 10/518,600, filed on Apr. 27, 2009.
U.S. Appl. No. 10/522,667, Internationally filed on Jan. 28, 2005 [Lampe et al.].
Preliminary Amendment for U.S. Appl. No. 10/522,667, filed on Jul. 27, 2006.
Non-Final Office Action for U.S. Appl. No. 10/522,667, mailed on Feb. 5, 2008, 12 pages.
Notice of Abandonment for U.S. Appl. No. 10/522,667, mailed on Aug. 29, 2008, 2 pages.
U.S. Appl. No. 11/690,762, filed on Mar. 23, 2007 [Endermann et al.].
Non-Final Office Action for U.S. Appl. No. 11/690,762, mailed on Jan. 24, 2008, 5 pages.
Amendment in Response to Non-Final Office Action for U.S. Appl. No. 11/690,762, filed on Apr. 21, 2008, 27 pages.
Notice of Allowance for U.S. Appl. No. 11/690,762, mailed on Jun. 26, 2008, 6 pages.
U.S. Appl. No. 11/904,550, filed on Sep. 26, 2007 [Endermann et al.].
First Preliminary Amendment and Response to Notice to File Missing Parts of Nonprovisional Application for U.S. Appl. No. 11/904,550, filed on Jul. 8, 2008, 5 pages.
U.S. Appl. No. 11/906,088, filed on Sep. 28, 2007 [Endermann et al.].
Non-Final Office Action for U.S. Appl. No. 11/906,088, mailed on Feb. 19, 2009, 6 pages.
Amendment for U.S. Appl. No. 11/906,088, filed on Jun. 15, 2009.
U.S. Appl. No. 12/008,662, filed on Jan. 11, 2008 [Endemann et al.].
First Preliminary Amendment and Response to Notice to File Missing Parts of Nonprovisional Application for U.S. Appl. No. 12/008,662, filed on Jul. 8, 2008, 5 pages.

* cited by examiner

ANTIBACTERIAL MACROCYCLES WITH SUBSTITUTED BIPHENYL

CROSS-REFERENCE TO RELATED APPLICATIONS

This application is a continuation of pending International Patent Application PCT/EP2004/013688, filed on Dec. 2, 2004 designating U.S., which claims priority from German Patent Application DE 103 58 824.8, filed on Dec. 16, 2003.

BACKGROUND OF THE INVENTION

The invention relates to antibacterial macrocycles with substituted biphenyl and processes for their preparation, their use for the treatment and/or prophylaxis of diseases, and their use for the production of medicaments for the treatment and/or prophylaxis of diseases, especially of bacterial infections.

In U.S. Pat. No. 3,452,136, thesis of R. U. Meyer, Stuttgart University, Germany 1991, thesis of V. Leitenberger, Stuttgart University, Germany 1991, Synthesis (1992), (10), 1025-30, J. Chem. Soc., Perkin Trans. 1 (1992), (1), 123-130, J. Chem. Soc., Chem. Commun. (1991), (10), 744, Synthesis (1991), (5), 409-13, J. Chem. Soc., Chem. Commun. (1991), (5), 275-7, J. Antibiot. (1985), 38(11), 1462-8, J. Antibiot. (1985), 38(11), 1453-61, the natural product biphenomycin B is described as having antibacterial activity. Some steps in the synthesis of biphenomycin B are described in Synlett (2003), 4, 522-526.

Chirality (1995), 7(4), 181-92, J. Antibiot. (1991), 44(6), 674-7, J. Am. Chem. Soc. (1989), 111(19), 7323-7, J. Am. Chem. Soc. (1989), 111(19), 7328-33, J. Org. Chem. (1987), 52(24), 5435-7, Anal. Biochem. (1987), 165(1), 108-13, J. Org. Chem. (1985), 50(8), 1341-2, J. Antibiot. (1993), 46(3), C-2, J. Antibiot. (1993), 46(1), 135-40, Synthesis (1992), (12), 1248-54, Appl. Environ. Microbiol. (1992), 58(12), 3879-8, J. Chem. Soc., Chem. Commun. (1992), (13), 951-3 describe a structurally related natural product, biphenomycin A, which has a further substitution with a hydroxy group on the macrocycle.

The natural products do not comply in terms of their properties with the requirements for antibacterial medicaments. Although structurally different agents with antibacterial activity are available on the market, the development of a resistance is a regular possibility. Novel agents for a good and more effective therapy are therefore desirable.

SUMMARY OF THE INVENTION

One object of the present invention is therefore to provide novel and alternative compounds having the same or improved antibacterial effect for the treatment of bacterial diseases in humans and animals.

It has surprisingly been found that certain derivatives of these natural products in which the carboxy group of the natural product is replaced with an amide group comprising a basic group have antibacterial activity on S. aureus strains (RN4220BiR and T17) which are resistant to biphenomycin.

In addition, these derivatives show an improved spontaneous resistance rate against S. aureus wild-type strains and biphenomycin-resistant S. aureus strains.

The invention relates to compounds of formula

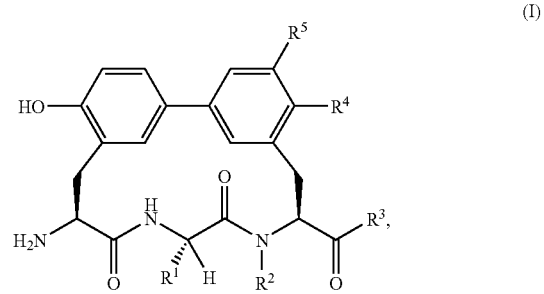

(I)

in which

R1 is alkyl, whereby alkyl is substituted with 1 to 3 substituents, whereby the substituents are selected independently of one another from the group consisting of amino, hydroxy, aminocarbonyl, hydroxycarbonyl, (C1-C6)-alkoxy, (C1-C6)-alkylamino, 5- to 7-membered heterocyclyl, 5- to 7-membered heteroaryl, $(C_1-C_6)$-alkylaminocarbonyl, guanidino and amidino, in which heterocyclyl and heteroaryl may be substituted with 1 to 2 substituents, whereby the substituents are selected independently of one another from the group consisting of amino and $(C_1-C_6)$-alkyl, $R^2$ is hydrogen, $(C_1-C_6)$-alkyl or $(C_3-C_7)$-cycloalkyl, $R^3$ is hydroxy or —$NR^6R^7$, $R^4$ is hydrogen, halogen, amino, hydroxy, aminocarbonyl, hydroxycarbonyl, nitro, trifluoromethyl, trifluoromethoxy, $(C_1-C_4)$-alkyl, $(C_1-C_4)$-alkoxy, $(C_1-C_6)$-alkylamino, amino or mono-$(C_1-C_4)$-alkylamino substituted mono-$(C_2-C_6)$-alkylaminocarbonyl or amino or mono-$(C_1-C_4)$-alkylamino substituted $(C_1-C_6)$-alkylcarbonylamino, $R^5$ is hydrogen, halogen, amino, hydroxy, aminocarbonyl, hydroxycarbonyl, nitro, trifluoromethyl, trifluoromethoxy, $(C_1-C_4)$-alkyl, $(C_1-C_4)$-alkoxy, $(C_1-C_6)$-alkylamino, amino or mono-$(C_1-C_4)$-alkylamino substituted mono-$(C_2-C_6)$-alkylaminocarbonyl or amino or mono-$(C_1-C_4)$-alkylamino substituted $(C_1-C_6)$-alkylcarbonylamino, whereby $R^5$ is halogen, amino, hydroxy, aminocarbonyl, hydroxycarbonyl, nitro, trifluoromethyl, trifluoromethoxy, $(C_1-C_4)$-alkyl, $(C_1-C_4)$-alkoxy, $(C_1-C_6)$-alkylamino, amino or mono-$(C_1-C_4)$-alkylamino substituted mono-$(C_2-C_6)$-alkylaminocarbonyl or amino or mono-$(C_1-C_4)$-alkylamino substituted $(C_1-C_6)$-alkylcarbonylamino if $R^4$ is hydroxy, $R^6$ is hydrogen, $(C_1-C_6)$-alkyl, $(C_3-C_7)$-cycloalkyl, 5- to 7-membered heterocyclyl, $(C_6-C_{10})$-aryl or 5- to 7-membered heteroaryl, whereby alkyl, cycloalkyl, heterocyclyl, aryl and heteroaryl may be substituted with 1 to 3 substituents, whereby the substituents are selected independently of one another from the group consisting of halogen, amino, hydroxy, aminocarbonyl, hydroxycarbonyl, nitro, cyano, trifluoromethyl, trifluoromethoxy, $(C_1-C_6)$-alkyl, $(C_1-C_6)$-alkoxy, $(C_1-C_6)$-alkylamino, $(C_3-C_7)$-cycloalkyl, 5- to 7-membered heterocyclyl, $(C_6-C_{10})$-aryl, 5- to 7-membered heteroaryl, $(C_1-C_6)$-alkoxycarbonyl, $(C_1-C_6)$-alkylaminocarbonyl, $(C_1-C_6)$-alkylsulfonylamino and $(C_6-C_{10})$-arylsulfonylamino, in which alkyl, alkylamino, cycloalkyl, heterocyclyl, aryl, heteroaryl, alkylaminocarbonyl, alkylsulfonylamino and arylsulfonylamino may be substituted with 1 to 3 substituents, whereby the substituents are selected independently of one another from the group consisting of amino, hydroxy, aminocarbonyl and hydroxycarbonyl, $R^7$ is hydrogen, ($C_1$-$C_6$)-alkyl or ($C_3$-$C_7$)-cycloalkyl,
whereby alkyl may be substituted with 1 to 2 substituents, whereby the substituents are selected independently of one another from the group consisting of amino, hydroxy and ($C_1$-$C_6$)-alkylamino, or $R^6$ and $R^7$ together with the nitrogen atom to which they are bonded form a piperidinyl, morpholinyl, piperazinyl or pyrrolidinyl, whereby piperidinyl, morpholinyl, piperazinyl and pyrrolidinyl may be substituted with 1 to 3 substituents, whereby the substituents are selected independently of one another from the group consisting of amino, hydroxy, aminocarbonyl, hydroxycarbonyl, optionally amino or hydroxy substituted ($C_1$-$C_6$)-alkyl, ($C_1$-$C_6$)-alkoxy, ($C_1$-$C_6$)-alkylamino and ($C_1$-$C_6$)-alkoxycarbonyl, and the salts thereof, the solvates thereof and the solvates of the salts thereof.

Compounds of the invention are the compounds of formula (I) and the salts, solvates and solvates of the salts thereof, and the compounds which are encompassed by formula (I) and are mentioned below as exemplary embodiment(s), and the salts, solvates and solvates of the salts thereof, insofar as the compounds which are encompassed by formula (I) and are mentioned below are not already salts, solvates and solvates of the salts.

The compounds of the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers by known processes such as chromatography on a chiral phase or crystallization using chiral amines or chiral acids.

The invention also relates, depending on the structure of the compounds, to tautomers of the compounds.

Salts preferred for the purposes of the invention are physiologically acceptable salts of the compounds of the invention.

Physiologically acceptable salts of the compounds (I) include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid, trifluoroacetic acid and benzoic acid.

Physiologically acceptable salts of the compounds (I) also include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dihydroabietylamine, arginine, lysine, ethylenediamine and methylpiperidine.

Solvates for the purposes of the invention refer to those forms of the compounds which form a complex in the solid or liquid state through coordination with solvent molecules. Hydrates are a special form of solvates in which coordination takes place with water.

For the purposes of the present invention, the substituents have the following meaning unless specified otherwise:

Alkyl per se and "alk" and "alkyl" in alkoxy, alkylamino, alkoxycarbonyl, alkylaminocarbonyl and alkylsulfonylamino represent a linear or branched alkyl radical usually having 1 to 6 ("$C_1$-$C_6$-alkyl"), preferably 1 to 4, particularly preferably 1 to 3 carbon atoms, by way of example and preferably methyl, ethyl, n-propyl, isopropyl, tert-butyl, n-pentyl and n-hexyl.

Alkoxy by way of example and preferably represents methoxy, ethoxy, n-propoxy, isopropoxy, tert-butoxy, n-pentoxy and n-hexoxy.

Alkylamino represents an alkylamino radical having one or two alkyl substituents (chosen independently of one another), by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino. $C_1$-$C_3$-Alkylamino represents for example a monoalkylamino radical having 1 to 3 carbon atoms or a dialkylamino radical having in 1 to 3 carbon atoms per alkyl substituent.

Alkoxycarbonyl by way of example and preferably represents methoxycarbonyl, ethoxycarbonyl, n-propoxycarbonyl, isopropoxycarbonyl, tert-butoxycarbonyl, n-pentoxycarbonyl and n-hexoxycarbonyl.

Alkylaminocarbonyl represents an alkylaminocarbonyl radical having one or two alkyl substituents (chosen independently of one another), by way of example and preferably methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert-butyl-N-methylaminocarbonyl, N-ethyl-N-n-pentylaminocarbonyl and N-n-hexyl-N-methylaminocarbonyl. $C_1$-$C_3$-Alkylaminocarbonyl represents for example a monoalkylaminocarbonyl radical having 1 to 3 carbon atoms or a dialkylaminocarbonyl radical having 1 to 3 carbon atoms per alkyl substituent.

Alkylsulfonylamino by way of example and preferably represents methylsulfonylamino, ethylsulfonylamino, n-propylsulfonylamino, isopropylsulfonylamino, tert-butylsulfonylamino, n-pentyl-sulfonylamino and n-hexylsulfonylamino.

Cycloalkyl represents a cycloalkyl group usually having 3 to 7, preferably 5 to 6 carbon atoms, by way of example and preferably cyclopropyl, cyclobutyl, cyclopentyl, cyclohexyl and cycloheptyl.

Aryl represents a mono- or bicyclic aromatic, carbocyclic radical usually having 6 to 10 carbon atoms; by way of example and preferably phenyl and naphthyl.

Arylsulfonylamino by way of example and preferably represents phenylsulfonylamino and naphthylsulfonylamino.

5- to 7-membered heterocyclyl in the context of the invention represents a mono- or bicyclic, saturated or partially unsaturated heterocycle having up to three heteroatoms from the series N, O and/or S, which is linked via a ring carbon atom or a nitrogen atom of the heterocycle. Mention may be made by way of example and preferably of: tetrahydrofuryl, dihydrofuryl, imidazolidinyl, thiolanyl, dioxolanyl, pyrrolidinyl, pyrrolinyl, tetrahydropyranyl, dihydropyranyl, piperidinyl, piperazinyl, morpholinyl, thiomorpholinyl and 1,4-diazepanyl.

5- to 7-membered heteroaryl in the context of the invention generally represents an aromatic, mono- or bicyclic radical having 5 to 7 ring atoms and up to 4 heteroatoms from the series S, O and/or N. 5- to 6-membered heteroaryls having up to 4 heteroatoms are preferred. The heteroaryl radical may be bonded via a carbon atom or a heteroatom. Mention may be made by way of example and preferably of: thienyl, furyl, pyrrolyl, thiazolyl, oxazolyl, imidazolyl, pyridyl, pyrimidyl, pyridazinyl, indolyl, indazolyl, benzofuranyl and benzothiophenyl.

Halogen represents fluorine, chlorine, bromine and iodine.

A symbol # on a carbon atom means that the compound is, in terms of the configuration at this carbon atom, in enantiopure form, by which is meant in the context of the present invention an enantiomeric excess of more than 90% (>90% ee).

In the formulae of groups which $R^6$ can represent, the end of the line besides which there is an * does not represent a carbon atom or a $CH_2$ group but is part of the bond to the nitrogen atom to which $R^6$ is bonded. $R^6$ is thus for example 2-aminoethyl in the case of k=0, l =1 and $R^9$=H, 3-amino-2-hydroxypropyl in the case of k=1, $R^8$=OH, l=1 and $R^9$=H, piperidin-4-ylmethyl in the case of q=1 and r=1 or piperidin-4-yl in the case of q=0 and r=1.

Preference is given in the context of the present invention to compounds of formula (I) in which $R^1$ is alkyl, whereby alkyl is substituted with 1 to 3 substituents, whereby the substituents are selected independently of one another from the group consisting of amino, hydroxy, aminocarbonyl, hydroxycarbonyl, $(C_1$-$C_6)$-alkoxy, $(C_1$-$C_6)$-alkylamino, 5- to 7-membered heterocyclyl, 5- to 7-membered heteroaryl, $(C_1$-$C_6)$-alkylaminocarbonyl, guanidino and amidino, in which heterocyclyl and heteroaryl may be substituted with 1 to 2 substituents, whereby the substituents are selected independently of one another from the group consisting of amino and $(C_1$-$C_6)$-alkyl, $R^2$ is hydrogen, $(C_1$-$C_6)$-alkyl or $(C_3$-$C_7)$-cycloalkyl, $R^3$ is hydroxy or —$NR^6R^7$, $R^4$ is hydrogen, halogen, amino, hydroxy, aminocarbonyl, hydroxycarbonyl, nitro, trifluoromethyl, trifluoromethoxy, $(C_1$-$C_4)$-alkyl, $(C_1$-$C_4)$-alkoxy or $(C_1$-$C_6)$-alkylamino, $R^5$ is hydrogen, halogen, amino, hydroxy, aminocarbonyl, hydroxycarbonyl, nitro, trifluoromethyl, trifluoromethoxy, $(C_1$-$C_4)$-alkyl, $(C_1$-$C_4)$-alkoxy or $(C_1$-$C_6)$-alkylamino, whereby $R^5$ is halogen, amino, hydroxy, aminocarbonyl, hydroxycarbonyl, nitro, trifluoromethyl, trifluoromethoxy, $(C_1$-$C_4)$-alkyl, $(C_1$-$C_4)$-alkoxy or $(C_1$-$C_6)$-alkylamino, if $R^4$ is hydroxy, $R^6$ is hydrogen, $(C_1$-$C_6)$-alkyl, $(C_3$-$C_7)$-cycloalkyl, 5- to 7-membered heterocyclyl, $(C_6$-$C_{10})$-aryl or 5- to 7-membered heteroaryl, whereby alkyl, cycloalkyl, heterocyclyl, aryl and heteroaryl may be substituted with 1 to 3 substituents, whereby the substituents are selected independently of one another from the group consisting of halogen, amino, hydroxy, aminocarbonyl, hydroxycarbonyl, nitro, cyano, trifluoromethyl, trifluoromethoxy, $(C_1$-$C_6)$-alkyl, $(C_1$-$C_6)$-alkoxy, $(C_1$-$C_6)$-alkylamino, $(C_3$-$C_7)$-cycloalkyl, 5- to 7-membered heterocyclyl, $(C_6$-$C_{10})$-aryl, 5- to 7-membered heteroaryl, $(C_1$-$C_6)$-alkoxycarbonyl, $(C_1$-$C_6)$-alkylaminocarbonyl, $(C_1$-$C_6)$-alkylsulfonylamino and $(C_6$-$C_{10})$-arylsulfonylamino, in which alkyl, alkylamino, cycloalkyl, heterocyclyl, aryl, heteroaryl, alkylaminocarbonyl, alkylsulfonylamino and arylsulfonylamino may be substituted with 1 to 3 substituents, whereby the substituents are selected independently of one another from the group consisting of amino, hydroxy, aminocarbonyl and hydroxycarbonyl, $R^7$ is hydrogen, $(C_1$-$C_6)$-alkyl or $(C_3$-$C_7)$-cycloalkyl, whereby alkyl may be substituted with 1 to 2 substituents, whereby the substituents are selected independently of one another from the group consisting of amino, hydroxy and $(C_1$-$C_6)$-alkylamino, or $R^6$ and $R^7$ together with the nitrogen atom to which they are bonded form a piperidinyl, morpholinyl, piperazinyl or pyrrolidinyl, whereby piperidinyl, morpholinyl, piperazinyl and pyrrolidinyl may be substituted with 1 to 3 substituents, whereby the substituents are selected independently of one another from the group consisting of amino, hydroxy, aminocarbonyl, hydroxycarbonyl, optionally amino- or hydroxy-substituted $(C_1$-$C_6)$-alkyl, $(C_1$-$C_6)$-alkoxy, $(C_1$-$C_6)$-alkylamino and $(C_1$-$C_6)$-alkoxycarbonyl, and the salts thereof, the solvates thereof and the solvates of the salts thereof.

Preference is also given in the context of the present invention to compounds of formula (I) in which $R^1$ is aminomethyl, 2-aminoethyl, 3-aminoprop-1-yl, 4-aminobut-1-yl, hydroxymethyl, 2-hydroxy-ethyl, aminocarbonylmethyl, 2-aminocarbonylethyl, 2-hydroxycarbonylethyl, 3-guanidinoprop-1-yl, 3-amino-2-hydroxyprop-1-yl or 4-amino-3-hydroxybut-1-yl, $R^2$ is hydrogen, methyl, ethyl or cyclopropyl, $R^3$ is hydroxy or —$NR^6R^7$, $R^4$ is hydrogen, halogen, amino, hydroxy, hydroxycarbonyl, aminocarbonyl, nitro or methyl, $R^5$ is hydrogen, halogen, amino, hydroxy, aminocarbonyl, hydroxycarbonyl, nitro or methyl, whereby $R^5$ is halogen, amino, hydroxy, aminocarbonyl, hydroxycarbonyl, nitro or methyl, if $R^4$ is hydroxy, $R^6$ is hydrogen, $(C_1$-$C_6)$-alkyl, $(C_5$-$C_6)$-cycloalkyl, 5- to 7-membered heterocyclyl or phenyl, whereby alkyl, cycloalkyl, heterocyclyl and phenyl may be substituted with 1 to 3 substituents, whereby the substituents are selected independently of one another from the group consisting of amino, hydroxy, aminocarbonyl, hydroxycarbonyl, $(C_1$-$C_4)$-alkyl, $(C_1$-$C_6)$-alkylamino, 5- to 7-membered heterocyclyl, phenyl, 5- or 6-membered heteroaryl, $(C_1$-$C_6)$-alkoxycarbonyl and $(C_1$-$C_6)$-alkylaminocarbonyl, in which alkyl, alkylamino, heterocyclyl, aryl, heteroaryl and alkylaminocarbonyl may be substituted with 1 to 3 substituents, whereby the substituents are selected independently of one another from the group consisting of amino, hydroxy, aminocarbonyl and hydroxycarbonyl, $R^7$ is hydrogen or $(C_1$-$C_4)$-alkyl, whereby alkyl may be substituted with 1 to 2 substituents, whereby the substituents are selected independently of one another from the group consisting of amino, hydroxy and $(C_1$-$C_6)$-alkylamino, or $R^6$ and $R^7$ together with the nitrogen atom to which they are bonded form a piperazinyl, whereby piperazinyl may be substituted with 1 to 3 substituents, whereby the substituents are selected independently of one another from the group consisting of amino, hydroxy, optionally amino substituted $(C_1-C_6)$-alkyl, and $(C_1-C_6)$-alkylamino, and the salts thereof, the solvates thereof and the solvates of the salts thereof.

Preference is also given in the context of the present invention to compounds of formula (I) in which $R^1$ is 2-aminoethyl, 3-aminoprop-1-yl, 4-aminobut-1-yl or 3-amino-2-hydroxyprop-1-yl, $R^2$ is hydrogen, methyl or ethyl, $R^3$ is —NR$^6$R$^7$, $R^4$ is hydrogen, fluorine, chlorine, amino, hydroxy or methyl, $R^5$ is hydrogen, fluorine or hydroxy, whereby $R^5$ is fluorine if $R^4$ is hydroxy, $R^6$ is a group of the formula

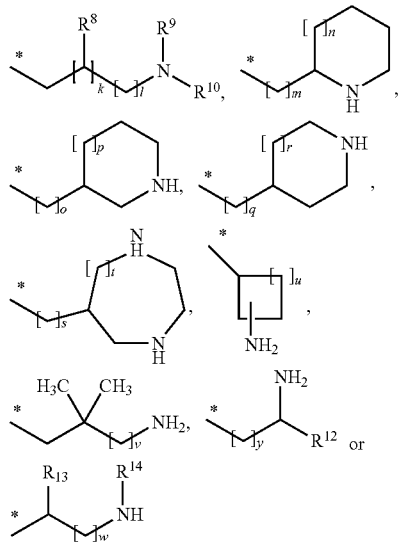

whereby $R^8$ is hydrogen or hydroxy, $R^9$ and $R^{14}$ are independently of one another hydrogen, methyl or a group of the formula

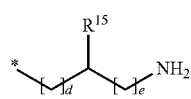

in which

* is the point of attachment to the nitrogen atom, $R^{15}$ is hydrogen or *—$(CH_2)_f$—$NH_2$, in which f is a number 1, 2 or 3, d is a number 0, 1, 2 or 3, and e is a number 1, 2 or 3, $R^{10}$ is hydrogen or aminoethyl, or $R^9$ and $R^{10}$ form together with the nitrogen atom to which they are bonded a piperazine ring, $R^{12}$ and $R^{13}$ are independently of one another a group of the formula *—$(CH_2)_{Z1}$—OH or *—$(CH_2)_{Z2}$—$NH_2$, in which

* is the point of attachment to the nitrogen atom,

Z1 and Z2 are independently of one another a number 1, 2, 3 or 4, k and t are independently of one another a number 0 or 1, l, w and y is independently of one another a number 1, 2, 3 or 4, m, r, s and v are independently of one another a number 1 or 2, n, o, p and q are independently of one another a number 0, 1 or 2, u is a number 0, 1, 2 or 3,

may independently of one another if w or y is 3 carry a hydroxy group on the middle carbon atom of the three-membered chain,

* is the point of attachment to the nitrogen atom, $R^7$ is hydrogen, and the salts thereof, the solvates thereof and the solvates of the salts thereof.

Preference is also given in the context of the present invention to compounds of formula (I) in which $R^1$ is 2-aminoethyl, 3-aminoprop-1-yl, 4-aminobut-1-yl or 3-amino-2-hydroxyprop-1-yl, $R^6$ is hydrogen, methyl or ethyl, $R^3$ is —NRR$^7$, $R^4$ is hydrogen, fluorine, chlorine, amino, hydroxy or methyl, $R^5$ is hydrogen, fluorine or hydroxy, whereby $R^5$ is fluorine if $R^4$ is hydroxy, $R^6$ is a group of the formula

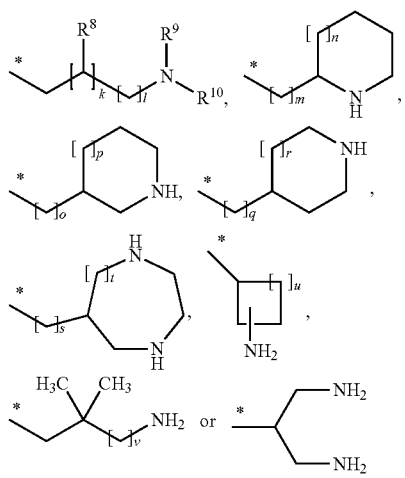

whereby $R^8$ is hydrogen or hydroxy, $R^9$ is hydrogen or methyl, $R^{10}$ is hydrogen, or $R^9$ and $R^{10}$ form together with the nitrogen atom to which they are bonded a piperazine ring k and t are independently of one another a number 0 or 1, l is a number 1, 2, 3 or 4, m, r, s and v are independently of one another a number 1 or 2, n, o, p and q are independently of one another a number 0, 1 or 2, u is a number 0, 1, 2 or 3,

* is the point of attachment to the nitrogen atom, $R^7$ is hydrogen, and the salts thereof, the solvates thereof and the solvates of the salts thereof.

Preference is given in the context of the present invention also to compounds of formula (I) in which
R$^1$ is 3-aminoprop-1-yl or 3-amino-2-hydroxyprop-1-yl,
R$^2$ is hydrogen or methyl,
R$^3$ is —NR$^6$R$^7$,
R$^4$ is hydrogen, fluorine, chlorine or methyl,
R$^5$ is hydrogen,
R$^6$ is a group of the formula

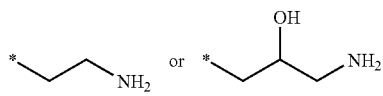

whereby
* is the point of attachment to the nitrogen atom,
R$^7$ is hydrogen,
and the salts thereof, the solvates thereof and the solvates of the salts thereof.

The invention further relates to a process for preparing the compounds of the formula (I) or the salts thereof, the solvates thereof or the solvates of the salts thereof, whereby in process

[A] compounds of formula

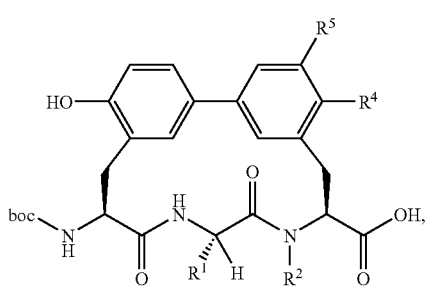

in which R$^1$, R$^2$, R$^4$ and R$^5$ have the meaning indicated above, and boc is tert-butoxycarbonyl,
are reacted in a two-stage process first in the presence of one or more dehydrating reagents with compounds of formula

HNR$^6$R$^7$     (III), in which R$^6$ and R$^7$ have the meaning indicated above,
and subsequently with an acid to give compounds of formula

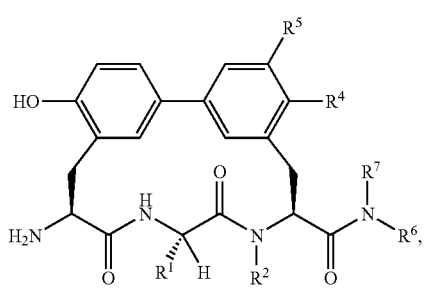

in which R$^1$, R$^2$, R$^4$ and R$^5$ have the meaning indicated above, or

[B] compounds of formula

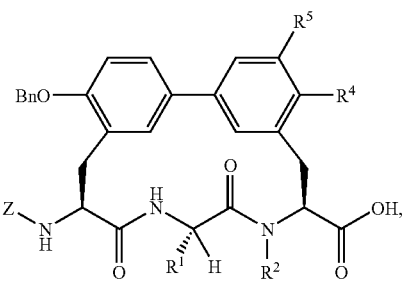

in which R$^1$, R$^2$, R$^4$ and R$^5$ have the meaning indicated above, and Z is benzyloxycarbonyl,
are reacted in a two-stage process first in the presence of one or more dehydrating reagents with compounds of formula (III) and subsequently with an acid or by hydrogenolysis to give compounds of formula (Ia), or

[C] compounds of formula (IV) are reacted with an acid or by hydrogenolysis to give compounds of formula

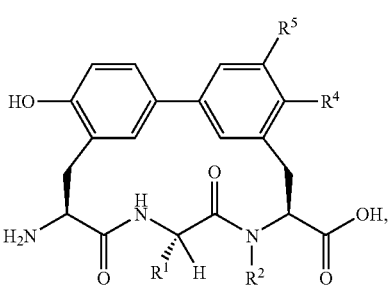

in which R$^1$, R$^2$, R$^4$ and R$^5$ have the meaning indicated above, or

[D] compounds of formula

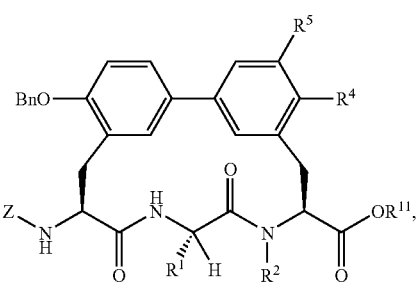

in which R$^1$, R$^2$, R$^4$ and R$^5$ have the meaning indicated above, and
R$^{11}$ is benzyl, methyl or ethyl,
are reacted with an acid or by hydrogenolysis, optionally by subsequent reaction with a base to hydrolyse the methyl or ethyl ester, to give compounds of formula (Ib).

Compounds of formula (I) are compounds of formulae (Ia) and (Ib).

The free base of the salts can be obtained for example by chromatography on a reversed phase column with an acetonitrile-water gradient with addition of a base, in particular by using an RP18 PHENOMENEX® LUNA™ C18(2) column and diethylamine as base.

The invention further relates to a process for preparing the compounds of formula (I) or the solvates thereof as claimed in claim 1, in which salts of the compounds or solvates of the salts of the compounds are converted into the compounds by chromatography with addition of a base.

A hydroxy group in the radical $R^1$ is optionally protected with a tert-butyldimethylsilyl group during the reaction with compounds of the formula (III), which group is removed in the second reaction step.

Reactive functionalities in the radicals $R^6$ and $R^7$ of compounds of formula (III) are introduced into the synthesis already protected, with preference for acid-labile protecting groups (e.g. boc).

The reaction in the first stage of processes [A] and [B] generally takes place in inert solvents, optionally in the presence of a base, preferably in a temperature range from 0° C. to 40° C. under atmospheric pressure.

Dehydrating reagents suitable hereby are, for example, carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium-3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or mixtures of these, or mixture of these together with bases.

Bases are, for example, alkali metal carbonates such as, for example, sodium or potassium carbonate, or bicarbonate, or organic bases such as trialkylamines, e.g. triethylamine, N-methylmorpholine, N-methylpiperidine, 4-dimethylaminopyridine or diisopropylethylamine.

The condensation is preferably carried out with HATU in the presence of a base, in particular diisopropylethylamine.

Inert solvents are, for example, halohydrocarbons such as dichloromethane or trichloromethane, hydrocarbon such as benzene, or nitromethane, dioxane, dimethylformamide or acetonitrile. It is also possible to employ mixtures of these solvents. Dimethylformamide is particularly preferred.

The reaction with an acid in the second stage of processes [A] and [B] and the reaction with an acid in processes [C] and [D] preferably takes place in a temperature range from 0° C. to 40° C. under atmospheric pressure.

Acids suitable hereby are hydrogen chloride in dioxane, hydrogen bromide in acetic acid or trifluoroacetic acid in methylene chloride.

The hydrogenolysis in the second stage of process [B] and the hydrogenolysis in processes [C] and [D] generally takes place in a solvent in the presence of hydrogen and palladium on activated carbon, preferably in a temperature range from 0° C. to 40° C. under atmospheric pressure.

Solvents are, for example, alcohols such as methanol, ethanol, n-propanol or isopropanol, in a mixture with water and glacial acetic acid, with preference for a mixture of ethanol, water and glacial acetic acid.

The hydrolysis in process [D] can for example take place as described for the reaction of the compounds of formula (V) to give compounds of formula (IV).

The compounds of formula (III) are known or can be prepared in analogy to known processes.

The compounds of formula (II) are known or can be prepared by reacting compounds of formula (Ib) with di(tert-butyl)dicarbonate in the presence of a base.

The reaction generally takes place in a solvent, preferably in a temperature range from 0° C. to 40° C. under atmospheric pressure.

Bases are, for example, alkali metal hydroxides such as sodium or potassium hydroxide, or alkali metal carbonates such as cesium carbonate, sodium or potassium carbonate, or other bases such as DBU, triethylamine or diisopropylethylamine, with preference for sodium hydroxide or sodium carbonate.

Solvents are, for example, halohydrocarbons such as methylene chloride or 1,2-dichloroethane, alcohols such as methanol, ethanol or isopropanol, or water.

The reaction is preferably carried out with sodium hydroxide in water or sodium carbonate in methanol.

The compounds of formula (IV) are known or can be prepared by hydrolysing the benzyl, methyl or ethyl ester in compounds of formula (V).

The reaction generally takes place in a solvent in the presence of a base, preferably in a temperature range from 0° C. to 40° C. under atmospheric pressure.

Bases are, for example, alkali metal hydroxides such as lithium, sodium or potassium hydroxide, with preference for lithium hydroxide.

Solvents are, for example, halohydrocarbons such as dichloromethane or trichloromethane, ethers such as tetrahydrofuran or dioxane, or alcohols such as methanol, ethanol or isopropanol, or dimethylformamide. It is also possible to employ mixtures of the solvents or mixtures of the solvents with water. Tetrahydrofuran or a mixture of methanol and water are particularly preferred.

The compounds of formula (V) are known or can be prepared by reacting compounds of formula

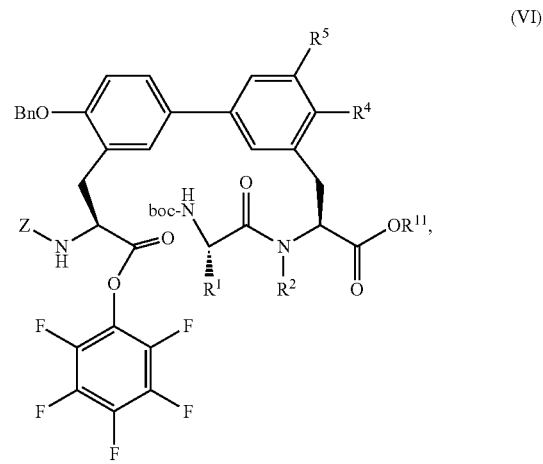

(VI)

in which $R^1$, $R^2$, $R^4$, $R^5$ and $R^{11}$ have the meaning indicated above, in the first stage with acids as described for the second stage of processes [A] and [B], and in the second stage with bases.

The reaction with bases in the second stage generally takes place in a solvent, preferably in a temperature range from 0° C. to 40° C. under atmospheric pressure.

Bases are, for example, alkali metal hydroxides such as sodium or potassium hydroxide, or alkali metal carbonates such as cesium carbonate, sodium or potassium carbonate, or other bases such as DBU, triethylamine or diisopropylethylamine, with preference for triethylamine.

Solvents are, for example halohydrocarbons such as chloroform, methylene chloride or 1,2-dichloroethane, or tetrahydrofuran, or mixtures of the solvents, with preference for methylene chloride or tetrahydrofuran.

The compounds of formula (VI) are known or can be prepared by reacting compounds of formula

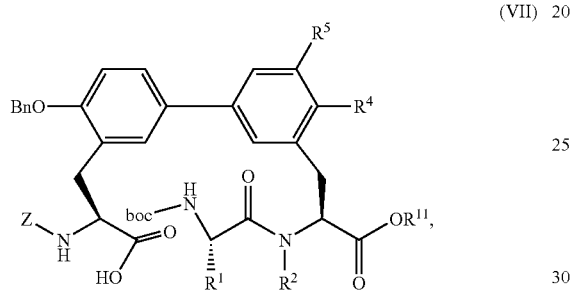

(VII)

in which $R^1$, $R^2$, $R^4$, $R^5$ and $R^{11}$ have the meaning indicated above,
with pentafluorophenol in the presence of dehydrating reagents as described for the first stage of processes [A] and [B].

The reaction preferably takes place with DMAP and EDC in dichloromethane in a temperature range from −40° C. to 40° C. under atmospheric pressure.

The compounds of formula (VII) are known or can be prepared by reacting compounds of formula

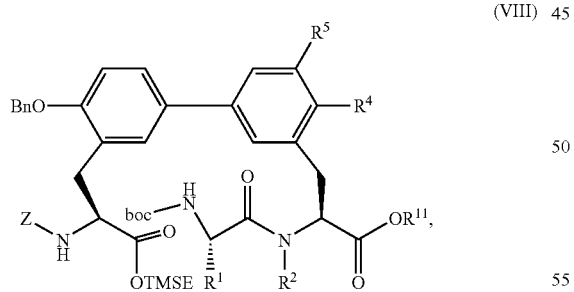

(VIII)

in which $R^1$, $R^2$, $R^4$, $R^5$ and $R^{11}$ have the meaning indicated above,
with fluoride, in particular with tetrabutylammonium fluoride.

The reaction generally takes place in a solvent, preferably in a temperature range from −10° C. to 30° C. under atmospheric pressure.

Inert solvents are, for example, halohydrocarbons such as dichloromethane, or hydrocarbons such as benzene or toluene, or ethers such as tetrahydrofuran or dioxane, or dimethylformamide. It is also possible to employ mixtures of the solvents. Preferred solvents are tetrahydrofuran and dimethylformamide.

The compounds of formula (VIII) are known or can be prepared by reacting compounds of formula

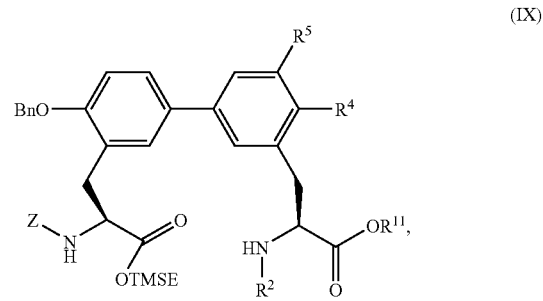

(IX)

in which $R^2$, $R^4$, $R^5$ and $R^{11}$ have the meaning indicated above,
with compounds of formula

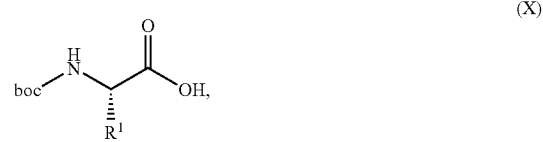

(X)

in which $R^1$ has the meaning indicated above,
in the presence of dehydrating reagents as described for the first stage of processes [A] and [B].

The compounds of formula (IX) are known or can be prepared in analogy to the processes described in the examples section.

The compounds of formula (X) are known or can be prepared in analogy to known processes.

The compounds of the invention show a valuable range of pharmacological and pharmacokinetic effects which could not have been predicted.

They are therefore suitable for use as medicaments for the treatment and/or prophylaxis of diseases in humans and animals.

The compounds of the invention can, because of their pharmacological properties, be employed alone or in combination with other active ingredients for the treatment and/or prophylaxis of infectious diseases, especially of bacterial infections.

For example, it is possible to treat and/or prevent local and/or systemic diseases caused by the following pathogens or by mixtures of the following pathogens:

gram-positive cocci, e.g. staphylococci (*Staph. aureus, Staph. epidermidis*) and streptococci (*Strept. agalactiae, Strept. faecalis, Strept. pneumoniae, Strept. pyogenes*); gram-negative cocci (*neisseria gonorrhoeae*) and gram-negative rods such as enterobacteriaceae, e.g. *Escherichia coli, Haemophilus influenzae, Citrobacter* (*Citrob. freundii, Citrob. divernis*), *Salmonella* and *Shigella*; also klebsiellas (*Klebs. pneumoniae, Klebs. oxytocy*), *Enterobacter* (*Ent. aerogenes, Ent. agglomerans*), *Hafnia, Serratia* (*Serr. marcescens*), *Proteus* (*Pr. mirabilis, Pr. rettgeri, Pr. vulgaris*), *Providencia, Yersinia*, and the genus *Acinetobacter*. The antibacterial range additionally includes the genus *Pseudomonas* (*Ps.*

*aeruginosa, Ps. maltophilia*) and strictly anaerobic bacteria such as *Bacteroides fragilis*, representatives of the genus *Peptococcus, Peptostreptococcus*, and the genus *Clostridium*; also *mycoplasmas* (*M. pneumoniae, M. hominis, M. urealyticum*) and *mycobacteria*, e.g. *Mycobacterium tuberculosis*.

The above list of pathogens is merely by way of example and is by no means to be interpreted to be limiting. Examples which may be mentioned of diseases which are caused by the pathogens mentioned or mixed infections and can be prevented, improved or healed by the topically applicable preparations of the invention, are:

infectious diseases in humans such as, for example, septic infections, bone and joint infections, skin infections, postoperative wound infections, abscesses, phlegmon, wound infections, infected burns, burn wounds, infections in the oral region, infections after dental operations, septic arthritis, mastitis, tonsillitis, genital infections and eye infections.

Apart from humans, bacterial infections can also be treated in other species. Examples which may be mentioned are:

Pigs: coli diarrhoea, enterotoxaemia, sepsis, dysentery, salmonellosis, metritis-mastitis-agalactiae syndrome, mastitis;

Ruminants (cattle, sheep, goats): diarrhoea, sepsis, bronchopneumonia, salmonellosis, pasteurellosis, mycoplasmosis, genital infections;

Horses: bronchopneumonias, joint ill, puerperal and post-puerperal infections, salmonellosis;

Dogs and cats: bronchopneumonia, diarrhoea, dermatitis, otitis, urinary tract infections, prostatitis;

Poultry (chickens, turkeys, quail, pigeons, ornamental birds and others): mycoplasmosis, *E. coli* infections, chronic airway diseases, salmonellosis, pasteurellosis, psittacosis.

It is also possible to treat bacterial diseases in the rearing and management of productive and ornamental fish, in which case the antibacterial spectrum is extended beyond the pathogens mentioned above to further pathogens such as, for example, *Pasteurella, Brucella, Campylobacter, Listeria, Erysipelothris, corynebacteria, Borellia, Treponema, Nocardia, Rikettsie, Yersinia*.

The present invention further relates to the use of the compounds of the invention for the treatment and/or prophylaxis of diseases, preferably of bacterial diseases, especially of bacterial infections.

The present invention further relates to the use of the compounds of the invention for, the treatment and/or prophylaxis of diseases, especially of the aforementioned diseases.

The present invention further relates to the use of the compounds of the invention for the production of a medicament for the treatment and/or prophylaxis of diseases, especially of the aforementioned diseases.

The present invention further relates to a method for the treatment and/or prophylaxis of diseases, especially of the aforementioned diseases, using of an antibacterially effective amount of the compounds of the invention.

The compounds of the invention may act systemically and/or locally. For this purpose, they can be administered in a suitable way such as, for example, orally, parenterally, pulmonaryly, nasally, sublingually, lingually, buccally, rectally, dermally, transdermally, conjuctivally or oticaly or as implant or stent.

The compounds of the invention can be administered in administration forms suitable for these administration routes.

Suitable for oral administration are administration forms which function according to the prior art and deliver the compounds of the invention rapidly and/or in modified fashion, and which contain the compounds of the invention in crystalline and/or amorphized and/or dissolved form, such as, for example, tablets (uncoated or coated tablets, for example having coatings which are resistant to gastric juice or dissolve with a delay or are insoluble and which control the release of the compound of the invention), tablets or films/wafers, which disintegrate rapidly in the oral cavity, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilisates or sterile powders.

Suitable for the other administration routes are, for example, pharmaceutical forms for inhalation (inter alia powder inhalers, nebulizers), nasal drops, solutions, sprays; tablets, films/wafers or capsules for lingual, sublingual or buccal administration, suppositories, preparations for the ears or eyes, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

The compounds of the invention can be converted into the stated administration forms. This can take place in a manner known per se by mixing with inert, nontoxic, pharmaceutically suitable excipients. These excipients include, inter alia, carriers (for example microcrystalline cellulose, lactose, mannitol), solvents (e.g. liquid polyethylene glycols), emulsifiers and dispersing or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and taste and/or odor corrigents.

The present invention further relates to medicaments which comprise at least one compound of the invention, normally together with one or more inert, nontoxic, pharmaceutically acceptable excipients, and to the use thereof for the aforementioned purposes.

It has generally proved advantageous on parenteral administration to administer amounts of about 5 to 250 mg/kg of body weight per 24 h to achieve effective results. The amount on oral administration is about 5 to 100 mg/kg of body weight per 24 h.

It may nevertheless be necessary where appropriate to deviate from the stated amounts depending on the body weight, administration route, individual behavior towards the active ingredient, nature of the preparation and time or interval over which administration takes place. Thus, it may be sufficient in some cases to make do with less than the aforementioned minimum amount, whereas in other cases the stated upper limit must be exceeded. Where larger amounts are administered, it may be advisable to divide these into a plurality of single doses over the day.

The percentage data in the following tests and examples are percentages by weight unless otherwise indicated; parts are parts by weight. Solvent ratios, dilution ratios and concentration data for liquid/liquid solutions are in each case based on volume.

DETAILED DESCRIPTION OF PREFERRED EMBODIMENTS

A. EXAMPLES

Abbreviations Used:
abs. absolute
aq. aqueous
Bn benzyl
Boc tert-butoxycarbonyl
$CDCl_3$ deuterochloroform
CH cyclohexane
D doublet (in $^1$H NMR)
Dd doublet of doublets (in $^1$H NMR)
DCC dicyclohexylcarbodiimide
DIC diisopropylcarbodiimide
DIEA diisopropylethylamine (Hünig's base)
DMSO dimethylsulfoxide
DMAP 4-N,N-dimethylaminopyridine
DMF dimethylformamide
EA ethyl acetate (acetic acid ethyl ester)
EDC N'-(3-dimethylaminopropyl)-N-ethylcarbodiimide×HCl
ESI electrospray ionization (in MS)
HATU O-(7-azabenzotriazol-1-yl)-N,N,N',N'-tetramethyluronium hexafluorophosphate
HBTU O-(benzotriazol-1-yl)-N,N,N,',N'-tetramethyluronium hexafluorophosphate
HOBt 1-hydroxy-1H-benzotriazole×$H_2O$
H hour(s)
HPLC high pressure, high performance liquid chromatography
LC-MS coupled liquid chromatography-mass spectroscopy
M multiplet (in $^1$H NMR)
Min minute
MS mass spectroscopy
NMR nuclear magnetic resonance spectroscopy
MTBE methyl tert-butyl ether
Pd/C palladium/carbon
Q quartet (in $^1$H NMR)
$R_f$ retention index (in TLC)
RP reverse phase (in HPLC)
RT room temperature
$R_t$ retention time (in HPLC)
S singlet (in $^1$H NMR)
sat saturated
T triplet (in $^1$H NMR)
TBS tert-butyldimethylsilyl
TFA trifluoroacetic acid
THF tetrahydrofuran
TMSE 2-(trimethylsilyl)ethyl
TPTU 2-(2-oxo-1(2H)-pyridyl)-1,1,3,3-tetramethyluronium tetrafluoroborate
Z benzyloxycarbonyl LC-MS and HPLC Methods:

Method 1 (LC-MS): Instrument: MICROMASS® Quattro LCZ mass spectrometer with HPLC Agilent series 1100; column: PHENOMENEX® SYNERGI™ 2 μ Hydro-RP Mercury (C18 with polar endcapping on 2 μ silica) 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 2 (LC-MS): MS instrument type: MICROMASS® ZQ mass spectrometer; HPLC instrument type: Waters Alliance 2795; column: PHENOMENEX® SYNERGI™ 2μ Hydro-RP Mercury (C18 with polar endcapping on 2 μ silica) 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 3 (LC-MS): MS instrument type: MICROMASS® ZQ mass spectrometer; HPLC instrument type: HP 1100 series; UV DAD; column: PHENOMENEX® SYNERGI™ 2 μ Hydro-RP Mercury (C18 with polar endcapping on 2μ silica) 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 4 (LC-MS): Instrument: MICROMASS® Platform LCZ mass spectrometer with HPLC Agilent series 1100; column: Grom-SIL120 ODS-4 HE, 50 mm×2.0 mm, 3 μm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 5 (LC-MS): MS instrument type: MICROMASS® ZQ mass spectrometer; HPLC instrument type: Waters Alliance 2795; column: Merck Chromolith SpeedROD RP-18e 50 mm×4.6 mm; eluent A: water+500 μl of 50% formic acid/1; eluent B: acetonitrile+500 μl of 50% formic acid/1; gradient: 0.0 min 10% B→3.0 min 95% B→4.0 min 95% B; oven: 35° C.; flow rate: 0.0 min 1.0 ml/min→3.0 min 3.0 ml/min→4.0 min 3.0 ml/min; UV detection: 210 nm.

Method 6 (LC-MS): MS instrument type: MICROMASS® ZQ mass spectrometer; HPLC instrument type: HP 1100 series; UV DAD; column: Grom-Sil 120 ODS-4 HE 50 mm×2 mm, 3.0 μm; eluent A: water+500 μl of 50% formic acid/1, eluent B: acetonitrile+500 μl of 50% formic acid/1; gradient: 0.0 min 70% B→4.5 min 90% B; oven: 50° C.; flow rate: 0.8 ml/min; UV detection: 210 nm.

Method 7 (LC-MS): MS instrument type: MICROMASS® ZQ mass spectrometer; HPLC instrument type: Waters Alliance 2790; column: Grom-Sil 120 ODS-4 HE 50 mm×2 mm, 3.0 μm; eluent A: water+500 μl of 50% formic acid/1, eluent B: acetonitrile+500 μl of 50% formic acid/1; gradient: 0.0 min 70% B→4.5 min 90% B; oven: 45° C.; flow rate: 0.8 ml/min; UV detection: 210 nm.

Method 8 (LC-MS): MS instrument type: MICROMASS® ZQ mass spectrometer; HPLC instrument type: HP 1100 series; UV DAD; column: Grom-Sil 120 ODS-4 HE 50 mm×2 mm, 3.0 μm; eluent A: water+500 μl of 50% formic acid/1, eluent B: acetonitrile+500 μl of 50% formic acid/1; gradient: 0.0 min 0% B→2.9 min 70% B→3.1 min 90% B→4.5 min 90% B; oven: 50° C.; flow rate: 0.8 ml/min; UV detection: 210 nm.

Method 9 (LC-MS): MS instrument type: MICROMASS® ZQ mass spectrometer; HPLC instrument type: Waters Alliance 2790; column: Grom-Sil 120 ODS-4 HE 50 mm×2 mm, 3.0 μm; eluent A: water+500 μl of 50% formic acid; eluent B: acetonitrile+500 μl of 50% formic acid/1; gradient: 0.0 min 5% B→2.0 min 40% B→4.5 min 90% B→5.5 min 90% B; oven: 45° C.; flow rate: 0.0 min 0.75 ml/min→4.5 min 0.75 ml/min 5.5 min→5.5 min 1.25 ml/min; UV detection: 210 nm.

Method 10 (LC-MS): MS instrument type: MICROMASS® ZQ mass spectrometer; HPLC instrument type: Waters Alliance 2790; column: Grom-Sil 120 ODS-4 HE 50 mm×2 mm, 3.0 μm; eluent A: water+500 μl of 50% formic acid/1, eluent B: acetonitrile+500 µl of 50% formic acid/1; gradient: 0.0 min 90% B→4.5 min 90% B; oven: 45° C.; flow rate: 0.8 ml/min; UV detection: 210 nm.

Method 11 (HPLC): Instrument: HP 1100 with DAD detection; column: Kromasil RP-18, 60 mm×2 mm, 3.5 µm; eluent A: 5 ml of HClO$_4$/1 of water, eluent B: acetonitrile; gradient: 0 min 2% B, 0.5 min 2% B, 4.5 min 90% B, 6.5 min 90% B; flow rate: 0.75 ml/min; oven: 30° C.; UV detection: 210 nm.

Method 12 (HPLC): Instrument: HP 1100 with DAD detection; column: Kromasil RP-18, 60 mm×2 mm, 3.5 µm; eluent A: 5 ml of HClO$_4$/1 of water, eluent B: acetonitrile; gradient: 0 min 2% B, 0.5 min 2% B, 4.5 min 90% B, 15 min 90% B; flow rate: 0.75 ml/min; oven: 30° C.; UV detection: 210 nm.

Method 13 (HPLC): Instrument: HP 1100 with DAD detection; column: Kromasil RP-18, 60 mm×2 mm, 3.5 µm; eluent A: 5 ml of HClO$_4$/1 of water, eluent B: acetonitrile; gradient: 0 min 2% B, 0.5 min 2% B, 4.5 min 90% B, 9 min 90% B; flow rate: 0.75 ml/min; oven: 30° C.; UV detection: 210 nm.

Method 14 (LC-MS): MS instrument type: MICROMASS® ZQ mass spectrometer; HPLC instrument type: Waters Alliance 2790; column: Grom-Sil 120 ODS-4 HE 50 mm×2 mm, 3.0 µm; eluent A: water+500 µl of 50% formic acid/1; eluent B: acetonitrile+500 µl of 50% formic acid/1; gradient: 0.0 min 0% B→0.2 min 0% B→2.9 min 70% B→3.1 min 90% B→4.5 min 90% B; flow rate: 0.8 ml/min; oven: 45° C.; UV detection: 210 nm.

Method 15 (LC-MS): Instrument: MICROMASS® Quattro LCZ mass spectrometer with HPLC Agilent series 1100; column: Grom-SIL120 ODS-4 HE, 50 mm×2.0 mm, 3 µm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 16 (LC-MS): MS instrument type: MICROMASS® ZQ mass spectrometer; HPLC instrument type: Waters Alliance 2795; column: Merck Chromolith SpeedROD RP-18e 50 mm×4.6 mm; eluent A: water+500 µl of 50% formic acid/1, eluent B: acetonitrile+500 µl of 50% formic acid/1; gradient: 0.0 min 10% B→2.0 min 95% B→4.0 min 95% B; oven: 35° C.; flow rate: 0.0 min 1.0 ml/min→2.0 min 3.0 ml/min→4.0 min 3.0 ml/min; UV detection: 210 nm.

Method 17 (LC-MS): Instrument: MICROMASS® Platform LCZ mass spectrometer with HPLC Agilent series 1100; column: Thermo HyPURITY Aquastar 3µ 50 mm ×2.1 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 18 (LC-MS): MS instrument type: MICROMASS® ZQ mass spectrometer; HPLC instrument type: Waters Alliance 2790; column: Grom-Sil 120 ODS-4 HE 50×2 mm, 3.0 µm; eluent B: acetonitrile+0.05% formic acid, eluent A: water+0.05% formic acid; gradient: 0.0 min 70% B→4.5 min 90% B→5.5 min 90% B; oven: 45° C.; flow rate: 0.0 min 0.75 ml/min→4.5 min 0.75 ml/min→5.5 min 1.25 ml/min; UV detection: 210 nm.

Starting Compounds

The letter designation in the starting compounds stand for the structural element of the head of the compounds of the invention in conjunction with a radical R$^1$ (e.g. ornithine (3-aminoprop-1-yl) or hydroxyornithine (3-amino-2-hydroxyprop-1-yl)), as described in the following table. The numbers stand for various reaction types.

| Series | Structural element | R$^1$ | R$^2$ |
|---|---|---|---|
| A | HO—⌬—⌬—F | ornithine | H |
| B | HO—⌬—⌬—Cl | hydroxyornithine | methyl |
| C | HO—⌬—⌬—Cl | hydroxyornithine | H |
| D | HO—⌬—⌬ | hydroxyornithine | H |
| E | HO—⌬—⌬—CH$_3$ | ornithine | H |
| F | HO—⌬—⌬ | ornithine | H |
| G | HO—⌬—⌬—CH$_3$ | hydroxyornithine | H |

-continued

| Series | Structural element | R¹ | R² |
|---|---|---|---|
| H | HO-⟨phenyl⟩-⟨phenyl(F)⟩-OH | hydroxyornithine | H |
| I | HO-⟨phenyl⟩-⟨phenyl⟩-NH₂ | hydroxyornithine | H |
| J | HO-⟨phenyl⟩-⟨phenyl(OH)⟩ | hydroxyornithine | H |
| K | HO-⟨phenyl⟩-⟨phenyl(OH)⟩ | ornithine | H |
| L | HO-⟨phenyl⟩-⟨phenyl⟩-F | hydroxyornithine | H |
| M | HO-⟨phenyl⟩-⟨phenyl⟩-Cl | ornithine | methyl |
| N | HO-⟨phenyl⟩-⟨phenyl-C(O)NHR⟩ | hydroxyornithine | H |
| O | HO-⟨phenyl⟩-⟨phenyl⟩-F | ornithine | methyl |
| P | HO-⟨phenyl⟩-⟨phenyl⟩-NH₂ | ornithine | H |

Example 1B (5-Bromo-2-chlorophenyl)methanol

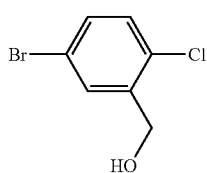

10 g (42.5 mmol) of 5-bromo-3-chlorobenzoic acid are dissolved in 135 ml of THF. At 0° C., 4.2 g (55.2 mmol, 5.24 ml) of borane-dimethyl sulfide complex are added dropwise. The mixture is then stirred at RT for 25 min and under reflux for 30 min. 40 ml of water and 15 ml of 2N hydrochloric acid are successively added dropwise while cooling in ice, followed by stirring at RT for 45 min. After a renewed addition of 15 ml of 2N hydrochloric acid the mixture is extracted several times with diethyl ether. The combined organic phase is washed successively with 1N hydrochloric acid, water, a saturated sodium bicarbonate solution and a saturated sodium chloride solution, dried over magnesium sulfate and concentrated in vacuo. The solid is dried under high vacuum to constant weight.

Yield: 9.1 g (97% of theory) HPLC (method 11): $R_t$=4.22 min MS (EI): m/z=220 (M)$^{+1}$H-NMR (300 MHz, CDCl$_3$): δ=1.90 (t, 1H), 4.75 (d, 2H), 7.20 (d, 1H), 7.35 (dd, 1H), 7.67 (d, 1H).

Example 2B

5-Bromo-2-chlorobenzaldehyde

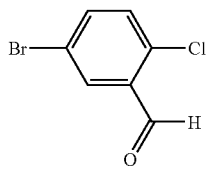

18 ml (0.26 mol) of DMSO are introduced into 64 ml of dichloromethane and, at −78° C., 16.1 g (0.127 mol, 11.1 ml) of oxalyl chloride are added. After 30 min, a solution of 13.1 g (59 mmol) of (5-bromo-2-chlorophenyl)methanol in 100 ml of chloroform is added dropwise. After 20 min, 40 ml of triethylamine are added and the reaction mixture is slowly warmed to RT. After the addition of 50 ml of water the mixture is extracted several times with ethyl acetate. The combined organic phases are washed successively with 2N hydrochloric acid, water, a saturated sodium bicarbonate solution and a saturated sodium chloride solution. The organic phase is dried over magnesium sulfate and concentrated in vacuo. The resulting solid is dried Yunder high vacuum to constant weight.

Yield: 12.7 g (94% of theory) HPLC (method 11): $R_t$=4.65 min MS (EI): m/z=218 (M)+ $^1$H-NMR (300 MHz, CDCl$_3$): δ=7.32 (d, 1H), 7.65 (dd, 1H), 8.03 (d, 1H), 10.4 (s, 1H).

Example 3H 2-(Benzyloxy)-3-fluorobenzaldehyde

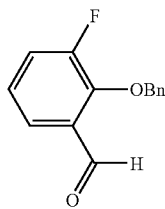

9.0 g (64 mmol) of 3-fluoro-2-hydroxybenzaldehyde are dissolved in 200 ml of DMF, 10.7 g (77.1 mmol) of potassium carbonate and 8.4 ml (12 g, 71 mmol) of benzyl bromide are added and the mixture stirred at 80° C. for 24 h. The mixture is poured into 600 ml of water, extracted several times with ethyl acetate, and the organic phase is dried over sodium sulfate, concentrated in vacuo and dried under high vacuum. The crude product is purified by silica gel chromatography (cyclohexane:ethyl acetate 2:1).

Yield: 14.3 g (97% of theory) HPLC (method 11): $R_t$=4.82 min. MS (DCI): m/z=231 (M+H)+ $^1$H-NMR (300 MHz, CDCl$_3$): δ=5.26 (s, 2H), 7.10 (m$_c$, 1H), 7.31-7.43 (m, 6H), 7.58 (dd, 1H), 10.25 (s, 1H).

Example 3J 3-(Benzyloxy)-5-hydroxybenzaldehyde

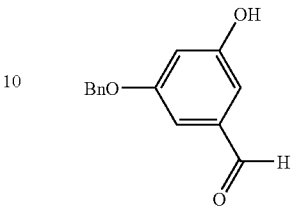

Preparation takes place in analogy to Example 3H from 5.0 g (36.2 mmol) of 3,5-dihydroxybenzaldehyde, 6.81 g (39.8 mmol) of benzyl bromide and 11.8 g (36.2 mmol) of cesium carbonate.

Yield: 2.8 g (34% of theory) LC-MS (method 8): $R_t$=3.31 min MS (EI): m/z=227 (M+H)+ $^1$H-NMR (300 MHz, CDCl$_3$): δ=5.10 (s, 2H), 5.21 (s, 1H), 6.75 (s, 1H), 6.96 (s, 1H), 7.08 (s, 1H), 7.25-7.45 (m, 5H), 9.88 (s, 1H).

Example 4A

Benzyl (2Z)-3-(5-bromo-2-fluorophenyl)-2-[(tert-butoxycarbonyl)amino]acrylate

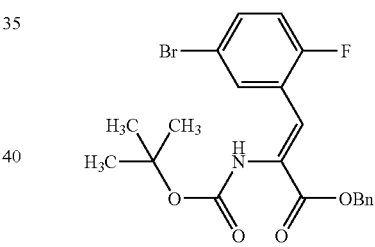

6.0 g (30 mmol) of 5-bromo-2-fluorobenzaldehyde and 12.7 g (34 mmol) of benzyl [(tert-butoxycarbonyl)amino](dimethoxyphosphoryl)acetate are introduced into 90 ml of THF and, while cooling with acetone/dry ice at −78° C., 3.91 g (34 mmol) of 1,1,3,3-tetramethylguanidine are added. After 4 h in the cold bath, the mixture is slowly warmed to RT and stirred at RT for a further 12 h. The solvent is distilled off in vacuo, and the crude product is taken up in ethyl acetate and washed once each with a saturated sodium bicarbonate solution and a saturated sodium chloride solution. The organic phase is dried over magnesium sulfate and evaporated to dryness in vacuo. The crude product is purified by chromatography (silica gel, cyclohexane/ethyl acetate 2:1).

Yield: 14 g (95% of theory) HPLC (method 11): $R_t$=5.47 min. MS (EI+): m/z=450 (M+H)+ $^1$H-NMR (300 MHz, CDCl$_3$): δ=1.39 (s, 9H), 5.30 (s, 2H), 6.53 (br. s, 1H), 6.94 (m, 1H), 7.28-7.46 (m, 6H), 7.67 (m, 1H).

Examples 4B, 4C, 4E, 4H to 4J and 4N and 4P listed in the following table are prepared from the appropriate precursors in analogy to the above method:

| Example No. | Structure | Prepared in analogy to Example No. | Analytical data |
|---|---|---|---|
| 4B | 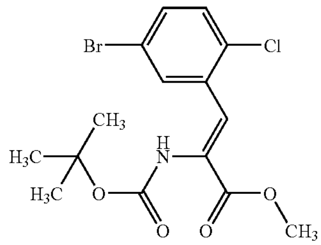 | 4A from Example 2B and methyl [(tert-butoxycarbonyl)-amino](dimethoxyphosphoryl) acetate | |
| 4C | 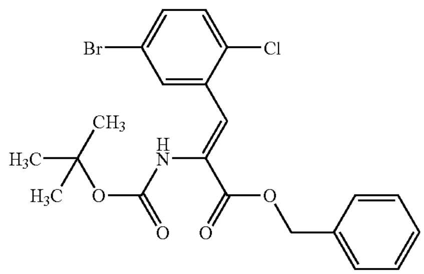 | 4A from Example 2B | LC-MS (method 2): $R_t$ = 2.97 min. MS (ES): m/z = 466 (M + H)$^+$ $^1$H-NMR (300 MHz, CDCl$_3$): δ = 1.36 (s, 9H), 5.32 (s, 2H), 6.47 (br. s, 1H), 7.2-7.5 (m, 7H), 7.70 (d, 1H). |
| 4E | 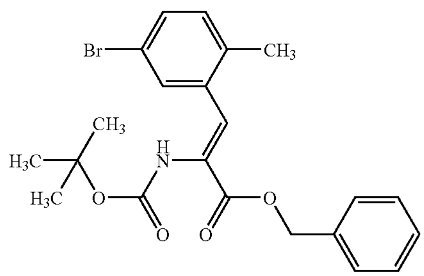 | 4A from 5-bromo-2-methylbenzaldehyde | LC-MS (method 4): $R_t$ = 3.38 min. MS (ES): m/z = 446 (M + H)$^+$ $^1$H-NMR (300 MHz, CDCl$_3$): δ = 1.35 (s, 9H), 2.28 (s, 3H), 5.30 (s, 2H), 6.21 (br. s, 1H), 7.04 (d, 1H), 7.21-7.46 (m, 7H), 7.10 (d, 1H). |
| 4H | 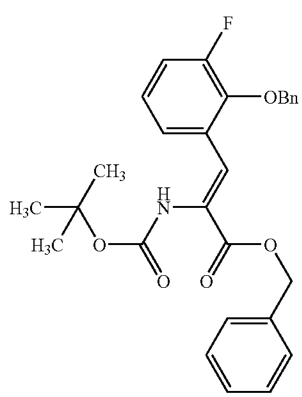 | 4A from Example 3H | LC-MS (method 13): $R_t$ = 5.52 min. MS (ESI): m/z = 478 (M + H)$^+$ $^1$H-NMR (300 MHz, CDCl$_3$): δ = 1.36 (s, 9H), 5.05 (s, 2H), 5.27 (s, 2H), 6.57 (br. s, 1H), 7.03 (m$_c$, 1H), 7.12-7.43 (m, 13H). |
| 4I | 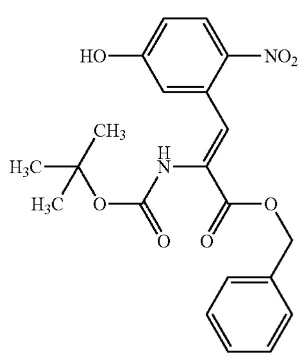 | 4A from 5-hydroxy-2-nitrobenzaldehyde | LC-MS (method 4): $R_t$ = 4.27 min. MS (ES): m/z = 415 (M + H)$^+$ $^1$H-NMR (300 MHz, CDCl$_3$): δ = 1.28 (s, 9H), 5.30 (s, 2H), 6.29 (s, 1H), 6.63 (br. s, 1H), 6.84 (dd, 1H), 6.96 (d, 1H), 7.3-7.45 (m, 4H), 7.65 (s, 1H), 8.12 (d, 1H). |

-continued

| Example No. | Structure | Prepared in analogy to Example No. | Analytical data |
|---|---|---|---|
| 4J | (structure) | 4A from Example 11J | HPLC (method 12): $R_t$ = 6.80 min. MS (ES): m/z = 590 (M + H)$^+$ |
| 4N | (structure) | 4A from Example 10N | HPLC (method 11): $R_t$ = 5.51 min. MS (DCI): m/z = 507 (M + NH$_4$)$^+$ $^1$H-NMR (400 MHz, CDCl$_3$): δ = 1.4 (s, 9H), 3.9 (s, 3H), 5.29 (s, 2H), 6.57 (br. s, 1H), 7.23 (s, 1H), 7.31-7.45 (m, 5H), 7.81 (s, 1H), 8.04 (s, 1H), 8.07 (s, 1H). |
| 4P | (structure) | 4A from 5-bromo-2-nitrobenzaldehyde (*Chem. Ber.* 1905, 38, 2812) | LC-MS (method 3): $R_t$ = 2.69 min. MS (ES): m/z = 402 (M + H)$^+$ $^1$H-NMR (300 MHz, DMSO-d$_6$): δ = 1.3 (s, 9H), 3.75 (s, 3H), 7.47 (s, 1H), 7.64 (s, 1H), 7.72 (d, 1H), 8.10 (d, 1H), 8.72 (br. s, 1H). |

Example 4O

Methyl (2Z)-3-(5-bromo-2-fluorophenyl)-2-[(tert-butoxycarbonyl)amino]acrylate

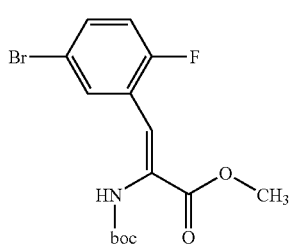

21.32 ml (169.9 mmol) of N,N,N,N-tetramethylguanidine are added to a solution, cooled to −70° C., of 30 g (147.8 mmol) of 5-bromo-2-fluorobenzaldehyde and 50.51 g (169.9 mmol) of methyl [(tert-butoxycarbonyl)amino](dimethoxyphosphoryl)acetate in 450 ml anhydrous tetrahydrofuran. After stirring at −70° C. for 4 h, the reaction mixture is stirred at RT for 15 h. 1000 ml of water and 1000 ml of ethyl acetate are added to the mixture. The organic phase is washed with water, dried over sodium sulfate and concentrated. The crude product is purified by column chromatography on silica gel (mobile phase: cyclohexane:ethyl acetate 4:1).

Yield: quant. HPLC (method 11): $R_t$=5.0 min. MS (DCI (NH$_3$)): m/z=391 (M+NH$_4$)$^+$. $^1$H-NMR (300 MHz, CDCl$_3$): δ=1.40 (s, 9H), 3.85 (s, 3H), 6.55 (br.s, 1H), 6.95 (dd, 1H), 7.26 (s, 1H), 7.35 (m, 1H), 7.58 (d, 1H).

Example 5A

Benzyl 3-bromo-N-(tert-butoxycarbonyl)-6-fluoro-L-phenylalaninate

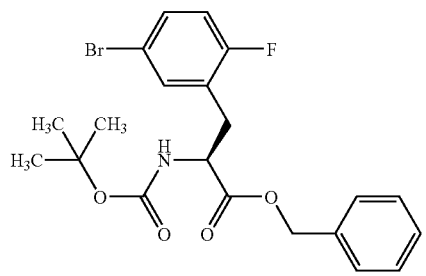

6.0 g (13.3 mmol) of benzyl (2Z)-3-(5-bromo-2-fluorophenyl)-2-[(tert-butoxycarbonyl)amino]acrylate are dissolved in 100 ml of ethanol. Under an argon atmosphere, 40 mg (0.055 mmol) of (+)-1,2-bis((2S,5S)-2,5-diethylphospholano)benzene(cyclooctadiene)rhodium(I)trifluoromethanesulfonate are added, and argon is passed through the solution for 30 min. The mixture is then hydrogenated under a pressure of 3 bar of hydrogen for 4 days. The mixture is filtered through silica gel, which is carefully washed with ethanol. The filtrate is concentrated in vacuo, and the crude product is dried under high vacuum.

Yield: 5.2 g (86% of theory) HPLC (method 11): $R_t$=5.40 min. MS (DCI(NH$_3$)): m/z=469 (M+NH$_4$)$^+$ $^1$H-NMR (300 MHz, CDCl$_3$): δ=1.41 (s, 9H), 3.01 (m$_c$, 1H), 3.19 (m$_c$, 1H), 4.60 (m$_c$, 1H), 5.09 (br. m, 1H), 5.09 (m, 2H), 6.87 (m$_c$, 1H), 7.20-7.42 (m, 7H).

Examples 5B, 5C, 5E, 5H to 5J and 5N and 5P listed in the following table are prepared from the appropriate precursors in analogy to the above method:

| Example No. | Structure | Prepared in analogy to Example No. | Analytical data |
|---|---|---|---|
| 5B | 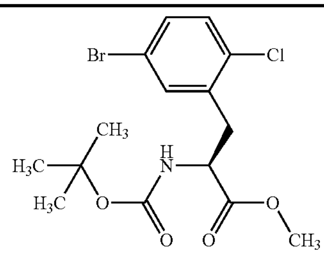 | 5A from Example 4B | LC-MS (method 2): $R_t$ = 2.59 min. MS (EI): m/z = 392 (M + H)$^+$ $^1$H-NMR (400 MHz, DMSO-d$_6$): δ = 1.30 (s, 9H), 2.89 (m$_c$, 1H), 3.22 (m$_c$, 1H), 3.65 (s, 3H), 4.30 (m$_c$, 1H), 7.3-7.5 (m, 2H), 7.57 (m, 1H). |
| 5C | 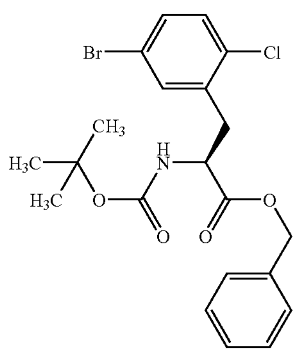 | 5A from Example 4C | LC-MS (method 1): $R_t$ = 3.07 min. MS (EI): m/z = 468 (M + H)$^+$ $^1$H-NMR (300 MHz, DMSO-d$_6$): δ = 1.30 (s, 9H), 2.95 (m$_c$, 1H), 3.23 (m$_c$, 1H), 4.33 (m$_c$, 1H), 5.13 (s, 2H), 7.27-7.52 (m, 7H), 7.57 (m, 1H). |
| 5E | 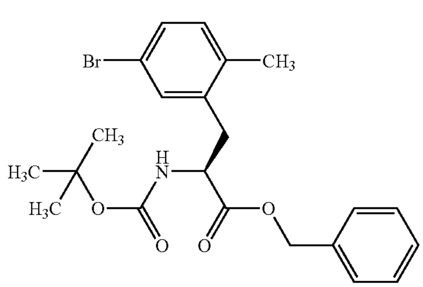 | 5A from Example 4E | LC-MS (method 8): $R_t$ = 3.81 min. MS (ES): m/z = 448 (M + H)$^+$ $^1$H-NMR (300 MHz, CDCl$_3$): δ = 1.39 (s, 9H), 2.24 (s, 3H), 2.83-3.15 (m, 2H), 4.57 (m$_c$, 1H), 5.00 (br. s, 1H), 5.09 (dd, 2H), 6.97 (d, 1H), 7.14-7.48 (m, 7H). |

-continued

| Example No. | Structure | Prepared in analogy to Example No. | Analytical data |
|---|---|---|---|
| 5H | 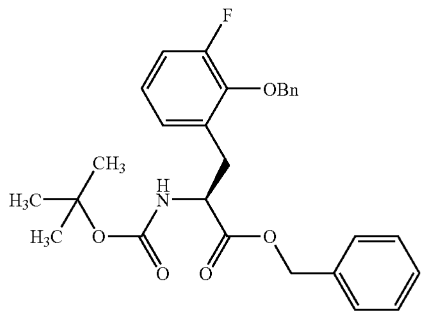 | 5A from Example 4H | $^1$H-NMR (200 MHz, CDCl$_3$): δ = 1.38 (s, 9H), 3.00 (m, 2H), 4.51 (m$_c$, 1H), 5.03 (s, 2H), 5.10 (s, 2H), partly overlaps 5.18 (m, 1H), 6.78-7.15 (m, 3H), 7.17-7.44 (m, 10H). |
| 5I | 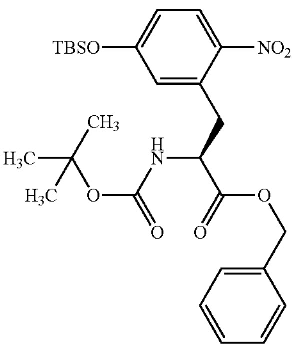 | 5A from Example 11I | LC-MS (method 5): R$_t$ = 3.19 min. MS (ES): m/z = 531 (M + H)$^+$ $^1$H-NMR (300 MHz, DMSO-d$_6$): δ = 0.25 (m, 6H), 0.95 (s, 9H), 1.28 (s, 9H), 2.97 (m$_c$, 1H), 3.53 (m$_c$, 1H), 4.42 (m$_c$, 1H), 5.14 (s, 2H), 6.87-7.0 (m, 2H), 7.27-7.41 (m, 5H), 7.98 (d, 1H). |
| 5J | 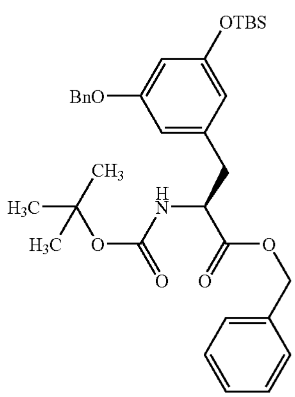 | 5A from Example 4J | LC-MS (method 7): R$_t$ = 2.88 min. MS (ES): m/z = 592 (M + H)$^+$ $^1$H-NMR (300 MHz, CDCl$_3$): δ = 0.0 (m, 6H), 0.82 (s, 9H), 1.28 (s, 9H), 3.36 (m$_c$, 2H), 4.45 (m$_c$, 1H), 4.47 (s, 2H), 4.85 (br. m, 1H), 4.96 (s, 2H), 6.09 (m, 1H), 6.18 (m, 2H), 7.15-7.35 (m, 10H). |
| 5N | 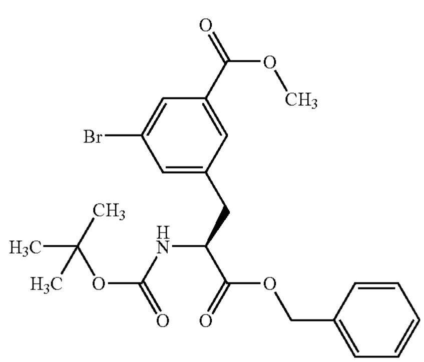 | 5A from Example 4N | HPLC (method 11): R$_t$ = 5.37 min. MS (DCI): m/z = 509 (M +NH$_4$)$^+$ $^1$H-NMR (300 MHz, CDCl$_3$): δ = 1.43 (s, 9H), 2.95-3.25 (m, 2H), 3.9 (s, 3H), 4.60 (m$_c$, 1H), 5.05 (m$_c$, 1H), 5.15 (s, 2H), 7.23-7.42 (m, 5H), 7.44 (s, 1H), 7.75 (s, 1H), 8.06 (s, 1H). |

| Example No. | Structure | Prepared in analogy to Example No. | Analytical data |
|---|---|---|---|
| 5P | 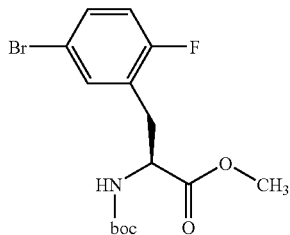 | 5A from Example 4P | LC-MS (method 3): $R_t$ = 2.69 min. MS (ES): m/z = 402 (M + H)$^+$ $^1$H-NMR (300 MHz, DMSO-$d_6$): δ = 1.28 (s, 9H), 2.95 ($m_c$, 1H), 3.48 ($m_c$, 1H), 3.65 (s, 3H), 4.42 ($m_c$, 1H), 7.31 (br. d, 1H), 7.7-7.8 (m, 2H), 7.95 (m, 1H). |

Example 5O

Methyl 3-bromo-N-(tert-butoxycarbonyl)-6-fluoro-L-phenylalaninate 20 g (53.45 mmol) of methyl (2Z)-3-(5-bromo-2-fluorophenyl)-2-[(tert-butoxycarbonyl)amino]acrylate (Example 4O) are dissolved in 300 ml of ethanol/dioxane (3:1). Under an argon atmosphere, 200 mg of (+)-1,2-bis((2S,5S)-2,5-diethylphospolano)benzene(cyclooctadiene)rhodium(I)trifluoromethanesulfonate are added, and argon is passed through the solution for 30 min. The mixture is then hydrogenated under a pressure of 3.5 bar of hydrogen for 3 days. The solvent is removed on a rotary evaporator, and the crude product is purified by column chromatography on silica gel (mobile phase: cyclohexane:ethyl acetate 2:2).

Yield: quant. HPLC (method 11): $R_t$=4.9 min. MS (DCI (NH$_3$)): m/z=393 (M+NH$_4$)$^+$. $^1$H-NMR (400 MHz, CDCl$_3$): δ=1.40 (s, 9H), 2.98 (dd, 1H), 3.20 (dd, 1H), 3.73 (s, 3H), 4.57 (m, 1H), 5.05 (m, 1H), 6.80 (dd, 1H), 7.25-7.40 (m, 2H).

Example 6H

Benzyl 2-(benzyloxy)-N-(tert-butoxycarbonyl)-3-fluoro-5-iodo-L-phenylalaninate

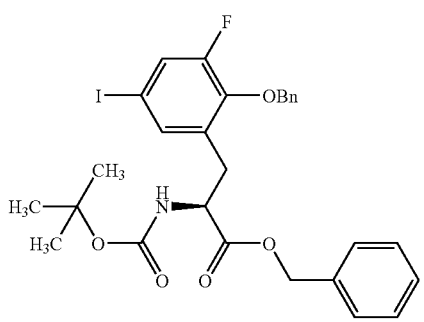

12.5 g (26.1 mmol) of benzyl 2-(benzyloxy)-N-(tert-butoxycarbonyl)-3-fluoro-L-phenylalaninate are introduced into 200 ml of dichloromethane, and 8.76 g (104 mmol) of sodium bicarbonate are added. 8.46 g (52.4 mmol) of iodine monochloride in 10 ml of dichloromethane are slowly added dropwise. After 72 h, 300 ml of a 5% sodium bisulfite solution are added. The phases are separated and the organic phase is extracted with water. The organic phase is concentrated and the residue is purified on silica gel (cyclohexane:ethyl acetate 6:1).

Yield: 7.0 g (35% of theory) HPLC (method 11): $R_t$=6.06 min. MS (ESI): m/z=606 [M+H]$^{+1}$H-NMR (200 MHz, CDCl$_3$): δ=1.38 (s, 9H), 2.70-3.11 (m, 2H), 4.52 ($m_c$, 1H), 5.04 ($m_c$, 4H) overlaps 5.05 (m, 1H), 6.78-7.09 (m, 2H), 7.15-7.48 (m, 10H).

Example 7D

Diethyl [(tert-butoxycarbonyl)amino](3-iodobenzyl)malonate

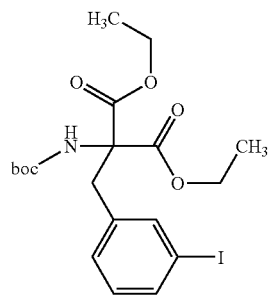

25 g (84.2 mmol) of 3-iodobenzyl bromide are added to a solution of 24.3 g (88.4 mmol) of diethyl [(tert-butoxycarbonyl)amino]malonate and 3.7 g (92.6 mmol) of sodium hydride in 300 ml of DMF while cooling in ice. After stirring the mixture at RT for 4 h, 5 ml of water are added cautiously while cooling in ice. The mixture is extracted several times with ethyl acetate, and the combined organic phases are washed with a saturated sodium chloride solution and water, dried over magnesium sulfate and concentrated in vacuo. The crude product is dried under high vacuum.

Yield: 43 g (99% of theory) HPLC (method 11): $R_t$=5.60 min. $^1$H-NMR (300 MHz, DMSO-$d_6$): δ=1.18 (t, 6H), 1.44 (s, 9H), 3.40 (s, 2H), 4.05-4.25 (m, 2H), 6.4 (br. s, 1H), 7.02 (d, 1H), 7.10 (t, 1H), 7.35 (s, 1H), 7.61 (d, 1H).

Example 8D

N-(tert-Butoxycarbonyl)-3-iodophenylalanine

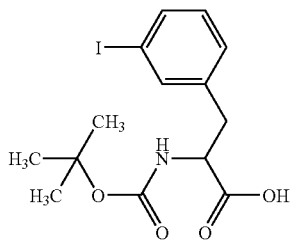

240 ml of a 1N sodium hydroxide solution are added to a suspension of 30.3 g (62 mmol) of diethyl[(tert-butoxycarbonyl)amino](3-iodobenzyl)malonate (Example 7D) in 440 ml of a mixture of ethanol and water (3:1). After 3 h under reflux and after cooling to RT, the pH of the reaction mixture is adjusted with concentrated hydrochloric acid to approx. pH 2. The reaction mixture is concentrated in vacuo. The residue is taken up in MTBE and water. The aqueous phase is extracted three times with MTBE. The combined organic phases are dried over sodium sulfate, filtered and concentrated. The residue is purified by RP-HPLC (acetonitrile/water gradient).

Yield: 16.2 g (67% of theory) HPLC (method 11): $R_t$=4.53 min. $^1$H-NMR (400 MHz, DMSO-d$_6$): δ=1.42 (s, 9H), 3.02 (m$_c$, 1H), 3.18 (m$_c$, 1H), 4.57 (br. m$_c$, 1H), 4.94 (br. m$_c$, 1H), 7.05 (t, 1H), 7.17 (d, 1H), 7.55 (s, 1H), 7.60 (d, 1H).

Example 9D

N-(tert-Butoxycarbonyl)-3-iodo-L-phenylalanine

The racemate from Example 8D is separated on a chiral stationary silica gel phase based on the selector from poly(N-methacryloyl-L-leucine dicyclopropylmethylamide), using a mixture of i-hexane/ethyl acetate as eluent. According to chromatographic comparison, the enantiomer eluted first corresponds to the (R)-enantiomer (97% ee), and the second, dextrorotatory ([α]$_D^{20}$:+18.8°, c=0.57, dichloromethane) enantiomer corresponds to the (S)-enantiomer (97% ee).

Example 10D

Berzyl N-(tert-butoxycarbonyl)-3-iodo-L-phenylalaninate

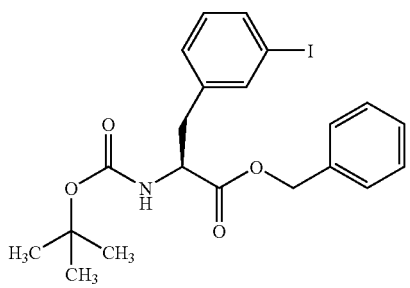

5.33 g (13.6 mmol) of N-(tert-butoxycarbonyl)-3-iodo-L-phenylalanine (from Example 9D) are dissolved in 110 ml of acetonitrile under argon. 166 mg (1.36 mmol) of 4-dimethylaminopyridine and 2.82 ml (27.2 mmol) of benzyl alcohol are added thereto. The mixture is cooled to −10° C., and 3.13 g (16.35 mmol) of EDC are added. The mixture is allowed slowly to reach RT and is stirred overnight. After about 16 h, the mixture is concentrated in vacuo on a rotary evaporator and the residue is purified by chromatography on RP-HPLC (mobile phase: acetonitrile/water gradient).

Yield: 4.78 g (73% of theory). LC-MS (method 8): $R_t$=3.77 min. MS (EI): m/z=482 (M+H)$^+$.

Example 11I

Benzyl (2Z)-2-[(tert-butoxycarbonyl)amino]-3-(5-{[tert-butyl(dimethyl)silyl]oxy}-2-nitrophenyl)acrylate

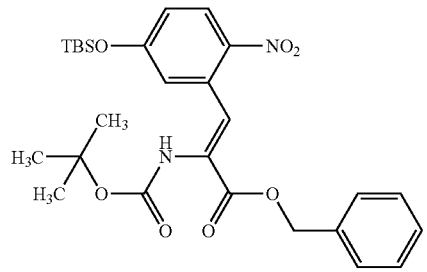

1.67 g (24.5 mol) of imidazole and 1.77 g (11.7 mmol) of tert-butyldimethylsilyl chloride are added to a solution of 6.76 g (9.8 mmol) of benzyl (2Z)-2-[(tert-butoxycarbonyl)amino]-3-(5-hydroxy}-2-nitrophenyl)acrylate (Example 4I) in 100 ml of dichloromethane while cooling in ice. The mixture is warmed to RT and stirred for 18 h. The organic phase is washed several times with water, dried over magnesium sulfate and concentrated in vacuo. The crude product purified by RP-HPLC (mobile phase: acetonitrile/water gradient).

Yield: 2.82 g (55% of theory) LC-MS (method 8): $R_t$=4.19 min. MS (EI$^+$): m/z=529 (M+H)$^{+1}$H-NMR (400 MHz, CDCl$_3$): δ=0.24 (s, 6H), 0.97 (s, 9H), 1.30 (s, 9H), 5.30 (s, 2H), 6.25 (br. s, 1H), 6.82 (dd, 1H), 6.93 (d, 1H), 7.30-7.46 (m, 5H), 7.60 (s, 1H), 8.12 (d, 1H).

Example 11J 3-(Benzyloxy)-5-{[tert-butyl(dimethyl)silyl]oxy}benzaldehyde

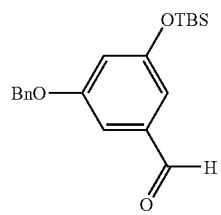

Preparation takes place in analogy to Example 11 from 2.8 g (12.3 mmol) of 3-(benzyloxy)-5-hydroxybenzaldehyde (Example 3J), 1.67 g (24.5 mmol) of imidazole and 3.57 g (13.5 mmol) of tert-butyldimethylsilyl trifluoromethanesulfonate.

Yield: 4.0 g (95% of theory) LC-MS (method 18): $R_t$=2.05 min MS (EI): m/z=343 (M+H)$^{+1}$H-NMR (400 MHz, CDCl$_3$):

δ=0.21 (s, 6H), 0.97 (s, 9H), 5.10 (s, 2H), 6.72 (s, 1H), 6.95 (s, 1H), 7.10 (s, 1H), 7.28-7.48 (m, 5H).

Example 10N

Methyl 3-bromo-5-formylbenzoate

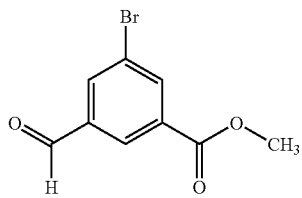

6.2 g (27.1 mmol) of 3-bromo-5-formylbenzoic acid (*J. Org. Chem.*, 2002, 67, 3548-3554) are dissolved in 110 ml of acetonitrile under argon. 330 mg (2.7 mmol) of 4-dimethylaminopyridine and 1.73 ml (54.2 mmol) of methanol are added thereto. The mixture is cooled to −10° C., and 6.23 g (32.5 mmol) of EDC are added. The mixture is slowly allowed to reach RT and is then stirred for 20 h. The solvent is then evaporated in vacuo, and the residue is purified by chromatography on silica gel (mobile phase: cyclohexane/ethyl acetate (6:1)).

Yield: 5.1 g (77% of theory). HPLC (method 11): $R_t$=4.41 min. $^1$H-NMR (200 MHz, CDCl$_3$): δ=3.95 (s, 3H), 8.20 (m, 1H), 8.43 (m, 1H), 8.47 (m, 1H), 10.03 (s, 1H).

Example 12I

Benzyl N-(tert-butoxycarbonyl)-3-hydroxy-6-nitro-L-phenylalaninate

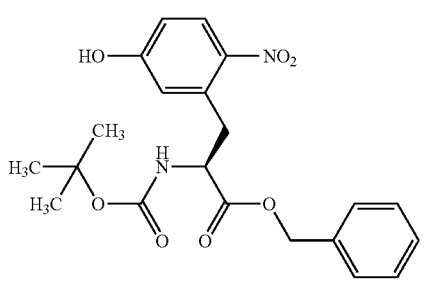

10.4 ml (10.4 mmol) of a 1N tetrabutylammonium fluoride solution in THF are added to a solution of 2.77 g (5.22 mmol) of benzyl N-(tert-butoxycarbonyl)-3-{[tert-butyl(dimethyl)silyl]oxy}-6-nitro-L-phenylalaninate (Example 5I) in 50 ml of THF, and the mixture is stirred at RT for 30 min. The solution is then poured into ice-water and extracted several times with ethyl acetate. The organic phase is dried over magnesium sulfate and concentrated in vacuo. The crude product is dried to constant weight under high vacuum.

Yield: 2.1 g (97% of theory) LC-MS (method 8): $R_t$=3.23 min. MS (EI$^+$): m/z=417 (M+H)$^+$ Example 12J Benzyl 3-(benzyloxy)-N-(tert-butoxycarbonyl)-5-hydroxy-L-phenylalaninate

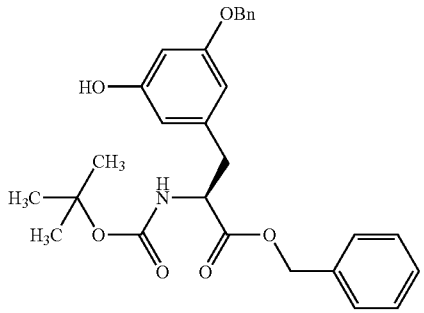

Preparation takes place in analogy to Example 12I from 1.30 g (2.2 mmol) of benzyl 3-(benzyloxy)-N-(tert-butoxycarbonyl)-5-{[tert-butyl(dimethyl)silyl]oxy}-L-phenylalaninate (Example 5J) and 4.4 ml (4.39 mmol) of a 1N tetrabutylammonium fluoride solution in THF.

Yield: 1.15 g (95% of theory) LC-MS (method 14): $R_t$=3.82 min MS (EI): m/z=478 (M+H)$^+$ Example 13I Benzyl N-(tert-butoxycarbonyl)-2-nitro-5-{[(trifluoromethyl)sulfonyl]oxy}-L-phenylalaninate

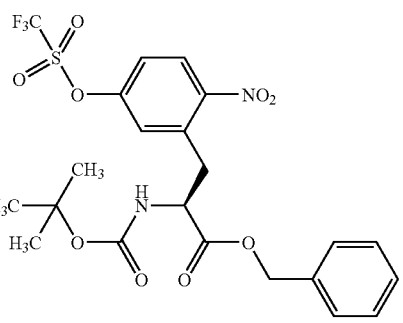

1.0 ml (6.01 mmol) of trifluoromethanesulfonic anhydride is added dropwise to a solution of 2.27 g (5.46 mmol) of benzyl N-(tert-butoxycarbonyl)-3-hydroxy-6-nitro-L-phenylalaninate (Example 12I) and 1.52 ml (10.9 mmol) of triethylamine in 150 ml of dichloromethane at −15° C. (acetone/dry ice bath). After 15 min, the mixture is warmed to RT, and water is added. The organic phase is separated, washed several times with water, dried over magnesium sulfate and concentrated in vacuo. The crude product is purified by RP-HPLC (mobile phase: acetonitrile/water gradient).

Yield: 1.88 g (63% of theory) HPLC (method 13): $R_t$=5.35 min. MS (DCI): m/z=566 (M+NH$_4$)$^{+1}$H-NMR (200 MHz, DMSO-d$_6$): δ=1.29 (s, 9H), 3.08 (m$_c$, 1H), 3.50 (m$_c$, 1H), 4.46 (m$_c$, 1H), 5.15 (s, 2H), 7.25-7.50 (m, 5H), 7.65-7.80 (m, 2H), 8.20 (m$_c$, 1H).

Example 13J

Benzyl 3-(benzyloxy)-N-(tert-butoxycarbonyl)-5-{[(trifluoromethyl)sulfonyl]oxy-L-phenylalaninate

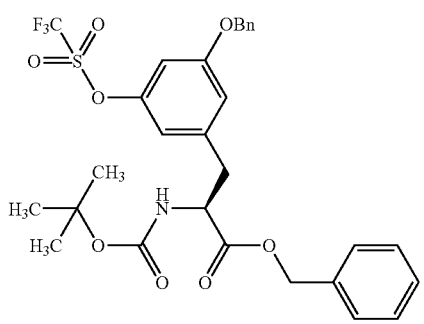

Preparation takes place in analogy to Example 13I from 1.15 g (2.41 mmol) of benzyl 3-(benzyloxy)-N-(tert-butoxycarbonyl)-5-hydroxy-L-phenylalaninate (Example 12J), 0.67 ml (4.82 mmol) of triethylamine and 0.45 ml (2.65 mmol) of trifluoromethanesulfonic anhydride.

Yield: 1.4 g (95% of theory) LC-MS (method 14): $R_t$=4.24 min MS (EI): m/z=610 (M+H)$^+$

Example 14B

Methyl 3-bromo-N-(tert-butoxycarbonyl)-6-chloro-N-methyl-L-phenylalaninate

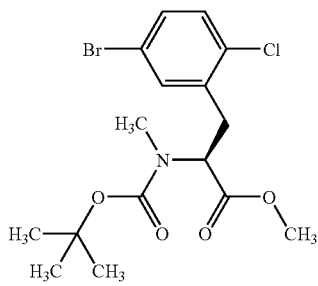

100 mg (0.25 mmol) of the compound from Example 5B are dissolved in 5 ml THF under argon and, at RT, 30 mg (0.76 mmol) of sodium hydride (60% dispersion in mineral oil) are added. After the addition of 290 mg (130 µl, 2.04 mmol) of methyl iodide the mixture is stirred at RT for 12 h. Then 20 ml each of ethyl acetate and water are added, and the pH is adjusted to 3 by adding 0.1N hydrochloric acid. The mixture is extracted several times with ethyl acetate, the organic phase is separated, dried over magnesium sulfate and evaporated to dryness in vacuo. The crude product is dissolved in 10 ml of methanol and, at 0° C. (ice-bath cooling) under argon, 50 mg (0.25 mmol) of EDC and 8 mg (0.057 mmol) of HOBt are added. The mixture is stirred at RT for 36 h. Methanol is evaporated in vacuo, and the crude mixture is mixed with water and extracted several times with ethyl acetate. The organic phase is dried over magnesium sulfate, evaporated to dryness in vacuo and purified by RP-HPLC (mobile phase: acetonitrile/water gradient).

Yield: 0.06 g (59% of theory) LC-MS (method 3): $R_t$=2.96 min. MS (EI): m/z=306 (M-boc+H)$^+$ $^1$H-NMR (400 MHz, DMSO-d$_6$): RT spectrum shows rotamers: δ=1.25 (s$_c$, 9H), 2.65 (s$_c$, 3H), 3.18 (m$_c$, 1H), 3.38 (m$_c$, 1H), 3.70 (s$_c$, 3H), 4.83 (m$_c$, 1H), 7.35-7.60 (m, 3H).

Example 14O

Methyl 3-bromo-N-(tert-butoxycarbonyl)-6-fluoro-N-methyl-L-phenylalaninate

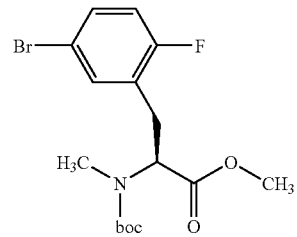

49.8 g (350.86 mmol) of iodomethane and 2.28 g (57.01 mmol) of sodium hydride are added to a solution of 16.5 g (43.86 mmol) of methyl 3-bromo-N-(tert-butoxycarbonyl)-6-fluoro-L-phenylalaninate (Example 5O) in 220 ml of anhydrous tetrahydrofuran. The reaction mixture is stirred at RT overnight. 1000 ml of water and 1000 ml of ethyl acetate are added to the mixture. The organic phase is washed successively with water and a saturated sodium chloride solution, dried over sodium sulfate and concentrated. The crude product is purified by column chromatography on silica gel (mobile phase: cyclohexane:ethyl acetate 3:1).

Yield: quant. HPLC (method 11): $R_t$=5.1 min. MS (DCI (NH$_3$)): m/z=390 (M+H)$^+$. $^1$H-NMR (400 MHz, CDCl$_3$): δ=1.48 (d, 9H), 2.23 (d, 3H), 3.09 (dd, 1H), 3.30 (dd, 1H), 3.75 (s, 3H), 4.70 (ddd, 1H), 6.92 (dd, 1H), 7.30 (m, 2H).

Example 15E

5-Bromo-2-methylbenzaldehyde

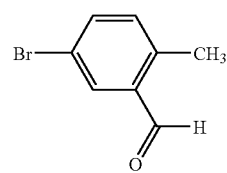

77.7 g (583 mmol) of aluminium trichloride are suspended in 200 ml of dichloromethane and cooled to 0° C. 40.0 g (333 mmol) of 2-methylbenzaldehyde are added dropwise over the course of 30 min. Then 53.2 g (333 mmol) of bromine are added at 0° C. over the course of 6 h, and the mixture is allowed to warm to RT and is stirred for 12 h. The reaction solution is added to 500 ml of ice-water. The aqueous phase is extracted several times with dichloromethane. The combined organic phases are washed successively with 2N hydrochloric acid, a saturated aqueous sodium bicarbonate solution and a saturated aqueous sodium chloride solution. The organic phase is dried over sodium sulfate and concentrated in vacuo. Purification is by silica gel chromatography and subsequently by crystallization from cyclohexane. The precipitated product is filtered off.

Yield: 3.2 g (5% of theory) LC-MS (method 9): $R_t$=3.26 min MS (EI): m/z=199 (M+H)$^+$ Example 16A 2-(Trimethylsilyl)ethyl-2-(benzyloxy)-N-[(benzyloxy)carbonyl]-5-(4,4,5,5-tetramethyl-1,3,2-dioxaborolan-2-yl)-L-phenylalaninate

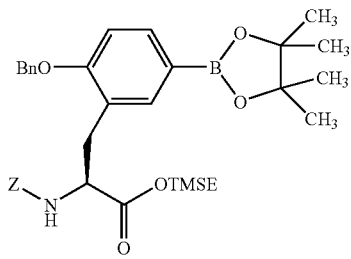

0.932 g (9.50 mmol) of potassium acetate are added to a solution of 2.00 g (3.17 mmol) of (2-trimethylsilyl)ethyl 2(S)-benzyloxycarbonylamino-3-(2-benzyloxy-5-iodophenyl)propionate in 30 ml of DMSO. The mixture is deoxygenated by passing argon through the vigorously stirred solution for 15 min. Then 0.924 g (3.64 mmol) of 4,4,4',4',5,5,5',5'-octamethyl-2,2'-bi-1,3,2-dioxaborolane and 0.116 g (0.160 mmol, 0.05 equivalents) of bis(diphenylphosphino)ferrocenepalladium(II)chloride are added. The mixture is heated under a gentle stream of argon to 80° C. and cooled again after 6 h. The mixture is filtered through silica gel (mobile phase: dichloromethane). The residue is purified by column chromatography on silica gel (mobile phase: cyclohexane:ethyl acetate 4:1).

LC-MS (method 22): $R_t$=4.50 min MS (EI): m/z=632 (M+H)$^+$ $^1$H-NMR (200 MHz, CDCl$_3$): δ=0.92 (dd, 2H), 1.31 (s, 12H), 2.95-3.95 (m, 2H), 4.11 (m$_c$, 2H), 4.55 (11 (m$_c$, 1H), 4.99 (s, 2H), 5.08 (s, 2H), 5.53 (d, 1H), 6.90 (d, 1H), 7.15-7.47 (m, 10 H), 7.58 (d, 1H), 7.67 (dd, 1H).

Example 17A 2-(Trimethylsilyl)ethyl-(2S)-3-(3'-{(2S)-3-(benzyloxy)-2-[(tert-butoxycarbonyl)amino]-3-oxopropyl}-4'-fluoro-4-hydroxybiphenyl-3-yl)-2-{[(benzyloxy)carbonyl]amino}propanoate

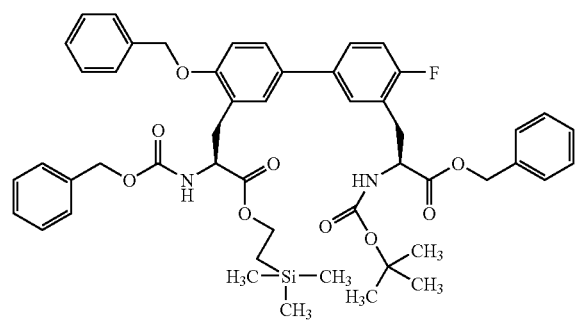

358 mg (0.79 mmol) of benzyl 3-bromo-N-(tert-butoxycarbonyl)-6-fluoro-L-phenylalaninate (Example 5A) are dissolved in 3 ml of abs. DMF, the solution is degassed in vacuo for 5 min and vented with argon, and the subsequent reaction is also carried out under a flow of argon. 58 mg (0.08 mmol) of bis(diphenylphosphino)ferrocenepalladium(II)chloride and 516 mg (1.58 mmol) of cesium carbonate are added to this solution while stirring. In parallel, 500 mg (0.79 mmol) of 2-(trimethylsilyl)ethyl 2-[(benzyloxy)carbonyl]-5-(4,4,5,5-tetramethyl-1,3,2-dioxaborolan-2-yl)-L-phenylalaninate (Example 16A) are dissolved in 3 ml of abs. DMF and degassed in vacuo for 5 min and subsequently argon is passed through the solution for 15 min. The solution prepared in this way is added under an argon atmosphere to the first solution, warmed to 40° C. and left to react overnight while stirring. The mixture is evaporated to dryness in vacuo and the residue is taken up in 10 ml of ethyl acetate and filtered to remove insolubles, and the organic phase is extracted three times with 3 ml of water. The organic phase is dried (sodium sulfate) and concentrated in vacuo, and the residue is separated by column chromatography (silica gel 60, mobile phase: cyclohexane/ethyl acetate=4/1). The main fraction affords 389 mg of product (47% yield); a further 72 mg (10% yield) are obtained from the mixed fraction by HPLC (acetonitrile/water).

Overall yield: 57% of theory LC-MS (method 4): $R_t$=5.0 min. MS (EI): m/z=876 [M+H]$^+$ Examples 17B to 17E, 17H to 17J, 17N and 17P listed in the following table are prepared from the appropriate precursors in analogy to the above method:

| Example No. | Structure | Prepared in analogy to Example No. | Analytical data |
|---|---|---|---|
| 17B | 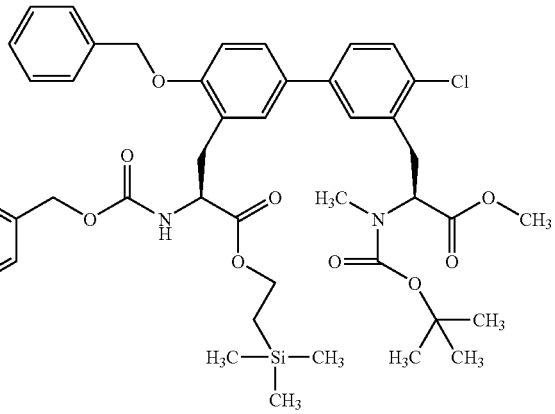 | 17A from Example 14B and 16A | LC-MS (method 3): $R_t$ = 3.55 min. MS (ES): m/z = 853 (M + Na)$^+$ |
| 17C | 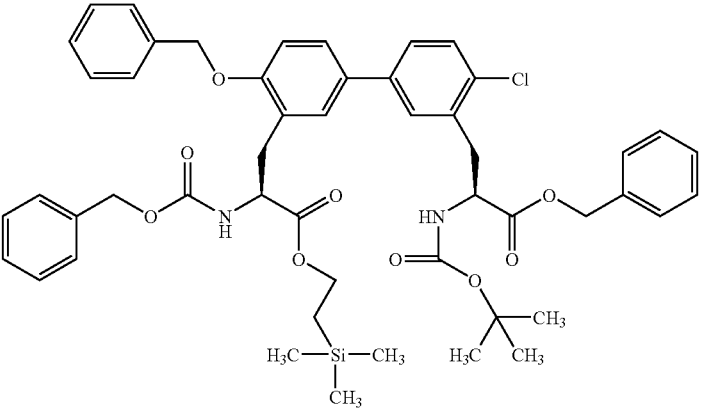 | 17A from Example 5C and 16A | HPLC (method 12): $R_t$ = 7.20 min. MS (ES): m/z = 893 (M + H)$^+$ $^1$H-NMR (200 MHz, DMSO-$d_6$): δ = 0.0 (s, 9H), 0.83 (m$_c$, 2H), 1.30 (s, 9H), 2.75-3.15 (m, 2H), 3.30 (m$_c$, 2H), 3.88 (s, 3H), 4.09 (m$_c$, 2H), 4.44 (m$_c$, 2H), 4.97 (m$_c$, 2H), 5.10-5.30 (m, 4H), 7.1-7.9 (m, 21H). |
| 17D | 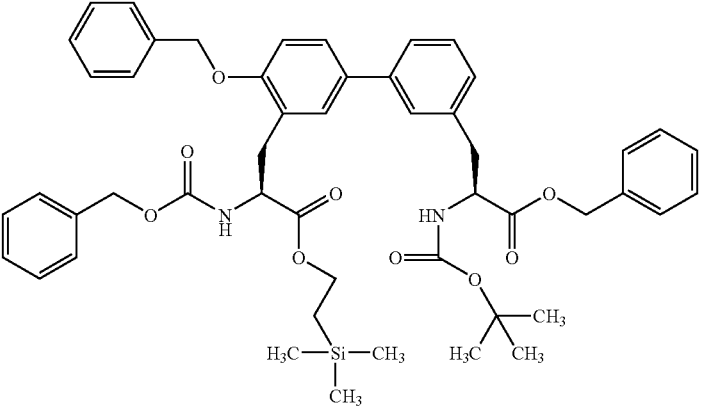 | 17A from Example 10D and 16A | LC-MS (method 9): $R_t$ = 5.35 min. MS (ES): m/z = 859 (M + H)$^+$ |

-continued

| Example No. | Structure | Prepared in analogy to Example No. | Analytical data |
|---|---|---|---|
| 17E | 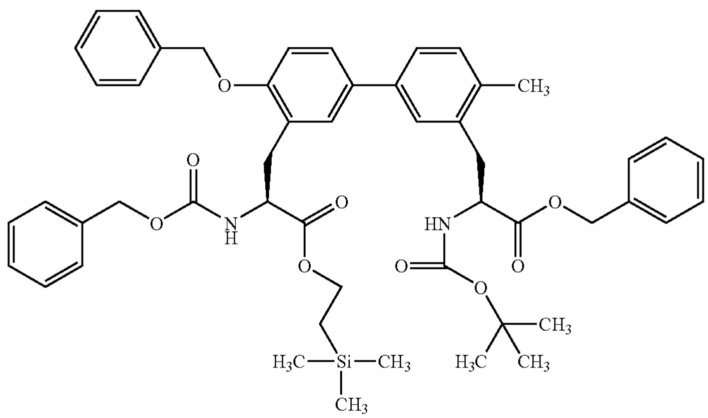 | 17A from Example 5E and 16A | LC-MS (method 18): $R_t$ = 4.01 min. MS (ES): m/z = 873 (M + H)$^+$ |
| 17H | 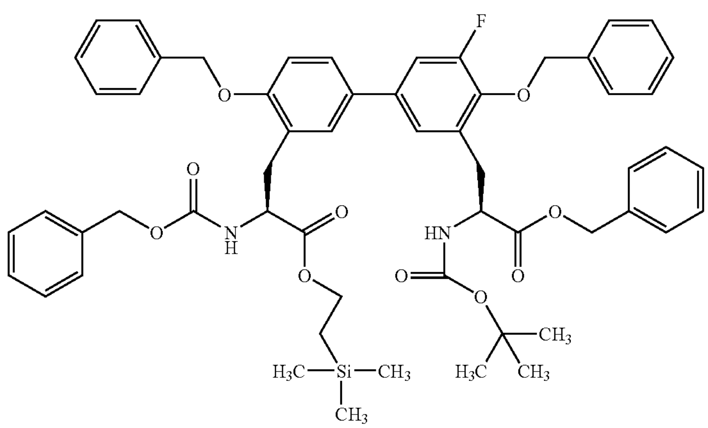 | 17A from Example 6H and 16A | LC-MS (method 18): $R_t$ = 3.79 min. MS (ES): m/z = 983 (M + H)$^+$ |
| 17I | 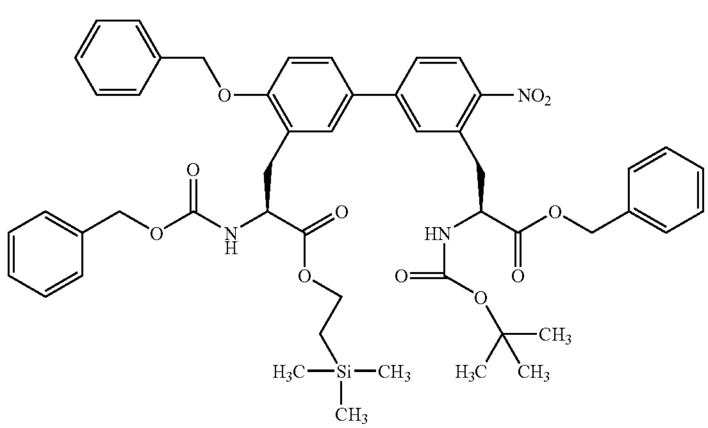 | 17A from Example 13I and 16A | LC-MS (method 7): $R_t$ = 2.93 min. MS (ES): m/z = 904 (M + H)$^+$ |

| Example No. | Structure | Prepared in analogy to Example No. | Analytical data |
|---|---|---|---|
| 17J | 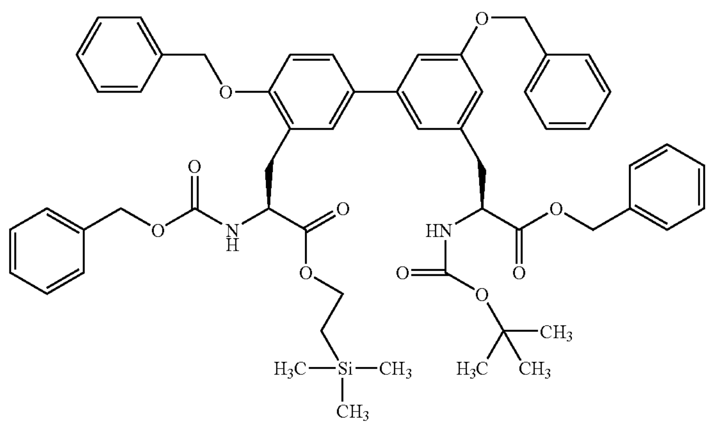 | 17A from Example 13J and 16A | LC-MS (method 7): $R_t$ = 3.73 min. MS (ES): m/z = 965 (M + H)$^+$ |
| 17N | 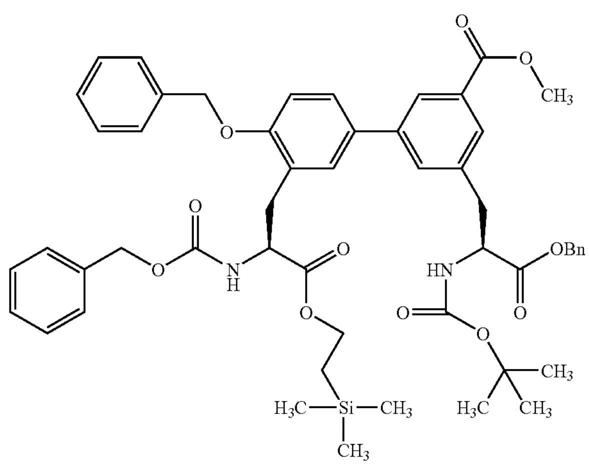 | 17A from Example 6N and 16A | LC-MS (method 5): $R_t$ = 3.36 min. MS (ES): m/z = 917 (M + H)$^+$ |
| 17P | 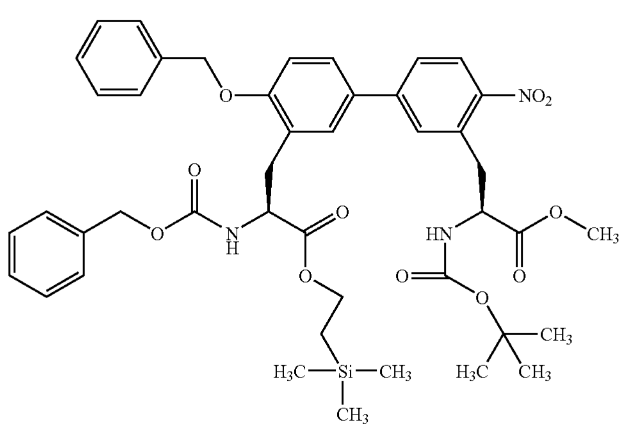 | 17A from Example 5P and 16A | LC-MS (method 1): $R_t$ = 3.40 min. MS (ES): m/z = 828 (M + H)$^+$ |

Example 17O

Methyl (2S)-3-(4'-(benzyloxy)-3'-{(2S)-2-{[(benzyloxy)carbonyl]amino}-3-oxo-3-[2-(trimethylsilyl)ethoxy]propyl}-4-fluorobiphenyl-3-yl)-2-[(tert-butoxycarbonyl)(methyl)amino]propanoate

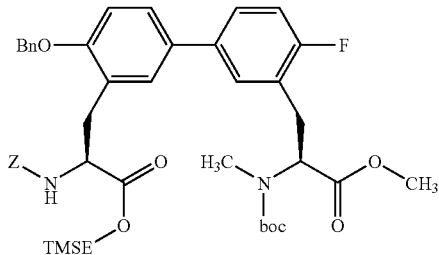

A solution of 1.68 g (4.09 mmol) of methyl 3-bromo-N-(tert-butoxycarbonyl)-6-fluoro-N-methyl-L-phenylalaninate (Example 14O) in 8 ml of 1-methyl-2-pyrrolidone is rendered inert and saturated with argon (pass argon through for about 30 min). Then 334 mg (0.41 mmol) of bis(diphenylphosphino)ferrocenepalladium(II)chloride ($PdCl_2$(dppf)) are added, and the mixture is stirred at RT for 10 min. Thereafter, 3.45 g (4.92 mmol) of 2-(trimethylsilyl)ethyl-2-(benzyloxy)-N-[(benzyloxy)carbonyl]-5-(4,4,5,5-tetramethyl-1,3,2-dioxaborolan-2-yl)-L-phenylalaninate (Example 16A) in 8 ml of 1-methyl-2-pyrrolidone and 2.67 g (8.19 mmol) of cesium carbonate are added. A gentle stream of argon is passed over the reaction mixture, which is stirred at 50° C. for 20 h. The mixture is cooled, taken up in dichloromethane and washed with water. The organic phase is dried over magnesium sulfate, and the solvent is concentrated in vacuo. The residue is purified by column chromatography on silica gel (cyclohexane:ethyl acetate 7:3).

Yield: 3.6 g (86% of theory). LC-MS (method 1): $R_t$=2.49 min MS (EI): m/z=1140 (M+H)$^+$.

Example 18A

Benzyl (2S)-2-amino-3-(4'-(benzyloxy)-3'-{(2S)-2-{[(benzyloxy)carbonyl]amino}-3-oxo-3-[2-(trimethylsilyl)ethoxy]propyl}-4-fluorobiphenyl-3-yl)propanoate hydrochloride

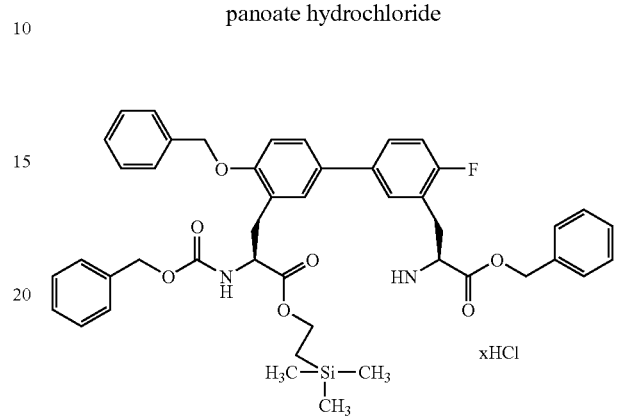

405 mg (0.46 mmol) of the compound from Example 17A are suspended in 2 ml of abs. dioxane, cooled to 0° C. and, while stirring, 12 ml of a 4N dioxane/hydrogen chloride solution are added. After 3 h, the mixture is evaporated to dryness in vacuo and dried to constant weight under high vacuum.

Yield: 395 mg (88% of theory) LC-MS (method 5): $R_t$=2.45 min. MS (EI): m/z=776 [M+H]$^+$ Examples 18B to 18E, 18H to 18J and 18N and 18P listed in the following table are prepared from the appropriate precursors in analogy to the above method:

| Example No. | Structure | Prepared in analogy to Example No. | Analytical data |
|---|---|---|---|
| 18B | (structure shown) | 18A from Example 17B | LC-MS (method 1): $R_t$ = 2.69 min. MS (ES): m/z = 731 (M − HCl + H)$^+$ |

-continued

| Example No. | Structure | Prepared in analogy to Example No. | Analytical data |
|---|---|---|---|
| 18C | 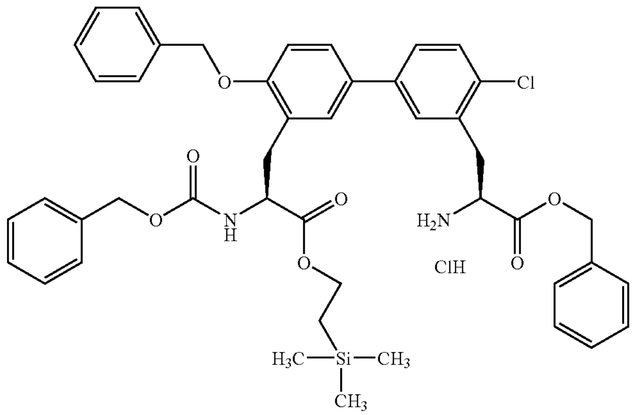 | 18A from Example 17C | LC-MS (method 5): $R_t$ = 2.50 min. MS (ES): m/z = 793 (M − HCl + H)$^+$ |
| 18D | 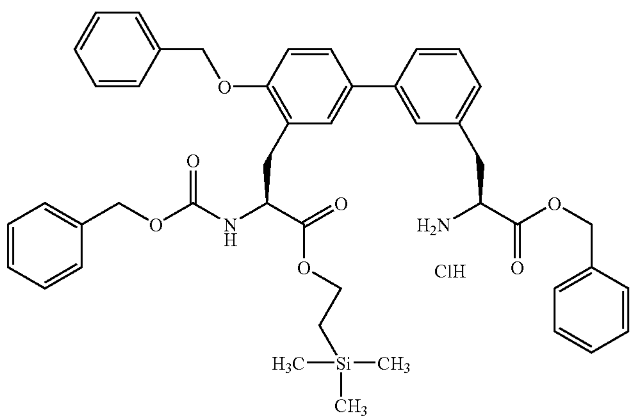 | 18A from Example 17D | LC-MS (method 5): $R_t$ = 2.36 min. MS (ES): m/z = 759 (M − HCl + H)$^+$ |
| 18E | 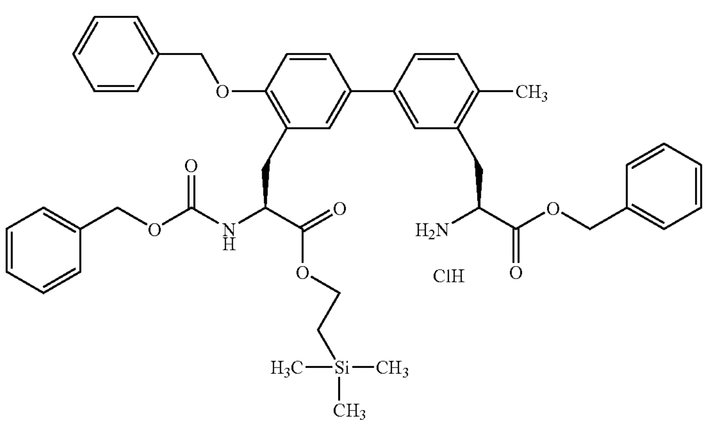 | 18A from Example 17E | LC-MS (method 8): $R_t$ = 3.10 min. MS (ES): m/z = 773 (M − HCl + H)$^+$ |

-continued

| Example No. | Structure | Prepared in analogy to Example No. | Analytical data |
|---|---|---|---|
| 18H | 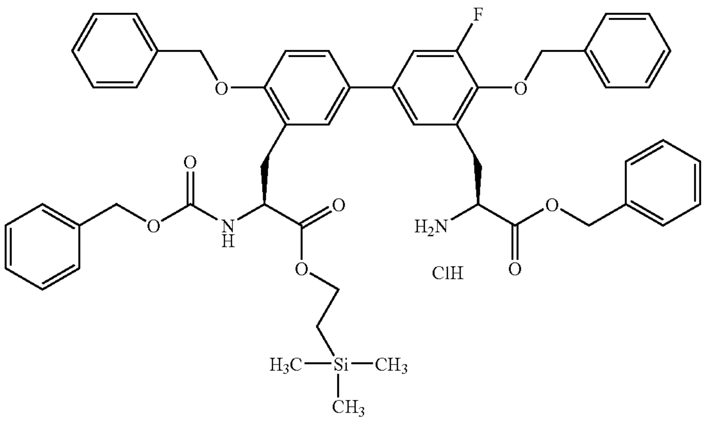 | 18A from Example 17H | LC-MS (method 18): $R_t$ = 1.28 min. MS (ES): m/z = 883 (M − HCl + H)$^+$ |
| 18I | 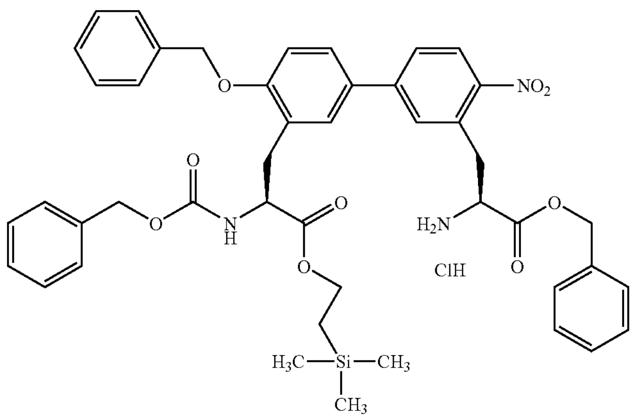 | 18A from Example 17I | LC-MS (method 14): $R_t$ = 3.45 min. MS (ES): m/z = 804 (M − HCl + H)$^+$ |
| 18J | 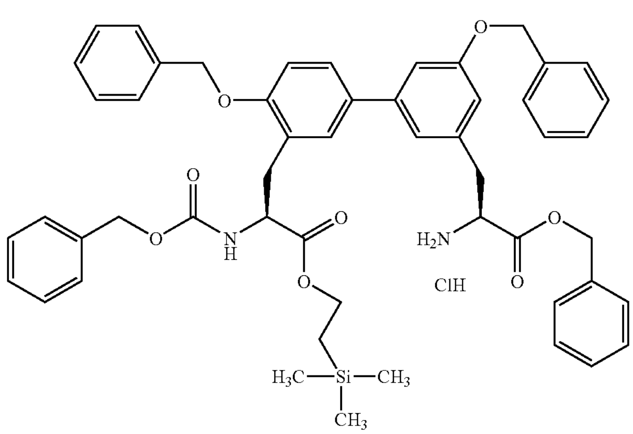 | 18A from Example 17J | LC-MS (method 14): $R_t$ = 3.61 min. MS (ES): m/z = 865 (M − HCl + H)$^+$ |

| Example No. | Structure | Prepared in analogy to Example No. | Analytical data |
|---|---|---|---|
| 18N | 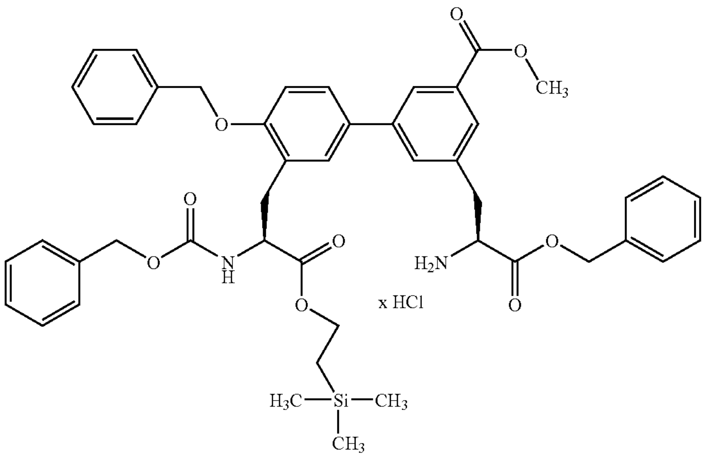 | 18A from Example 17N | LC-MS (method 5): $R_t$ = 2.42 min. MS (ES): m/z = 817 (M − HCl + H)$^+$ |
| 18P | 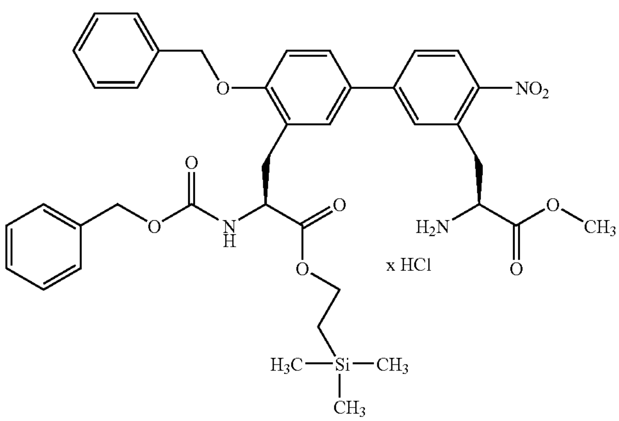 | 18A from Example 17P | LC-MS (method 1): $R_t$ = 2.39 min. MS (ES): m/z = 728 (M − HCl + H)$^+$ |

Example 18O 2-(Trimethylsilyl)ethyl (2S)-2-{[(benzyloxy)carbonyl]amino}-3-{4-(benzyloxy)-4'-fluoro-3'-[(2,9-3-methoxy-2-(methylamino)propyl]biphenyl-3-yl}propanoate hydrochloride

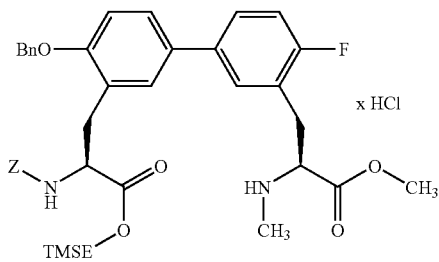

23 ml of a 4M hydrogen chloride/dioxane solution are added to a solution, cooled to 0° C., of 1.2 g (1.47 mmol) of methyl (2S)-3-(4'-(benzyloxy)-3'-{(2S)-2-{[(benzyloxy)carbonyl]amino}-3-oxo-3-[2-(trimethylsilyl)ethoxy]propyl}-4-fluorobiphenyl-3-yl)-2-[(tert-butoxycarbonyl)(methyl)amino]propanoate (Example 17O) in 6 ml of anhydrous dioxane. After stirring for 3 h, the solvent is evaporated in vacuo, coevaporated several times with dichloromethane and dried under high vacuum. The crude product is reacted without further purification.

Yield: quant. LC-MS (method 2): $R_t$=2.62 min. MS (EI): m/z=715 (M+H)$^+$.

Example 19A 2-(Trimethylsilyl)ethyl (2S)-3-{3'-[(2S)-3-(benzyloxy)-2-({(2S)-5-{[(benzyloxy)carbonyl]amino}-2-[(tert-butoxycarbonyl)amino]pentanoyl}amino)-3-oxopropyl]-4'-fluoro-4-hydroxybiphenyl-3-y}-2-{[(benzyloxy)carbonyl]amino}propanoate

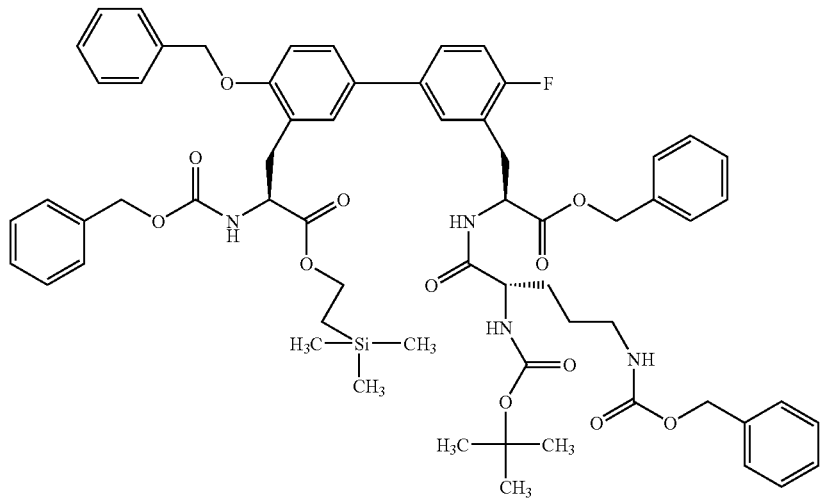

90 mg (0.12 mmol) of the compound from Example 18A and 42.4 mg (0.12 mmol) of $N^5$-[(benzyloxy)carbonyl]-$N^2$-(tert-butoxycarbonyl)-L-ornithine are dissolved in 3 ml of abs. DMF, cooled to 0° C., and 44 mg (0.12 mmol) of HATU and 16.2 mg (0.13 mmol) of Hünig's base are added. The mixture is stirred at this temperature for 30 min. and then a further 32.4 mg (0.26 mmol) of Hünig's base are added, and the temperature is allowed to rise to RT. After reaction overnight, the mixture is evaporated to dryness in vacuo, and the residue is purified by column chromatography (silica gel 60, mobile phase: dichloromethane/methanol=100/5).

Yield: 98 mg (75% of theory) LC-MS (method 6): $R_t$=3.84 min. MS (EI): m/z=1124 (M+H)$^+$

Example 19B 2-(Trimethylsilyl)ethyl (2S)-3-(4-(benzyloxy)-3'-{(2S)-2-[((2S,4R)-5-{[(benzyloxy)carbonyl]amino}-2-[(tert-butoxycarbonyl)amino]-4-{[tert-butyl(dimethyl)silyl]oxy}pentanoyl)(methyl)amino]-3-methoxy-3-oxopropyl}-4'-chlorobiphenyl-3-yl)-2-{[(benzyloxy)carbonyl]amino}-propanoate

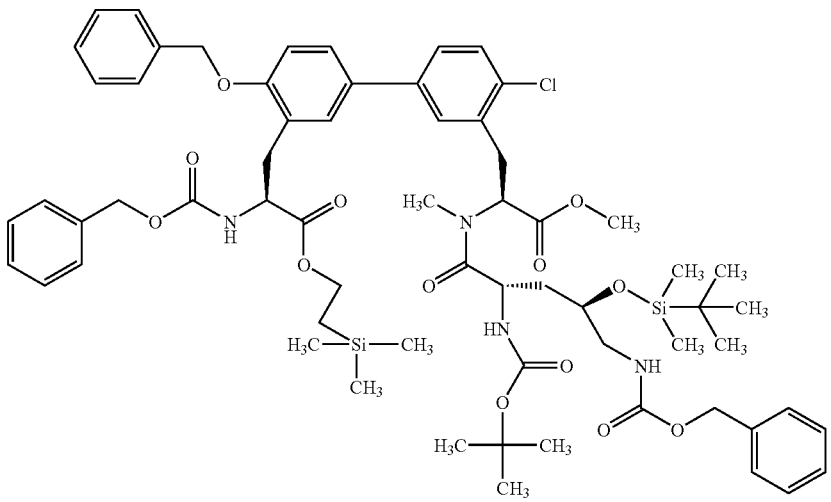

320 mg (0.43 mmol) of the compound from Example 18B and 320 mg (0.52 mmol) of (2S,4R)-5-{[(benzyloxy)carbonyl]amino}-2-[(tert-butoxycarbonyl)amino]-4-{[tert-butyl(dimethyl)silyl]oxy}pentanoic acid are dissolved in 6 ml of abs. DMF, cooled to 0° C., and 20 mg (0.52 mmol) of HATU and 19.2 mg (1.51 mmol) of Hünig's base are added. The mixture is stirred at this temperature for 30 min., then a further 3.2 mg (0.06 mmol) of Hünig's base are added, and the temperature is allowed to rise to RT. After reaction overnight, the mixture is evaporated to dryness in vacuo, and the crude product is purified by HPLC (mobile phase: acetonitrile/methanol gradient).

Yield: 303 mg (58% of theory) LC-MS (method 3): $R_t$=3.81 min. MS (EI): m/z=1209 (M+H)$^+$ Examples 19C to 19N and 19P listed in the following table are prepared from the appropriate precursors in analogy to the indicated methods:

| Example No. | Structure | Prepared in analogy to Example No. | Analytical data |
|---|---|---|---|
| 19C | 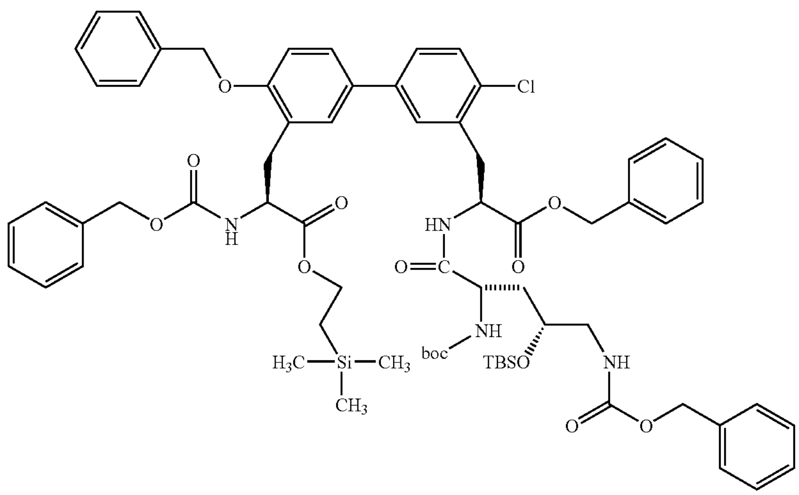 | 19B from Example 18C | LC-MS (method 2): $R_t$ = 3.69 min. MS (ES): m/z = 1271 (M + H)$^+$ |
| 19D | 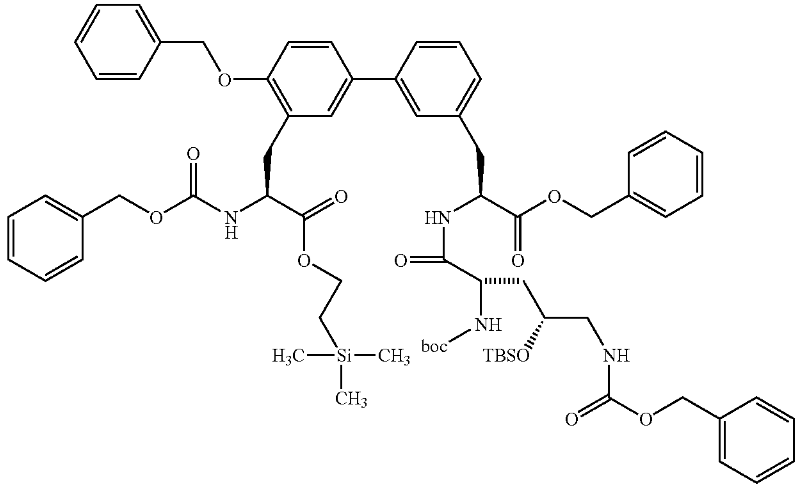 | 19B from Example 18D | LC-MS (method 2): $R_t$ = 3.64 min. MS (ES): m/z = 1271 (M + H)$^+$ |

-continued

| Example No. | Structure | Prepared in analogy to Example No. | Analytical data |
|---|---|---|---|
| 19E | 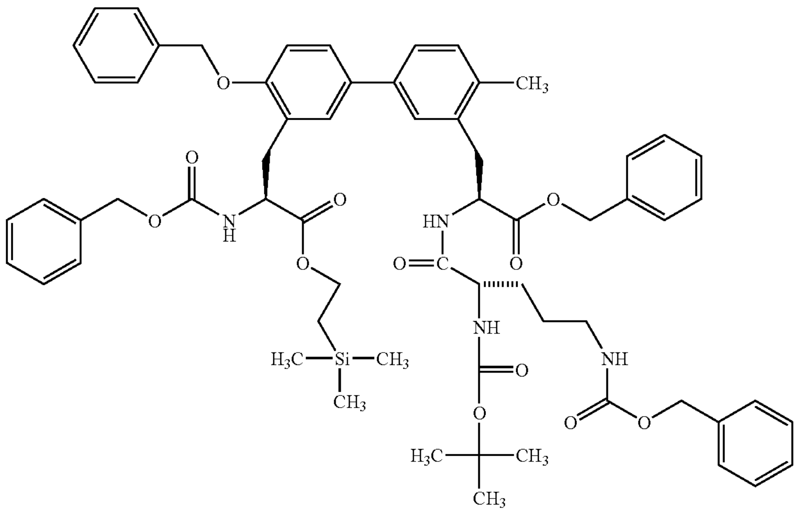 | 19A from Example 18E | LC-MS (method 3): $R_t$ = 3.54 min. MS (ES): m/z = 1271 (M + H)$^+$ |
| 19F | 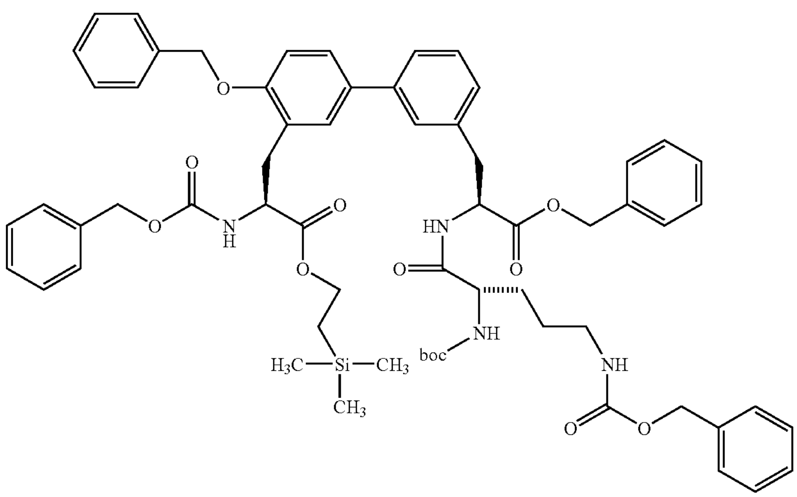 | 19A from Example 18D | LC-MS (method 9): $R_t$ = 5.35 min. MS (ES): m/z = 1271 (M + H)$^+$ |
| 19G | 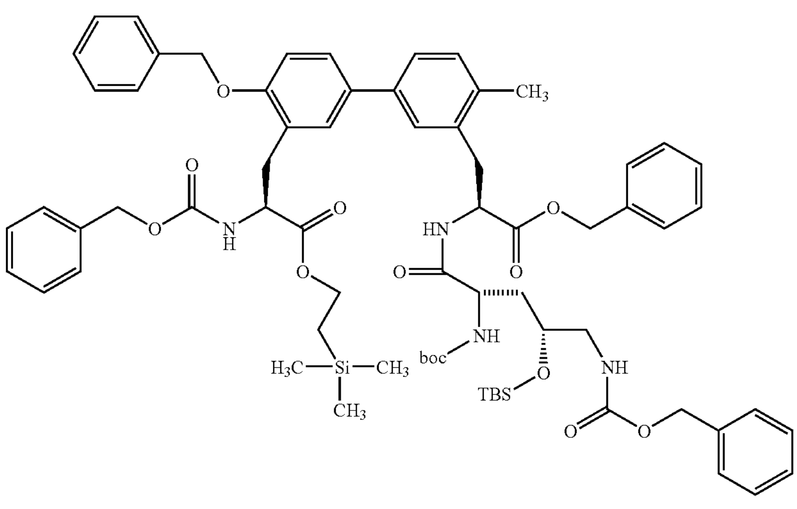 | 19B from Example 18E | LC-MS (method 5): $R_t$ = 3.89 min. MS (ES): m/z = 1271 (M + H)$^+$ |

-continued

| Example No. | Structure | Prepared in analogy to Example No. | Analytical data |
|---|---|---|---|
| 19H | 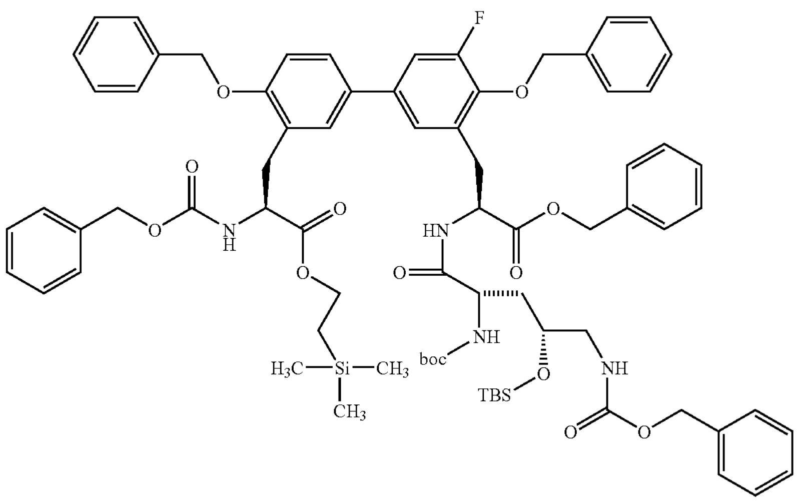 | 19B from Example 18H | LC-MS (method 10): $R_t$ = 1.34 min. MS (ES): m/z = 1271 $(M + H)^+$ |
| 19I | 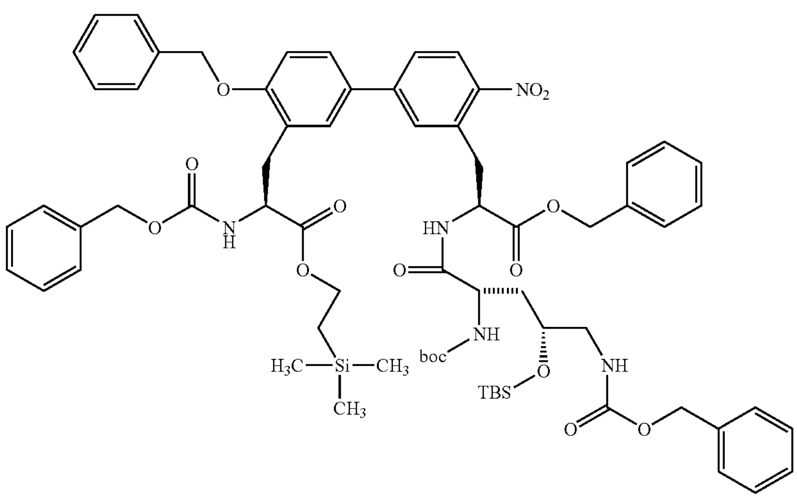 | 19B from Example 18I | LC-MS (method 10): $R_t$ = 1.04 min. MS (ES): m/z = 1271 $(M + H)^+$ |
| 19J | 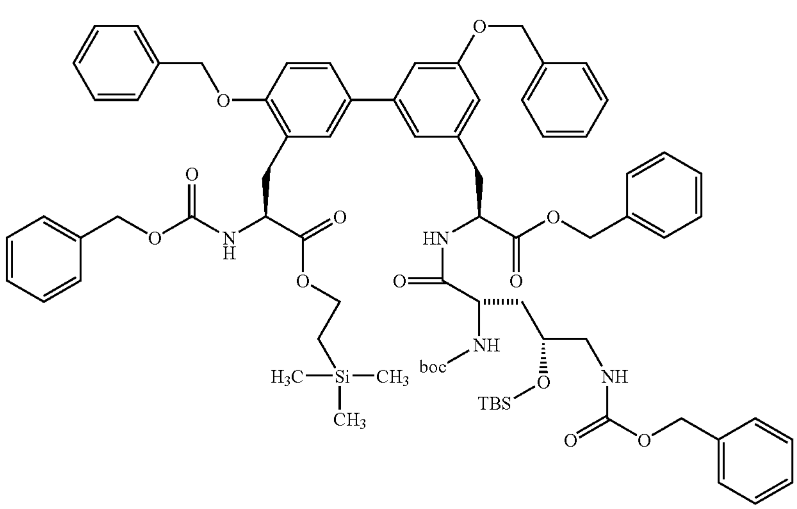 | 19B from Example 18J | LC-MS (method 10): $R_t$ = 1.38 min. MS (ES): m/z = 1271 $(M + H)^+$ |

-continued

| Example No. | Structure | Prepared in analogy to Example No. | Analytical data |
|---|---|---|---|
| 19K | 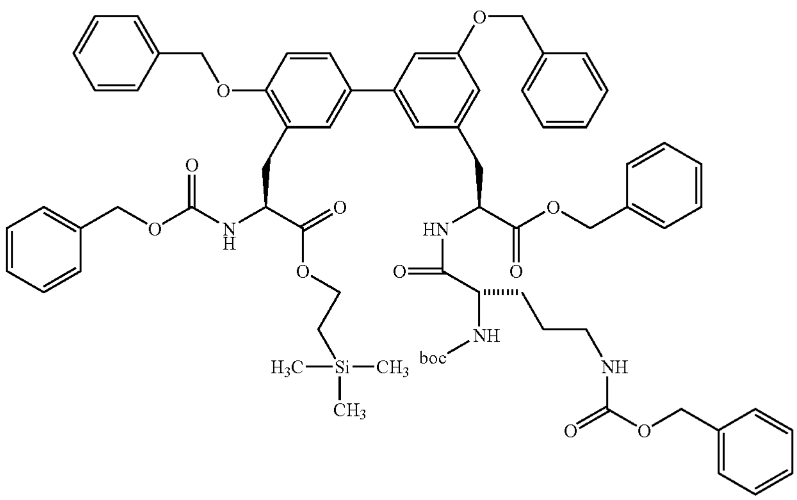 | 19A from Example 18J | LC-MS (method 7): $R_t$ = 3.58 min. MS (ES): m/z = 1271 $(M + H)^+$ |
| 19L | 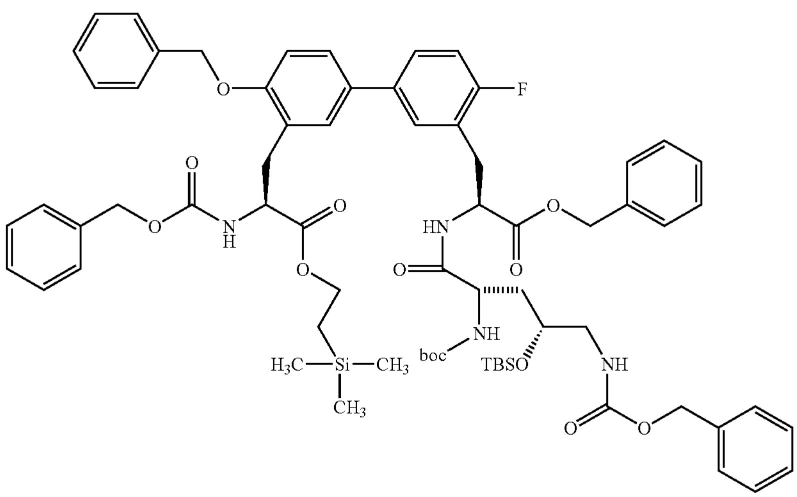 | 19B from Example 18A | LC-MS (method 3): $R_t$ = 3.87 min. MS (ES): m/z = 1271 $(M + H)^+$ |
| 19M | 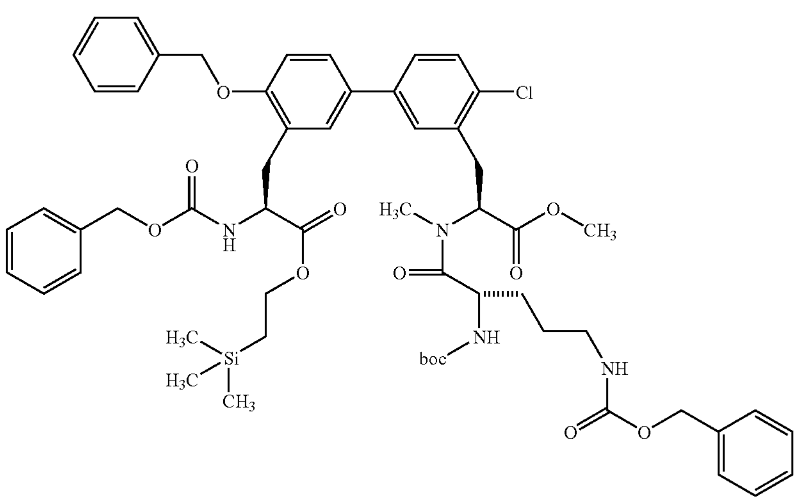 | 19A from Example 18B | LC-MS (method 2): $R_t$ = 3.38 min. MS (ES): m/z = 1271 $(M + H)^+$ |

-continued

| Example No. | Structure | Prepared in analogy to Example No. | Analytical data |
|---|---|---|---|
| 19N | 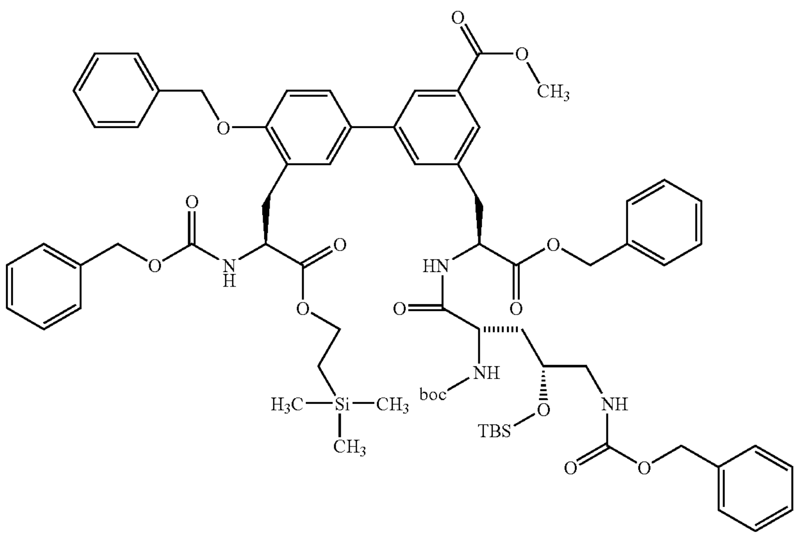 | 19B from Example 18N | LC-MS (method 16): $R_t$ = 2.88 min. MS (ES): m/z = 1271 (M + H)$^+$ |
| 19P | 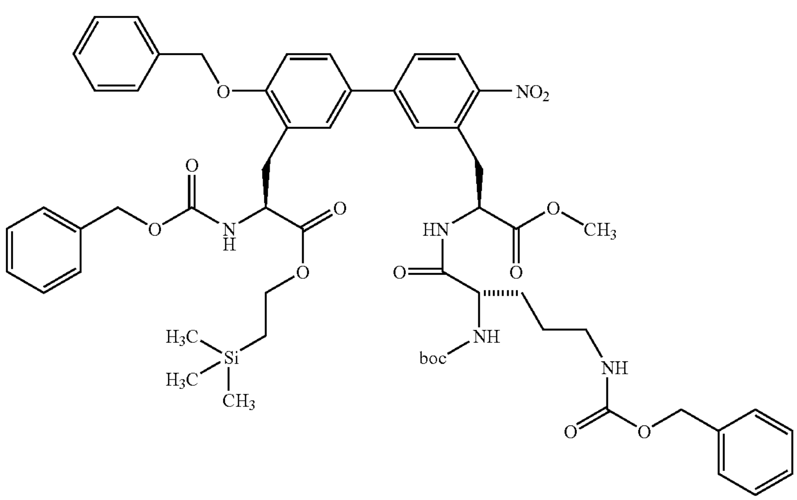 | 19A from Example 18P | LC-MS (method 2): $R_t$ = 3.23 min. MS (ES): m/z = 1271 (M + H)$^+$ |

Example 19O 2-(Trimethylsilyl)ethyl (2S)-3-(4-(benzyloxy)-3'-{(2S)-2-[{(2R)-5-{[(benzyloxy)carbonyl]amino}-2-[(tert-butoxycarbonyl)amino]pentanoyl}(methyl)amino]-3-methoxy-3-oxopropyl}-4'-fluorobiphenyl-3-yl)-2-{[(benzyloxy)carbonyl]amino}propanoate

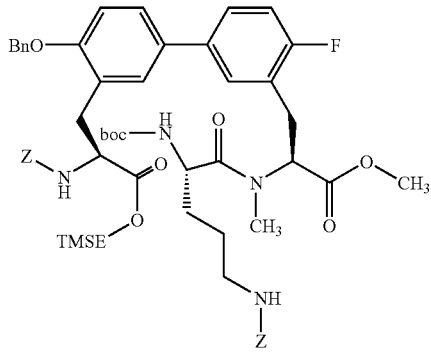

0.73 g (1.91 mmol) of HATU and 0.22 g (1.72 mmol) of N,N-diisopropylethylamine are added to a solution, cooled to 0° C., of 1.05 g (crude product, approx. 1.47 mmol) of 2-(trimethylsilyl)ethyl (2S)-2-{[(benzyloxy)carbonyl]amino}-3-{4-(benzyloxy)-4'-fluoro-3'-[(2S)-3-methoxy-2-(methylamino)propyl]biphenyl-3-yl}propanoate hydrochloride (Example 18O) and 0.64 g (1.77 mmol) of $N^5$-[(benzyloxy)carbonyl]-$N^2$-t-butoxycarbonyl)-L-omithine in 20 ml of anhydrous DMF. After stirring at 0° C. for 30 min, an additional 0.44 g (3.45 mmol) of N,N-diisopropylethylamine are added. The reaction mixture is stirred at RT for 15 h. The solvent is then evaporated and the residue is taken up in dichloromethane. The organic phase is washed with water, dried over sodium sulfate and concentrated. The crude product is purified by preparative HPLC.

Yield 0.89 g (57% of theory) LC-MS (method 3): $R_t$=3.45 min. MS (EI): m/z=1064 (M+H)$^+$.

Example 20B (2S)-3-(4-(Benzyloxy)-3'-{(2S)-2-[{(2S,4R)-5-{[(benzyloxy)carbonyl]amino}-2-[(tert-butoxycarbonyl)amino]-4-hydroxypentanoyl}-(methyl)amino]-3-methoxy-3-oxopropyl}-4'-chlorobiphenyl-3-yl)-2-{[(benzyloxy)carbonyl]amino}propanoic acid

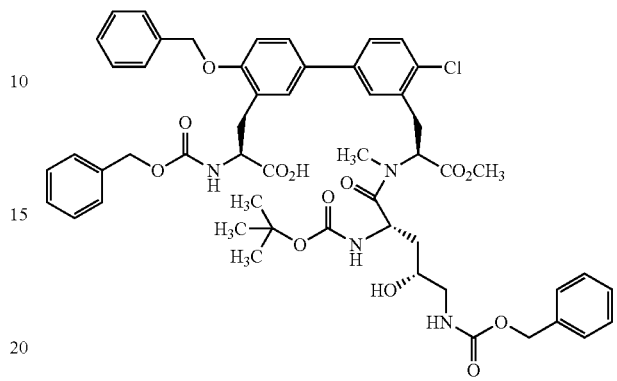

282.3 mg (0.23 mmol) of 2-(trimethylsilyl)ethyl (2S)-3-(4-benzyloxy)-3'-{(2S)-2-[(benzyloxy)carbonyl]amino}-2-[(tert-butoxycarbonyl)amino]-4-{[tert-butyl(dimethyl)silyl]-oxy}pentanoyl)(methyl)amino]-3-methoxy-3-oxopropyl}-4'-chlorobiphenyl-3-yl)-2-{[benzyloxy)carbonyl]amino}propanoate (Example 19B) are introduced into 20 ml of abs. DMF and, while stirring, 0.7 ml (183 mg, 0.7 mmol) of tetra-n-butylammonium fluoride solution is added and the mixture is stirred at RT for 20 min. The mixture is cooled to 0° C. and 60 ml of water and 0.5 ml of 1N hydrochloric acid are added. A precipitate precipitates. The mixture is stirred for a further 60 min, the precipitate is filtered off and washed with a little water, and the precipitate is dried to constant weight in vacuo.

Yield: 236 mg (98% of theory) LC-MS (method 1): $R_t$=3.07 min. MS (EI): m/z=994 [M+H]$^+$ Examples 20A, 20C to 20N and 20P listed in the following table are prepared from the appropriate precursors in analogy to the indicated methods:

| Example No. | Structure | Prepared in analogy to Example No. | Analytical data |
|---|---|---|---|
| 20A | 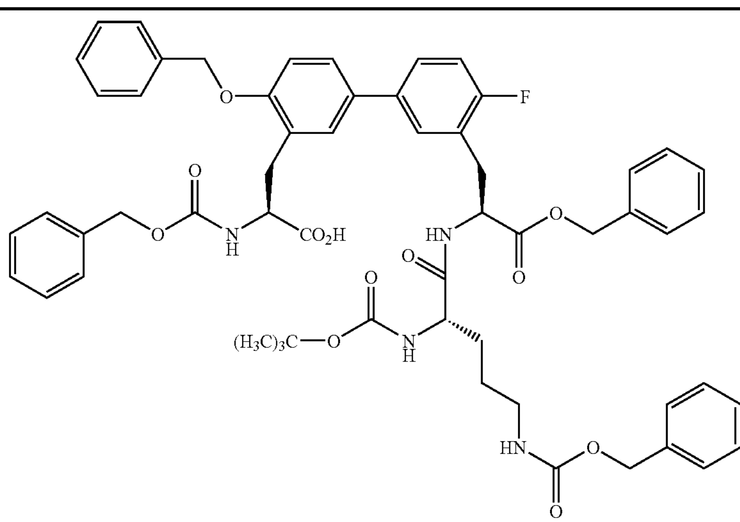 | 20B from Example 19A | LC-MS (method 7): $R_t$ = 0.91 min. MS (EI): m/z = 1024 (M + H)$^+$ |

-continued

| Example No. | Structure | Prepared in analogy to Example No. | Analytical data |
|---|---|---|---|
| 20C | 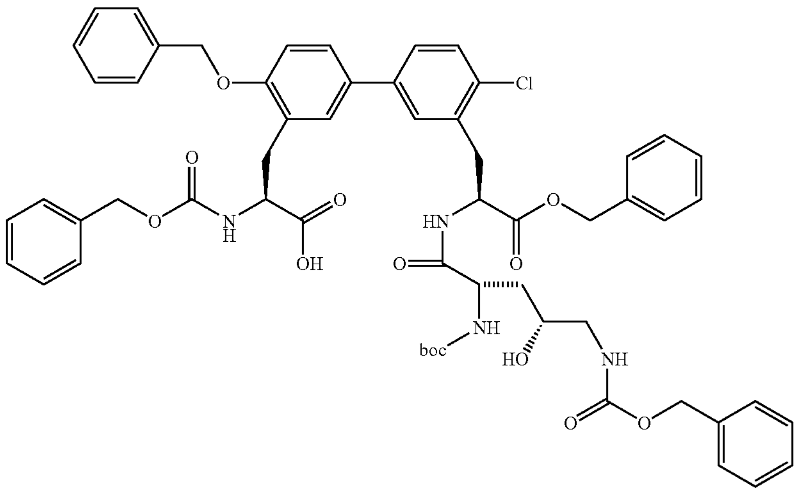 | 20B from Example 19C | LC-MS (method 5): $R_t$ = 2.93 min. MS (ES): m/z = 1057 $(M + H)^+$ |
| 20D | 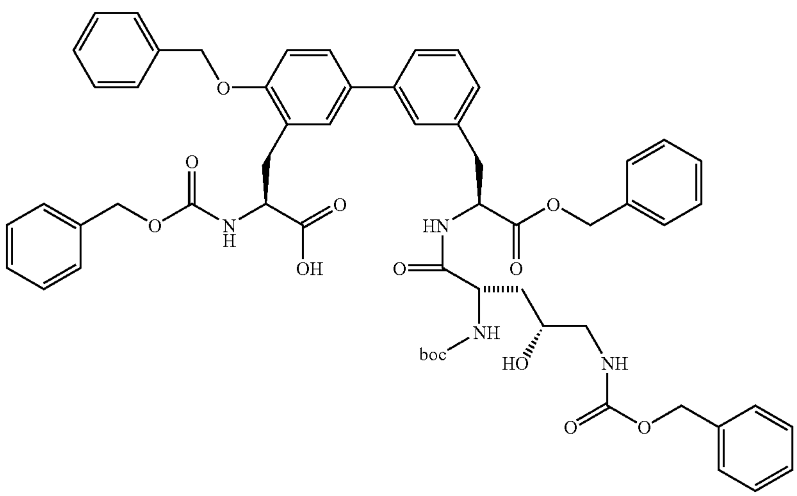 | 20B from Example 19D | LC-MS (method 15): $R_t$ = 4.59 min. MS (ES): m/z = 1023 $(M + H)^+$ |
| 20E | 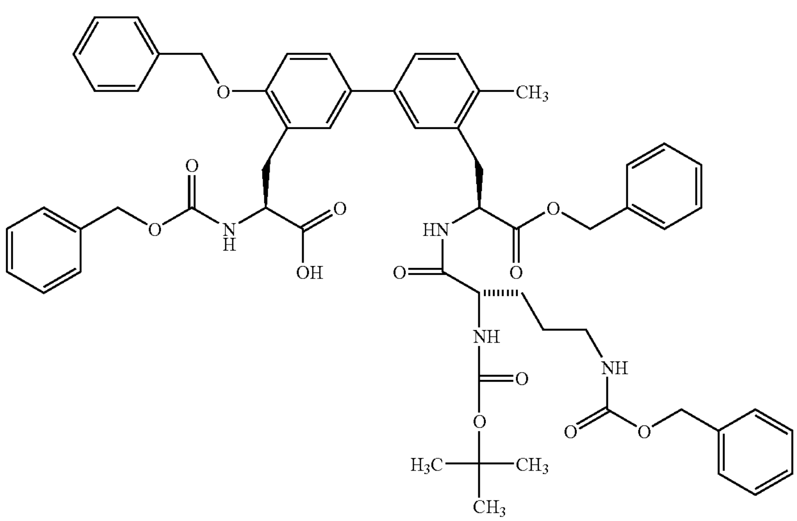 | 20B from Example 19E | LC-MS (method 8): $R_t$ = 3.90 min. MS (ES): m/z = 1021 $(M + H)^+$ |

| Example No. | Structure | Prepared in analogy to Example No. | Analytical data |
|---|---|---|---|
| 20F | 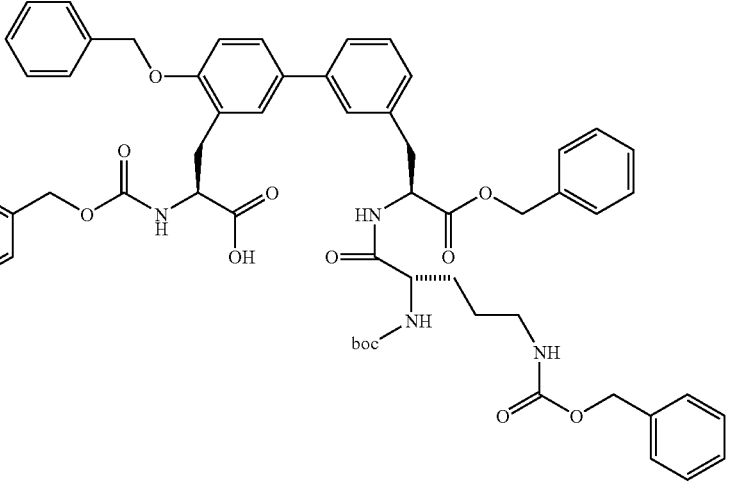 | 20B from Example 19F | LC-MS (method 8): $R_t$ = 4.23 min. MS (ES): m/z = 1007 $(M + H)^+$ |
| 20G | 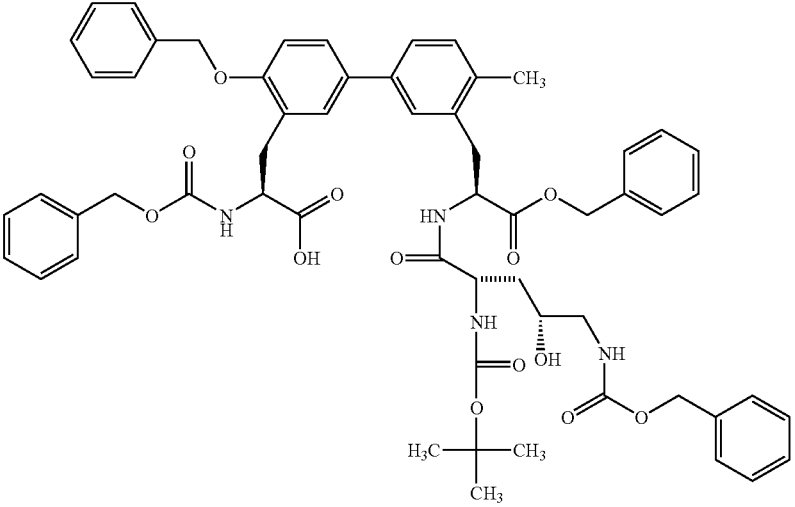 | 20B from Example 19G | LC-MS (method 8): $R_t$ = 3.84 min. MS (ES): m/z = 1037 $(M + H)^+$ |
| 20H | 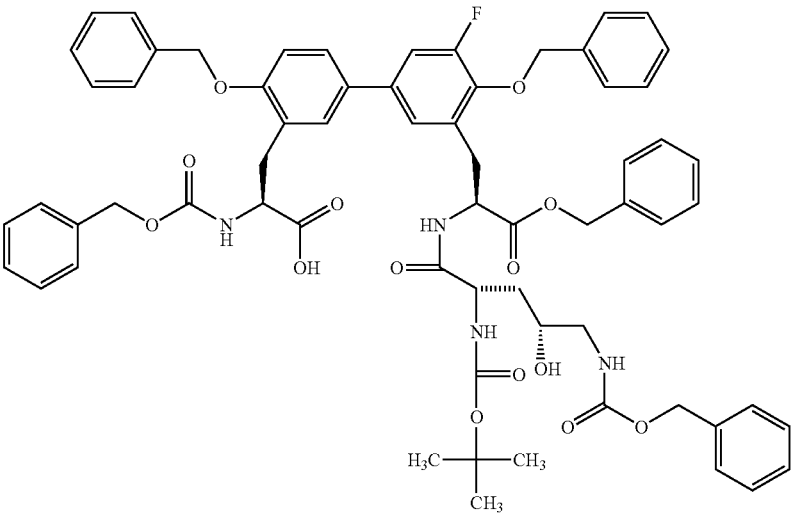 | 20B from Example 19H | |

-continued

| Example No. | Structure | Prepared in analogy to Example No. | Analytical data |
|---|---|---|---|
| 20I | 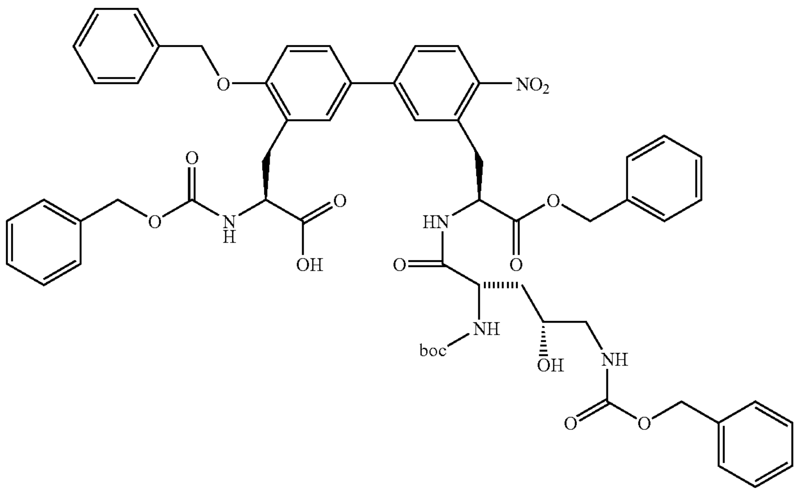 | 20B from Example 19I | LC-MS (method 14): $R_t$ = 4.07 min. MS (ES): m/z = 1068 $(M + H)^+$ |
| 20J | 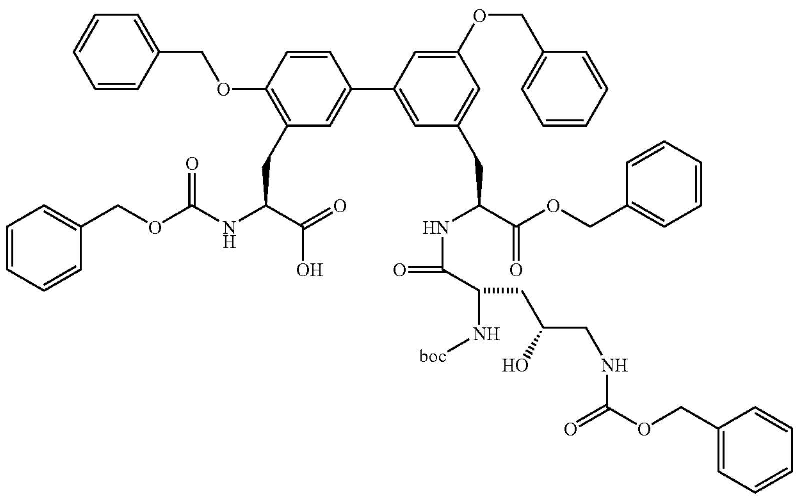 | 20B from Example 19J | LC-MS (method 14): $R_t$ = 4.16 min. MS (ES): m/z = 1129 $(M + H)^+$ |
| 20K | 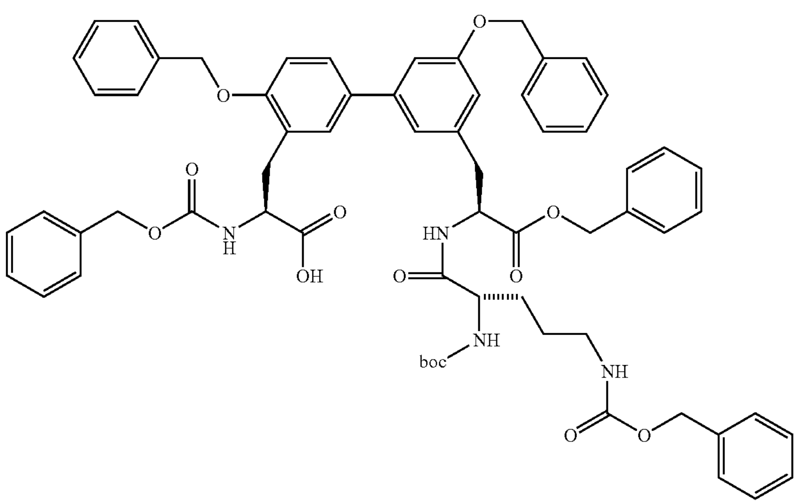 | 20B from Example 19K | LC-MS (method 14): $R_t$ = 4.21 min. MS (ES): m/z = 1113 $(M + H)^+$ |

-continued

| Example No. | Structure | Prepared in analogy to Example No. | Analytical data |
|---|---|---|---|
| 20L | 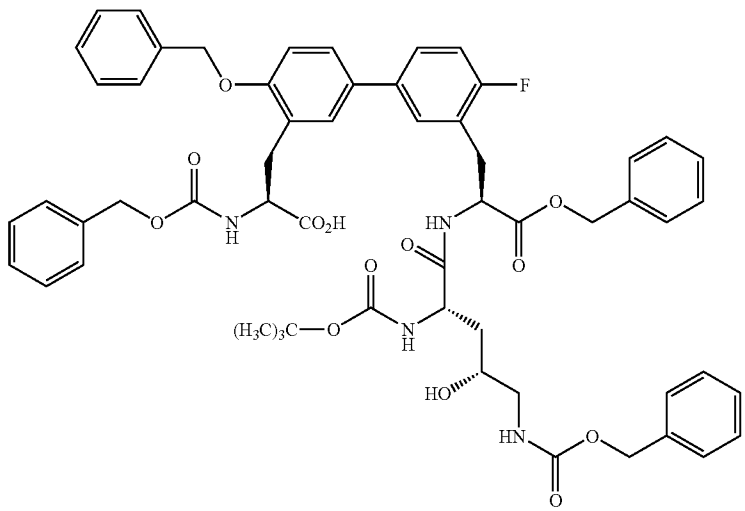 | 20B from Example 19L | LC-MS (method 14): $R_t$ = 4.08 min. MS (EI): m/z = 1041 $(M + H)^+$ |
| 20M | 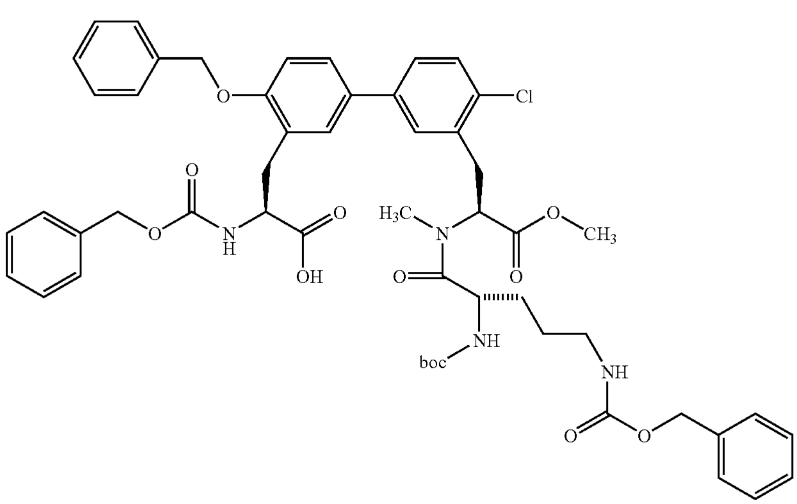 | 20B from Example 19M | LC-MS (method 2): $R_t$ = 3.04 min. MS (ES): m/z = 979 $(M + H)^+$ |

-continued

| Example No. | Structure | Prepared in analogy to Example No. | Analytical data |
|---|---|---|---|
| 20N | 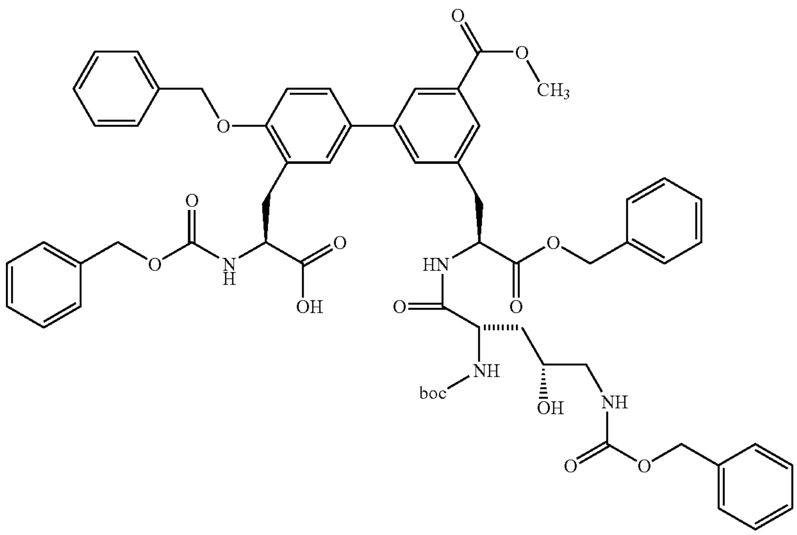 | 20B from Example 19N | LC-MS (method 5): $R_t$ = 2.82 min. MS (ES): m/z = 1081 (M + H)$^+$ |
| 20P | 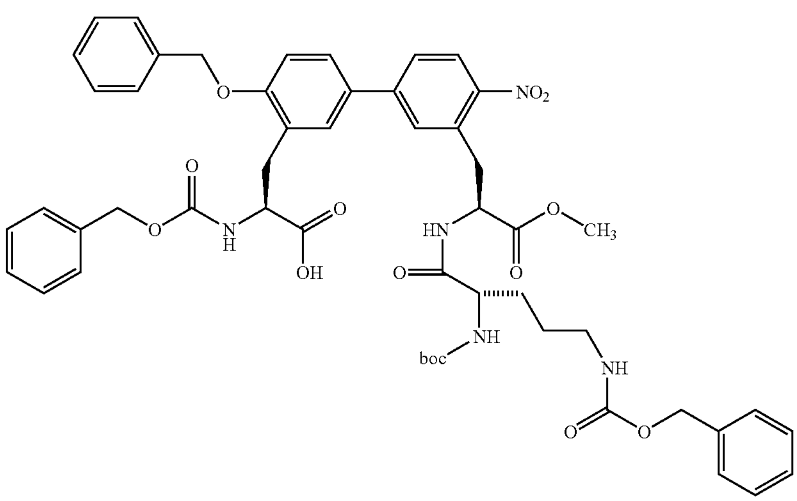 | 20B from Example 19P | LC-MS (method 3): $R_t$ = 3.03 min. MS (ES): m/z = 976 (M + H)$^+$ |

Example 20O (2S)-3-(4-(Benzyloxy)-3'-{(2S)-2-[{(2R)-5-{[(benzyloxy)carbonyl]amino}-2-[(tert-butoxycarbonyl)amino]pentanoyl}(methyl)-amino]-3-methoxy-3-oxopropyl}-4'-fluorobiphenyl-3-yl)-2-{[(benzyloxy)carbonyl]amino}propionic acid

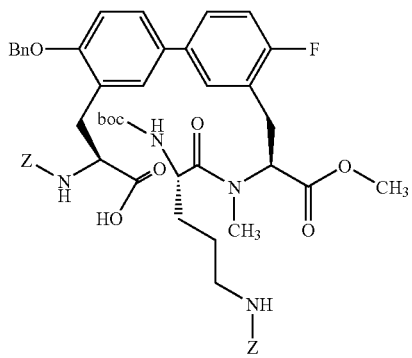

1.9 ml of 1N tetrabutylammonium fluoride in THF are added dropwise to a solution of 980 mg (0.922 mmol) of 2-(trimethylsilyl)ethyl (2S)-3-(4-(benzyloxy)-3'-{(2S)-2-[{(2R)-5-{[(benzyloxy)carbonyl]amino}-2-[(tert-butoxycarbonyl)amino]pentanoyl}(methyl)amino]-3-methoxy-3-oxopropyl}-4'-fluorobiphenyl-3-yl)-2-{[(benzyloxy)carbonyl]amino}propanoate (Example 19O) in 20 ml of absolute DMF. After 60 min at RT, the mixture is cooled to 0° C., and ice-water is added. The mixture is immediately extracted with dichloromethane. The organic phase is dried over magnesium sulfate, concentrated in vacuo and dried under high vacuum. The crude product is reacted without further purification.

Yield: quant LC-MS (method 2): $R_t$=2.91 min. MS (EI): m/z=964 (M+H)$^+$.

Example 21B

Pentafluorophenyl (2S)-3-(4-(benzyloxy)-3'-{(2S)-2-[2-[{(2S,4S)-5-{[(benzyloxy)carbonyl]amino}-2-[(tert-butoxycarbonyl)amino]-4-hydroxypentanoyl}(methyl)amino]-3-methoxy-3-oxopropyl-4'-chlorobiphenyl-3-yl)-2-{[(benzyloxy)carbonyl]amino}propanoate

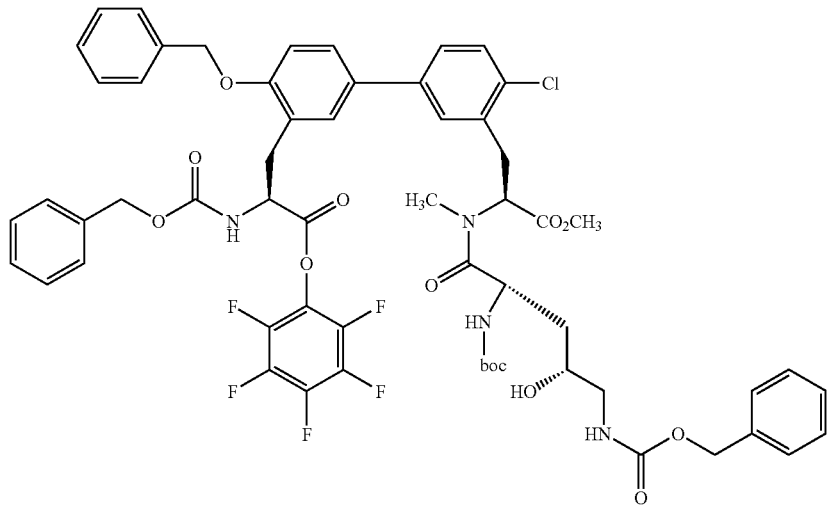

235 mg (0.24 mmol) of the compound from Example 20B are dissolved in 10 ml of abs. Dichloromethane, cooled to −20° C. and, while stirring, 217 mg (1.18 mmol) of pentafluorophenyl, 2.9 mg (0.02 mmol) of DMAP and 49.8 mg (0.26 mmol) of EDC are added. The temperature is allowed to rise slowly to RT, and the mixture is stirred overnight. The mixture is concentrated in vacuo and the crude product is dried to constant weight under high vacuum.

Yield: 219 mg (57% of theory) LC-MS (method 2): $R_t$=3.25 min. MS (EI): m/z=1160 [M+H]$^+$ Examples 21A, 21C to 21N and 21P listed in the table following are prepared from the appropriate precursors in analogy to the methods indicated:

| Example No. | Structure | Prepared in analogy to Example No. | Analytical data |
|---|---|---|---|
| 21A | 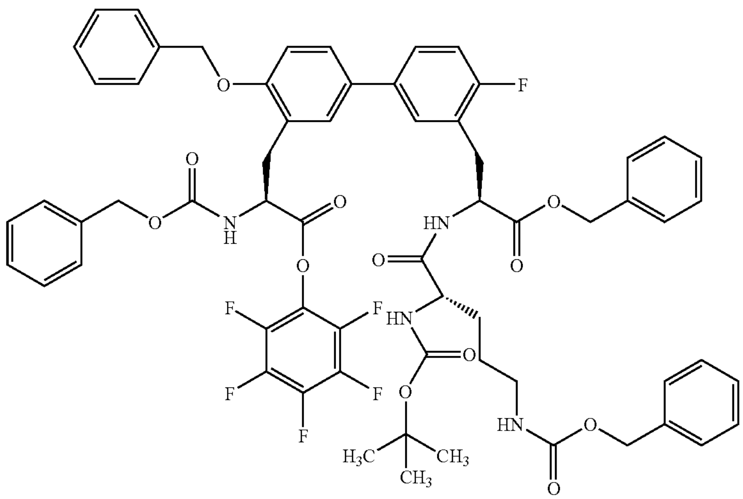 | 21B from Example 20B | LC-MS (method 2): $R_t$ = 3.27 min. MS (EI): m/z = 1190 $(M + H)^+$ |
| 21C | 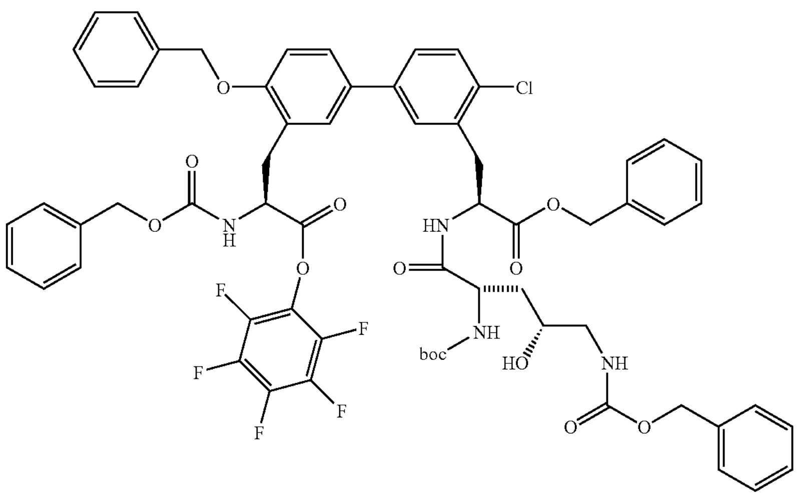 | 21B from Example 20C | LC-MS (method 5): $R_t$ = 3.28 min. MS (ES): m/z = 1223 $(M + H)^+$ |
| 21D | 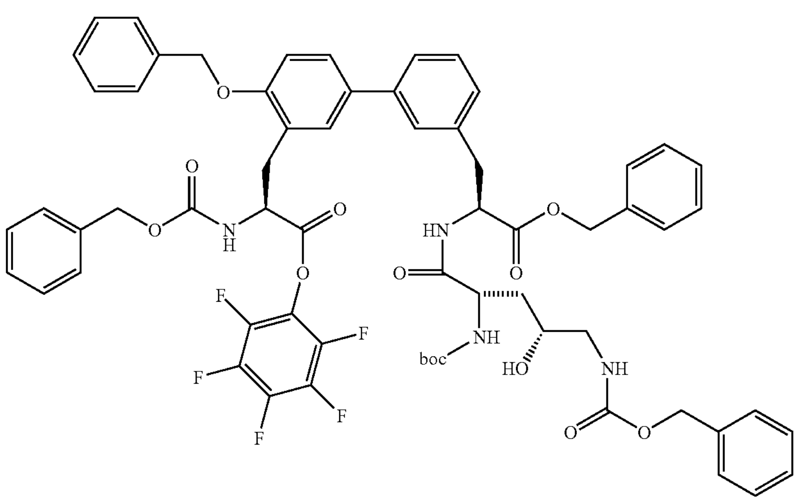 | 21B from Example 20D | LC-MS (method 8): $R_t$ = 4.72 min. MS (ES): m/z = 1189 $(M + H)^+$ |

| Example No. | Structure | Prepared in analogy to Example No. | Analytical data |
|---|---|---|---|
| 21E | 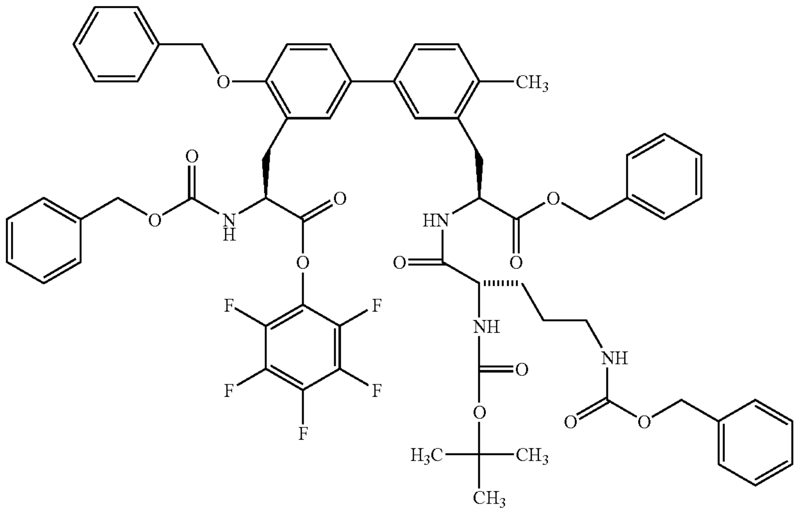 | 21B from Example 20E | LC-MS (method 5): $R_t$ = 3.32 min. MS (ES): m/z = 1187 $(M + H)^+$ |
| 21F | 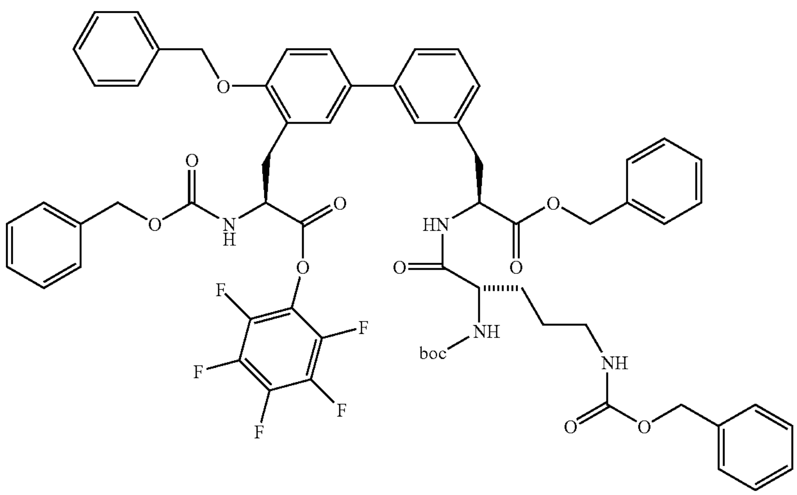 | 21B from Example 20F | LC-MS (method 6): $R_t$ = 3.59 min. MS (ES): m/z = 1173 $(M + H)^+$ |
| 21G | 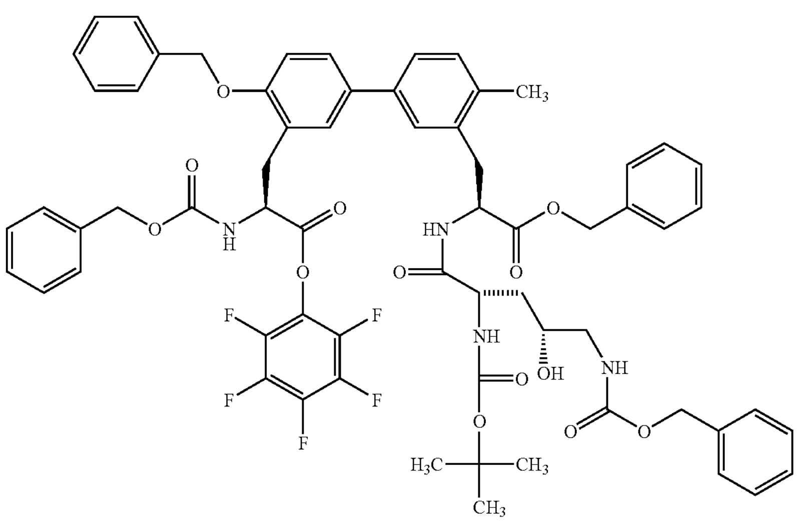 | 21B from Example 20G | |

-continued

| Example No. | Structure | Prepared in analogy to Example No. | Analytical data |
|---|---|---|---|
| 21H | 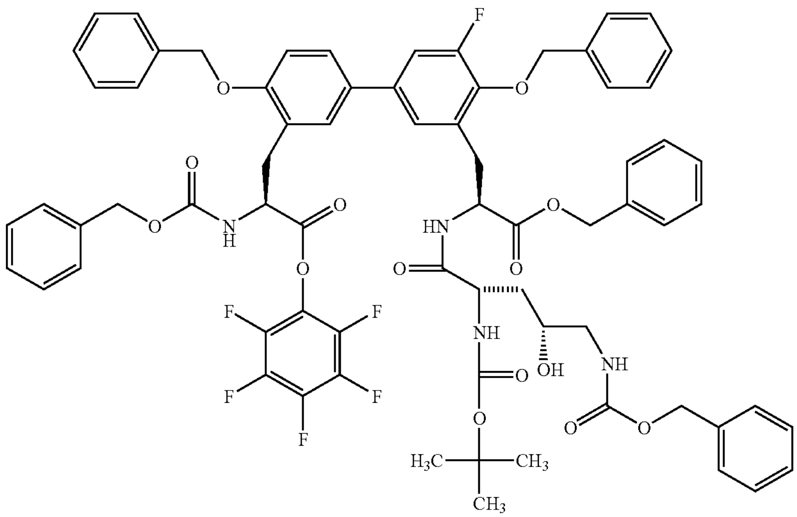 | 21B from Example 20H | |
| 21I | 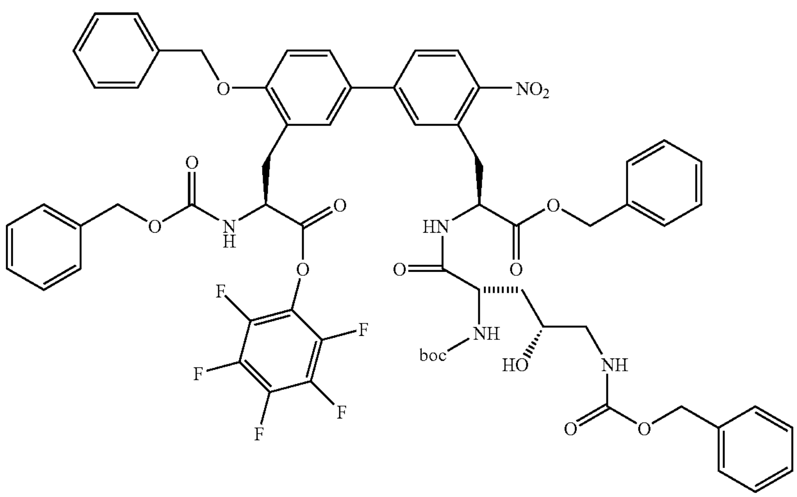 | 21B from Example 20I | LC-MS (method 14): $R_t$ = 4.39 min. MS (ES): m/z = 1234 (M + H)$^+$ |
| 21J | 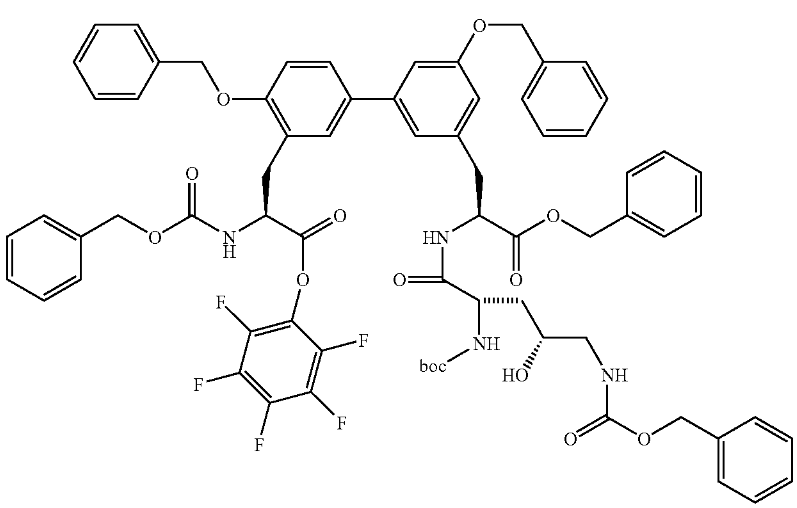 | 21B from Example 20J | |

-continued

| Example No. | Structure | Prepared in analogy to Example No. | Analytical data |
|---|---|---|---|
| 21K | 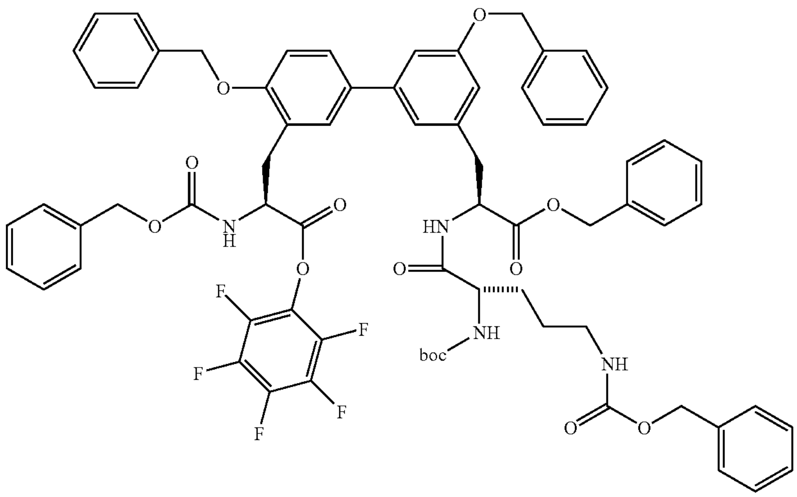 | 21B from Example 20K | |
| 21L | 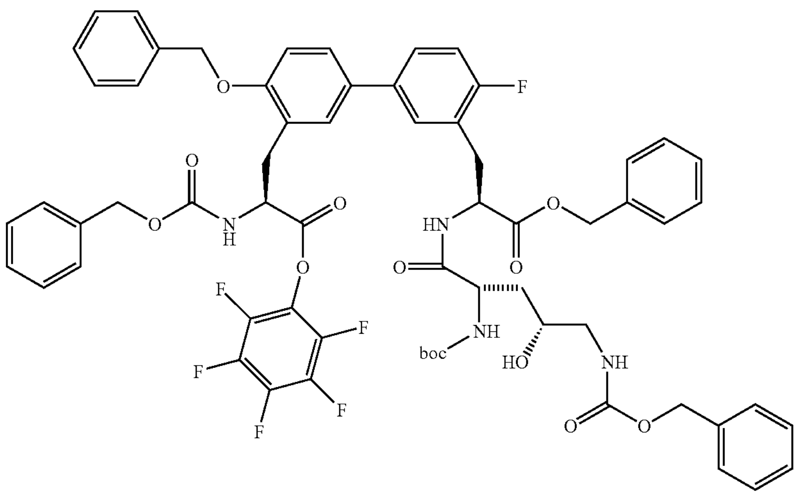 | 21B from Example 20L | LC-MS (method 1): $R_t$ = 3.42 min. MS (EI): m/z = 1207 (M + H)$^+$ |
| 21M | 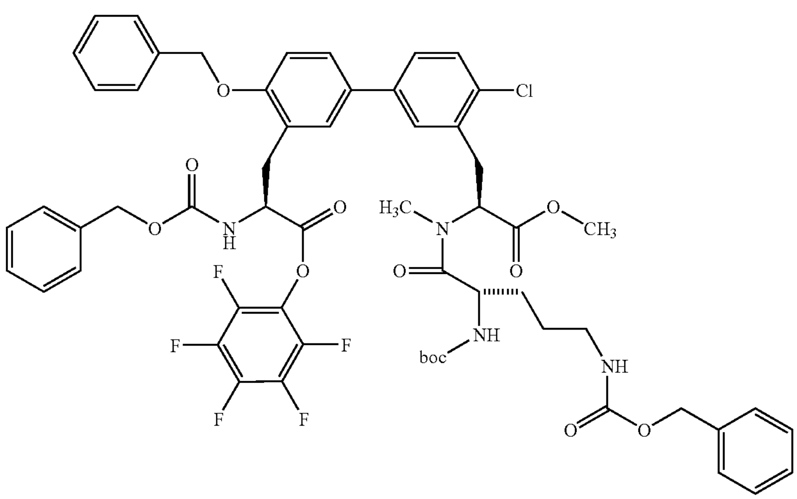 | 21B from Example 20M | LC-MS (method 3): $R_t$ = 3.45 min. MS (ES): m/z = 1145 (M + H)$^+$ |

-continued

| Example No. | Structure | Prepared in analogy to Example No. | Analytical data |
|---|---|---|---|
| 21N | 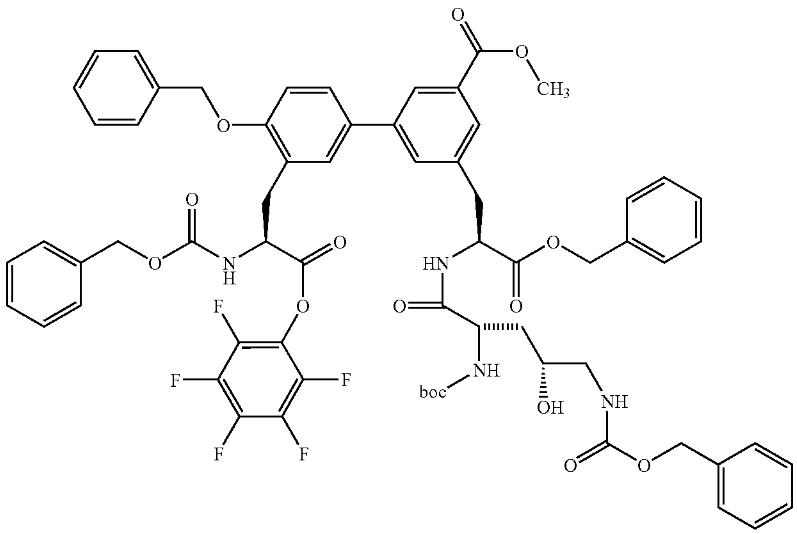 | 21B from Example 20N | LC-MS (method 4): $R_t$ = 4.01 min. MS (ES): m/z = 1247 (M + H)$^+$ |
| 21P | 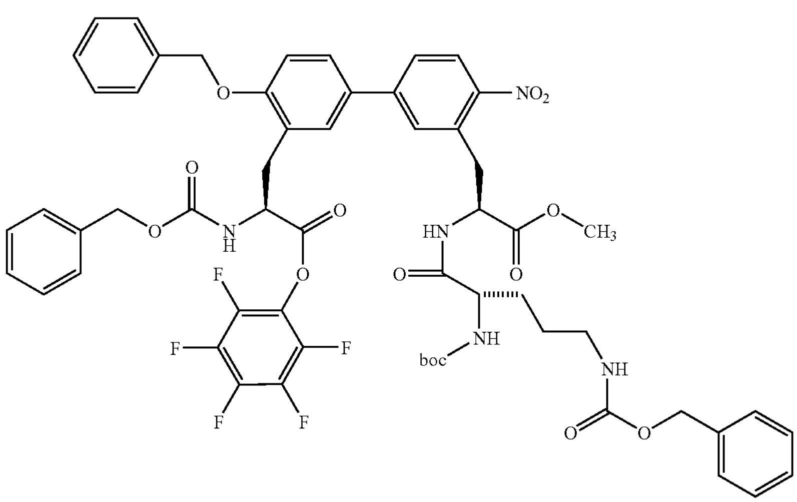 | 21B from Example 20P | LC-MS (method 3): $R_t$ = 3.37 min. MS (ES): m/z = 1142 (M + H)$^+$ |

Example 21O

Pentafluorophenyl (2S)-3-(4-(benzyloxy)-3'-{(2S)-2-[{(2R)-5{[(benzyloxy)carbonyl]amino}-2-[(tert-butoxycarbonyl)amino]-pentanoyl}(methyl)amino]-3-methoxy-3-oxopropyl}-4'-fluorobi-phenyl-3-yl)-2-{[(benzyloxy)carbonyl]amino}propanoate

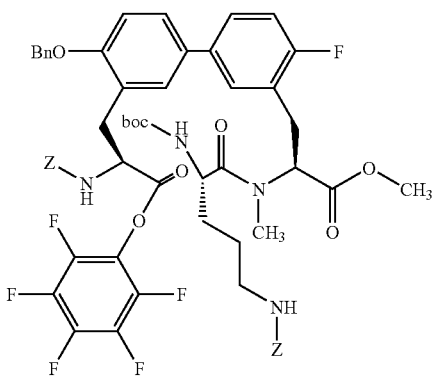

0.89 g (crude product, about 0.922 mmol) of (2S)-3-(4-(benzyloxy)-3'-{(2S)-2-[{(2R)-5-{[(benzyloxy)carbonyl]amino}-2-[(tert-butoxycarbonyl)amino]pentanoyl}(methyl)amino]-3-methoxy-3-oxopropyl}-4'-fluorobiphenyl-3-yl)-2-{[(benzyloxy)carbonyl]amino}-propionic acid (Example 20O) are introduced into 50 ml of dichloromethane. At −25° C., 0.85 g (4.61 mmol) of pentafluorophenol, 0.21 g (1.11 mmol) of EDC and 45 mg (0.37 mmol) of DMAP are added under argon. The mixture slowly warms to RT overnight. The reaction mixture is concentrated in vacuo and briefly dried under high vacuum. The crude product is reacted without further purification.

Yield: quant. LC-MS (method 3): $R_t$=3.41 min. MS (EI): m/z=1130 (M+H)$^+$.

Example 22B

Methyl (2S)-2-[{(2S,4S)-2-amino-5-{[(benzyloxy)carbonyl]amino}-4-hydroxypentanoyl}(methyl)amino]-3-{4'-(benzyloxy)-3'-[(2S)-2-{[(benzyloxy)carbonyl]amino}-3-oxo-3-(pentafluorophenoxy)propyl]-4-chlorobiphenyl-3-yl}propanoate hydrochloride

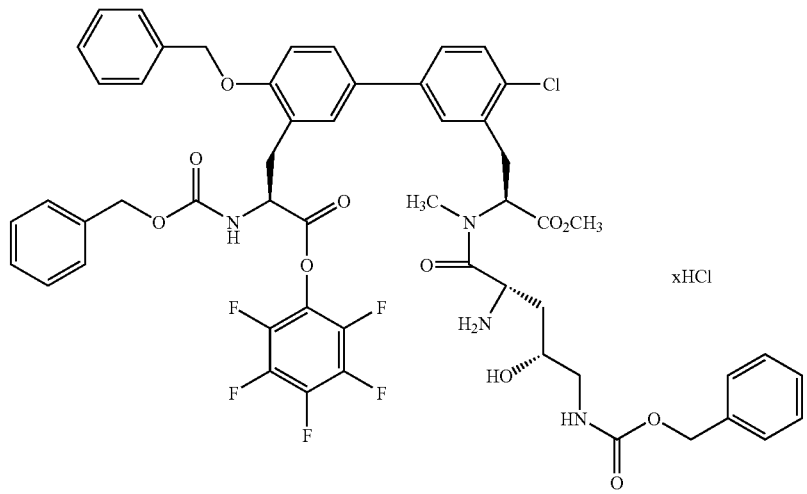

219 mg (0.14 mmol) of the compound from Example 21B are dissolved in 2.3 ml of dioxane and, while stirring at 0° C., 6 ml of a 4N hydrogen chloride/dioxane solution are added. The mixture is stirred at this temperature for 30 min, the temperature is allowed to rise to RT and the mixture stirred for a further hour, and then the mixture is evaporated to dryness in vacuo. The product is obtained after drying to constant weight under high vacuum.

Yield: 207 mg (quantitative) LC-MS (method 2): $R_t$=3.25 min. MS (EI): m/z=1060 (M-HCl+H)$^+$ Examples 22A, 22C to 22N and 22P listed in the following table are prepared from the appropriate precursors in analogy to the indicated methods:

| Example No. | Structure | Prepared in analogy to Example No. | Analytical data |
|---|---|---|---|
| 22A | 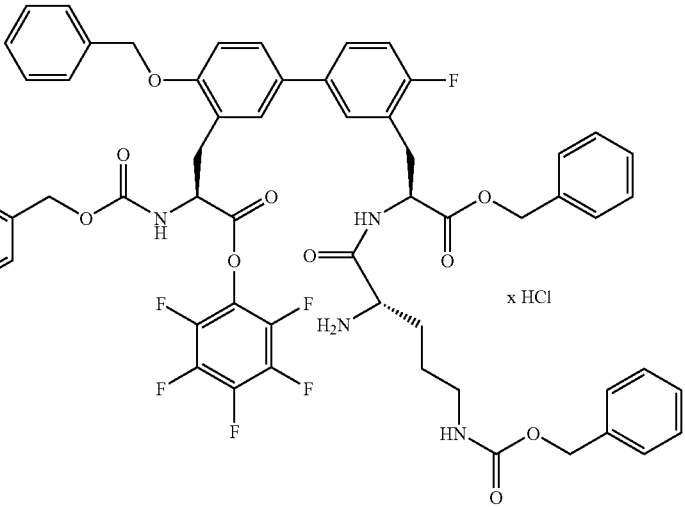 | 22B from Example 21A | LC-MS (method 6): $R_t$ = 0.35 min. MS (EI): m/z = 1090 (M − HCl + H)⁺ |
| 22C | 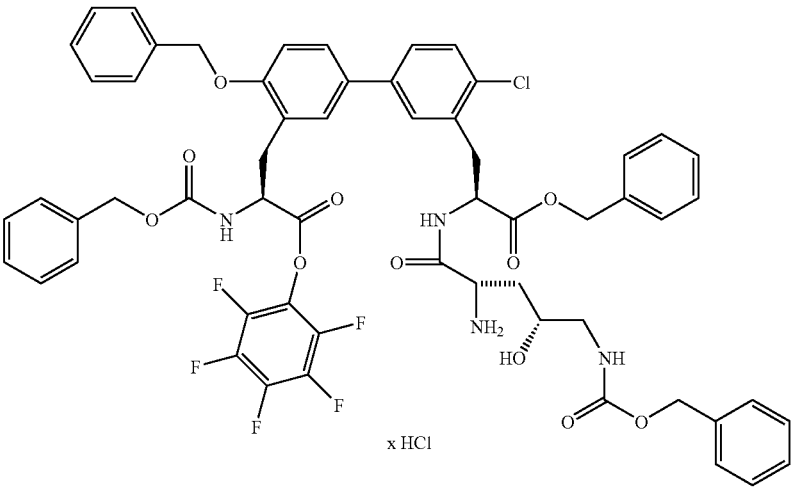 | 22B from Example 21C | LC-MS (method 5): $R_t$ = 2.54 min. MS (ES): m/z = 1123 (M − HCl + H)⁺ |
| 22D | 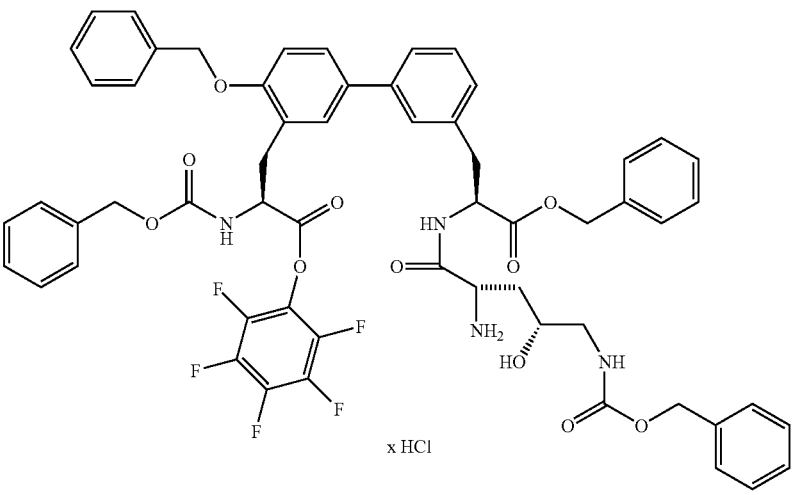 | 22B from Example 21D | LC-MS (method 14): $R_t$ = 3.45 min. MS (ES): m/z = 1189 (M − HCl + H)⁺ |

-continued

| Example No. | Structure | Prepared in analogy to Example No. | Analytical data |
|---|---|---|---|
| 22E | 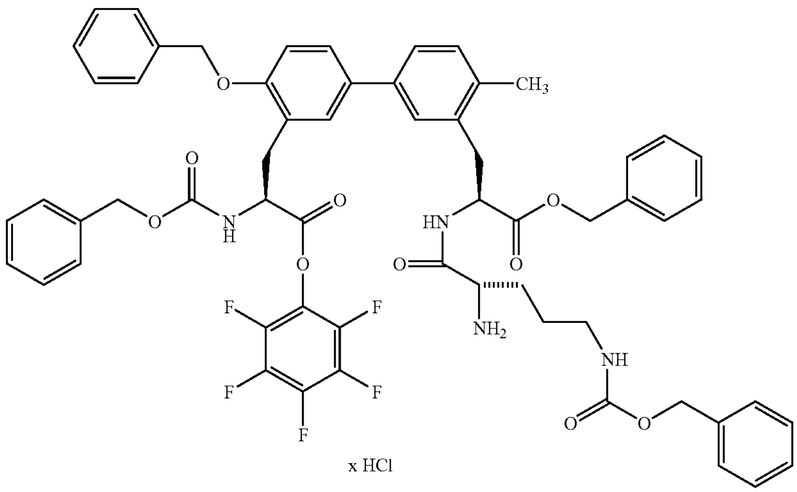 | 22B from Example 21E | LC-MS (method 5): $R_t$ = 3.32 min. MS (ES): m/z = 1087 $(M - HCl + H)^+$ |
| 22F | 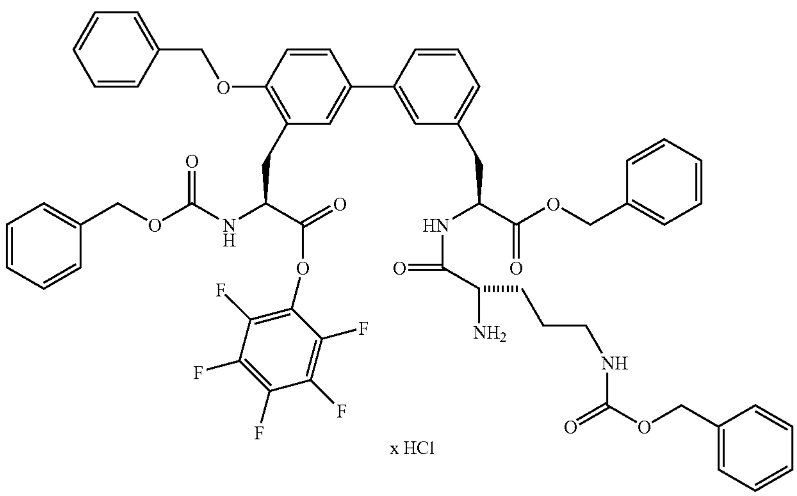 | 22B from Example 21F | LC-MS (method 5): $R_t$ = 2.51 min. MS (ES): m/z = 1073 $(M - HCl + H)^+$ |
| 22G | 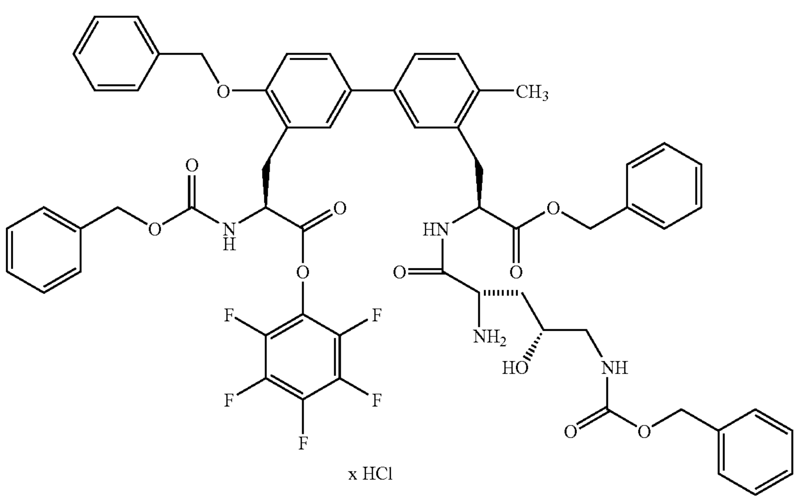 | 22B from Example 21G | LC-MS (method 5): $R_t$ = 2.60 min. MS (ES): m/z = 1104 $(M - HCl + H)^+$ |

| Example No. | Structure | Prepared in analogy to Example No. | Analytical data |
|---|---|---|---|
| 22H | 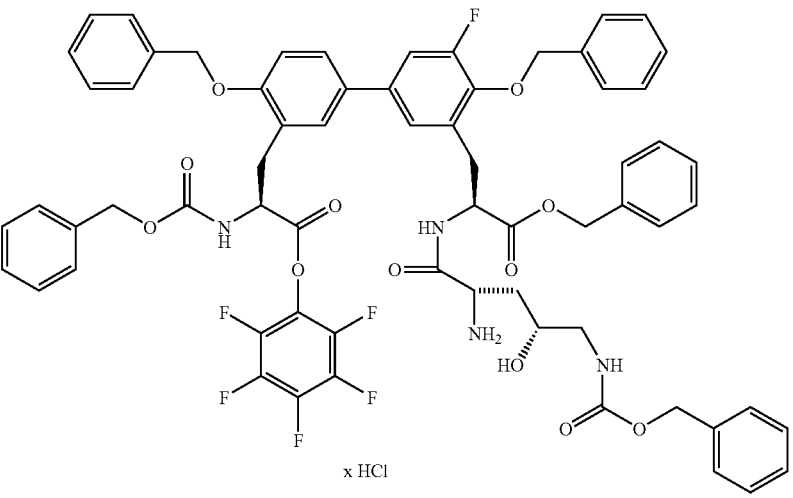 x HCl | 22B from Example 21H | |
| 22I | 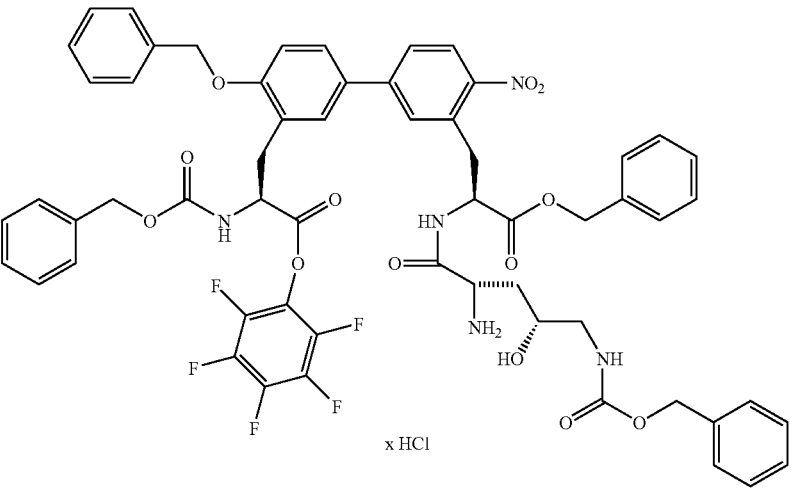 x HCl | 22B from Example 21I | LC-MS (method 14): $R_t$ = 3.46 min. MS (ES): m/z = 1134 (M − HCl + H)$^+$ |
| 22J | 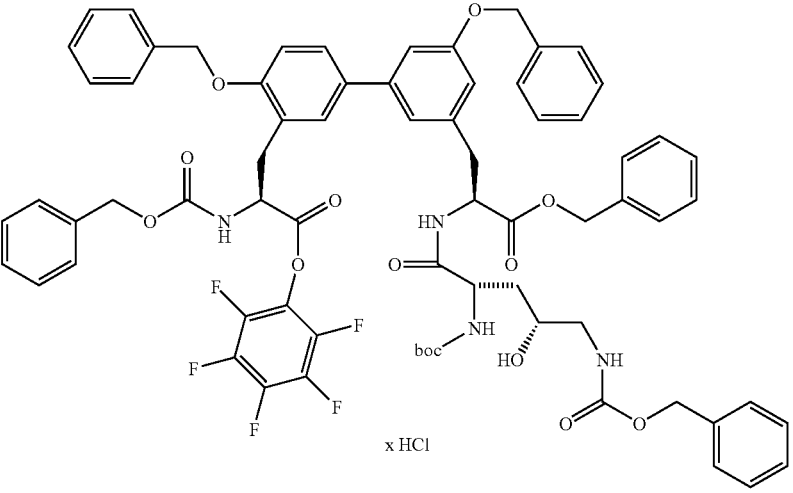 x HCl | 22B from Example 21J | |

-continued
| Example No. | Structure | Prepared in analogy to Example No. | Analytical data |
|---|---|---|---|
| 22K | 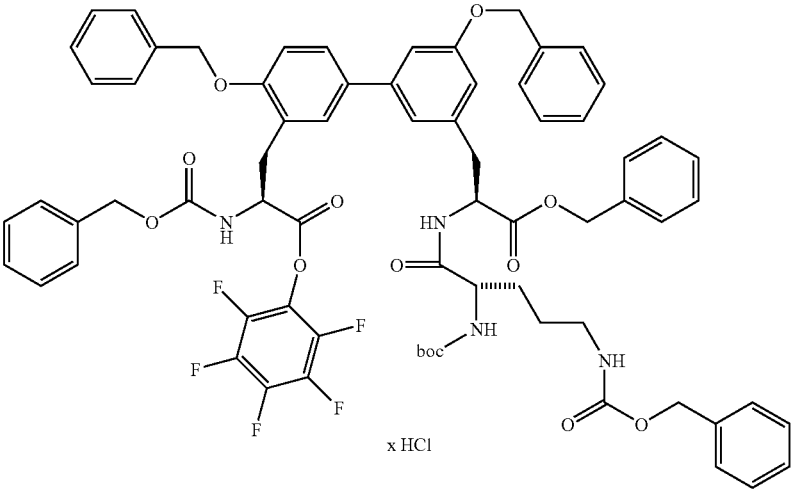 | 22B from Example 21K | |
| 22L | 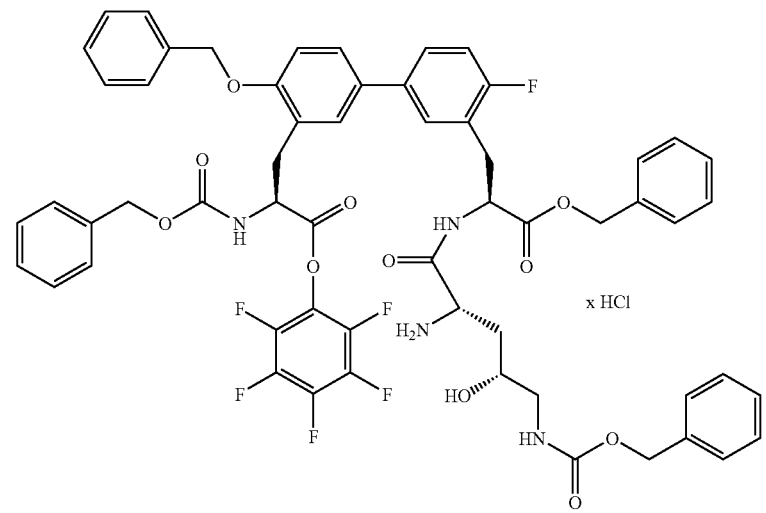 | 22B from Example 21L | LC-MS (method 2): $R_t$ = 2.40 min. MS (EI): m/z = 1107 (M − HCl + H)$^+$ |
| 22M | 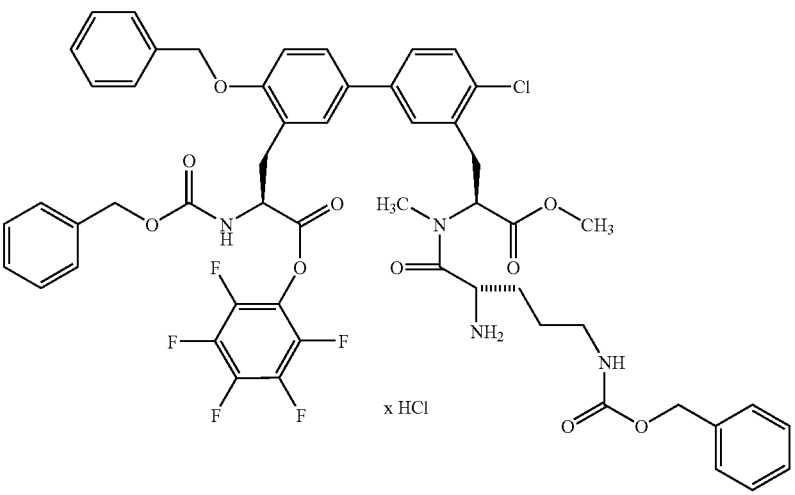 | 22B from Example 21M | LC-MS (method 3): $R_t$ = 2.99 min. MS (ES): m/z = 1045 (M − HCl + H)$^+$ |

-continued
| Example No. | Structure | Prepared in analogy to Example No. | Analytical data |
|---|---|---|---|
| 22N | 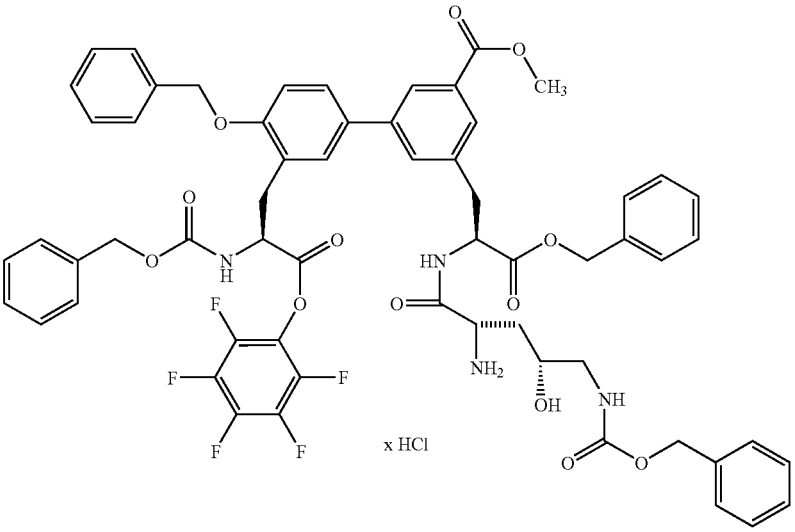 | 22B from Example 21N | LC-MS (method 5): $R_t$ = 2.53 min. MS (ES): m/z = 1147 (M − HCl + H)$^+$ |
| 22P | 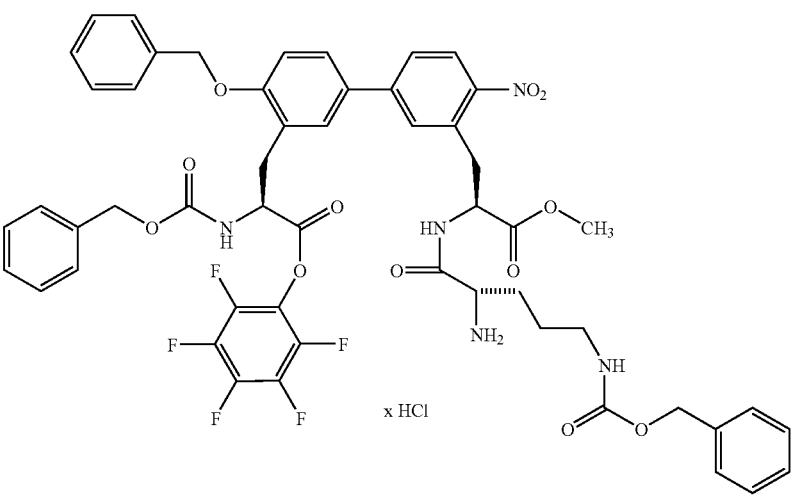 | 22B from Example 21P | LC-MS (method 3): $R_t$ = 2.77 min. MS (ES): m/z = 1042 (M − HCl + H)$^+$ |

Example 22O

Methyl (2S)-2-[((2R)-2-amino-5-{[(benzyloxy)carbonyl]amino}pen-tanoyl)(methyl)amino]-3-{4'-(benzyloxy)-3'-[(2S)-2-{[(benzyloxy)carbonyl]amino}-3-oxo-3-(pentafluorophenoxy)propyl]-4-fluorobiphenyl-3-yl}propanoate hydrochloride

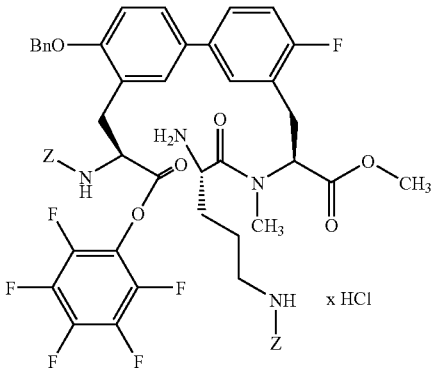

37 ml of a 4M hydrogen chloride-dioxane solution are added to a solution of 1.038 g (crude product, about 0.92 mmol) of pentafluorophenyl (2S)-3-(4-(benzyloxy)-3'-{(2S)-2-[{(2R)-5-{[(benzyloxy)carbonyl]amino}-2-[(tert-butoxycarbonyl)amino]-pentanoyl}(methyl)amino]-3-methoxy-3-oxopropyl}-4'-fluorobiphenyl-3-yl)-2-{[(benzyloxy)carbonyl]amino}propanoate (Example 21O) in 19 ml of anhydrous dioxane at 0° C. After 1 h at 0° C., the reaction solution is concentrated in vacuo, coevaporated several times with dichloromethane and dried under high vacuum. The crude product is reacted without further purification.

Yield: quant. LC-MS (method 2): $R_t$=2.54 min. MS (EI): m/z=1029 (M+H)$^+$.

Example 23B

Methyl (8S,11S,14S)-17-(benzyloxy)-14-{[(benzyloxy)carbonyl]amino}-11-((2R)-3-{[(benzyloxy)carbonyl]amino}-2-hydroxypro-pyl)-5-chloro-10,13-dioxo-9,12-diazatricyclo[14.3.1.1$^{2,6}$]henicosa-1(20,2(21),3,5,16,18-hexaene-8-carboxylate

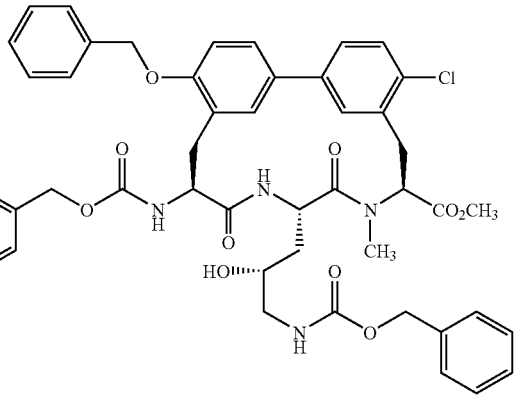

207 mg (0.18 mmol) of the compound from Example 22B are dissolved in 250 ml of abs. chloroform and, while stirring vigorously, 1.8 ml (1.3 g, 12.9 mmol) of triethylamine in 30 ml of chloroform are added dropwise in 20 min. Stirring is continued overnight and the mixture is concentrated in vacuo (bath temperature≦40° C.). The residue is separated by preparative HPLC (acetonitrile/water).

Yield: 77 mg (46% of theory) LC-MS (method 2): $R_t$=2.96 min. MS (EI): m/z=876 (M+H)$^+$ Examples 23A, 23C to 23N and 23P listed in the following table are prepared from the appropriate precursors in analogy to the indicated methods:

| Example No. | Structure | Prepared in analogy to Example No. | Analytical data |
|---|---|---|---|
| 23A | 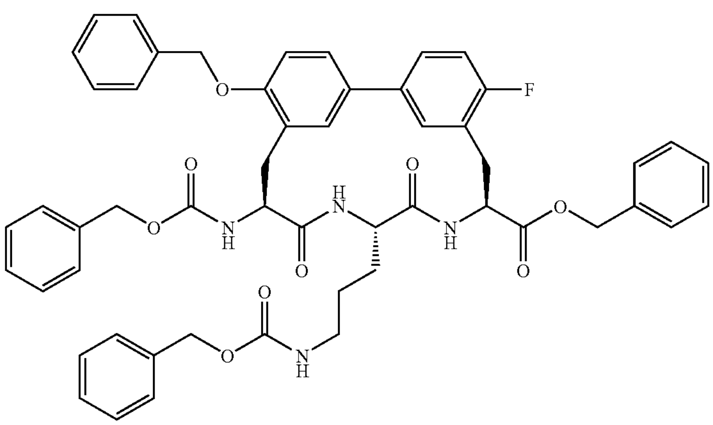 | 23B from Example 22A | LC-MS (method 8): $R_t$ = 4.35 min. MS (EI): m/z = 906 (M + H)$^+$ |

-continued
| Example No. | Structure | Prepared in analogy to Example No. | Analytical data |
|---|---|---|---|
| 23C | 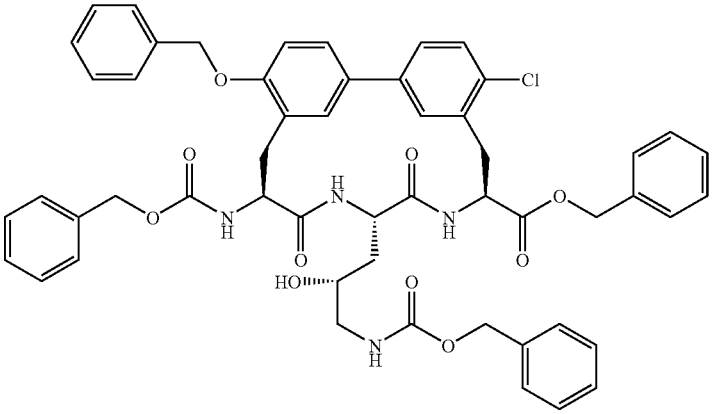 | 23B from Example 22C | LC-MS (method 8): $R_t$ = 4.03 min. MS (EI): m/z = 939 (M + H)$^+$ |
| 23D | 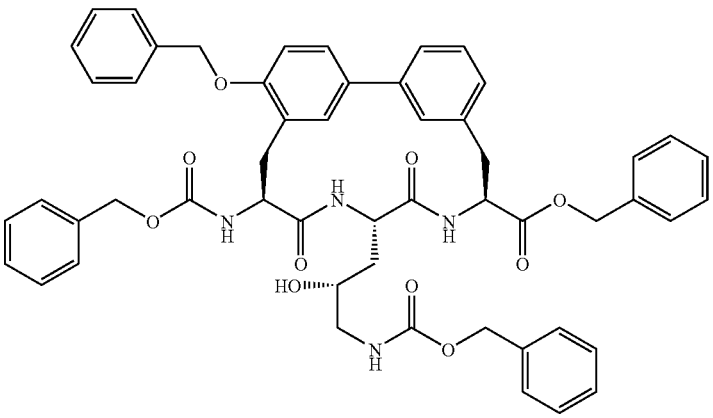 | 23B from Example 22D | LC-MS (method 8): $R_t$ = 3.85 min. MS (EI): m/z = 905 (M + H)$^+$ |
| 23E | 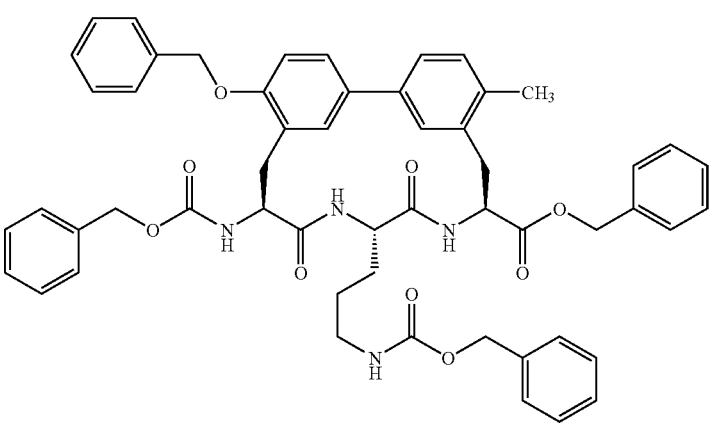 | 23B from Example 22E | LC-MS (method 1): $R_t$ = 3.23 min. MS (EI): m/z = 903 (M + H)$^+$ |

-continued
| Example No. | Structure | Prepared in analogy to Example No. | Analytical data |
|---|---|---|---|
| 23F | 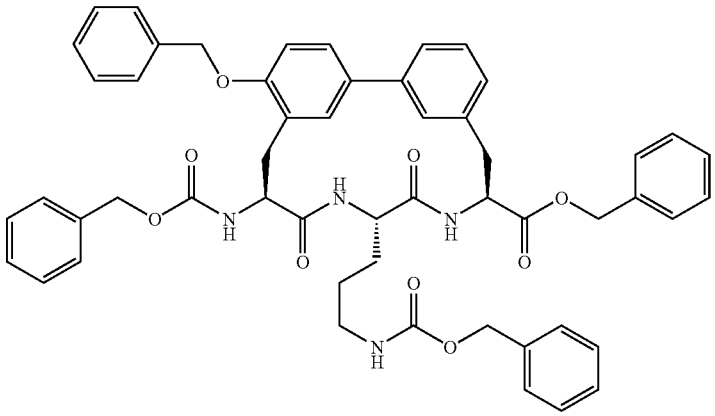 | 23B from Example 22F | LC-MS (method 6): $R_t$ = 1.51 min.<br>MS (EI): m/z = 889 (M + H)+ |
| 23G | 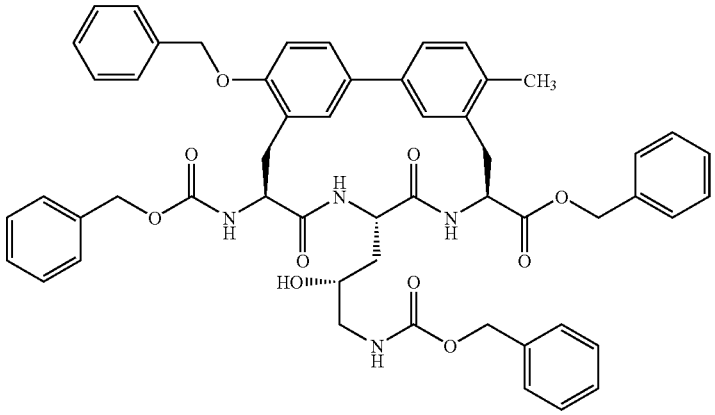 | 23B from Example 22G | LC-MS (method 5): $R_t$ = 2.96 min.<br>MS (EI): m/z = 919 (M + H)+ |
| 23H | 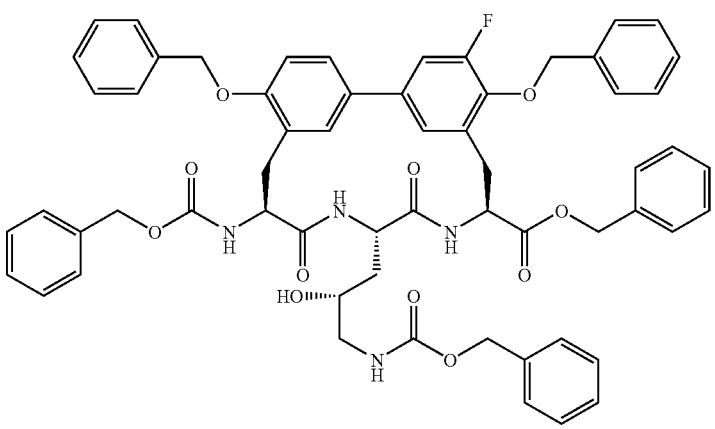 | 23B from Example 22H | LC-MS (method 6): $R_t$ = 2.80 min.<br>MS (EI): m/z = 1029 (M + H)+ |

-continued

| Example No. | Structure | Prepared in analogy to Example No. | Analytical data |
|---|---|---|---|
| 23I | 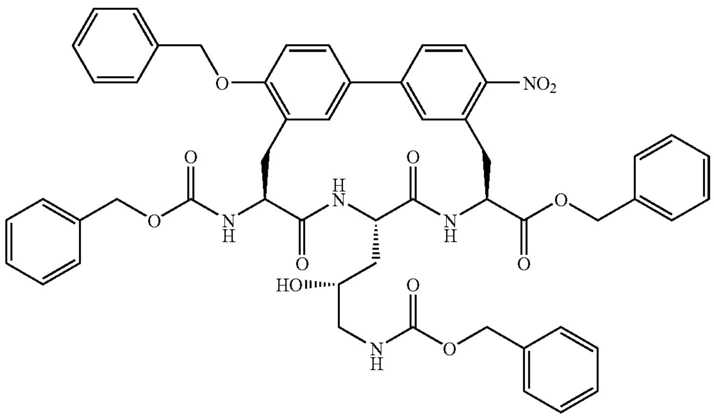 | 23B from Example 22I | LC-MS (method 7): $R_t$ = 0.99 min. MS (EI): m/z = 950 (M + H)$^+$ |
| 23J | 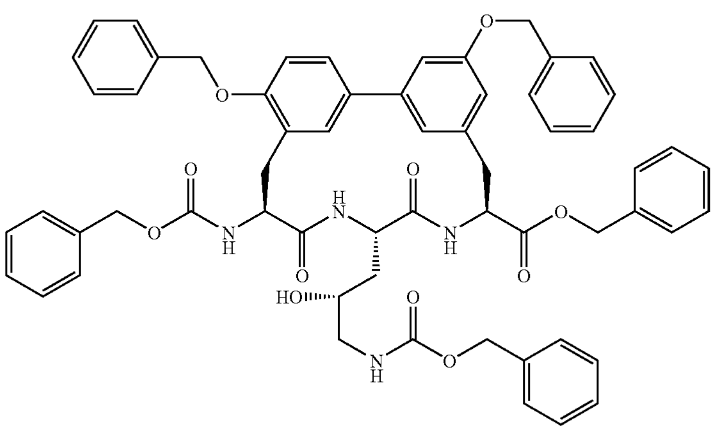 | 23B from Example 22J | LC-MS (method 14): $R_t$ = 4.18 min. MS (EI): m/z = 1011 (M + H)$^+$ |
| 23K | 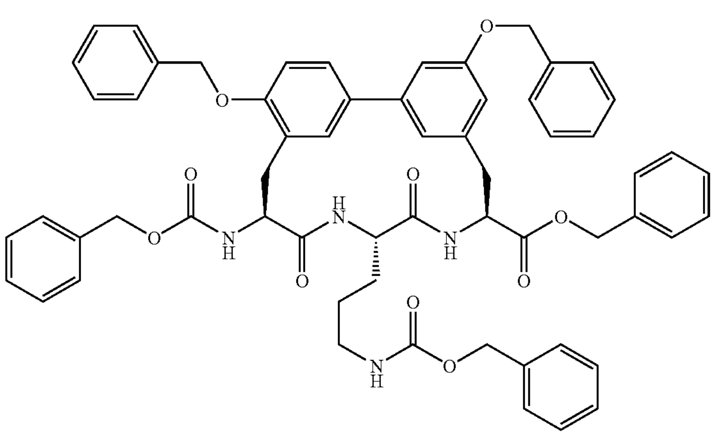 | 23B from Example 22K | LC-MS (method 14): $R_t$ = 4.22 min. MS (EI): m/z = 995 (M + H)$^+$ |

-continued
| Example No. | Structure | Prepared in analogy to Example No. | Analytical data |
|---|---|---|---|
| 23L | 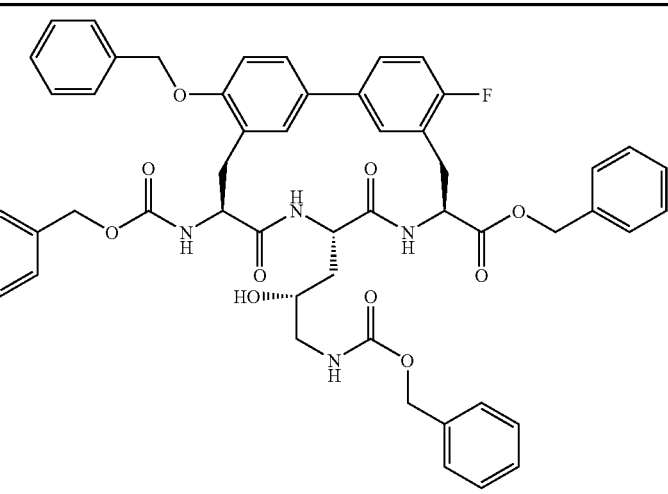 | 23B from Example 22L | LC-MS (method 2): $R_t$ = 3.05 min.<br>MS (EI): m/z = 923 (M + H)$^+$ |
| 23M | 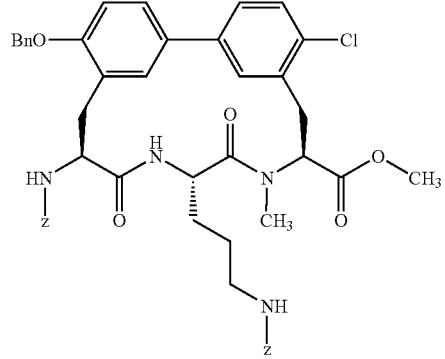 | 23B from Example 22M | LC-MS (method 3): $R_t$ = 3.26 min.<br>MS (ES): m/z = 861 (M + H)$^+$ |
| 23N | 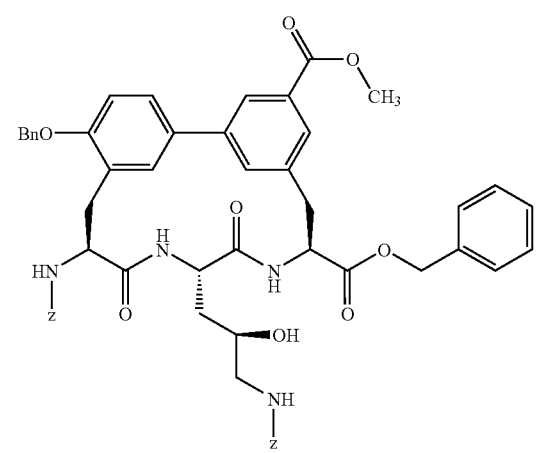 | 23B from Example 22N | LC-MS (method 5): $R_t$ = 2.86 min.<br>MS (ES): m/z = 963 (M + H)$^+$ |

-continued

| Example No. | Structure | Prepared in analogy to Example No. | Analytical data |
|---|---|---|---|
| 23P | 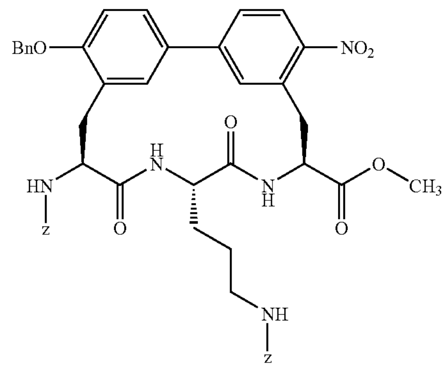 | 23B from Example 22P | LC-MS (method 2): $R_t$ = 2.84 min. MS (ES): m/z = 858 (M + H)$^+$ |

Example 23O

Methyl (8S,11S,14S)-17-(benzyloxy)-14-{[(benzyloxy)carbonyl-amino}-11-(3-{[(benzyloxy)carbonyl]amino}propyl)-5-fluoro-9-methyl-10,13-dioxo-9,12-diazatricyclo[14.3.1.1$^{2,6}$]henicosa-1(20),2(21),3,5,16,18-hexaene-8-carboxylate

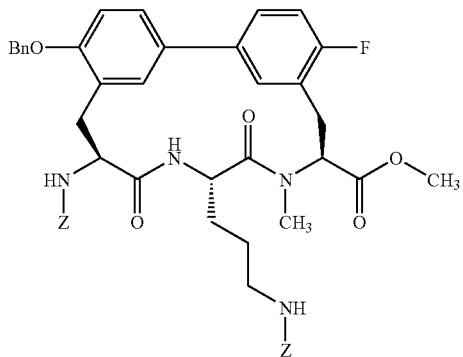

777 mg (crude product, about 0.92 mmol) of methyl (2S)-2-[((2R)-2-amino-5-{[(benzyloxy)carbonyl]amino}pentanoyl)(meth-yl)amino]-3-{4'-(benzyloxy)-3'-[(2S)-2-{[(benzyloxy)carbonyl]-amino}-3-oxo-3-pentafluorophenoxy)propyl]-4-fluorobiphenyl-3-yl}propanoate hydrochloride (Example 22O) are dissolved in 1.4 l of dichloromethane, and 14 ml of triethylamine are added dropwise. The mixture is stirred at RT overnight. For workup, the mixture is concentrated in vacuo on a rotary evaporator under mild conditions and taken up in dichloromethane. Water is added, and the pH is adjusted to 10 by adding a 0.1N sodium hydroxide solution. The organic phase is washed with water, dried over sodium sulfate and concentrated. The crude product is purified by preparative HPLC.

Yield: 450 mg (57% of theory, over four stages starting from Example 190). LC-MS (method 3): $R_t$=3.15 min. MS (EI): m/z=845 (M+H)$^+$.

Example 24B

Methyl (8S,11S,14S)-14-amino-11-[(2R)-3-amino-2-hydroxypropyl]-5-chloro-17-hydroxy-10,13-dioxo-9,12-diazatricyclo[14.3.1.1$^{2,6}$]henicosa-1(20),2(21),3,5,16,18-hexaene-8-carboxylate dihydrobromide

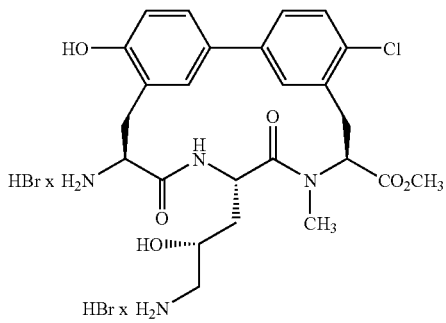

73 mg (0.08 mmol) of the compound from Example 23B are stirred with 2 ml of glacial acetic acid/hydrogen bromide (33%) at RT for 15 min. The mixture is then cautiously evaporated (bath temperature max. 40° C.) to dryness, the residue is taken up in 3 ml of toluene and evaporated to dryness, and this procedure is repeated once more. The residue is dried to constant weight under high vacuum.

Yield: 69 mg of a mixture of 58% product and 19% of the O-acetyl product LC-MS (method 1): $R_t$=1.36 min. (product) and 1.44 min. (O-acetyl product) MS (EI): m/z=518 (M-2HBr+H)$^+$ and 560 (MOAc-2HBr+H)$^+$

Example 24M

Methyl (8S,11S,14S)-14-amino-11-(3-aminopropyl)-5-chloro-17-hydroxy-10,13-dioxo-9,12-diazatricyclo[14.3.1.1$^{2,6}$]henicosa-1(20),2(21),3,5,16,18-hexaene-8-carboxylate dihydrobromide

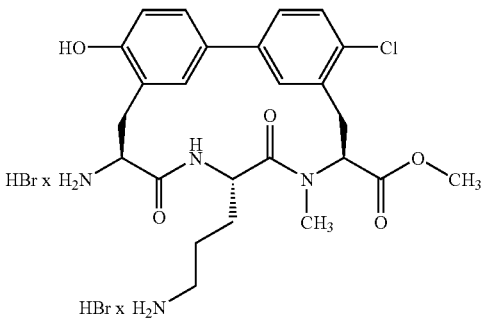

200 mg (0.23 mmol) of the compound from Example 23M are stirred with 2 ml of glacial acetic acid/hydrogen bromide (33%) at RT for 45 min. The mixture is then cautiously evaporated (bath temperature max. 40° C.) to dryness, and the residue is dried to constant weight under high vacuum.

Yield: quant. LC-MS (method 17): $R_t$=2.76 min MS (EI): m/z=503 (M−2HBr+H)$^+$

Example 25C

Benzyl (8S,11S,14S)-17-(benzyloxy)-14-{[(benzyloxy)carbonyl]-amino}-11-((2R)-3-{[(benzyloxy)carbonyl]amino}-2-{[tert-butyl-(dimethyl)silyl]oxy}propyl)-5-chloro-10,13-dioxo-9,12-diazatricyclo[14.3.1.1$^{2,6}$]henicosa-1(20),2(21),3,5,16,18-hexaene-8-carboxylate

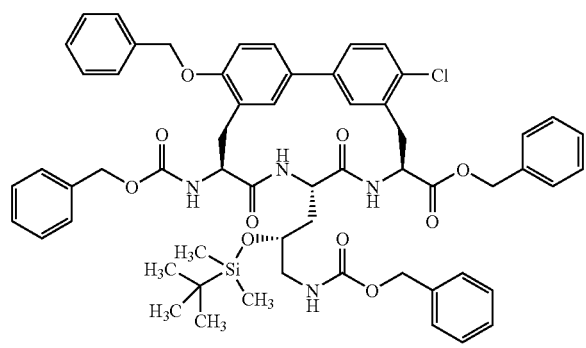

200 mg (0.21 mmol) of the compound from Example 23C are dissolved in 27 ml of absolute DMF and, at 0° C., 230 mg (0.85 mmol) of tert-butyldimethylsilyl trifluoromethanesulfonate, 0.12 ml (0.85 mmol) of triethylamine and 30 mg (0.21 mmol) of DMAP are added. The mixture is stirred at RT for 1 day. The mixture is cautiously concentrated to a volume of 1 ml in vacuo. After the addition of 20 ml of methylene chloride, the organic phase is cautiously washed with 10 ml of a saturated sodium bicarbonate solution and 10 ml of water. The organic phase is evaporated to dryness, and the residue is dried under high vacuum.

Yield: 220 mg (99% of theory) LC-MS (method 1): $R_t$=3.55 min. MS (EI): m/z=1053 (M+H)$^+$

Example 26C1

(8S,11S,14S)-17-(Benzyloxy)-14-{[(benzyloxy)carbonyl]amino}-11-((2R)-3-{[(benzyloxy)carbonyl]amino}-2-{[tert-butyl(dimethyl)-silyl]oxy}propyl)-5-chloro-10,13-dioxo-9,12-diazatricyclo-[14.3.1.1$^{2,6}$]henicosa-1(20),2(21),3,5,16,18-hexaene-8-carboxylic acid

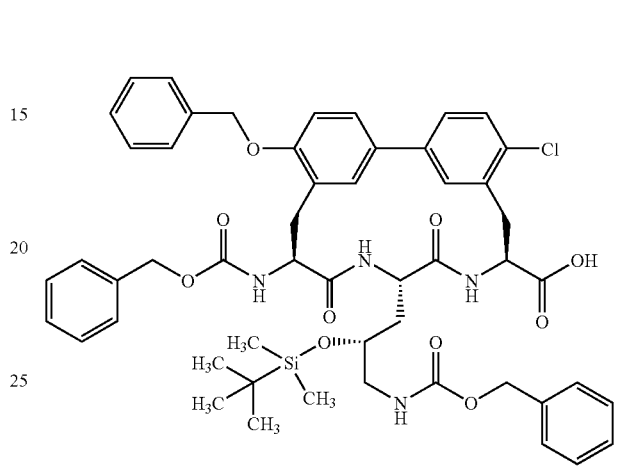

220 mg (0.21 mmol) of the compound from Example 25C are dissolved in 11 ml of THF, and 3 ml each of water and methanol are added. After the addition of 10.2 mg (0.43 mmol) of lithium hydroxide the mixture is stirred at RT for 24 h. The reaction solution is then concentrated in vacuo, and the crude product is dried under high vacuum.

Yield: 200 mg (99% of theory) LC-MS (method 2): $R_t$=3.18 min. MS (EI): m/z=963 (M+H)$^+$

Example 26C2

8S,11S,14S)-17-(Benzyloxy)-14-{[(benzyloxy)carbonyl]amino}-11-{(2R)-3-{[(benzyloxy)carbonyl]amino}-2-hydroxypropyl}-5-chloro-10,13-dioxo-9,12-diatricyclo[14.3.1.1$^{2,6}$]henicosa-1(20),2(21),3,5,16,18-hexaene-8-carboxylic acid

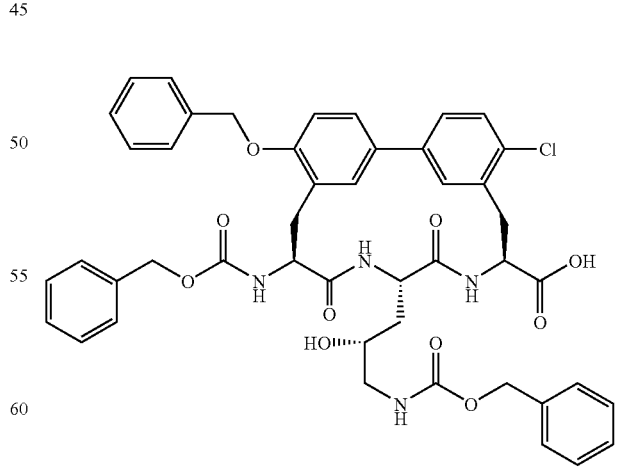

Preparation follows in analogy to Example 26C1 from 169 mg (0.18 mmol) of the compound from Example 23C and 7.7 mg (0.32 mmol) of lithium hydroxide in 12 ml of THF:methanol:water 4:1:1.

Yield: 135 mg (99% of theory) LC-MS (method 1): $R_t$=2.85 min. MS (EI): m/z=849 (M+H)$^+$

Example 26E (8S,11S,14S)-17-(Benzyloxy)-14-{[(benzyloxy)carbonyl]amino}-11-(3-{[(benzyloxy)carbonyl]amino}propyl)-5-methyl-10,13-dioxo-9,12-diazatricyclo[14.3.1.1$^{2,6}$]henicosa-1(20),2(21),3,5,16,18-hexaene-8-carboxylic acid

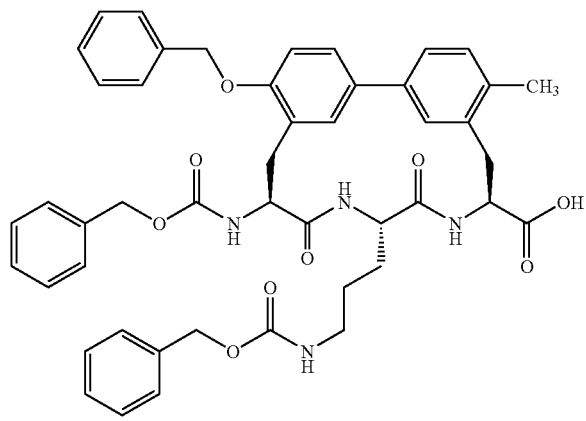

0.21 g (0.23 mmol) of the compound from Example 23E are suspended at RT in a THF:methanol:water mixture (28 ml, 4:1:2), and 11.0 mg (0.47 mmol) of lithium hydroxide are added. After 12 h at room temperature, the mixture is concentrated in vacuo, and the residue is suspended in 100 ml of water. The pH is adjusted to 3 with 1N hydrochloric acid, whereby the product precipitates in crystalline form. The product is filtered off and dried in vacuo.

Yield: 179 mg (94% of theory) LC-MS (method 2): $R_t$=2.70 min. MS (EI): m/z=813 [M+H]$^+$

Example 26F1

(8S,11S,14S)-17-(Benzyloxy)-14-{[(benzyloxy)carbonyl]amino}-11-(3-{[(benzyloxy)carbonyl]amino}propyl)-10,13-dioxo-9,12-diazatricyclo[14.3.1.1$^{2,6}$]henicosa-1(20),2(21),3,5,16,18-hexaene-8-carboxylic acid

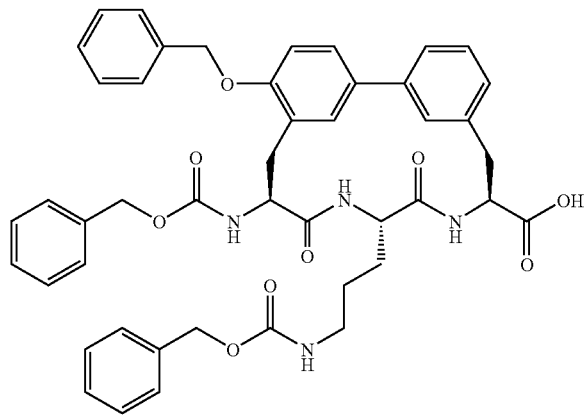

Preparation follows in analogy to Example 26E from 250 mg (0.28 mmol) of the compound from Example 23F and 13.5 mg (0.56 mmol) of lithium hydroxide in THF:methanol:water.

Yield: 194 mg (86% of theory) LC-MS (method 5): $R_t$=2.61 min. MS (EI): m/z=799 (M+H)$^+$

Example 26F2

O-Benzyl-N-{[(8S,11S,14S)-17-(benzyloxy)-14-{[(benzyloxy)carbonyl]amino}-11-(3-{[(benzyloxy)carbonyl]amino}propyl)-10,13-dioxo-9,12-diazatricyclo[14.3.1.12,6]henicosa-1(20),2(21),3,5,16,18-hexaen-8-yl]carbonyl}-L-tyrosine

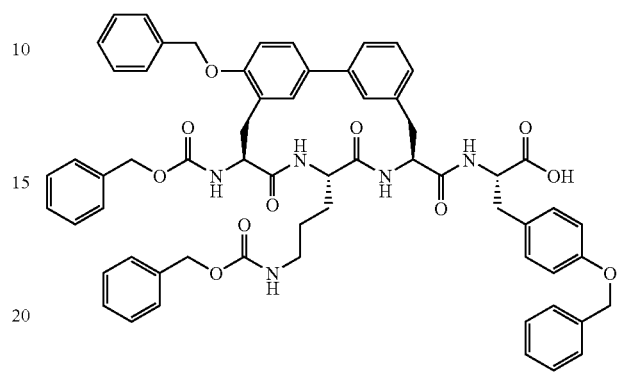

Preparation follows in analogy to Example 26F1 from 58 mg (0.05 mmol) of the compound from Example 27F3 and 2.4 mg (0.1 mmol) of lithium hydroxide in 12 ml of THF:methanol:water 4:1:1.

Yield: 53 mg (99% of theory) LC-MS (method 5): $R_t$=2.86 min. MS (EI): m/z=1052 (M+H)$^+$

Example 26O (8S,11S,14S)-17-(Benzyloxy)-14-{[(benzyloxy)carbonyl]amino}-11-(3-{[(benzyloxy)carbonyl]amino}propyl)-5-fluoro-9-methyl-10,13-dioxo-9,12-diazatricyclo[14.3.1.1$^{2,6}$]henicosa-1(20),2(21),3,5,16,18-hexaene-8-carboxylic acid

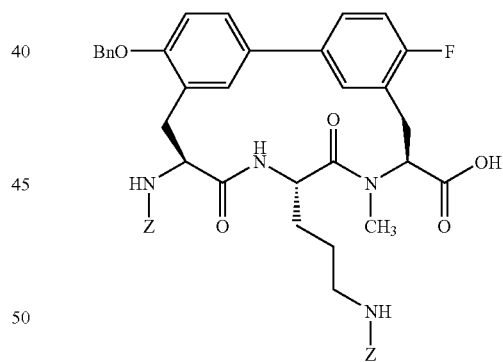

6.6 ml (0.66 mmol) of a 0.1N aqueous lithium hydroxide solution are added to a suspension of 280 mg (0.331 mmol) of methyl (8S,11S,14S)-17-(benzyloxy)-14-{[(benzyloxy)carbonyl]amino}-11-(3-{[(benzyloxy)carbonyl]amino}propyl)-5-fluoro-9-methyl-10,13-dioxo-9,12-diazatricyclo[1.4.3.1.1$^{2,6}$]henicosa-1(20),2(21),3,5,16,18-hexaene-8-carboxylate (Example 23O) in 125 ml of dioxane/water (4:1) at 0° C. The mixture is stirred at RT for 12 h. The pH is adjusted to 2 by adding 0.1N hydrochloric acid. The reaction mixture is concentrated in vacuo and dried under high vacuum. The crude product is reacted without further purification.

LC-MS (method 2): $R_t$=2.75 min. MS (EI): m/z=831(M+H)$^+$.

Example 27E

Benzyl {3-[(8S,11S,14S)-17-(benzyloxy)-14-{[(benzaloxy)carbonyl]amino}-8-{[(2-{[(benzyloxy)carbonyl]amino}ethyl)amino]carbonyl}-5-methyl-10,13-dioxo-9,12-diazatricyclo[14.3.1.1$^{2,6}$]-henicosa-1(20),2(21),3,5,16,18-hexaen-11-yl]propyl}carbamate 25 mg (0.030 mmol) of the compound from Example 26E are suspended in DMF (2.0 ml) under argon at RT, and 18.0 mg (0.090 mmol) of benzyl(2-aminoethyl)carbamate, 8 mg (0.06 mmol) of N,N-diisopropylethylamine and 23 mg (0.060 mmol) of HATU are added. After 12 h at room temperature, 18.0 mg (0.090 mmol) of benzyl(2-aminoethyl)carbamate, 8 mg (0.06 mmol) of N,N-diisopropylethylamine and 23 mg (0.060 mmol) of HATU are again added, and the mixture is stirred at RT for 4 h. 50 ml of water are added, whereby the product precipitates in crystalline form. The product is filtered off, washed with water and stirred in 50 ml of acetonitrile:methanol. It is dried to constant weight in vacuo.

Yield: 19 mg (62% of theory) LC-MS (method 2): R$_t$=2.90 min. MS (EI): m/z=989 [M+H]$^+$ Examples 27C1 to 27C10 and 27F1 to 27F4 listed in the following table are prepared from the appropriate precursors in analogy to the above method:

| Example No. | Structure | Prepared in analogy to Example No. | Analytical data |
|---|---|---|---|
| 27C1 | 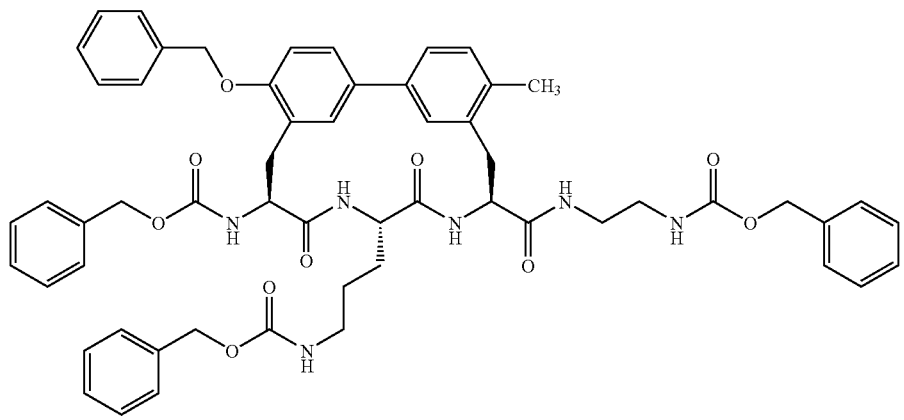 | 27E from Example 26C1 and glycinamide | LC-MS (method 16): R$_t$ = 2.21 min. MS (EI): m/z = 1019 (M + H)$^+$ |

-continued

| Example No. | Structure | Prepared in analogy to Example No. | Analytical data |
|---|---|---|---|
| 27C2 | 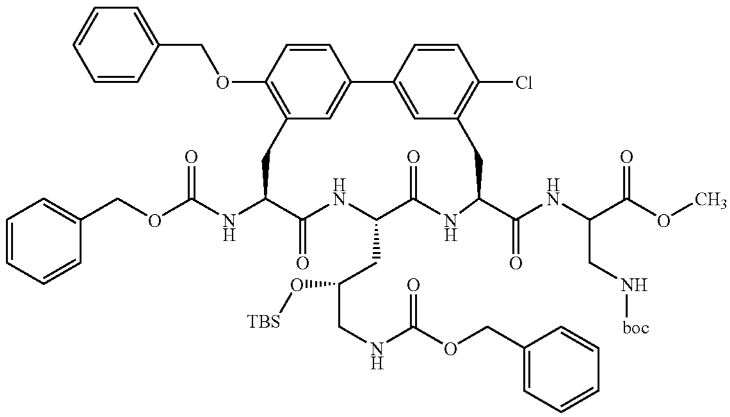 | 27E from Example 26C1 and methyl 3-[(tert-butoxycarbonyl)-amino]-L-alaninate | LC-MS (method 2): $R_t$ = 3.28 min. MS (EI): m/z = 1163 $(M + H)^+$ |
| 27C3 | 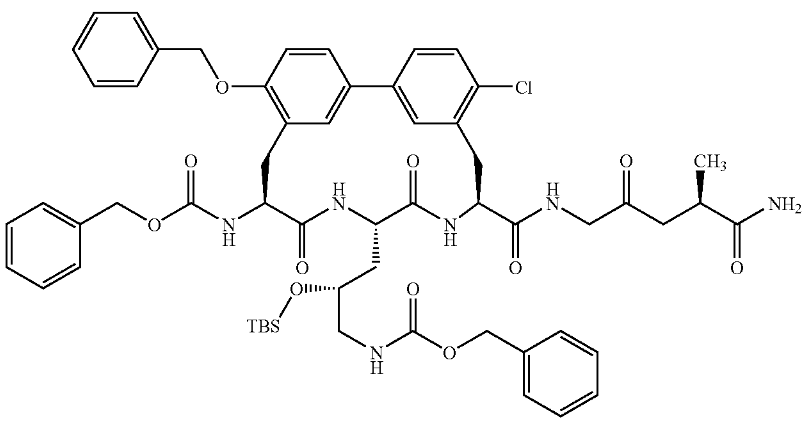 | 27E from Example 26C1 and glycyl-L-alaninamide | LC-MS (method 2): $R_t$ = 3.01 min. MS (EI): m/z = 1090 $(M + H)^+$ |
| 27C4 | 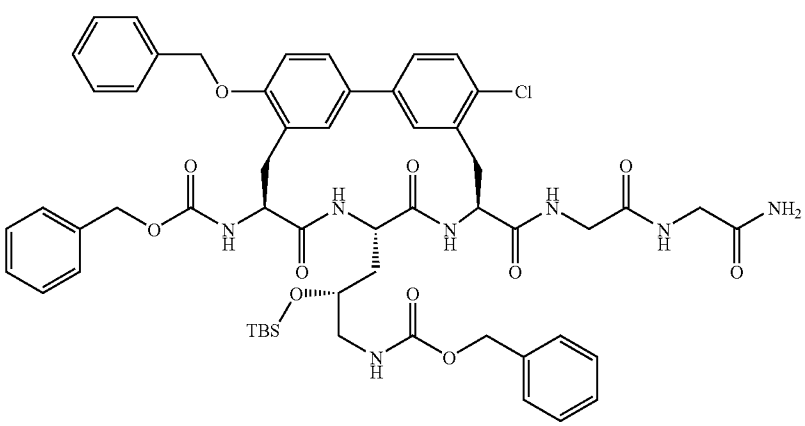 | 27E from Example 26C1 and glycylglycinamide | LC-MS (method 2): $R_t$ = 2.97 min. MS (EI): m/z = 1076 $(M + H)^+$ |

-continued

| Example No. | Structure | Prepared in analogy to Example No. | Analytical data |
|---|---|---|---|
| 27C5 | 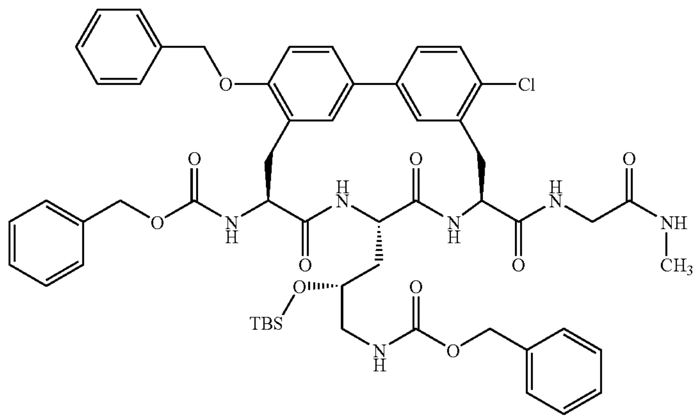 | 27E from Example 26C1 and N¹-methylglycinamide | LC-MS (method 2): $R_t$ = 3.12 min. MS (EI): m/z = 1033 $(M + H)^+$ |
| 27C6 | 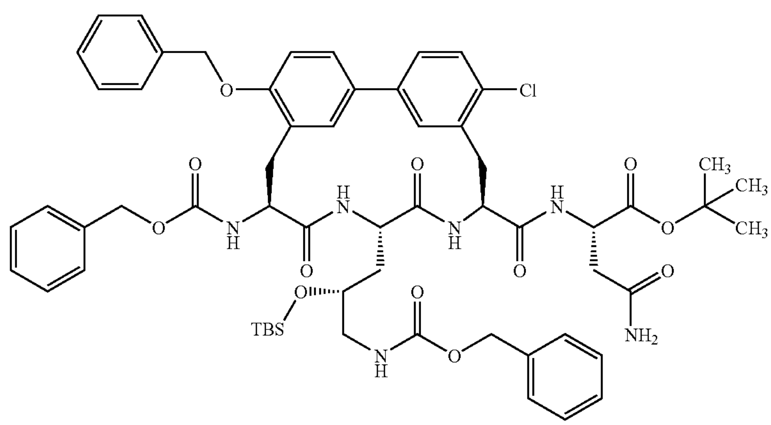 | 27E from Example 26C1 and tert-butyl L-aspartate | LC-MS (method 3): $R_t$ = 3.35 min. MS (EI): m/z = 1133 $(M + H)^+$ |
| 27C7 | 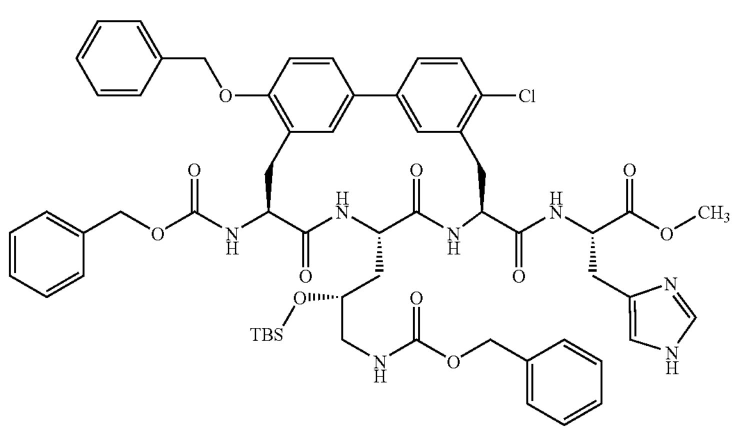 | 27E from Example 26C1 and methyl L-histidinate | LC-MS (method 3): $R_t$ = 2.94 min. MS (EI): m/z = 1114 $(M + H)^+$ |

-continued

| Example No. | Structure | Prepared in analogy to Example No. | Analytical data |
|---|---|---|---|
| 27C8 | 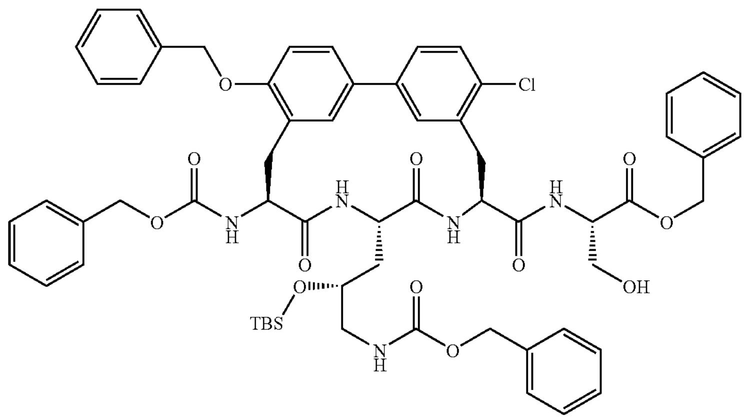 | 27E from Example 26C1 and benzyl L-serinate | LC-MS (method 2): R$_t$ = 3.28 min. MS (EI): m/z = 1140 (M + H)$^+$ |
| 27C9 | 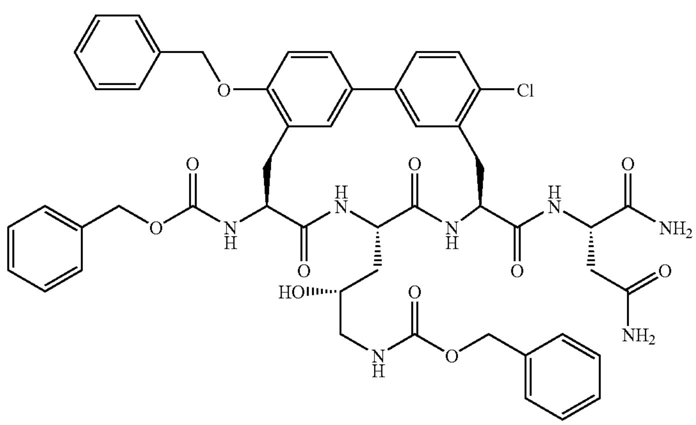 | 27E from Example 26C2 and aspartamide | LC-MS (method 1): R$_t$ = 2.61 min. MS (EI): m/z = 962 (M + H)$^+$ |
| 27C10 | 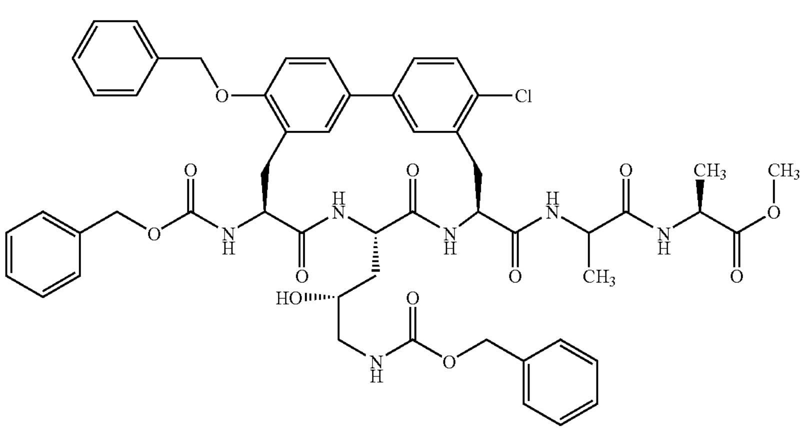 | 27E from Example 26C2 and methyl D-alanyl-d-alanylate | LC-MS (method 1): R$_t$ = 2.89 min. MS (EI): m/z = 1005 (M + H)$^+$ |

-continued

| Example No. | Structure | Prepared in analogy to Example No. | Analytical data |
|---|---|---|---|
| 27C11 | 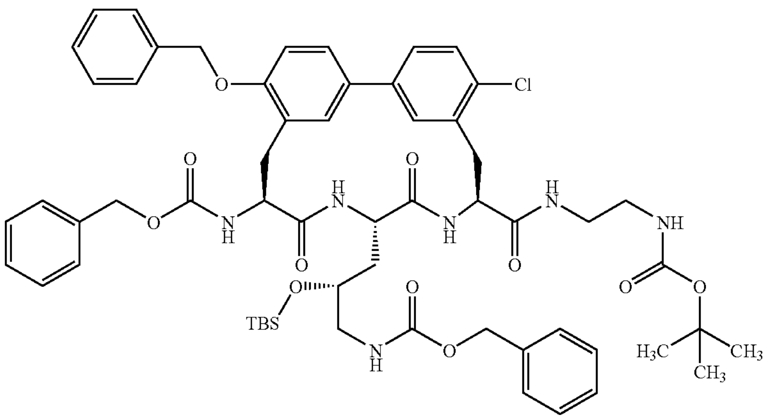 | 27E from Example 26C1 and tert-butyl (2-aminoethyl)-carbamate | LC-MS (method 1): $R_t$ = 3.43 min. MS (EI): m/z = 1105 $(M + H)^+$ |
| 27F1 | 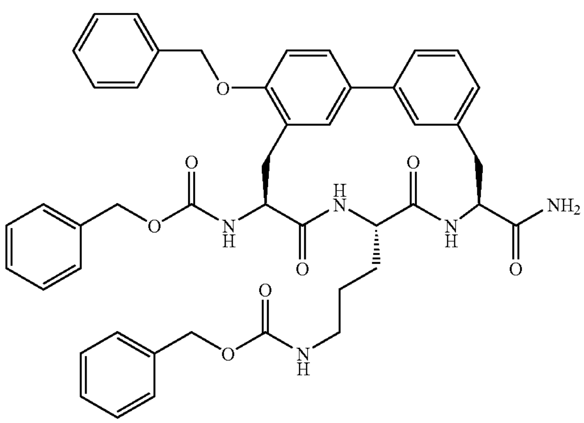 | 27E from Example 26F and ammonia | LC-MS (method 5): $R_t$ = 2.55 min. MS (EI): m/z = 798 $(M + H)^+$ |
| 27F2 | 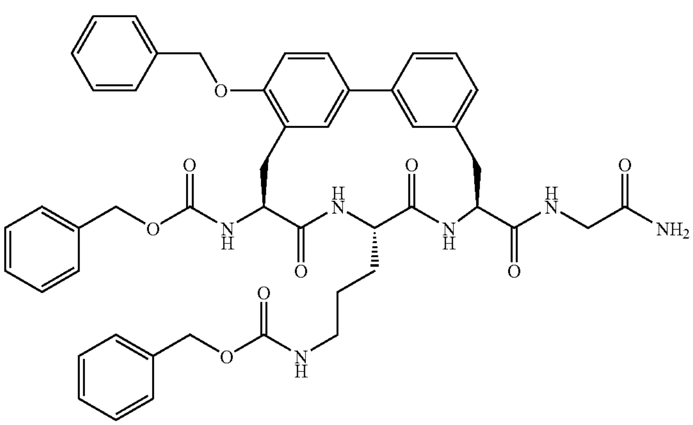 | 27E from Example 26F and glycinamide | LC-MS (method 5): $R_t$ = 2.47 min. MS (EI): m/z = 855 $(M + H)^+$ |

-continued

| Example No. | Structure | Prepared in analogy to Example No. | Analytical data |
|---|---|---|---|
| 27F3 | 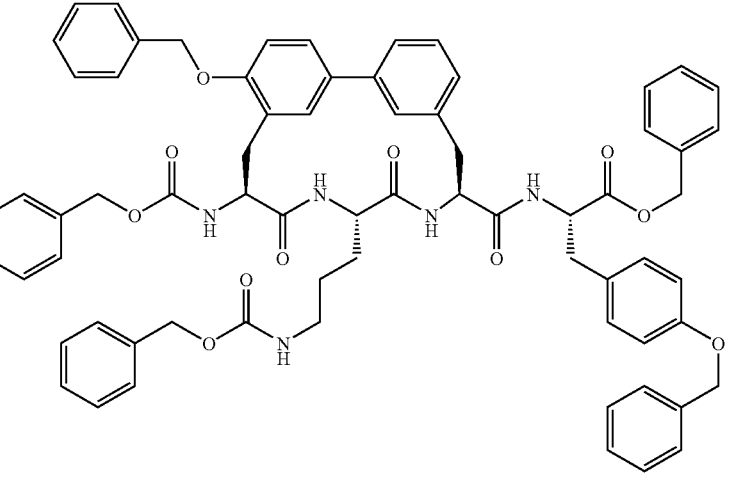 | 27E from Example 26F1 and benzyl O-benzyl-L-tyrosinate | LC-MS (method 5): $R_t$ = 3.14 min. MS (EI): m/z = 1142 (M + H)$^+$ |
| 27F4 | 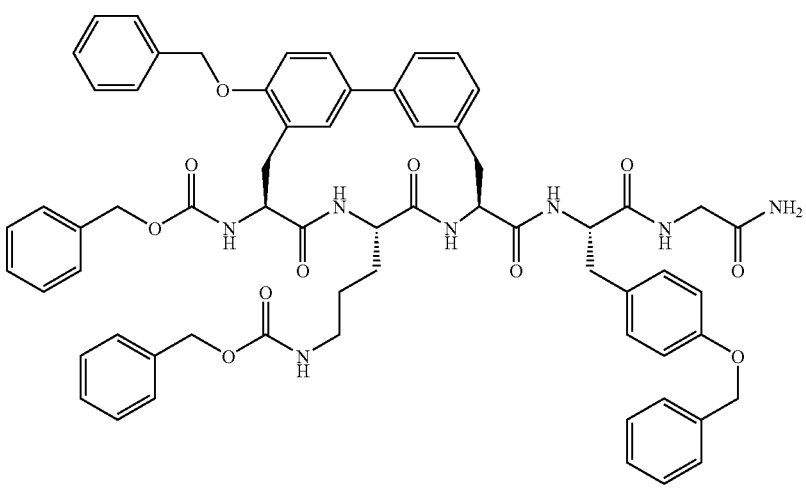 | 27E from Example 26F2 and glycinamide | LC-MS (method 3): $R_t$ = 3.00 min. MS (EI): m/z = 1109 (M + H)$^+$ |

Example 28A (8S,11S,14S)-14-[(tert-Butoxycarbonyl)amino]-11-{3-[(tert-butoxycarbonyl)amino]propyl}-5-fluoro-17-hydroxy-10,13-dioxo-9,12-diazatricyclo[14.3.1.1$^{2,6}$]henicosa-1(20),2(21),3,5,16,18-hexaene-8-carboxylic acid

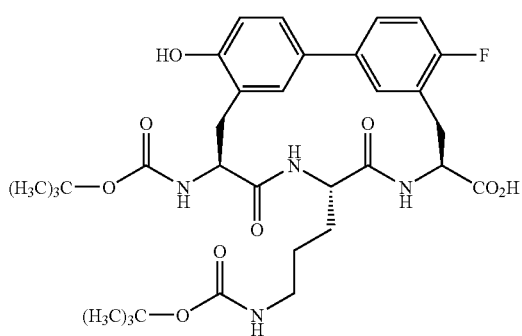

33 mg (0.06 mmol) of the compound from Example 1 are dissolved in 0.28 ml of a 0.1N sodium hydroxide solution and, while stirring, 40.7 mg (0.19 mmol) of di-tert-butyl dicarbonate are added, and the mixture is stirred overnight. The pH is adjusted to 4 with 0.1N hydrochloric acid, and the mixture is extracted twice with ethyl acetate. The organic phases are combined, dried with sodium sulfate and evaporated to dryness in vacuo.

Yield: 33 mg (77% of theory) LC-MS (method 3): $R_t$=2.24 min. MS (EI): m/z=658 (M+H)$^+$ A product mixture composed of the target compound and the corresponding phenyl carbonates (m/z=757 and m/z=857) results and is used without further separation for subsequent reactions.

Example 28J (8S,11S,14S)-14-[(tert-Butoxycarbonyl)amino]-11-
{(2R)-3-[(tert-butoxycarbonyl)amino]-2-hydrox-
ypropyl}-4,17-dihydroxy-10,13-dioxo-9,12-diazatri-
cyclo]14.3.1.1$^{2,6}$]henicosa-1(20),2(21),3,5,16,18-
hexaene-8-carboxylic acid 17 mg (0.03 mmol) of the compound from Example 34 are introduced into 1.0 ml of methanol:water (9:1), 1.0 ml of a saturated aqueous sodium bicarbonate solution and 27.5 mg (0.12 mmol) of di-tert-butyl carbonate in 0.15 ml of methanol:water (9:1) are added and the mixture is stirred at RT for 12 h. The reaction solution is concentrated in vacuo, mixed with water and extracted with ethyl acetate. After phase separation, the aqueous phase is adjusted to pH 4 by adding 0.1N hydrochloric acid and is extracted several times with ethyl acetate. The combined organic phases are dried over sodium sulfate and evaporated to dryness in vacuo.

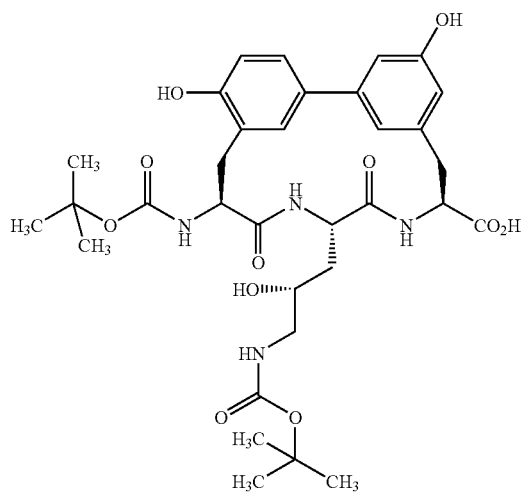

Yield: 21 mg (quantitative), LC-MS (method 15): $R_t$=2.44 min. MS (EI): m/z=673 (M+H)$^+$ A product mixture composed of target compound and the corresponding phenyl carbonates (m/z=772 and m/z=872) results and is used without further separation for subsequent reactions.

Examples 28B, 28D and 28K to 28N listed in the following table are prepared from the appropriate precursors in analogy to the indicated methods:

| Example No. | Structure | Prepared in analogy to Example No. | Analytical data |
|---|---|---|---|
| 28B | 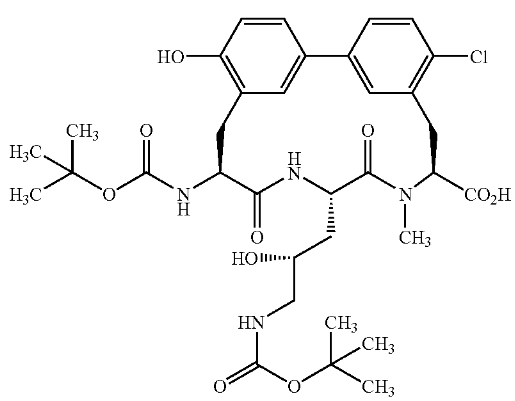 | 28A from Example 4 | LC-MS (method 2): $R_t$ = 2.08 min. MS (EI): m/z = 704 (M + H)$^+$ |

-continued

| Example No. | Structure | Prepared in analogy to Example No. | Analytical data |
|---|---|---|---|
| 28D | 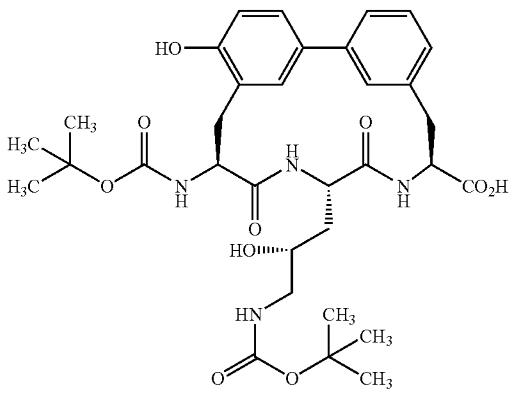 | 28J from Example 25 | |
| 28F | 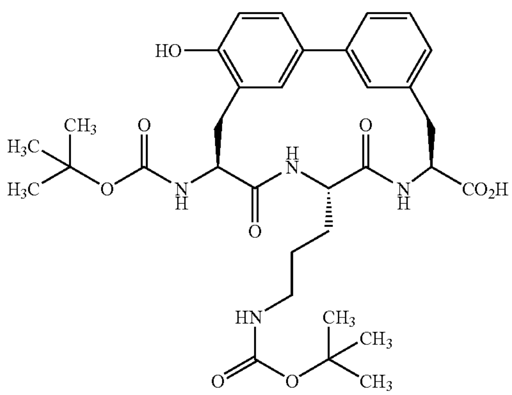 | 28A from Example 35 | LC-MS (method 1): $R_t$ = 2.19 min. MS (EI): m/z = 640 (M + H)$^+$ |
| 28K | bisphenyl carbonate as main compound | 28J from Example 2 | LC-MS (method 15): $R_t$ = 3.33 min. MS (EI): m/z = 857 (M + H)$^+$ |

-continued

| Example No. | Structure | Prepared in analogy to Example No. | Analytical data |
|---|---|---|---|
| 28L | 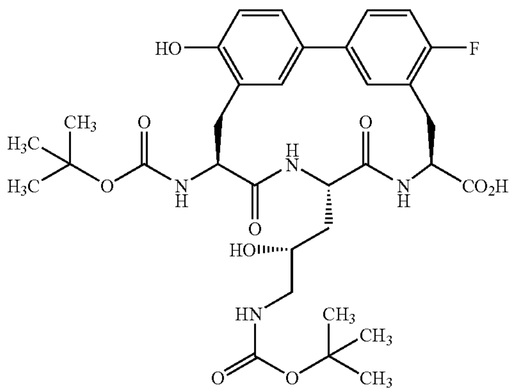 | 28A from Example 3 | LC-MS (method 17): $R_t$ = 3.20 min. MS (EI): m/z = 675 (M + H)$^+$ |
| 28M | 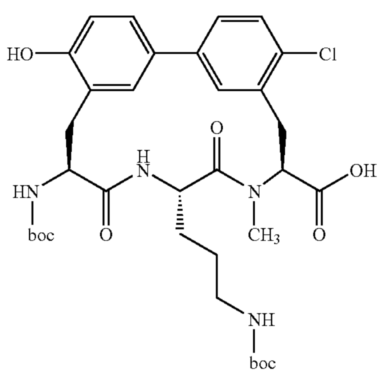 | 28O from Example 24M | LC-MS (method 1): $R_t$ = 2.39 min. MS (ES): m/z = 689 (M + H)$^+$ |
| 28N | 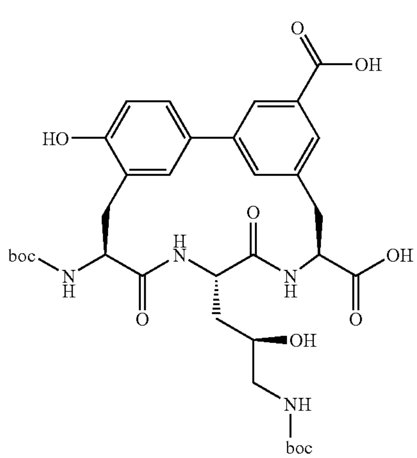 | 28O from Example 31N | LC-MS (method 3): $R_t$ = 1.89 min. MS (ES): m/z = 701 (M + H)$^+$ |

Example 28O (8S,11S,14S)-14-[(tert-Butoxycarbonyl)amino]-11-{3-[(tert-butoxycarbonyl)amino]propyl}-5-fluoro-17-hydroxy-9-methyl-10,13-dioxo-9,12-diazatricyclo[14.3.1.1$^{2,6}$]henicosa-1(20),2(21),3,5,16,18-hexaene-8-carboxylic acid

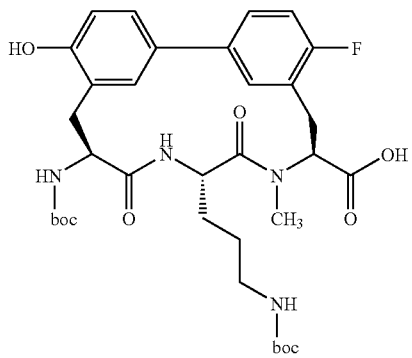

180 mg (0.330 mmol) (8S,11S,14S)-14-amino-11-(3-aminopropyl)-5-fluoro-17-hydroxy-9-methyl-10,13-dioxo-9,12-diazatricyclo-[14.3.1.1$^{2,6}$]henicosa-1(20),2(21),3,5,16,18-hexaene-8-carboxylic acid dihydrochloride (Example 40) are dissolved in 1.6 ml (1.6 mmol) of a 1N sodium hydroxide solution and 2 ml of water and, while stirring at room temperature, 216 mg (0.99 mmol) of di-tert-butyl dicarbonate dissolved in 1 ml of methanol are added. The mixture is stirred at RT overnight. The pH is adjusted to 3 by dropwise addition of 0.1N hydrochloric acid. The aqueous phase is extracted with ethyl acetate, and the organic phase is dried over magnesium sulfate and evaporated to constant weight in vacuo. The product is reacted without further purification.

LC-MS (method 2): $R_t$=2.11 min. MS (EI): m/z=673 (M+H)$^+$.

Example 28P1

(8S,11S,14S)-5,14-Bis[(tert-butoxycarbonyl)amino]-11-{3-[(tert-butoxycarbonyl)amino]propyl}-17-hydroxy-10,13-dioxo-9,12-diazatricyclo[14.3.1.1$^{2,6}$]henicosa-1(20),2(21),3,5,16,18-hexaene-8-carboxylic acid

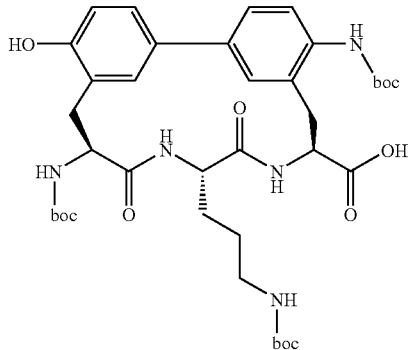

170 mg (0.26 mmol) of the compound from Example 31P are dissolved in 1.29 ml (1.29 mmol) of a 1N sodium hydroxide solution and 0.85 ml of water and, while stirring at room temperature, 170 mg (0.78 mmol) of di-tert-butyl dicarbonate dissolved in 0.3 ml of methanol are added. The mixture is stirred at RT for 1 h and then 170 mg (0.78 mmol) of di-tert-butyl dicarbonate and 1.29 ml (1.29 mmol) of a 1N sodium hydroxide solution are again added, and stirring is continued at RT for 2 h. The pH is adjusted to 3 by dropwise addition of 0.1N hydrochloric acid, resulting in a precipitate. The mixture is first extracted with ethyl acetate, and the organic phase is separated. The organic phase is dried over magnesium sulfate and evaporated to constant weight in vacuo. The product is reacted without further purification. The remaining aqueous phase is filtered and the residue is dried to constant weight in vacuo (see Example 28P2).

Yield: 140 mg (70% of theory) LC-MS (method 2): $R_t$=2.32 min. MS (ES): m/z=756 (M+H)$^+$

Example 28P2

(8S,11S,14S)-5-Amino-14-[(tert-butoxycarbonyl)amino]-11-{3-[(tert-butoxycarbonyl)amino]propyl}-17-hydroxy-10,13-dioxo-9,12-diazatricyclo[4.3.1.1$^{2,6}$]henicosa-1(20),2(21),3,5,16,18-hexaene-8-carboxylic acid hydrochloride

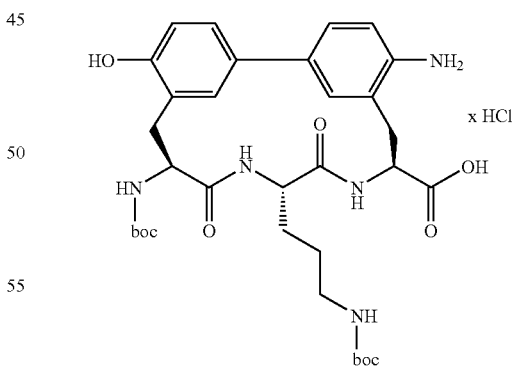

Example 28P2 is formed as by-product in the preparation of Example 28P1.

Yield: 20 mg (12% of theory) LC-MS (method 2): $R_t$=1.67 min. MS (ES): m/z=656 (M-HCl+H)$^+$

Example 29A1 tert-Butyl {3-[(8S,11S,14S)-14-[(tert-butoxycarbonyl)amino]-8-[({2-[(tert-butoxycarbonyl)amino]ethyl}amino)carbonyl]-5-fluo-ro-17-hydroxy-10,13-dioxo-9,12-diazatricyclo[14.3.1.1$^{2,6}$]henico-sa-1(20),2(21),3,5,16,18-hexaen-11-yl]propyl}carbamate

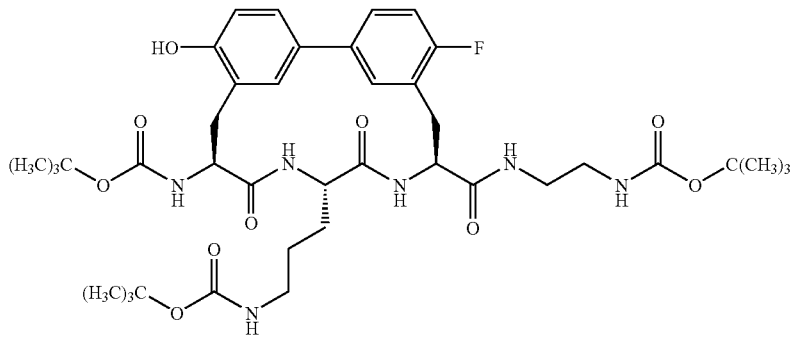

15 mg (0.02 mmol) of the compound from Example 28A and 4.38 mg (0.03 mmol) of tert-butyl (2-aminoethyl)carbamate are dissolved in 1 ml of abs. DMF and cooled to 0° C., and 10,4 mg (0.03 mmol) of HATU and 3.4 mg (0.03 mmol) of Hünig's base are added. The mixture is stirred at 0° C. for 30 min, the temperature is then allowed to rise to RT, a further 6.8 mg (0.05 mmol) of Hünig's base are added, and reaction is allowed to continue overnight. The mixture is evaporated to dryness in vacuo, and the residue is separated by preparative HPLC (acetonitrile/water).

Yield: 6.5 mg (36% of theory) LC-MS (method 3): $R_t$=2.48 min. MS (EI): m/z=800 (M+H)$^+$ Examples 29A2, 29B1, 29B2, 29D, 29F1, 29F2, 29J, 29K, 29L, 29F4, 29M1, 29M2, 29N, 29O1, 29P1 and 29P2 listed in the following table are prepared from the appropriate precursors in analogy to the indicated methods:

| Example No. | Structure | Prepared in analogy to Example No. | Analytical data |
|---|---|---|---|
| 29A2 | 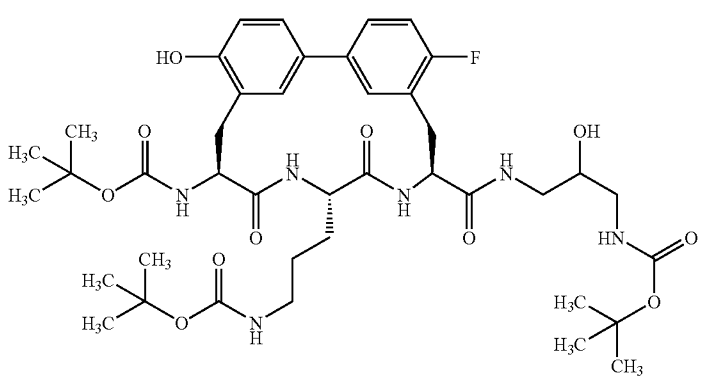 | 29A1 from Example 28A and tert-butyl (3-amino-2-hydroxypropyl)-carbamate | LC-MS (method 3): $R_t$ = 2.39 min. MS (EI): m/z = 830 (M = H)$^+$ |

| Example No. | Structure | Prepared in analogy to Example No. | Analytical data |
|---|---|---|---|
| 29B1 | 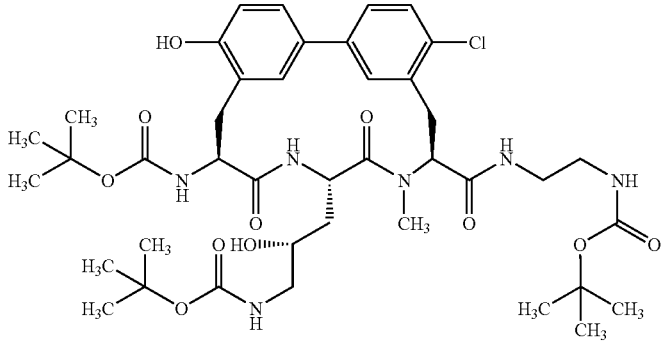 | 29A1 from Example 28B and tert-butyl (2-aminoethyl)-carbamate | LC-MS (method 2): $R_t$ = 2.41 min. MS (EI): m/z = 846 [M = H]$^+$ |
| 29B2 | 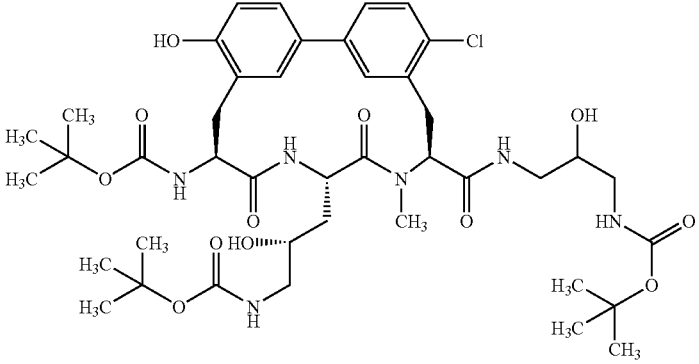 | 29A1 from Example 28B and tert-butyl (3-amino-2-hydroxypropyl)-carbamate | LC-MS (method 2): $R_t$ = 2.30 min. MS (EI): m/z = 876 [M = H]$^+$ |
| 29D | 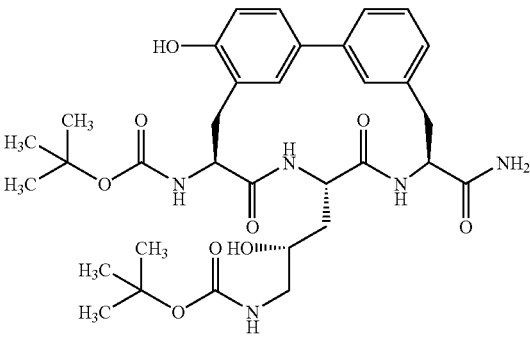 | 29A1 from Example 28D and ammonia | LC-MS (method 8): $R_t$ = 2.65 min. MS (EI): m/z = 656 (M = H)$^+$ |
| 29F1 | 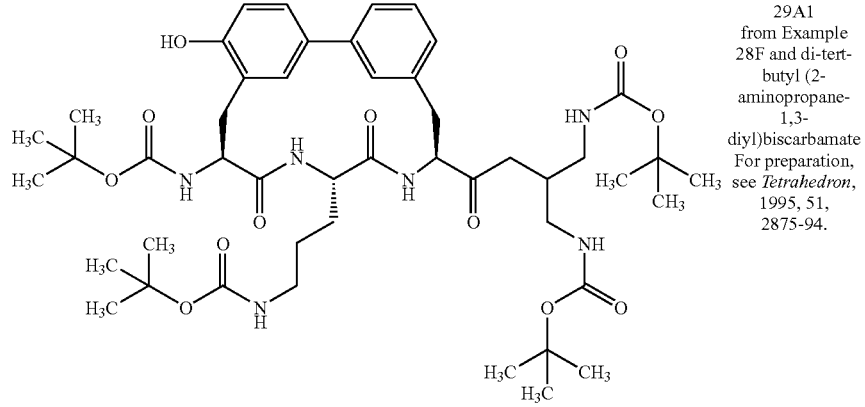 | 29A1 from Example 28F and di-tert-butyl (2-aminopropane-1,3-diyl)biscarbamate For preparation, see *Tetrahedron*, 1995, 51, 2875-94. | LC-MS (method 1): $R_t$ = 2.63 min. MS (EI): m/z = 912 (M = H)$^+$ |

-continued
| Example No. | Structure | Prepared in analogy to Example No. | Analytical data |
|---|---|---|---|
| 29F2 | 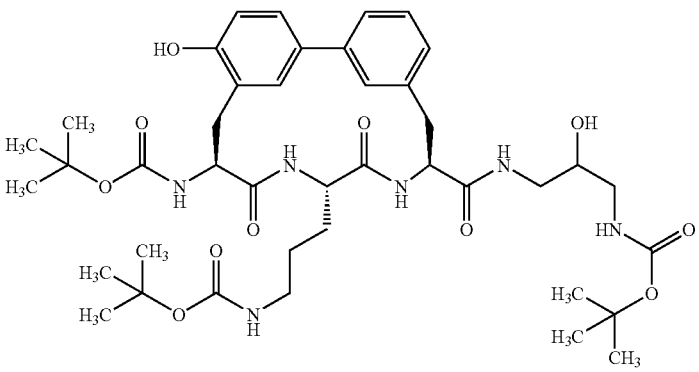 | 29A1 from Example 28F and tert-butyl (3-amino-2-hydroxypropyl)-carbamate | LC-MS (method 2): $R_t$ = 2.17 min. MS (EI): m/z = 813 (M = H)$^+$ |
| 29J | 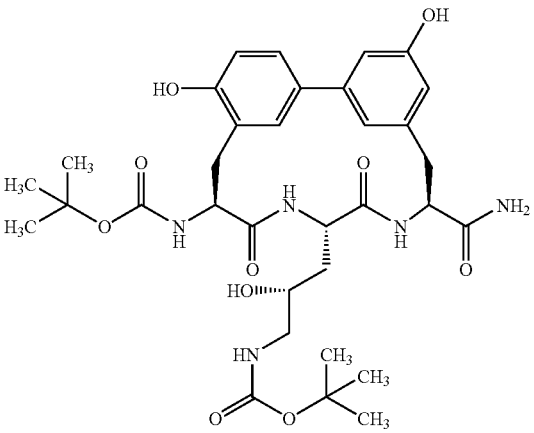 | 29A1 from Example 28J and ammonia | LC-MS (method 8): $R_t$ = 2.40 min. MS (EI): m/z = 672 (M = H)$^+$ |
| 29K | 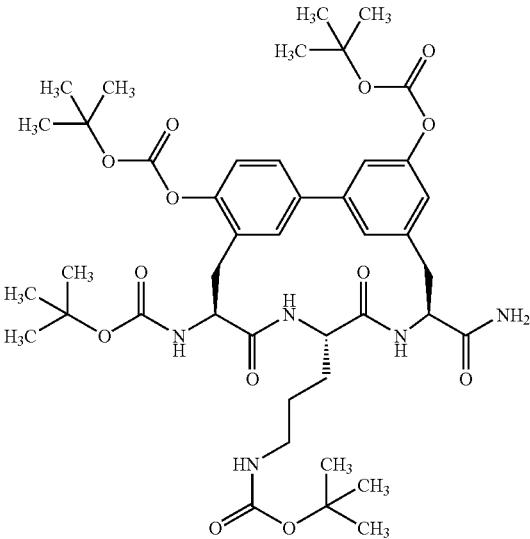 | 29A1 from Example 28K and ammonia | LC-MS (method 8): $R_t$ = 3.58 min. MS (EI): m/z = 856 (M = H)$^+$ |

-continued

| Example No. | Structure | Prepared in analogy to Example No. | Analytical data |
|---|---|---|---|
| 29L | 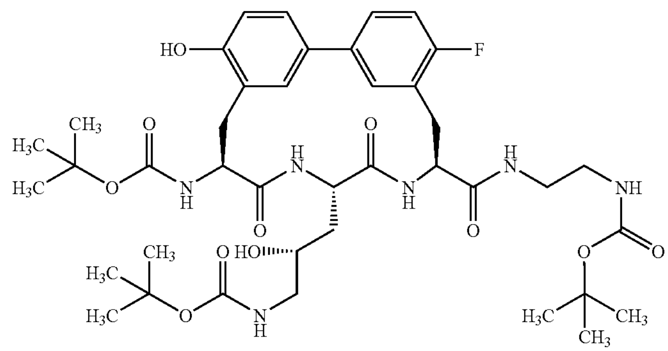 | 29A1 from Example 28L and tert-butyl (2-aminoethyl)-carbamate | LC-MS (method 2): $R_t$ = 2.23 min. MS (EI): m/z = 817 (M = H)+ |
| 29F4 | 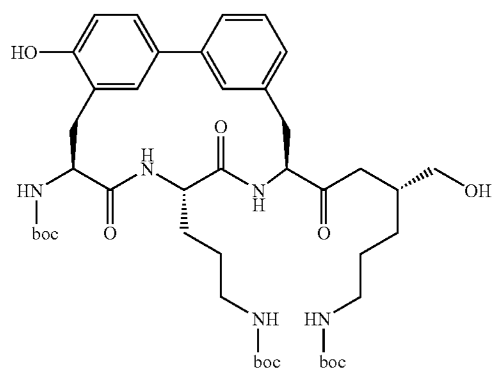 | 29F3 from Example 28F and Example Z5 | LC-MS (method 3): $R_t$ = 2.37 min. MS (EI): m/z = 841 (M = H)+ |
| 29M1 | 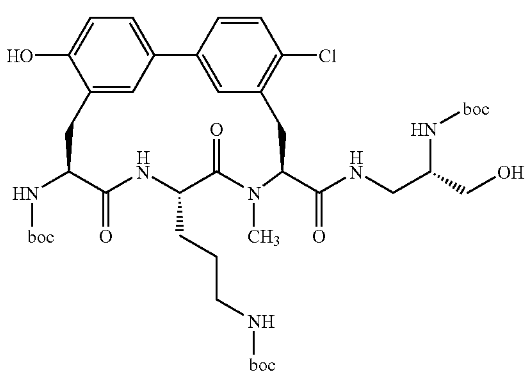 | 29F3 from Example 28M and Example Z11 | LC-MS (method 2): $R_t$ = 2.33 min. MS (EI): m/z = 861 (M = H)+ |
| 29M2 | 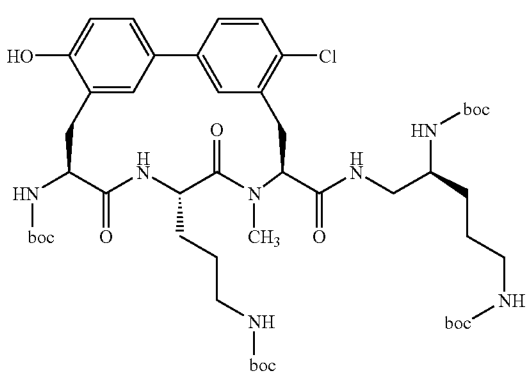 | 29F3 from Example 28M and Example Z9 | LC-MS (method 3): $R_t$ = 2.91 min. MS (EI): m/z = 988 (M = H)+ |

-continued

| Example No. | Structure | Prepared in analogy to Example No. | Analytical data |
|---|---|---|---|
| 29N | 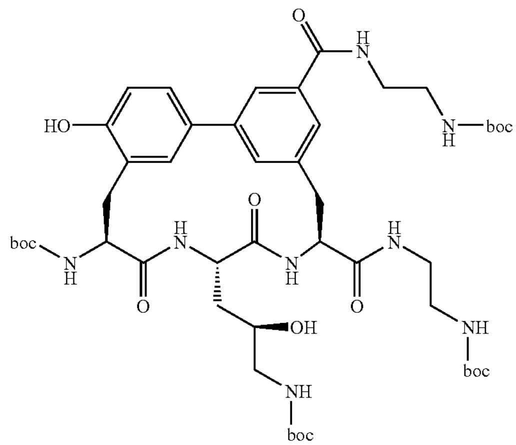 | 29F3 from Example 28N and tert-butyl (aminoethyl)-carbamate | LC-MS (method 3): $R_t$ = 2.35 min. MS (EI): m/z = 985 (M = H)$^+$ |
| 29O1 | 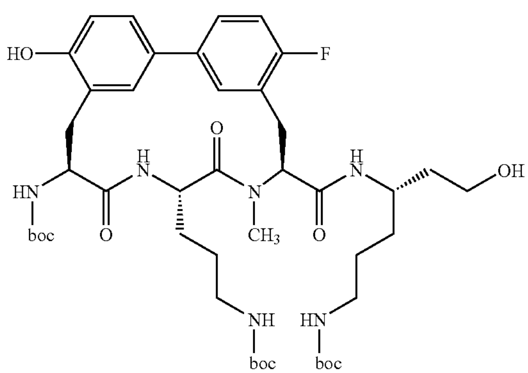 | 29F3 from Example 28O and Example Z3 | LC-MS (method 3): $R_t$ = 2.49 min. MS (EI): m/z = 887 (M = H)$^+$ |
| 29P1 | 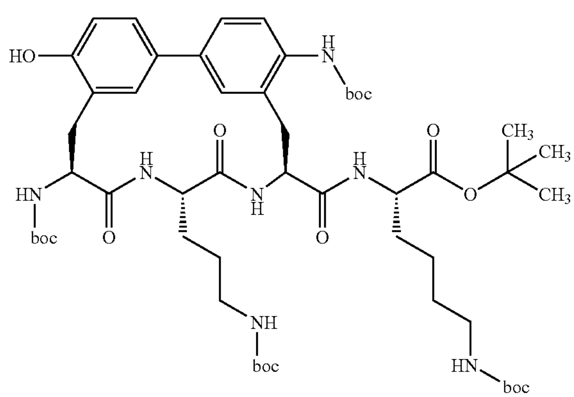 | 29F3 from Example 28P and tert-butyl N$^6$-(tert-butoxycarbonyl)-L-lysinate | LC-MS (method 2): $R_t$ = 2.91 min. MS (EI): m/z = 1040 (M = H)$^+$ |

-continued

| Example No. | Structure | Prepared in analogy to Example No. | Analytical data |
|---|---|---|---|
| 29P2 | 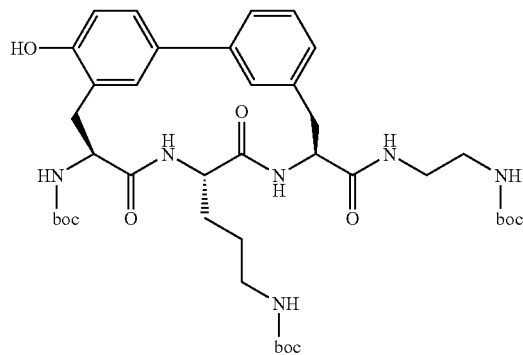 | 29F3 from Example 28P and L-alaninamide | LC-MS (method 2): $R_t$ = 2.49 min. MS (EI): m/z = 826 (M = H)+ |

Example 29F3 tert-Butyl {3-[(8S,11S,14S)-14-[(tert-butoxycarbonyl)amino]-8-[({2-[(tert-butoxycarbonyl)amino]ethyl}amino)carbonyl]-17-hydroxy-10,13-dioxo-9,12-diazatricyclo[14.3.1.1$^{2,6}$]henicosa-1(20),2(21),3,5,16,18-hexaen-11-yl]propyl}carbamate

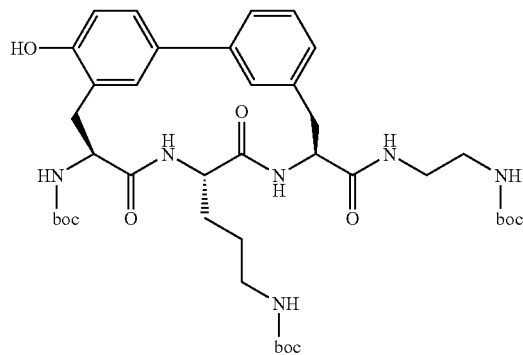

24 mg (0.037 mmol) of the compound from Example 28F and 7.8 mg (0.048 mmol) of tert-butyl (2-aminoethyl)carbamate are dissolved in 1 ml of dimethylformamide under argon. Then, at 0° C. (ice bath), 9.2 mg (0.048 mmol) of EDC and 1.5 mg (0.011 mmol) of HOBt are added. The mixture is slowly warmed to RT and stirred at RT for 12 h. The solution is concentrated in vacuo, and the residue is stirred with water. The remaining solid is filtered off with suction and dried under high vacuum.

Yield: 18 mg (63% of theory) LC-MS (method 17): $R_t$=2.41 min. MS (EI): m/z=783 (M+H)+

Example 29P3

(8S,11S,14S)-14-[(tert-Butoxycarbonyl)amino]-11-{3-[(tert-butoxycarbonyl)amino]propyl}-5-{[N-(tert-butoxycarbonyl)glycyl]-amino}-17-hydroxy-10,13-dioxo-9,12-diazatricyclo[14.3.1.1$^{2,6}$-henicosa-1(20),2(21),3,5,16,18-hexaene-8-carboxylic acid

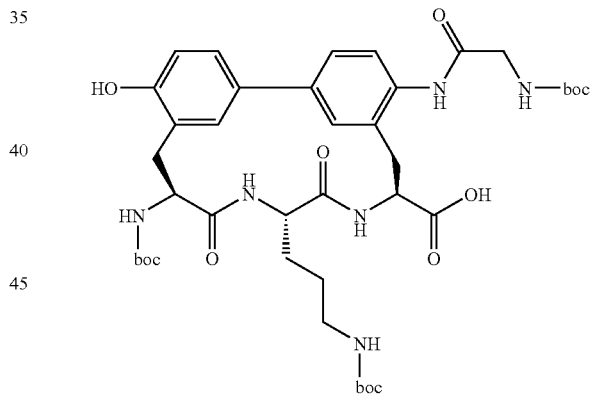

4.4 mg (0.025 mmol) of N-(tert-butoxycarbonyl)glycine are dissolved in 1.7 ml of dimethylformamide under argon. Then, at 0° C. (ice bath), 5.3 mg (0.027 mmol) of EDC and 1.0 mg (0.007 mmol) of HOBt are added. 20 mg (0.032 mmol) of the compound from Example 28P2 are subsequently added. The mixture is slowly warmed to RT and stirred at RT for 12 h. The solution is concentrated in vacuo, and the residue is purified by chromatography on Sephadex-LH20 (mobile phase: methanol/acetic acid (0.25%)).

Yield: 8.8 mg (44% of theory) LC-MS (method 1): $R_t$=2.17 min. MS (EI): m/z=813 (M+H)+

Example 30M1

Benzyl {3-[(8S,11S,14S)-17-(benzyloxy)-14-{[(benzyloxy)carbonyl]amino}-8-[({2-[bis(2-aminoethyl)amino]ethyl}amino)carbonyl]-5-chloro-9-methyl-10,13-dioxo-9,12-diazatricyclo-[14.3.1.1²,⁶]henicosa-1(20),2(21),3,5,16,18-hexaen-11-yl]propyl}-carbamate

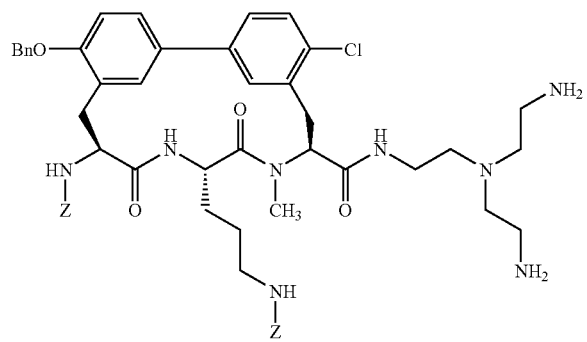

0.76 mg (0.012 mmol) of potassium cyanide are added to a solution of 100 mg (0.036 mmol) of the compound from Example 23M in 0.25 ml of N,N-bis(2-aminoethyl)ethane-1,2-diamine. The mixture is stirred at RT for 16 h. Water is added to the mixture. The precipitated solid is filtered off and dried under high vacuum.

Yield: 102 mg (87% of theory) LC-MS (method 3): $R_t$=2.03 min. MS (EI): m/z=975 (M+H)$^+$.

Example 30O

Benzyl {3-[(8S,11S,14S)-8-{[(2-aminoethyl)amino]carbonyl}-17-(benzyloxy)-14-{[(benzyloxy)carbonyl]amino}-5-fluoro-9-methyl-10,13-dioxo-9,12-diazatricyclo[14.3.1.1²,⁶]henicosa-1(20),2(21),3,5,16,18-hexaen-11-yl]propyl}carbamate

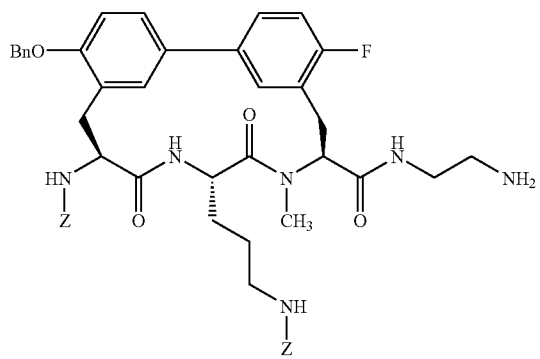

0.46 mg (0.007 mmol) of potassium cyanide are added to a solution of 30 mg (0.036 mmol) of methyl (8S,11S,14S)-17-(benzyloxy)-14-{[(benzyloxy)carbonyl]amino}-11-(3-{[(benzyloxy)-carbonyl]amino}propyl)-5-fluoro-9-methyl-10,13-dioxo -9,12-diazatricyclo[14.3.1.1²,⁶]henicosa-1(20),2(21),3,5,16,18-hexaene-8-carboxylate (Example 23O) in 0.6 ml of 1,2-diaminoethane. The mixture is stirred at RT for 16 h. Water is added to the mixture. The precipitated solid is filtered off and dried under high vacuum.

Yield: 28 mg (89% of theory) LC-MS (method 2): $R_t$=2.13 min. MS (EI): m/z=873 (M+H)$^+$.

Examples 30M2 and 30P listed in the following table are prepared from the appropriate precursors in analogy to the indicated methods:

| Example No. | Structure | Prepared in analogy to Example No. | Analytical data |
|---|---|---|---|
| 30M2 | (structure shown) | 30O from Example 23M | LC-MS (method 1): $R_t$ = 2.51 min. MS (ES): m/z = 889 (M + H)$^+$ |

| Example No. | Structure | Prepared in analogy to Example No. | Analytical data |
|---|---|---|---|
| 30P | 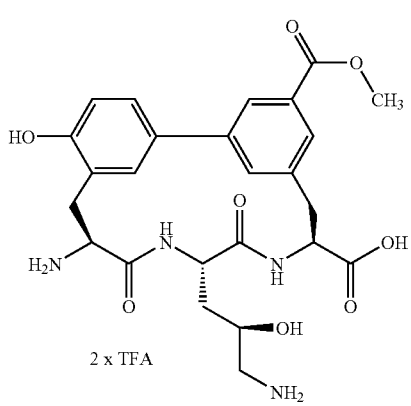 | 30O from Example 23P | LC-MS (method 1): $R_t$ = 2.30 min. MS (ES): m/z = 886 (M + H)$^+$ |

Example 31N (8S,11S,14S)-14-Amino-11-[(2R)-3-amino-2-hydroxypropyl]-17-hydroxy-4-(methoxycarbonyl-10, 13-dioxo-9,12-diazatricyclo-[4.3.1.1$^{2,6}$]henicosa-1 (20),2(21),3,5,16,18-hexaene-8-carboxylic acid di(hydrotrifluoroacetate)

Example 31O

Methyl (8S,11S,14S)-14-amino-11-(3-aminopropyl)-5-fluoro-17-hydroxy-9-methyl-10,13-dioxo-9,12-diazatricyclo[14.3.1.1$^{2,6}$]henicosa-1(20),2(21),3,5, 16,18-hexaene-8-carboxylate

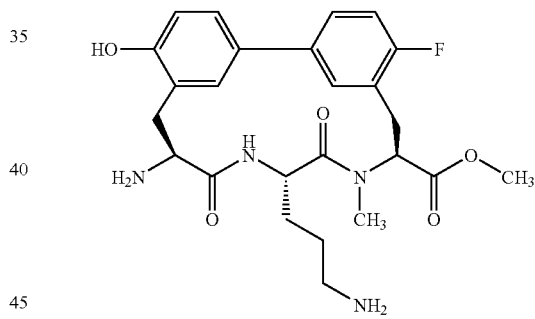

Preparation takes place in analogy to Example 39 from Example 23N.

LC-MS (method 3): $R_t$=1.08 min. MS (ES): m/z=515 (M-2TFA+H)$^+$ $^1$H-NMR (400 MHz, D$_2$O): δ=1.8 (m$_c$, 1H), 1.96 (m$_c$, 1H), 2.75-3.2 (m, 5H), 3.48 (m$_c$, 1H), 3.84 (s, 3H), 3.86 (m$_c$, 1H), 4.38 (m$_c$, 1H), 4.57 (m$_c$, 1H), 4.80 (m$_c$, 1H), 6.83 (s, 1H), 6.88 (d, 1H), 7.37 (d, 1H), 7.40 (s, 1H), 7.65 (s, 1H), 7.84 (s, 1H).

A solution of 50 mg (0.059 mmol) of methyl (8S,11S,14S)-17-(benzyloxy)-14-{[(benzyloxy)carbonyl]amino}-11-(3-{[(benzyloxy)carbonyl]amino}propyl)-5-fluoro-9-methyl-10,13-dioxo-9,12-di-azatricyclo[14.3.1.1$^{2,6}$]henicosa-1(20), 2(21),3,5,16,18-hexaene-8-carboxylate (Example 23O) in ethanol is hydrogenated after the addition of 5 mg of palladium on activated carbon (10%) under atmospheric pressure at RT for 12 h. The mixture is filtered through kieselguhr, and the residue is washed with ethanol. The filtrate is evaporated to dryness in vacuo.

Yield: quant. LC-MS (method 3): $R_t$=1.34 min. MS (EI): m/z=487 (M+H)$^+$.

Example 31P

Methyl (8S,11S,14S)-5,14-diamino-11-(3-aminopropyl)-17-hydroxy-10,13-dioxo-9,12-diazatricyclo[14.3.1.1²,⁶]henicosa-1(20),2(21),3,5,16,18-hexaene-8-carboxylate trihydroacetate

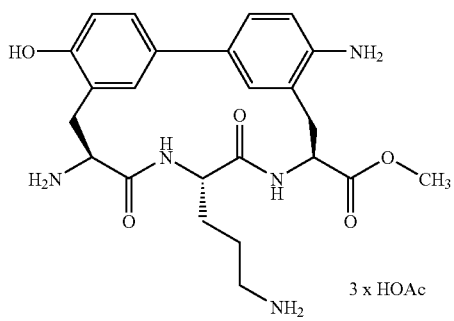

150 mg of the compound from Example 23P are added to a mixture of 17 ml acetic acid/water/ethanol (4:1:1). 30 mg of palladium on activated carbon (10%) are added, and then the mixture is hydrogenated under atmospheric pressure at RT for 72 h. The reaction mixture is filtered through prewashed kieselguhr, washed with ethanol, and the filtrate is concentrated in vacuo on a rotary evaporator. The remaining solid is dried under high vacuum.

Yield: 100 mg (88% of theory) LC-MS (method 17): $R_t$=2.16 min. MS (EI): m/z=470 (M-3HOAc+H)⁺. ¹H-NMR (400 MHz, $D_2O$): δ=1.6-1.9 (m, 4H), 2.85-3.25 (m, 5H), 3.48 ($m_c$, 1H), 3.75 (s, 3H), 4.37 ($m_c$, 1H), 4.6-4.7 (m, 1H, under $D_2O$), 4.92 ($m_c$, 1H), 6.75-6.95 (m, 3H), 7.09 (s, 1H), 7.32 (d, 1H), 7.42 (d, 1H).

Example Z1

(3S)-3-{[(Benzyloxy)carbonyl]amino}-6-[(tert-butoxycarbonyl)-amino]hexanoyl methyl carbonate

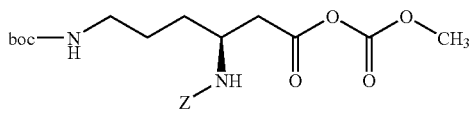

2 g (5.26 mmol) of (3S)-3-{[(benzyloxy)carbonyl]amino}-6-[(tert-butoxycarbonyl) amino]hexanoic acid and 0.56 g (5.73 mmol) of triethylamine are dissolved in 30 ml of THF under argon and cooled to 0° C. 0.59 g (5.73 mmol) of ethyl chloroformate are added, and the mixture is stirred at 0° C. for 3 hours. The reaction mixture is filtered through kieselguhr, and the filtrate is reacted directly.

Example Z2

Benzyl [(1S)-4-[(tert-butoxycarbonyl)amino]-1-(2-hydroxyethyl)-butyl]carbamate

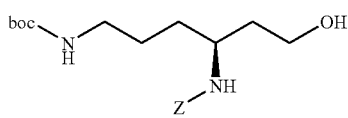

The filtrate of (3S)-3-{[(benzyloxy)carbonyl]amino}-6-[(tert-butoxycarbonyl) amino]hexanoyl methyl carbonate (Example Z1) is added dropwise to a suspension of 0.49 g (13.14 mmol) of sodium borohydride in 0.6 ml of water at 0° C. The mixture slowly warms to RT and is stirred overnight. The reaction solution is concentrated, and the residue is mixed with ethyl acetate and water. The organic phase is dried over magnesium sulfate, concentrated and dried under high vacuum. The crude product is reacted without further purification.

Yield: 570 mg (30% of theory over two stages) LC-MS (method 1): $R_t$=2.09 min. MS (EI): m/z=367 (M+H)⁺

Example Z3 tert-Butyl [(4S)-4-amino-6-hydroxyhexyl]carbamate

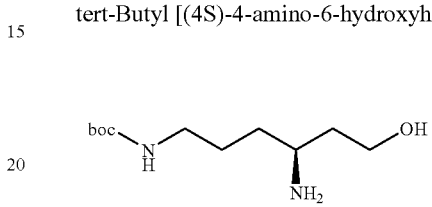

620 mg (1.69 mmol) of benzyl [(1S)-4-[(tert-butoxycarbonyl) -amino]-1-(2-hydroxyethyl)butyl]-carbamate (Example Z2) are dissolved in 60 ml of ethanol. 100 mg of palladium on activated carbon (10%) are added thereto, and the mixture is hydrogenated under atmospheric pressure at RT for 15 h. The reaction mixture is filtered through prewashed kieselguhr, washed with ethanol, and the filtrate is concentrated on a rotary evaporator. The product is reacted without further purification.

Yield: quant. ¹H-NMR (400 MHz, $D_2O$): δ=1.2-1.6 (m, 6H), 1.4 (s, 9H), 2.6-3.0 (m, 1H), 3.0-3.2 (m, 2H), 3.7-3.9 (m, 2H), 4.6 (br.s, 1H)

Example Z4

Benzyl [(1S)-4-[(tert-butoxycarbonyl)amino]-1-(hydroxymethyl)-butyl]carbamate

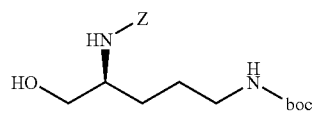

157 mg (1.56 mmol) of 4-methylmorpholine and 169 mg (1.56 mmol) of ethyl chloroformate are added to a solution of 570 mg (1.56 mmol) of $N^2$-[(benzyloxy)carbonyl]-$N^5$-(tert-butoxycarbonyl)-L-ornithine in 10 ml of tetrahydrofuran at −10° C., and the mixture is stirred for 30 min. At this temperature, 3.11 ml (3.11 mmol) of a 1M solution of lithium aluminium hydride in tetrahydrofuran are slowly added dropwise. The mixture is slowly warmed to RT and stirred at RT for 12 h. While cooling in ice, 0.2 ml of water and 0.3 ml of a 4.5% sodium hydroxide solution are cautiously added, and stirring is continued at RT for 3 h. The mixture is filtered and the filtrate is concentrated in vacuo. The residue is dissolved in ethyl acetate, washed with water, dried over magnesium sulfate and again evaporated to dryness in vacuo. The product is reacted without further purification.

Yield: 170 mg (31% of theory) LC-MS (method 2): $R_t$=1.88 min. MS (EI): m/z=353 (M+H)⁺.

Example Z5 tert-Butyl [(4S)-4-amino-5-hydroxypentyl]carbamate

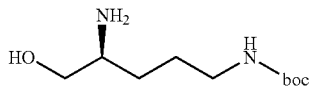

A solution of 169 mg (0.48 mmol) of benzyl [(1S)-4-[(tert-butoxycarbonyl)amino]-1-(hydroxymethyl)butyl]carbamate (Example Z4) in 50 ml of ethanol is hydrogenated after the addition of 17 mg of palladium on activated carbon (10%) under atmospheric pressure at RT for 4 h. The mixture is filtered through kieselguhr, and the residue is washed with ethanol. The filtrate is evaporated to dryness in vacuo. The product is reacted without further purification.

Yield: 104 mg (99% of theory) MS (DCI): m/z=219 (M+H)⁺

Example Z6 tert-Butyl [(1S)-4-[(tert-butoxycarbonyl)amino]-1-hydroxymethyl)butyl]carbamate

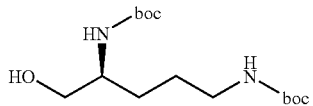

91 mg (0.90 mmol) of 4-methylmorpholine and 98 mg (0.90 mmol) of ethyl chloroformate are added to a solution of 300 mg (0.90 mmol) of $N^2,N^5$-bis(tert-butoxycarbonyl)-L-ornithine in 10 ml of tetrahydrofuran at −10° C., and the mixture is stirred for 30 min. At this temperature, 1.81 ml (1.81 mmol) of a 1M solution of lithium aluminium hydride in tetrahydrofuran are slowly added dropwise. The mixture is slowly warmed to RT and stirred at RT for 12 h. While cooling in ice, 0.1 ml of water and 0.15 ml of a 4.5% sodium hydroxide solution are cautiously added, and stirring is continued at RT for 3 h. The mixture is filtered and the filtrate is concentrated in vacuo. The residue is dissolved in ethyl acetate, washed with water, dried over magnesium sulfate and again evaporated to dryness in vacuo. The product is reacted without further purification.

Yield: 239 mg (83% of theory) MS (ESI): m/z=319 (M+H)⁺; 341(M+Na)⁺·

Example Z7

(2S)-2,5-Bis[(tert-butoxycarbonyl)amino]pentyl-methanesulfonate

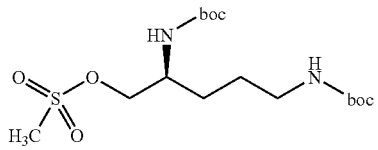

103 mg (0.90 mmol) of methanesulfonyl chloride and 0.21 ml (1.5 mmol) of triethylamine are added to a solution of 240 mg (0.75 mmol) of tert-butyl [(1S)-4-[(tert-butoxycarbonyl)amino]-1-(hydroxymethyl)butyl]carbamate (Example Z6) in 20 ml of dichloromethane and the mixture is stirred at RT for 16 h. The mixture is diluted with dichloromethane and washed twice with 0.1N hydrochloric acid. The organic phase is dried over magnesium sulfate and evaporated to dryness in vacuo. The product is reacted without further purification.

Yield: 218 mg (73% of theory) MS (ESI): m/z=419 (M+Na)⁺·

Example Z8 tert-Butyl {(4S)-5-azido-4-[(tert-butoxycarbonyl)amino]pentyl}-carbamate

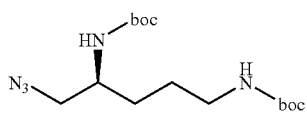

36 mg (0.55 mmol) of sodium azide are added to a solution of 218 mg (0.55 mmol) of (2S)-2,5-bis[(tert-butoxycarbonyl)amino]pentyl methanesulfonate (Example Z7) in 15 ml of dimethylformamide and the mixture is stirred at 70° C. for 12 h. Most of the solvent is distilled off in vacuo, and the residue is diluted with ethyl acetate. The solution is washed several times with a saturated sodium bicarbonate solution, dried over magnesium sulfate and evaporated to dryness in vacuo. The product is reacted without further purification.

Yield: 188 mg (99% of theory) MS (ESI): m/z=344 (M+H)⁺.

Example Z9 tert-Butyl {(4S)-5-amino-4-[(tert-butoxycarbonyl)amino]pentyl}-carbamate

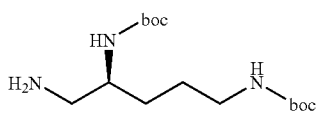

A solution of 188 mg (0.55 mmol) of tert-butyl-{(4S)-5-azido-4-[(tert-butoxycarbonyl) amino]pentyl}carbamate (Example Z8) in ethanol is hydrogenated after the addition of 20 mg of palladium on activated carbon (10%) under atmospheric pressure at RT for 12 h. The mixture is filtered through kieselguhr, and the residue is washed with ethanol. The filtrate is evaporated to dryness in vacuo. The product is reacted without further purification.

Yield: 102 mg (59% of theory) MS (ESI): m/z=318 (M+H)+; 340 (M+Na)+.

Examples Z10 and Z11 listed in the following table are prepared from the appropriate precursors in analogy to the indicated methods:

| Example No. | Structure | Prepared in analogy to Example No. | Analytical data |
|---|---|---|---|
| Z10 | HN-boc, HO, NH-Z | Z4 from 3-{[(benzyloxy)carbonyl]-amino}-N-(tert-butoxycarbonyl)-L-alanine | LC-MS (method 12): $R_t$ = 1.79 min. MS (EI): m/z = 325 (M + H)+ |
| Z11 | HN-boc, HO, NH$_2$ | Z5 from Example Z10 | MS (DCI): m/z = 191 (M + H)+ |

Examplary Embodiments

Example 1

(8S,11S,14S)-14-Amino-11-(3-aminopropyl)-5-fluoro-17-hydroxy-10,13-dioxo-9,12-diazatricyclo[14.3.1.1$^{2,6}$]henicosa-1(20),2(21),3,5,16,18-hexaene-8-carboxylic acid dihydrochloride

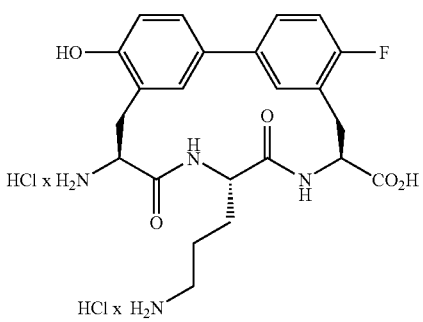

30 mg (0.03 mmol) of the compound from Example 23A are suspended in 30 ml of glacial acetic acid/water/ethanol=4/1/1 and, 15 mg of Pd/C catalyst (10%) are added and the mixture is hydrogenated at RT for 24 h. The catalyst is filtered off, and the filtrate is mixed with 5 ml of 0.1N hydrochloric acid and evaporated in vacuo and dried under high vacuum.

Yield: 18 mg (quantitative) LC-MS (method 14): $R_t$=1.78 min. MS (EI): m/z=458 (M-2HCl+H)+

Example 2

(8S,11S,14S)-14-Amino-11-(3-aminopropyl)-4,17-dihydroxy-10,13-dioxo-9,12-diazatricyclo[14.3.1.1$^{2,6}$]henicosa-1(20),2(21),3,5,16,18-hexaene-8-carboxylic acid dihydrochloride

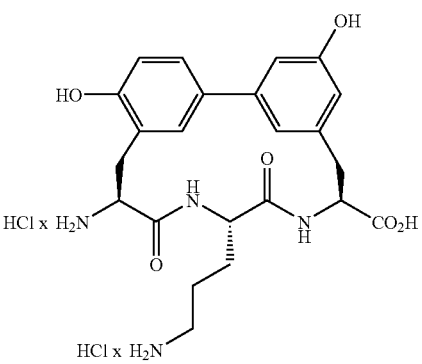

Preparation takes place in analogy to Example 1 from 22 mg (0.02 mmol) of the compound from Example 23K in 4 ml of glacial acetic acid/water/ethanol=4/1/1 with 8 mg of Pd/C catalyst (10%).

Yield: 11 mg (97% of theory) LC-MS (method 15): $R_t$=1.24 min. MS (EI): m/z=457 (M-2HCl+H)+

Example 3

(8S,11S,14S)-14-Amino-11-[(2R)-3-amino-2-hydroxypropyl]-5-fluoro-17-hydroxy-10,13-dioxo-9,12-diazatricyclo[14.3.1.1$^{2,6}$]henicosa-1(20),2(21),3,5,16,18-hexaene-8-carboxylic acid dihydrochloride

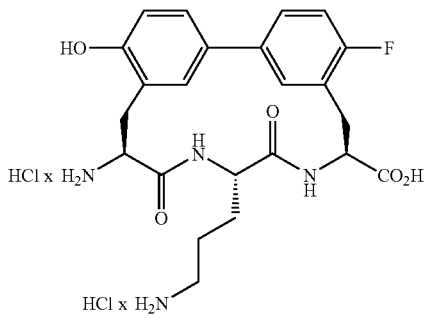

Preparation takes place in analogy to Example 1 from 55 mg (0.06 mmol) of the compound from Example 23L in 55 ml of glacial acetic acid/water/ethanol=4/1/1 with 34 mg of Pd/C catalyst (10%).

Yield: 33 mg (quantitative) LC-MS (method 2): $R_t$=1.37 min. MS (EI): m/z=475 (M-2HCl+H)+

Example 4

(8S,11S,14S)-14-Amino-11-[(2R)-3-amino-2-hydroxypropyl]-5-chloro-17-hydroxy-9-methyl-10,13-dioxo-9,12-diazatricyclo-[14.3.1.1$^{2,6}$]henicosa-1(20),2(21),3,5,16,18-hexaene-8-carboxylic acid

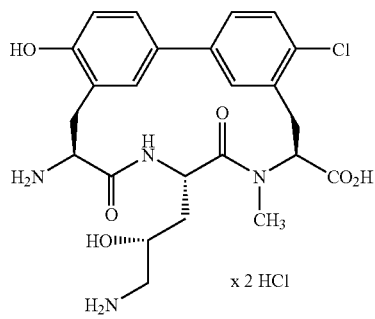

69 mg (approx. 0.077 mmol) of the mixture from Example 24B are suspended in 2 ml of THF/methanol (1/1) and, while stirring, 4.85 mg (0.2 mmol) of lithium hydroxide are added. A solution results. Stirring is continued for half an hour and, after addition of 0.22 ml of 0.1N hydrochloric acid, the mixture is evaporated to dryness in vacuo.

Yield: 80 mg of a mixture of 44% product and 18% of the O-acetyl product LC-MS (method 3): $R_t$=1.33 min. (product) and 1.51 min. (O-acetyl product) MS (EI): m/z=504 (M-2HCl+H)$^+$ and 546 (MOAc-2HCl+H)$^+$

Example 5

(8S,11S,14S)-14-Amino-N-(2-aminoethyl)-11-(3-aminopropyl)-5-fluoro-17-hydroxy-10,13-dioxo-9,12-diazatricyclo[14.3.1.1$^{2,6}$]-henicosa-1(20),2(21),3,5,16,18-hexaene-8-carboxamide trihydro-chloride

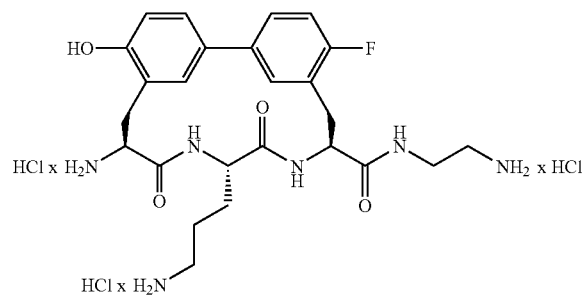

1 ml of a 4N dioxane/hydrogen chloride solution is poured onto 6.5 mg (0.01 mmol) of the compound from Example 29A1 at RT, and the mixture is stirred for 2 h. The mixture is evaporated to dryness in vacuo and dried to constant weight under high vacuum.

Yield: 5 mg (quantitative) LC-MS (method 3): $R_t$=0.27 min. MS (EI): m/z=500 (M-3HCl+H)$^+$

Example 6

(8S,11S,14S)-14-Amino-11-[(2R)-3-amino-2-hydroxypropyl]-17-hydroxy-10,13-dioxo-9,12-diazatricyclo[4.3.1.1$^{2,6}$]henicosa-1(20),2(21),3,5,16,18-hexaene-8-carboxamide di(hydrotrifluoroacetate)

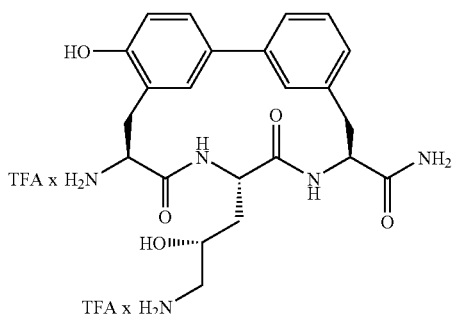

Preparation takes place in analogy to Example 5 from 16.1 mg (0.025 mmol) of the compound from Example 29D with 0.4 ml of a 4N dioxane/hydrogen chloride solution. The crude product is purified by HPLC (Kromasil 1000C18, mobile phase acetonitrile/0.2% aqueous TFA 1:3).

Yield: 1 mg (5% of theory) LC-MS (method 5): $R_t$=1.14 min. MS (EI): m/z=456 (M-2TFA+H)$^+$ $^1$H-NMR (400 MHz, D$_2$O): δ=1.83 (m$_c$, 1H), 1.95 (m$_c$, 1H), 2.85 (m$_c$, 1H), 2.9-3.2 (m, 4H), 3,54 (m$_c$, 1H), 3.80 (m$_c$, 1H), 4.38 (m$_c$, 1H), 4.6 (m, 1H, under D$_2$O signal), 4.84 (m$_c$, 1H), 6.85-7.0 (m, 2H), 7.14 (d, 1H), 7.24-7.48 (m, 4H).

Examples 7 to 12 listed in the following table are prepared from the appropriate precursors in analogy to the methods detailed above:

| Example No. | Structure | Prepared in analogy to Example No. | Analytical data |
|---|---|---|---|
| 7 | 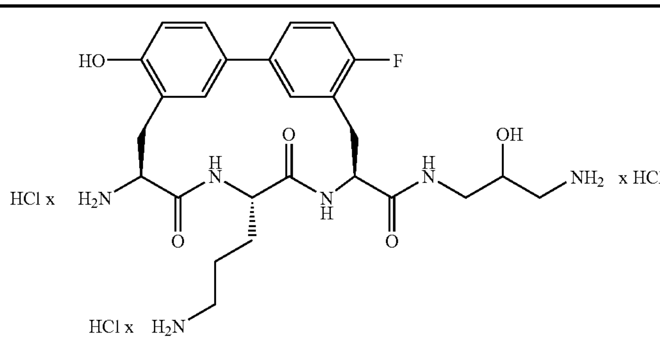 | 5 from Example 29A2 Yield: 99% of theory | LC-MS (method 3): $R_t$ = 0.25 min. MS (EI): m/z = 530 (M − 3HCl + H)$^+$ |

-continued

| Example No. | Structure | Prepared in analogy to Example No. | Analytical data |
|---|---|---|---|
| 8 | 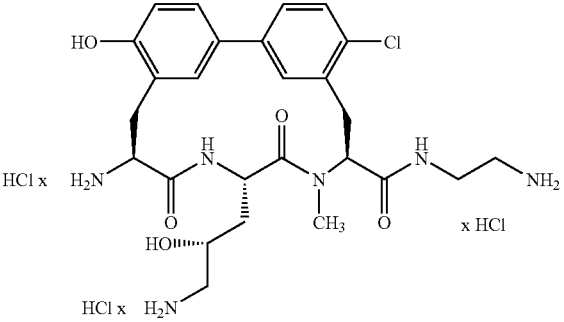 | 5 from Example 29B1 Yield: 99% of theory | LC-MS (method 2): $R_t$ = 0.48 min. MS (EI): m/z = 546 (M − 3HCl + H)$^+$ |
| 9 | 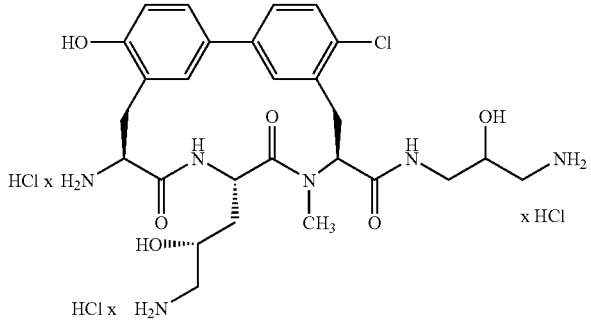 | 5 from Example 29B2 Yield: 97% of theory | LC-MS (method 3): $R_t$ = 0.29 min. MS (EI): m/z = 576 (M − 3HCl + H)$^+$ |
| 10 | 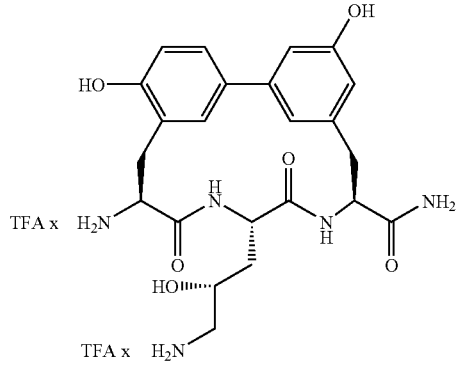 | 6 from Example 29J Yield: 38% of theory | LC-MS (method 5): $R_t$ = 0.77 min. MS (EI): m/z = 470 (M − 2TFA − H)$^-$ |
| 11 | 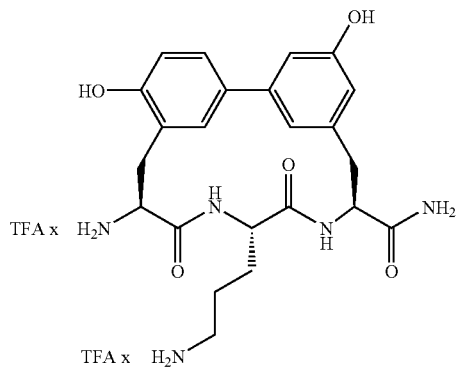 | 6 from Example 29K Yield: 45% of theory | LC-MS (method 8): $R_t$ = 1.41 min. MS (EI): m/z = 456 (M − 2TFA + H)$^+$ |

| Example No. | Structure | Prepared in analogy to Example No. | Analytical data |
|---|---|---|---|
| 12 | 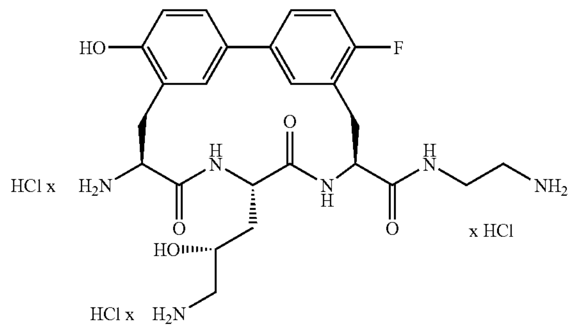 | 5 from Example 29L Yield: 99% of theory | LC-MS (method 17): $R_t$ = 2.20 min. MS (EI): m/z = 517 (M − 3HCl + H)$^+$ |

Example 13

(8S,11S,14S)-14-Amino-11-[(2R)-3-amino-2-hydroxypropyl]-N-(2-amino-2-oxoethyl)-5-chloro-17-hydroxy-10,13-dioxo-9,12-diazatricyclo[14.3.1.1$^{2,6}$] henicosa-1(20),2(21),3,5,16,18-hexaene-8-carboxamide di(hydrotrifluoroacetate)

41 mg (0.04 mmol) of the compound from Example 27C1 are dissolved in 0.5 ml of a 33% solution of hydrogen bromide in acetic acid and stirred at RT for 45 min. The mixture is then cautiously (bath temperature max. 40° C.) evaporated to dryness, and the crude product is taken up in 7 ml of THF/methanol/water (4:2:1). 2 mg (0.08 mmol) of lithium hydroxide are added, and the mixture is stirred at RT for 12 h, The mixture is concentrated in vacuo, taken up in 3 ml of 0.1N hydrochloric acid and stirred at RT for 15 min. The solvent is evaporated in vacuo and the crude product is purified by HPLC (Kromasil 100C18, mobile phase acetonitrile/0.2% aqueous TFA, gradient).

Yield: 8.25 mg (29% of theory) LC-MS (method 1): $R_t$=1.15 min MS (EI): m/z=547 (M-2TFA+H)$^{+1}$H-NMR (400 MHz, D$_2$O): δ=1.83 (m$_c$, 1H), 1.97 (m$_c$, 1H), 2.84 (m$_c$, 1H), 2.93-3.08 (m, 3H), 3.40 (m$_c$, 1H), 3.53 (m$_c$, 1H), 3.75-4.0 (m, 3H), 4.38 (m$_c$, 1H), 4.78 (m$_c$, 1H), 4.85 (m$_c$, 1H), 6.90 (d, 1H), 6.97 (s, 1H), 7.30 (s, 1H), 7.33-7.50 (m, 3H).

Example 14

Methyl 3-amino-N-{[(8S,11S,14S)-14-amino-11-[(2R)-3-amino-2-hydroxypropyl]-5-chloro-17-hydroxy-10,13-dioxo-9,12-diazatricy-clo[14.3.1.1$^{2,6}$] henicosa-1(20),2(21),3,5,16.18-hexaen-8-yl]carbonyl}-L-alaninate tri(hydrotrifluoroacetate)

51 mg (0.044 mmol) of the compound from Example 27C2 are dissolved in 1 ml of a 33% solution of hydrogen bromide in acetic acid and stirred at RT for 45 min. The solution is then concentrated in vacuo, and the crude product is dissolved in 2 ml of DMF and 2 mg of lithium hydroxide are added. The mixture is stirred at RT for 12 h. The solvent is evaporated in vacuo and the crude product is purified by HPLC (Kromasil 100C18, mobile phase acetonitrile/0.2% aqueous TFA, gradient).

Yield: 17.8 mg (43% of theory) LC-MS (method 3): $R_t$=0.57 min MS (EI): m/z=591(M-3TFA+H)$^{+1}$H-NMR (400 MHz, D$_2$O): δ=1.85 (m$_c$, 1H), 1.97 (m$_c$, 1H), 2.84 (m$_c$, 1H), 2.95-3.12 (m, 3H), 3.30 (m$_c$, 1H), 3.4-3.6 (m, 4H), 3.75 (s, 3H), 3.85 (m$_c$, 1H), 4.38 (m$_c$, 1H), 4.78 (m$_c$, 1H), 4.87 (m$_c$, 1H), 6.90 (d, 1H), 7.0 (s, 1H), 7.34 (s, 1H), 7.37-7.55 (m, 3H).

Example 15

3-Amino-N-{[(8S,11S,14S)-14-amino-11-[(2R)-3-amino-2-hydroxypropyl]-5-chloro-17-hydroxy-10,13-dioxo-9,12-diazatricyclo-[14.3.1.1$^{2,6}$]henicosa-1(20),2(21),3,5,16,18-hexaen-8-yl]carbonyl}-L-alanine tri(hydrotrifluoroacetate)

Example 16

N-{[(8S,11S,14S)-14-Amino-11-[(2R)-3-amino-2-hydroxypropyl]-5-chloro-17-hydroxy-10,13-dioxo-9,12-diazatricyclo[14.3.1.1$^{2,6}$]-henicosa-1(20),2(21),3,5,16,18-hexaen-8-yl]carbonyl}-L-serine di(hydrotrifluoroacetate)

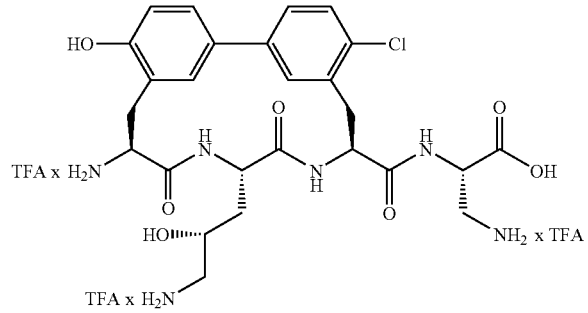

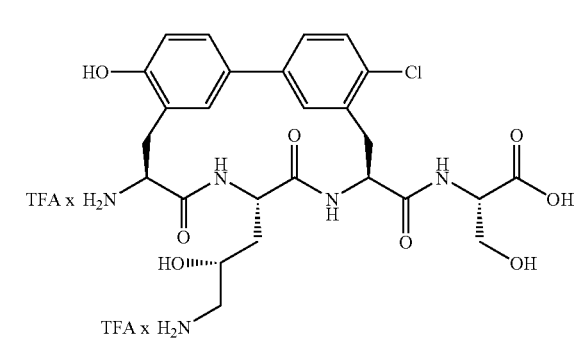

Example 15 is formed as by-product of the reaction to give Example 14 and is likewise isolated by HPLC (Kromasil 100C18, mobile phase acetonitrile/0.2% aqueous TFA, gradient).

Yield: 3.8 mg (8% of theory) LC-MS (method 3): R$_t$=0.76 min MS (EI): m/z=577 (M-3TFA+H)$^{+1}$H-NMR (400 MHz, D$_2$O): δ=1.85 (m$_c$, 1H), 1.96 (m$_c$, 1H), 2.86 (m$_c$, 1H), 2.95-3.14 (m, 3H), 3.23 (m$_c$, 1H), 3.27-3.6 (m, 4H), 3.85 (m$_c$, 1H), 4.38 (m$_c$, 1H), 4.78 (m$_c$, 1H), 4.87 (m$_c$, 1H), 6.90 (d, 1H), 6.98 (s, 1H), 7.28 (s, 1H), 7.33-7.53 (m, 3H).

51 mg (0.044 mmol) of the compound from Example 27C8 are dissolved in 1 ml of a 33% solution of hydrogen bromide in acetic acid and stirred at RT for 45 min. The solution is then concentrated in vacuo, and the crude product is dissolved in 2 ml of DMF and 2 mg of lithium hydroxide are added. The mixture is stirred at 60° C. for 12 h. The solvent is evaporated in vacuo and the crude product is purified by HPLC (Kromasil 100C18, mobile phase acetonitrile/0.2% aqueous TFA, gradient).

Yield: 3.86 mg (11% of theory) LC-MS (method 2): R$_t$=0.91 min MS (EI): m/z=578 (M-2TFA+H)$^{+1}$H-NMR (400 MHz, D$_2$O): δ=1.84 (m$_c$, 1H), 1.97 (m$_c$, 1H), 2.68-3.10 (m, 3H), 3.37 (m$_c$, 1H), 3.53 (m$_c$, 1H), 3.85 (m$_c$, 1H), 4.38 (m$_c$, 1H), 4.47 (m$_c$, 1H), 4.76 (m$_c$, 1H), 4.96 (m$_c$, 1H), 6.86 (d, 1H), 6.94 (s, 1H), 7.27 (s, 1H), 7.3-7.5 (m, 3H).

Examples 17 to 24 listed in the following table are prepared from the appropriate precursors in analogy to the methods detailed above:

| Example No. | Structure | Prepared in analogy to Example No. | Analytical data |
|---|---|---|---|
| 17 | 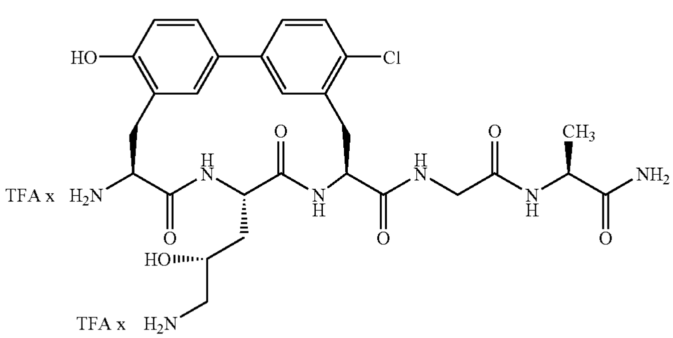 | 13 from Example 27C3 Yield: 25% of theory | LC-MS (method 2): R$_t$ = 0.92 min. MS (EI): m/z = 618 (M − 2TFA + H)$^+$ $^1$H-NMR (400 MHz, D$_2$O): δ = 1.33 (d, 3H), 1.83 (m$_c$, 1H), 1.98 (m$_c$, 1H), 2.85 (m$_c$, 1H), 2.95-3.1 (m, 3H), 3.4 (m$_c$, 1H), 3.53 (m$_c$, 1H), 3.83 (m$_c$, 1H), 3.95 (m$_c$, 2H), 4.22 (q, 1H), 4.38 (m$_c$, 1H), 4.77 (m$_c$, 1H), 4.84 (m$_c$, 1H), 6.90 (d, 1H), 6.96 (s, 1H), 7.3 (s, 1H), 7.35-7.5 (m, 3H). |

-continued

| Example No. | Structure | Prepared in analogy to Example No. | Analytical data |
|---|---|---|---|
| 18 | (structure) | 14 from Example 27C4 Yield: 59% of theory | LC-MS (method 3): $R_t$ = 1.13 min. MS (EI): m/z = 604 (M − 2TFA + H)⁺ 1H-NMR (400 MHz, D$_2$O): δ = 1.83 (m$_c$, 1H), 1.98 (m$_c$, 1H), 2.85 (m$_c$, 1H), 2.95-3.1 (m, 3H), 3.4 (m$_c$, 1H), 3.53 (m$_c$, 1H), 3.83 (m$_c$, 1H), 3.95 (m$_c$, 2H), 4.22 (q, 1H), 4.38 (m$_c$, 1H), 4.77 (m$_c$, 1H), 4.84 (m$_c$, 1H), 6.87 (d, 1H), 6.95 (s, 1H), 7.27 (s, 1H), 7.3-7.5 (m, 3H). |
| 19 | (structure) | 14 from Example 27C5 Yield: 59% of theory | LC-MS (method 3): $R_t$ = 1.19 min. MS (EI): m/z = 561 (M − 2TFA + H)⁺ 1H-NMR (400 MHz, D$_2$O): δ = 1.83 (m$_c$, 1H), 1.98 (m$_c$, 1H), 2.66 (s, 3H), 2.85 (m$_c$, 1H), 2.92-3.08 (m, 3H), 3.4 (m$_c$, 1H), 3.52 (m$_c$, 1H), 3.75-3.95 (m, 3H), 4.37 (m$_c$, 1H), 4.76 (m$_c$, 1H), 4.84 (m$_c$, 1H), 4.84 (m$_c$, 1H), 6.88 (d, 1H), 6.95 (s, 1H), 7.29 (s, 1H), 7.35-7.5 (m, 3H). |
| 20 | (structure) | 14 from Example 27C6 Yield: 40% of theory | LC-MS (method 2): $R_t$ = 0.91 min. MS (EI): m/z = 605 (M − 2TFA + H)⁺ 1H-NMR (400 MHz, d$_2$O): δ = 1.83 (m$_c$, 1H), 1.98 (m$_c$, 1H), 2.66-3.08 (m, 6H), 3.32 (m$_c$, 1H), 3.53 (m$_c$, 1H), 3.82 (m$_c$, 1H), 4.37 (m$_c$, 1H), 4.56 (m$_c$, 1H), 4.76 (m$_c$, 1H), 4.84 (m$_c$, 1H), 6.8-6.95 (m, 2H), 7.21 (s, 1H), 7.3-7.45 (m, 3H). |
| 21 | (structure) | 14 from Example 27C7 Yield: 21% of theory | MS (EI): m/z = 628 (M − 3TFA + H)⁺ 1H-NMR (400 MHz, D$_2$O): δ = 1.80 (m$_c$, 1H), 1.95 (m$_c$, 1H), 2.75-3.2 (m, 6H), 3.27 (m$_c$, 1H), 3.50 (m$_c$, 1H), 3.81 (m$_c$, 1H), 4.37 (m$_c$, 1H), 4.48 (m$_c$, 1H), 4.68 (m$_c$, 1H), 4.75 (m$_c$, 1H), 6.83-6.97 (m, 2H), 7.21 (s, 1H), 7.26 (s, 1H), 7.3-7.5 (m, 3H), 8.57 (s, 1H). |

-continued

| Example No. | Structure | Prepared in analogy to Example No. | Analytical data |
|---|---|---|---|
| 22 | 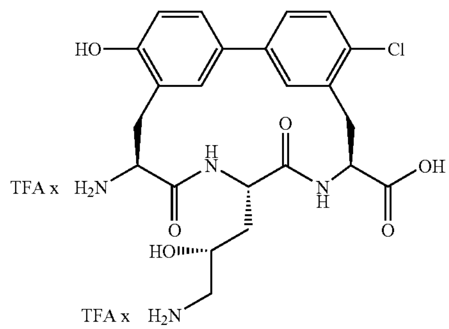 | 14 from Example 23C Yield: 25% of theory | LC-MS (method 8): $R_t$ = 1.67 min. MS (EI): m/z = 491 (M − 2TFA + H)$^+$ 1H-NMR (400 MHz, D$_2$O): δ = 1.81 (m$_c$, 1H), 1.97 (m$_c$, 1H), 2.83 (m$_c$, 2H), 2.96 (m$_c$, 1H), 3.05 (m$_c$, 1H), 3.48 (m$_c$, 2H), 3.88 (m$_c$, 1H), 4.35 (m$_c$, 1H), 4.57 (m$_c$, 1H), 4.75 (m$_c$, 1H), 6.8-6.93 (m, 2H), 7.20 (s, 1H), 7.25-7.45 (m, 3H). |
| 23 | 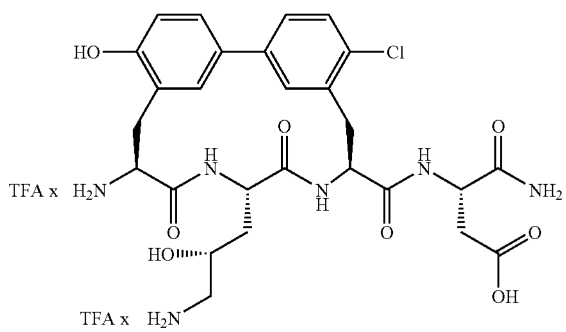 | 14 from Example 27C9 Yield: 9% of theory | LC-MS (method 2): $R_t$ = 0.92 min. MS (EI): m/z = 605 (M − 2TFA + H)$^+$ 1H-NMR (400 MHz, D$_2$O): δ = 1.83 (m$_c$, 1H), 1.98 (m$_c$, 1H), 2.66-3.1 (m, 6H), 3.28 (m$_c$, 1H), 3.54 (m$_c$, 1H), 3.82 (m$_c$, 1H), 4.40 (m$_c$, 1H), 4.7-4.8 (m, 2H, under D$_2$O signal), 4.85 (m$_c$, 1H), 6.8-6.93 (m, 2H), 7.20 (s, 1H), 7.25-7.47 (m, 3H). |
| 24 | 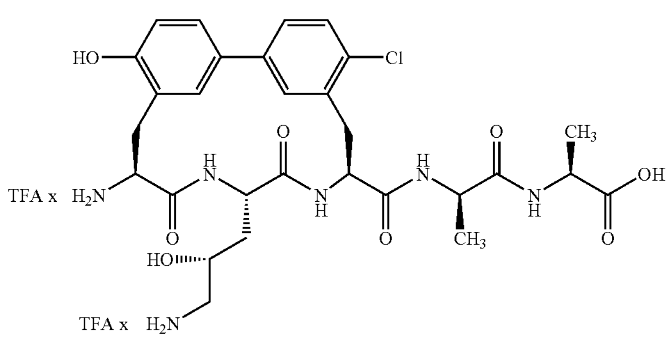 | 14 from Example 27C10 Yield: 18% of theory | LC-MS (method 3): $R_t$ = 0.32 min. MS (EI): m/z = 633 (M − 2TFA + H)$^+$ 1H-NMR (400 MHz, D$_2$O): δ = 1.28 (d, 3H), 1.35 (d, 3H), 1.80 (m$_c$, 1H), 1.98 (m$_c$, 1H), 2.84 (m$_c$, 1H), 2.93-3.1 (m, 3H), 3.35 (m$_c$, 1H), 3.53 (m$_c$, 1H), 3.77 (m$_c$, 1H), 4.06 (q, 1H), 4.24 (q, 1H), 4.37 (m$_c$, 1H), 4.67-4.85 (m, 2H, under D$_2$O signal), 6.90 (d, 1H), 7.0 (s, 1H), 7.31 (s, 1H), 7.35-7.52 (m, 3H). |

Example 25

(8S,11S,14S)-14-Amino-11-[(2R)-3-amino-2-hydroxypropyl]-17-hydroxy-10,13-dioxo-9,12-diazatricyclo[14.3.1.1$^{2,6}$]henicosa-1(20),2(21),3,5,16,18-hexaene-8-carboxylic acid di(hydrotrifluoroacetate)

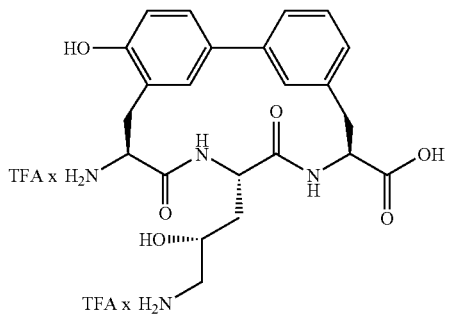

30 mg (0.03 mmol) of the compound from Example 23D are suspended in 50 ml of glacial acetic acid:water:THF=4:1:1 and, after the addition of 10 mg of Pd/C (10%) catalyst, hydrogenated under atmospheric pressure at RT for 1 day. The crude product is purified by HPLC (Kromasil 100C18, mobile phase acetonitrile/0.2% aqueous TFA 1:3).

Yield: 25 mg (95% of theory) LC-MS (method 14): $R_t$=1.69 min MS (EI): m/z=457 (M-2TFA+H)$^{+1}$H-NMR (400 MHz, D$_2$O): δ=1.83 (m$_c$, 1H), 1.95 (m$_c$, 1H), 2.83 (m$_c$, 1H), 2.9-3.1(m, 3H), 3.16 (m$_c$, 1H), 3,52 (m$_c$, 1H), 3.88 (m$_c$, 1H), 4.38 (m$_c$, 1H), 4.52 (m$_c$, 1H), 4.72 (m$_c$, 1H), 6.85-7.0 (m, 2H), 7.14 (d, 1H), 7.24-7.48 (m, 4H).

Example 26

(8S,11S,14S)-14-Amino-N-(2-aminoethyl)-11-(3-aminopropyl)-17-hydroxy-5-methyl-10,13-dioxo-9,12-diazatricyclo[14.3.1.1$^{2,6}$]-henicosa-1(20),2(21),3,5,16,18-hexaene-8-carboxamide trihydrochloride

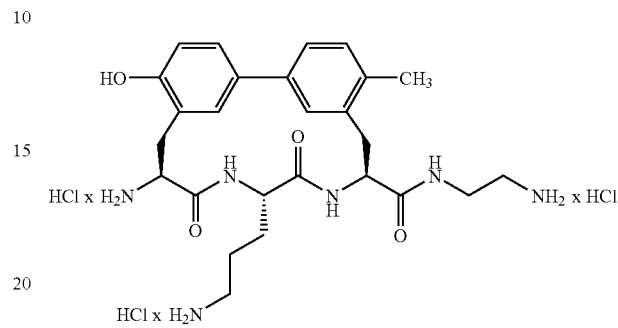

19 mg (0.020 mmol) of the compound from Example 27E are suspended in 12 ml of glacial acetic acid:water:ethanol=4:1:1 and, after the addition of 10 mg of Pd/C (10%) catalyst, hydrogenated under atmospheric pressure at room temperature for 2 days. The catalyst is filtered off, and the filtrate is mixed with 0.5 ml of 0.1N hydrochloric acid, evaporated in vacuo and dried under high vacuum. The residue is stirred with 2.5 ml of dioxane:methanol (4:1), and the product is filtered off.

Yield: 2.9 mg (5% of theory) LC-MS (method 2): $R_t$=0.31 min. MS (EI): m/z=497 (M-3HCl+H)$^+$ Examples 27 to 34 listed in the following table are prepared from the appropriate precursors in analogy to the methods detailed above:

| Example No. | Structure | Prepared in analogy to Example No. | Analytical data |
|---|---|---|---|
| 27 | 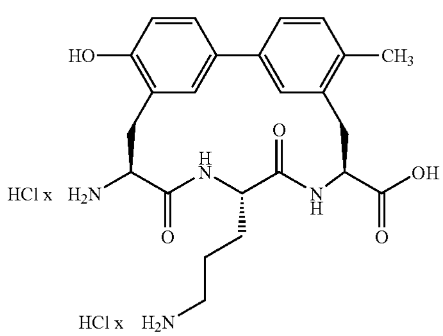 | 26 from Example 23E Yield: 72% of theory | LC-MS (method 5): $R_t$ = 1.23 min. MS (EI): m/z = 455 (M − 2HCl + H)$^+$ |

-continued

| Example No. | Structure | Prepared in analogy to Example No. | Analytical data |
|---|---|---|---|
| 28 | 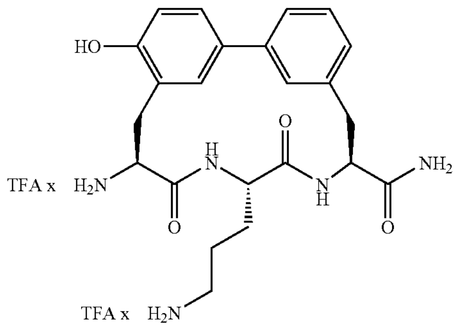 | 25 from Example 27F1 Yield: 15% of theory | MS (EI): m/z = 440 (M − 2TFA + H)+ 1H-NMR (400 MHz, D2O): δ = 1.5-1.8 (m, 4H), 2.8-3.2 (m, 5H), 3.54 (mc, 1H), 4.42 (mc, 1H), 4.65∝4.8 (m, 2H, under D2O signal), 6.85-7.0 (m, 2H), 7.13 (d, 1H), 7.25-7.48 (m, 4H). |
| 29 | 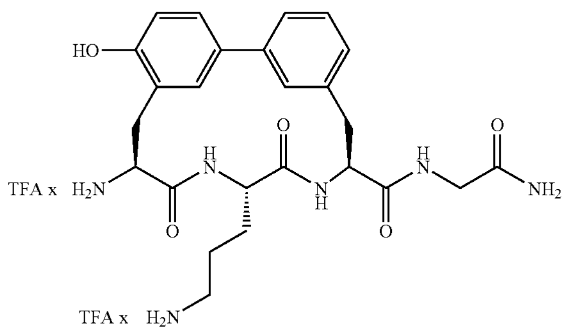 | 25 from Example 27F2 Yield: 68% of theory | MS (EI): m/z = 497 (M − 2TFA + H)+ 1H-NMR (400 MHz, D2O): δ = 1.5-1.9 (m, 4H), 2.85-3.15 (m, 5H), 3.54 (mc, 1H), 3.88 (mc, 2H), 4.42 (mc, 1H), 4.7 (m, 1H, under D2O signal), 4.78 (mc, 1H), 6.85-7.0 (m, 2H), 7.13 (d, 1H), 7.25-7.48 (m, 4H). |
| 30 | 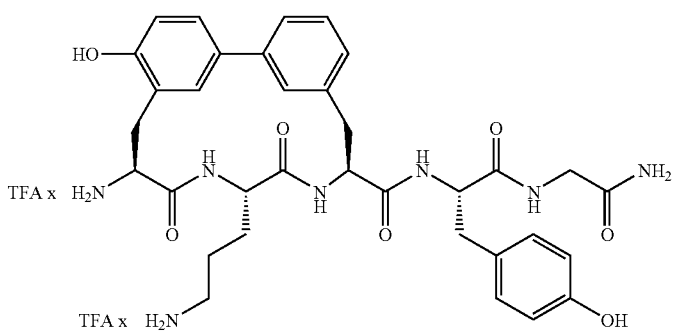 | 25 from Example 27F4 Yield: 21% of theory | MS (EI): m/z = 660 (M − 2TFA + H)+ 1H-NMR (400 MHz, D2O): δ = 1.4-1.7 (m, 4H), 2.75-3.1 (m, 7H), 3.54 (mc, 1H), 3.80 (mc, 2H), 4.42 (mc, 1H), 4.53 (mc, 1H), 4.58 (mc, 1H), 4.7 (m, 1H, under D2O signal), 6.73 (d, 2H), 6.85-7.0 (m, 2H), 7.03-7.13 (m, 3H), 7.22 (s, 1H), 7.28 (t, 1H), 7.33-7.46 (m, 2H). |
| 31 | 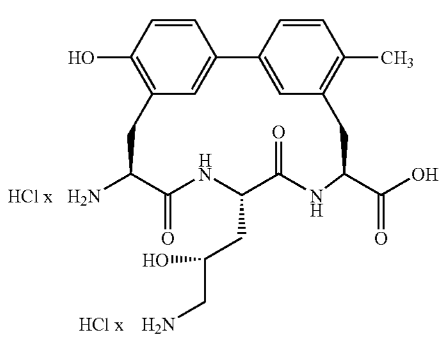 | 26 from Example 23G Yield: 57% of theory | LC-MS (method 5): Rt = 1.24 min. MS (EI): m/z = 471 (M − 2HCl + H)+ |

-continued

| Example No. | Structure | Prepared in analogy to Example No. | Analytical data |
|---|---|---|---|
| 32 | 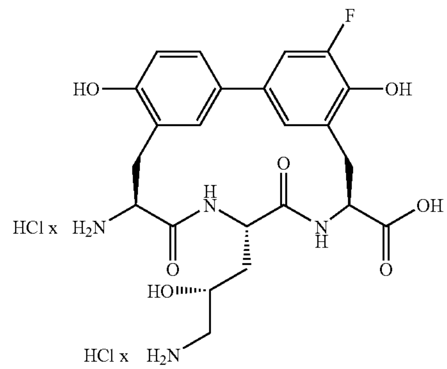 | 26 from Example 23H Yield: 76% of theory | LC-MS (method 5): $R_t$ = 0.98 min. MS (EI): m/z = 491 [M + H]$^+$ |
| 33 | 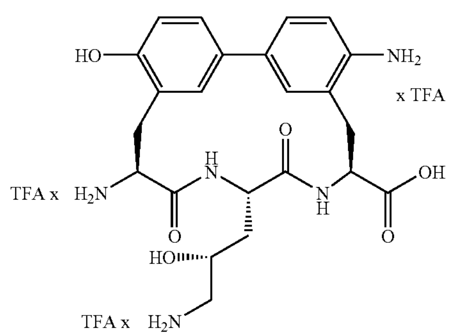 | 25 from Example 23I Yield: 49% of theory | MS (EI): m/z = 472 (M − 3TFA + H)$^+$ 1H-NMR (400 MHz, D$_2$O): δ = 1.83 (m$_c$, 1H), 1.96 (m$_c$, 1H), 2.75-3.1 (m, 4H), 3.22 (m$_c$, 1H), 3.54 (m$_c$, 1H), 3.85 (m$_c$, 1H), 4.38 (m$_c$, 1H), 4.53 (m$_c$, 1H), 4.78 (m$_c$, 1H), 6.90 (d, 1H), 6.97 (s, 1H), 7.29 (d, 1H), 7.38-7.53 (m, 3H). |
| 34 | 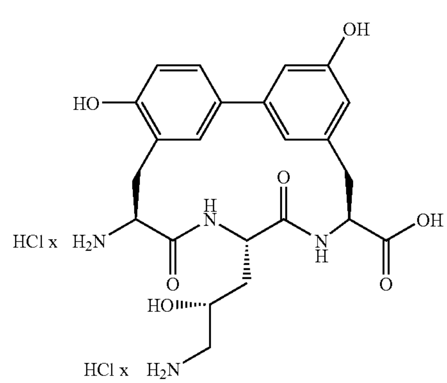 | 26 from Example 23J Yield: 98% of theory | LC-MS (method 8): $R_t$ = 1.42 min. MS (EI): m/z = 473 (M − 2HCl + H)$^+$ |

Example 35

(8S,11S,14S)-14-Amino-11-(3-aminopropyl)-17-hydroxy-10,13-di-oxo-9,12-diazatricyclo[14.3.1.1$^{2,6}$]henicosa-1(20),2(21),3,5,16,18-hexaene-8-carboxylic acid dihydrochloride

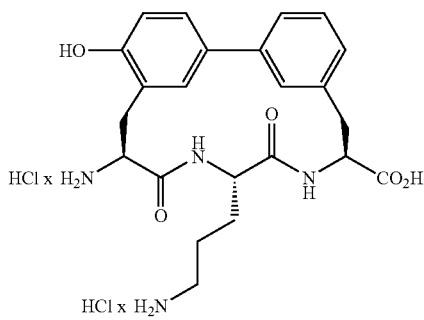

Preparation takes place in analogy to Example 1 from 140 mg (0.16 mmol) of the compound from Example 23F in 150 ml of glacial acetic acid/water/ethanol=4/1/1 with 50 mg of Pd/C catalyst (10%).

Yield: 80 mg (95% of theory) LC-MS (method 14): $R_t$=1.53 min. MS (EI): m/z=441 (M-2HCl+H)$^{+1}$H-NMR (400 MHz, D$_2$O): δ=1.79 (m$_c$, 3H), 1.94 (m$_c$, 1H), 2.8-3.3 (m, 5H), 3.63 (m$_c$, 1H), 4.51(m$_c$, 1H), 4.65-4.85 (m, 2H), 7.0 (d, 1H), 7.05 (s, 1H), 7.25 (d, 1H), 7.35-7.54 (m, 4H).

Example 36

(8S,11S,14S)-14-Amino-N-(2-aminoethyl)-11-[(2R)-3-amino-2-hydroxypropyl]-17-hydroxy-10,13-dioxo-9,12-diazatricyclo-[14.3.1.1$^{2,6}$]henicosa-1(20),2(21),3,5,16,18-hexaene-8-carboxamide tri (hydrotrifluoroacetate)

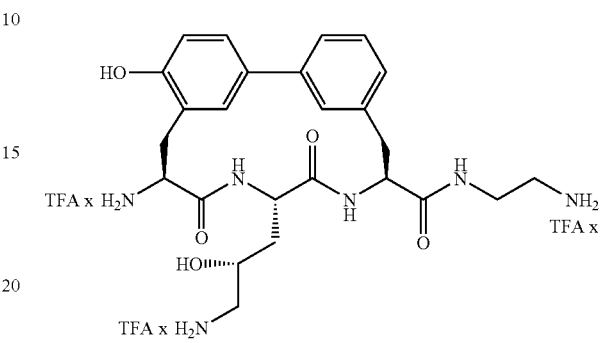

43 mg (0.04 mmol) of the compound from Example 27C11 are suspended in 23 ml of glacial acetic acid/water/ethanol (4/1/1) and, after the addition of 8 mg of Pd/C catalyst (10%), hydrogenated under atmospheric pressure at RT for 24 h. The catalyst is removed on a membrane filter, and the filtrate is concentrated in vacuo. The crude product is taken up in 0.1 ml of a 4N dioxane/hydrogen chloride solution and stirred at RT for 2 h. The solvent is evaporated in vacuo and the crude product is purified by HPLC (Kromasil 100C18, mobile phase acetonitrile/0.2% aqueous TFA, gradient).

Yield: 6.1 mg (29% of theory) LC-MS (method 17): $R_t$=2.19 min MS (EI): m/z=499 (M-3TFA+H)$^{+1}$H-NMR (400 MHz, D$_2$O): δ=1.87 (m$_c$, 1H), 1.97 (m$_c$, 1H), 2.86 (m$_c$, 1H), 3.0-3.15 (m, 6H), 3,50 (m$_c$, 2H), 3,55 (m$_c$, 1H), 3.85 (m$_c$, 1H), 4.42 (m$_c$, 1H), 4.73 (m$_c$, 1H), 4.85 (m$_c$, 1H), 6.94 (d, 1H), 6.98 (s, 1H), 7.13 (s, 1H), 7.25-7.37 (m, 2H), 7.4-7.48 (m, 2H).

Examples 37 and 38 listed in the following table are prepared from the appropriate precursors in analogy to the methods detailed above:

| Example No. | Structure | Prepared in analogy to Example No. | Analytical data |
|---|---|---|---|
| 37 | 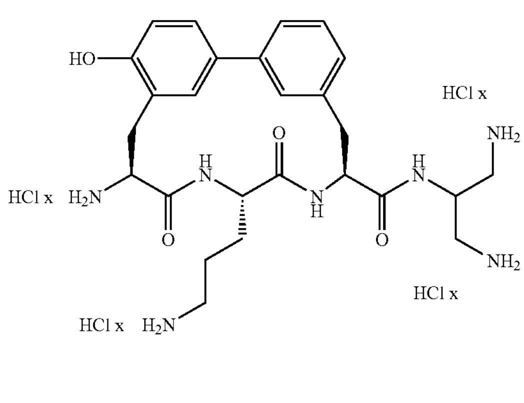 | 5 from Example 29F1 | LC-MS (method 2): $R_t$ = 0.24 min. MS (EI): m/z = 512 (M − 4HCl + H)$^+$ |

| Example No. | Structure | Prepared in analogy to Example No. | Analytical data |
|---|---|---|---|
| 38 | 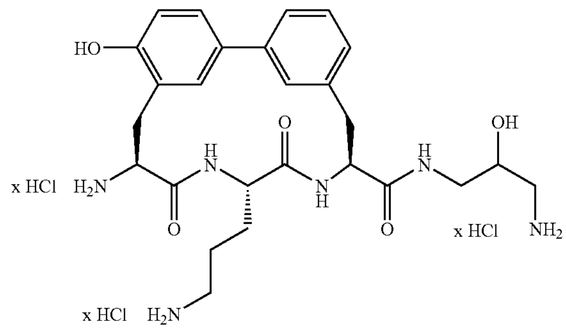 | 5 from Example 29F2 | LC-MS (method 17): $R_t$ = 2.32 min. MS (EI): m/z = 513 (M – 3HCl + H)$^+$ |

Example 39

(8S,11S,14S)-14-Amino-N-(2-aminoethyl)-11-(3-aminopropyl)-5-fluoro-17-hydroxy-9-methyl-10,13-dioxo-9,12-diazatricyclo-[14.3.1.1$^{2,6}$]henicosa-1(20),2(21),3,5,16,18-hexaene-8-carbox-amide tri (hydrotrifluoroacetate)

25 mg (0.029 mmol) of benzyl {3-[(8S,11S,14S)-8-{[(2-aminoethyl)amino]carbonyl}-17-(benzyloxy)-14-{[(benzyloxy)carbonyl]-amino}-5-fluoro-9-methyl-10,13-dioxo-9,12-diazatricyclo[14.3.1.1$^{2,6}$]henicosa-1(20),2(21),3,5,16,18-hexaen-11-yl]pro-pyl}carbamate (Example 30O) are added into a mixture of 5 ml of acetic acid/water/ethanol (4:1:1) mixture. 10 mg of palladium on activated carbon (10%) are added, and the mixture is hydrogenated under atmospheric pressure at RT for 15 h. The reaction mixture is filtered through prewashed kieselguhr, washed with ethanol, and the filtrate is concentrated in vacuo on a rotary evaporator. The residue is mixed with 0.1N hydrochloric acid and concentrated in vacuo. The remaining solid is dried under high vacuum. The trihydrochloride is converted into the tri(hydrotrifluoroacetate) by preparative HPLC (Kromasil 100C18, mobile phase acetonitrile/0.2% aqueous trifluoroacetic acid 5:95→95:5).

Yield: 11 mg (45% of theory) LC-MS (method 17): $R_t$=2.18 min. MS (EI): m/z=515 (M-3CF$_3$CO$_2$H+H)$^+$. 1H-NMR (400 MHz, D$_2$O): δ=1.56-1.94 (m, 8H), 2.85-3.60 (m, 9H), 2.92 (s, 3H), 5.70 (m, 1H), 6.90 (d, 1H), 6.96 (s, 1H), 7.10-7.20 (m, 2H), 7.40-7.60 (m, 2H).

Example 40

(8S,11S,14S)-14-Amino-11-(3-aminopropyl)-5-fluoro-17-hydroxy-9-methyl-10,13-dioxo-9,12-diazatricyclo[14.3.1.1$^{2,6}$]henicosa-1(20),2(21),3,5,16,18-hexaene-8-carboxylic acid dihydrochloride 275 mg (0.331 mmol) of (8S,11S,14S)-17-(benzyloxy)-14-{[(benzyloxy)carbonyl]amino}-11-(3-{[(benzyloxy)carbonyl]-amino}propyl)-5-fluoro-9-methyl-10,13-dioxo-9,12-diazatricyclo[14.3.1.1$^{2,6}$]henicosa-1(20),2(21),3,5,16,18-hexaene-8-carboxylic acid (Example 26O) are added into a mixture of 90 ml of acetic acid/water/ethanol (4:1:1). 300 mg of palladium on activated carbon (10%) are added, and the mixture is then hydrogenated under atmospheric pressure at RT for 15 h. The reaction mixture is filtered through prewashed kieselguhr, washed with ethanol, and the filtrate is concentrated in vacuo on a rotary evaporator. The residue is mixed with 0.1N hydrochloric acid and concentrated. The remaining solid is dried under high vacuum.

Yield: quant. LC-MS (method 17): $R_t$=2.47 min. MS (EI): m/z=473 (M-2HCl+H)$^+$.

Example 41

(8S,11S,14S)-14-Amino-11-(3-aminopropyl)-5-chloro -N-[(2S)-2,5-diaminopentyl]-17-hydroxy-9-methyl-10,13-dioxo-9,12-diazatricyclo[14.3.1.1$^{2,6}$]henicosa-1(20),2(21),3,5,16,18-hexaene-8-carboxamide tetrahydrochloride

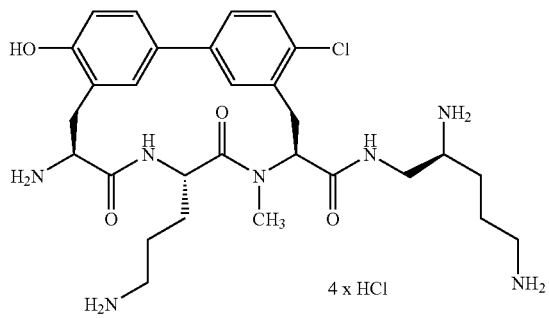

11.4 mg (0.012 mmol) of the compound from Example 29M2 are dissolved in 0.05 ml of dioxane at RT, and 0.175 ml of a 4N hydrogen chloride/dioxane solution are added and the mixture is stirred for 2 h. The mixture is evaporated to dryness in vacuo and dried to constant weight under high vacuum.

Yield: 7.9 mg (93% of theory) MS (ESI): m/z=588 (M-4HCl+H)$^+$ $^1$H-NMR (400 MHz, D$_2$O): δ=1.55-1.95 (m, 8H), 2.85 (s, 3H), 2.9-3.1(m, 6H), 3.25-3.75 (m, 7H), 4.45 (m$_c$, 1H), 4.78 (m$_c$, 1H), 5.70 (m$_c$, 1H), 6.92 (d, 1H), 7.0 (s, 1H), 7.15 (s, 1H), 7.45 (d, 1H), 7.51(d, 1H), 7.57 (d, 1H).

Example 42

(8S,11S,14S)-14-Amino-11-(3-aminopropyl)-N-{2-[bis(2-aminoethyl)amino]ethyl}-5-chloro-17-hydroxy-9-methyl-10,13-dioxo-9,12-diazatricyclo[14.3.1.1$^{2,6}$]henicosa-1(20),2(21)3,5,16,18-hexaene-8-carboxamide penta(hydrotrifluoroacetate)

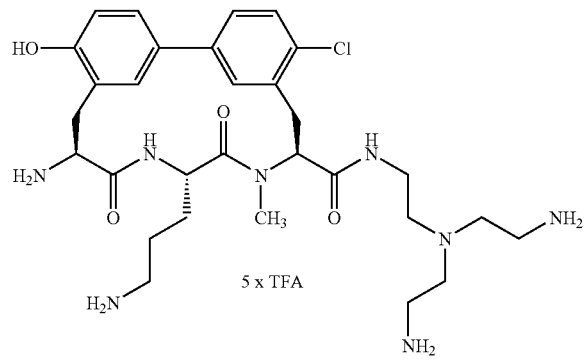

110 mg (0.113 mmol) of the compound from Example 30M1 are dissolved in 2 ml of a 33% solution of hydrogen bromide in acetic acid and stirred at RT for 45 min. The mixture is then concentrated in vacuo and the crude product is purified by HPLC (Kromasil 100C18, mobile phase acetonitrile/0.2% aqueous trifluoroacetic acid, gradient).

Yield: 64.1 mg (53% of theory) MS (ESI): m/z=617 (M-5TFA+H)$^{+1}$H-NMR (400 MHz, D$_2$O): δ=1.57-1.74 (m, 3H), 1.78-1.91 (m, 1H), 2.68 (t, 2H), 2.79 (m$_c$, 4H), 2.88 (s, 3H), 2.92 (m$_c$, 2H), 3.0-3.1(m, 5H), 3.15-3,5 (m, 4H), 3,57 (m$_c$, 1H), 4.44 (m$_c$, 1H), 4.80 (m$_c$, 1H), 5.63 (m$_c$, 1H), 6.91 (d, 1H), 6.98 (s, 1H), 7.13 (s, 1H), 7.43 (d, 1H), 7.50 (d, 1H), 7.56 (d, 1H).

Example 43

(8S,11S,14S)-5,14-Diamino-N-(2-aminoethyl)-11-(3-aminopropyl)-17-hydroxy-10,13-dioxo-9,12-diazatricyclo[14.3.1.1$^{2,6}$]henicosa-1(20),2(21),3,5,16,18-hexaene-8-carboxamide tetrahydrochloride

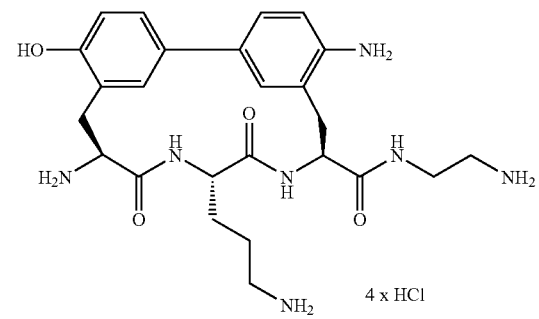

30 mg of the compound from Example 30P are added into a mixture of 28 ml acetic acid/water/ethanol (4:1:1). 16 mg of palladium on activated carbon (10%) are added and the mixture is then hydrogenated under atmospheric pressure at RT for 48 h. The reaction mixture is filtered through prewashed kieselguhr, washed with ethanol, and the filtrate is concentrated in vacuo on a rotary evaporator. The residue is mixed with 1.2 ml of 0.1N hydrochloric acid and again concentrated in vacuo. The remaining solid is dried under high vacuum.

Yield: 21 mg (96% of theory) LC-MS (method 17): R$_t$=0.73 min. MS (EI): m/z=498 (M-4HCl+H)$^+$ $^1$H-NMR (400 MHz, D$_2$O): δ=1.5-1.9 (m, 4H), 2.85-3.2 (m, 7H), 3.3-3.6(m, 3H), 4.42 (m$_c$, 1H), 4.6-4.7 (m, 1H, under D$_2$O), 4.87 (m$_c$, 1H), 6.90 (d, 1H), 7.01(s, 1H), 7.23 (d, 1H), 7.45 (s, 1H), 7.45-7.55 (m, 2H).

The trihydrochloride is converted into the tri(hydrotrifluoroacetate) by preparative HPLC (Kromasil 100C18, mobile phase acetonitrile/0.2% aqueous trifluoroacetic acid 5:95→95:5).

| Example No. | Structure | Prepared in analogy to Example No. | Analytical data |
|---|---|---|---|
| 44 | 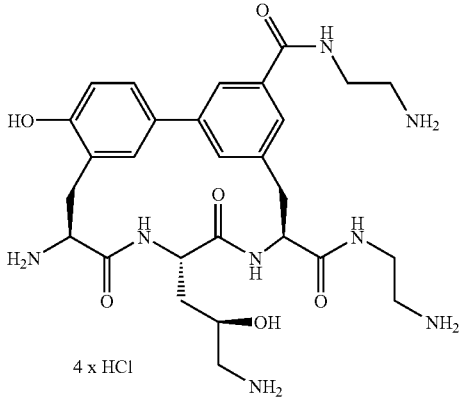 4 x HCl | 5 from Example 29N | LC-MS (method 17): $R_t$ = 1.88 min. MS (ES): m/z = 585 (M − 4HCl + H)$^+$ 1H-NMR (400 MHz, D$_2$O): δ = 1.8-2.0 (m, 2H), 2.75 (m$_c$, 1H), 2.95-3.23 (m, 6H), 3.4-3.75 (m, 6H), 3.86 (m$_c$, 1H), 4.40 (m$_c$, 1H), 4.7 (m, 1H, under D$_2$O), 4.83 (m$_c$, 1H), 6.9-7.0 (m, 2H), 7.4-7.55 (m, 3H), 7.78 (s, 1H). |
| 45 | 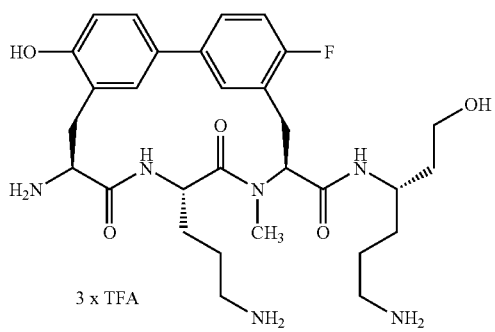 3 x TFA | 39 from Example 29O1 | LC-MS (method 17): $R_t$ = 2.18 min. MS (EI): m/z = 587 (M − 3TFA + H)$^+$ 1H-NMR (400 MHz, D$_2$O): δ = 1.53-1.87 (m, 10H), 2.64-3.62 (m, 12H), 4.53 (m, 1H), 4.92-4.97 (m, 1H), 5.66 (dd, 1H), 6.94 (d, 1H), 6.99 (s, 1H), 7.11-7.19 (m, 2H), 7.48-7.58 (m, 2H). |
| 46 | 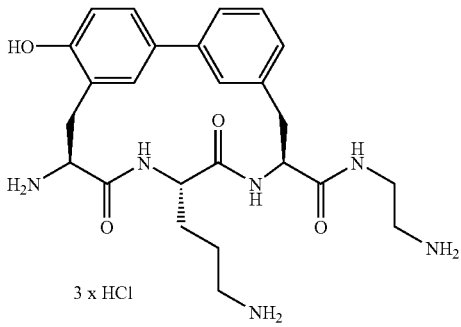 3 x HCl | 5 from Example 29F3 | LC-MS (method 17): $R_t$ = 2.04 min. MS (EI): m/z = 486 (M − 3HCl + H)$^+$ 1H-NMR (400 MHz, D$_2$O): δ = 1.55-1.9 (m, 4H), 2.93 (m$_c$, 2H), 2.97-3.17 (m, 5H), 3.45-3.6 (m, 3H), 4.41 (m$_c$, 1H), 4.6-4.8 (m, 2H under D$_2$O), 6.87-6.97 (m, 2H), 7.12 (m$_c$, 1H), 7.24-7.36 (m, 2H), 7.37-7.48 (m, 2H). |
| 47 | 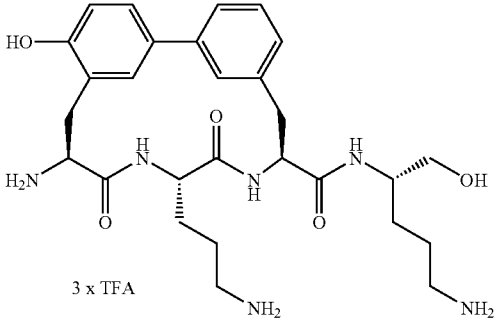 3 x TFA | 39 from Example 29F4 | LC-MS (method 17): $R_t$ = 1.85 min. MS (EI): m/z = 541 (M − 3TFA + H)$^+$ 1H-NMR (400 MHz, D$_2$O): δ = 1.5-1.9 (m, 8H), 3.85-3.15 (m, 7H), 3.45-3.9 (m, 4H), 4.41 (m$_c$, 1H), 4.6-4.8 (m, 2H under D$_2$O), 6.85-6.97 (m, 2H), 7.12 (m$_c$, 1H), 7.22-7.48 (m, 4H). |

-continued

| Example No. | Structure | Prepared in analogy to Example No. | Analytical data |
|---|---|---|---|
| 48 | (structure) 3 x TFA | 45 from Example 30M2 | LC-MS (method 17): $R_t$ = 2.30 min.<br>MS (EI): m/z = 531 (M − 3TFA + H)$^+$<br>1H-NMR (400 MHz, D$_2$O): δ = 1.5-1.9 (m, 4H), 2.87 (s, 3H), 2.95 (m$_c$, 2H), 3.03-3.15 (m, 3H), 3.26 (m$_c$, 1H), 3.38-3.6 (m, 4H), 4.43 (m$_c$, 1H), 4.88 (m$_c$, 1H), 5.66 (m$_c$, 1H), 6.87 (d, 1H), 6.98 (s, 1H), 7.12 (s, 1H), 7.38-7.6 (m, 3H). |
| 49 | (structure) 3 x TFA | 39 from Example 29M1 | LC-MS (method 17): $R_t$ = 2.40 min.<br>MS (EI): m/z = 561 (M − 3TFA + H)$^+$<br>1H-NMR (400 MHz, D$_2$O): δ = 1.58-1.75 (m, 3H), 1.78-1.92 (m, 1H), 2.85 (s, 3H), 2.94 (m$_c$, 2H), 3.05 (m$_c$, 1H), 3.28 (m$_c$, 1H), 3.38-3.68 (m, 7H), 3.75 (m$_c$, 1H), 4.44 (m$_c$, 1H), 4.80 (m$_c$, 1H), 5.70 (m$_c$, 1H), 6.90 (d, 1H), 7.0 (s, 1H), 7.15 (s, 1H), 7.43 (d, 1H), 7.50 (d, 1H), 7.56 (d, 1H). |
| 50 | (structure) 4 x HCl | 5 from Example 29P1 | MS (ESI): m/z = 584 (M − 4HCl + H)$^+$<br>1H-NMR (400 MHz, D$_2$O): δ = 1.5-1.9 (m, 4H), 2.6-3.1 (m, 8H), 3.15-3.35 (m, 3H), 3.45-3.75 (m, 3H), 3.9 (m$_c$, 1H), 4.40 (m$_c$, 1H), 4.6-4.7 (m, 1H, under D$_2$O), 4.78 (m$_c$, 1H), 6.85-6.93 (m, 2H), 6.96 (s, 1H), 7.25 (s, 1H), 7.33 (d, 1H), 7.40 (d, 1H) |
| 51 | (structure) 3 x TFA | 39 from Example 29P2 | LC-MS (method 17): $R_t$ = 1.90 min.<br>MS (EI): m/z = 526 (M − 3TFA + H)$^+$ |

| Example No. | Structure | Prepared in analogy to Example No. | Analytical data |
|---|---|---|---|
| 52 | 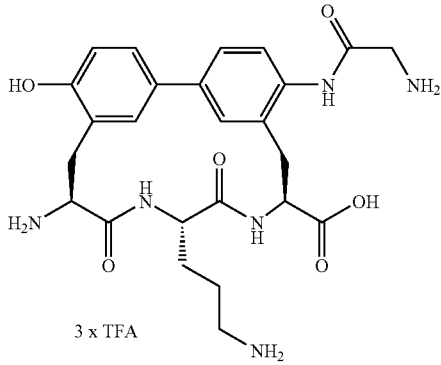 3 x TFA | 39 from Example 28P2 | LC-MS (method 17): $R_t$ = 1.37 min. MS (EI): m/z = 513 (M − 3TFA + H)$^+$ 1H-NMR (400 MHz, $D_2O$): δ = 1.63-1.95 (m, 4H), 2.85 ($m_c$, 1H), 2.98 ($m_c$, 2H), 3.10 ($m_c$, 1H), 3.25 ($m_c$, 1H), 3.58 (m, 1H), 4.04 (s, 2H), 4.45 ($m_c$, 1H), 4.57 ($m_c$, 1H), 4.6-4.8 (m, 1H, under $D_2O$), 6.96 (d, 1H), 7.07 (s, 1H), 7.30 (d, 1H), 7.4-7.6 (m, 3H). |

B. Assessment of the Physiological Activity

Abbreviations used:
AMP adenosine monophosphate
ATP adenosine triphosphate
BHI medium brain heart infusion medium
CoA coenzyme A
DMSO dimethylsulfoxide
DTT dithiothreitol
EDTA ethylenediaminetetraacetic acid
KCl potassium chloride
$KH_2PO_4$ potassium dihydrogenphosphate
$MgSO_4$ magnesium sulfate
MIC minimum inhibitory concentration
MTP microtitre plate
NaCl sodium chloride
$Na_2HPO_4$ disodium hydrogenphosphate
$NH_4Cl$ ammonium chloride
NTP nucleotide triphosphate
PBS phosphate-buffered saline
PCR polymerase chain reaction
PEG polyethylene glycol
PEP phosphoenolpyruvate
Tris tris[hydroxymethyl]aminomethane The in vitro effect of the compounds of the invention can be shown in the following assays:

In vitro Transcription-Translation with *E. coli* Extracts

In order to prepare an S30 extract logarithmically growing *Escherichia coli* MRE 600 (M. Müller; Freiburg University), are harvested, washed and employed as described for the in vitro transcription-translation assay (Müller, M. and Blobel, G. Proc Natl Acad Sci USA (1984) 81, pp. 7421-7425).

1 µl of cAMP (11.25 mg/ml) are additionally added per 50 µl of reaction mix to the reaction mix for the in vitro transcription-translation assay. The assay mixture amounts to 105 µl, with 5 µl of the substance to be tested being introduced in 5% DMSO. 1 µg/100 µl of mixture of the plasmid pBESTluc (Promega, Germany) are used as transcription templates. After incubation at 30° C. for 60 min, 50 µl of luciferin solution (20 mM tricine, 2.67 mM $MgSO_4$, 0.1 mM EDTA, 33.3 mM DTT pH 7.8, 270 µM CoA, 470 µM luciferin, 530 µM ATP) are added, and the resulting bioluminescence is measured in a luminometer for 1 minute. The concentration of an inhibitor which leads to 50% inhibition of the translation of firefly luciferase is indicated as the $IC_{50}$.

In Vitro Transcription-Translation with *S. aureus* Extracts

Construction of an *S. aureus* Luciferase Reporter Plasmid

In order to construct a reporter plasmid which can be used in an in vitro transcription -translation assay from *S. aureus* the plasmid pBESTluc (Promega Corporation, USA) is used. The *E. coli* tac promoter present in this plasmid in front of the firefly luciferase is replaced by the capA1 promoter with appropriate Shine-Dalgarno sequence from *S. aureus*. The primers CAPFor 5'-CGGCCAAGCTTACTCGGATCCA-GAGTTTGCAAAATATACAGGGGATTAT -ATATAATG-GAAAACAAGAAAGGAAAATAGGAGGTT-TATATGGAAGACGCCA-3' and CAPRev 5'-GTCATCGTCGGGAAGACCTG-3' are used for this. The primer CAPFor contains the capA1 promoter, the ribosome binding site and the 5' region of the luciferase gene. After PCR using pBESTluc as template it is possible to isolate a PCR product which contains the firefly luciferase gene with the fused capA1 promoter. This is, after restriction with ClaI and HindIII, ligated into the vector pBESTluc which has likewise been digested with ClaI and HindIII. The resulting plasmid pla can be replicated in *E. coli* and be used as template in the *S. aureus* in vitro transcription-translation assay.

Preparation of S30 Extracts from *S. aureus*

Six liters of BHI medium are inoculated with a 250 ml overnight culture of a *S. aureus* strain and allowed to grow at 37° C. until the OD600 nm is 2-4. The cells are harvested by centrifugation and washed in 500 ml of cold buffer A (10 mM Tris acetate, pH 8.0, 14 mM magnesium acetate, 1 mM DTT, 1 M KCl). After renewed centrifugation, the cells are washed in 250 ml of cold buffer A with 50 mM KCl, and the resulting pellets are frozen at −20° C. for 60 min. The pellets are thawed on ice in 30 to 60 min and taken up to a total volume of 99 ml in buffer B (10 mM Tris acetate, pH 8.0, 20 mM magnesium acetate, 1 mM DTT, 50 mM KCl). 1.5 ml lysostaphin (0.8 mg/ml) in buffer B are introduced into 3 precooled centrifuge cups each and each mixed with 33 ml of the cell suspension. The samples are incubated at 37° C., shaking occasionally, for 45 to 60 min, before 150 µl of a 0.5 M DTT solution are added. The lysed cells are centrifuged at 30 000×g and 4° C. for 30 min. The cell pellet is taken up in buffer B and then centrifuged again under the same conditions, and the collected supernatants are combined. The supernatants are centrifuged again under the same conditions, and 0.25 volumes of buffer C (670 mM Tris acetate, pH 8.0, 20 mM magnesium acetate, 7 mM $Na_3$ phosphoenolpyruvate, 7 mM DTT, 5.5 mM ATP, 70 µM amino acids (complete from Promega), 75 µg of pyruvate kinase (Sigma, Germany)/ml are added to the upper ⅔ of the supernatant. The samples are incubated at 37° C. for 30 min. The supernatants are dialysed against 2 l of dialysis buffer (10 mM Tris acetate, pH 8.0, 14 mM magnesium acetate, 1 mM DTT, 60 mM potassium acetate) in a dialysis tube with a 3500 Da cut-off with one buffer change at 4° C. overnight. The dialysate is concentrated to a protein concentration of about 10 mg/ml by covering the dialysis tube with cold PEG 8000 powder (Sigma, Germany) at 4° C. The S30 extracts can be stored in aliquots at −70° C.

Determination of the $IC_{50}$ in the *S. aureus* In Vitro Transcription-Translation Assay Inhibition of protein biosynthesis of the compounds can be shown in an in vitro transcription-translation assay. The assay is based on the cell-free transcription and translation of firefly luciferase using the reporter plasmid pla as template and cell-free S30 extracts obtained from *S. aureus*. The activity of the resulting luciferase can be detected by luminescence measurement.

The amount of S30 extract or plasmid plato be employed must be tested anew for each preparation in order to ensure an optimal concentration in the assay. 3 µl of the substance to be tested, dissolved in 5% DMSO, are introduced into an MTP. Then 10 µl of a suitably concentrated plasmid solution p1 a are added. Then 46 µl of a mixture of 23 µl of premix (500 mM Potassium acetate, 87.5 mM Tris acetate, pH 8.0, 67.5 mM ammonium acetate, 5 mM DTT, 50 µg of folic acid/ml, 87.5 mg of PEG 8000/ml, 5 mM ATP, 1.25 mM each NTP, 20 µM each amino acid, 50 mM PEP ($Na_3$ salt), 2.5 mM cAMP, 250 µg each *E. coli* tRNA/ml) and 23 µl of a suitable amount of *S. aureus* S30 extract are added and mixed. After incubation at 30° C. for 60 min, 50 µl of luciferin solution (20 mM tricine, 2.67 mM $MgSO_4$, 0:1 mM EDTA, 33.3 mM DTT pH 7.8, 270 µM CoA, 470 µM luciferin, 530 µM ATP) are added, and the resulting bioluminescence is measured in a luminometer for 1 min. The concentration of an inhibitor which leads to 50% inhibition of the translation of firefly luciferase is indicated as the $IC_{50}$.

Determination of the Minimum Inhibitory Concentration (MIC)

The minimum inhibitory concentration (MIC) is the minimum concentration of an antibiotic with which the growth of a test microbe is inhibited over 18-24 h. The inhibitor concentration can in these cases be determined by standard microbiological methods (see, for example, The National Committee for Clinical Laboratory Standards. Methods for dilution antimicrobial susceptibility tests for bacteria that grow aerobically; approved standard-fifth edition. NCCLS document M7-A5 [ISBN 1-56238-394-9]. NCCLS, 940 West Valley Road, Suite 1400, Wayne, Pa. 19087-1898 USA, 2000). The MIC of the compounds of the invention is determined in the liquid dilution test on the 96-well microtitre plate scale. The bacterial microbes are cultivated in a minimal medium (18.5 mM $Na_2HPO_4$, 5.7 mM $KH_2PO_4$, 9.3 mM $NH_4Cl$, 2.8 mM $MgSO_4$, 17.1 mM NaCl, 0.033 µg/ml thiamine hydrochloride, 1.2 µg/ml nicotinic acid, 0.003 µg/ml biotin, 1% glucose, 25 µg/ml of each proteinogenic amino acid with the exception of phenylalanine; [H.-P. Kroll; unpublished]) with addition of 0.4% BH broth (test medium). In the case of *Enterococcus faecium* L4001, heat-inactivated fetal calf serum (FCS; GibcoBRL, Germany) is added to the test medium in a final concentration of 10%. Overnight cultures of the test microbes are diluted to an $OD_{578}$ of 0.001 (to 0.01 in the case of *enterococci*) in fresh test medium, and incubated 1:1 with dilutions of the test substances (1:2 dilution steps) in test medium (200 µl final volume). The cultures are incubated at 37° C. for 18-24 hours; enterococci in the presence of 5% $CO_2$.

The lowest substance concentration in each case at which bacterial growth was no longer visible is defined as the MIC. The MIC values in µM of some compounds of the invention for a series of test microbes are listed by way of example in the table below. The compounds show a graded antibacterial effect against most of the test microbes.

TABLE A (with Comparative Example biphenomycin B)

| Ex. No. | MIC *S. aureus* 133 | MIC *S. aureus* T17 | MIC *E. faecium* L4001 | $IC_{50}$ *S. aureus* 133 Translation |
|---|---|---|---|---|
| 9 | 0.35 | 0.7 | 11 | 0.3 |
| 12 | 0.16 | 0.6 | 20 | 0.8 |
| 36 | 0.4 | 0.8 | >25 | 0.36 |
| Biphenomycin B | 0.1 | >25 | >25 | 1.5 |

All concentration data in µM.

Alternative Method for Determining the Minimum Inhibitory Concentration (MIC)

The minimum inhibitory concentration (MIC) is the minimum concentration of an antibiotic with which the growth of a test microbe is inhibited over 18-24 h. The inhibitor concentration can be determined by standard microbiological methods using modified medium in an agar dilution test (see, for example, the National Committee for Clinical Laboratory Standards. Methods for dilution antimicrobial susceptibility tests for bacteria that grow aerobically; approved standard-fifth edition. NCCLS document M7-A5 [ISBN 1-56238-394-9]. NCCLS, 940 West Valley Road, Suite 1400, Wayne, PA. 19087-1898 USA, 2000). The bacterial microbes are cultivated on 1.5% agar plates containing 20% defibrinated horse blood. The test microbes, which are incubated on Columbia blood agar plates (Becton-Dickinson) overnight, are diluted in PBS, adjusted to a microbe count of about $5 \times 10^5$ microbes/ml and placed as drops (1-3 µl) on test plates. The test substances contain various dilutions of the test substances (1:2 dilution stages). The cultures are incubated at 37° C. in the presence of 5% $CO_2$ for 18-24 hours.

The lowest concentration of each substance at which no visible bacterial growth occurs is defined as the MIC and is reported in µg/ml.

TABLE B (with Comparative Example biphenomycin B)

| Ex. No. | MIC *S. aureus* 133 | MIC *S. aureus* T17 | MIC *E. faecium* L4001 | $IC_{50}$ *S. aureus* 133 Translation |
|---|---|---|---|---|
| 9 | 2 | 4 | 16 | 0.3 |
| 12 | 1 | 1 | 16 | 0.8 |
| 36 | 1 | 2 | 8 | 0.36 |
| 42 | 2 | 2 | 32 | 0.08 |
| 43 | 2 | 4 | >32 | 0.9 |
| Biphenomycin B | <0.03 | >32 | 0.5 | 1.5 |

Concentration data: MIC in µg/ml; $IC_{50}$ in µM.

Systemic Infection with S. aureus 133

The suitability of the compounds of the invention for treating bacterial infections can be shown in varius animal models. For this purpose, the animals are generally infected with a suitable virulent microbe and then treated with the compound to be tested, which is in a formulation which is adapted to the particular therapy model. The suitability of the compounds of the invention can be demonstrated specifically for the treatment of bacterial infections in a mouse sepsis model after infection with S. aureus.

For this purpose, S. aureus 133 cells are cultured overnight in BH broth (Oxoid, Germany overnight culture was diluted 1:100 in fresh BH broth and expanded for 3 hours. The bacteria which are in the logarithmic phase of growth are centrifuged and washed twice with buffered physiological saline solution. A cell suspension in saline solution with an extinction of 50 units is then adjusted in a photometer (Dr Lange LP 2W). After a dilution step (1:15), this suspension is mixed 1:1 with a 10% strength mucine suspension. 0.2 ml of this infection solution is administered i.p. per 20 g of mouse. This corresponds to a cell count of about $1\text{-}2\times10^6$ microbes/mouse. The i.v. therapy takes place 30 minutes after the infection. Female CFW1 mice are used for the infection test. The survival of the animals is recorded for 6 days. The animal model is adjusted so that untreated animals die within 24 h after the infection.

Determination of the Spontaneous Resistance Rates to S. aureus

The spontaneous resistance rates for the compounds of the invention are determined as follows: the bacterial microbes are cultivated in 30 ml of a minimal medium (18.5 mM $Na_2HPO_4$, 5.7 mM $KH_2PO_4$, 9.3 mM $NH_4Cl$, 2.8 mM $MgSO_4$, 17.1 mM NaCl, 0.033 µg/ml thiamine hydrochloride, 1.2 µg/ml nicotinic acid, 0.003 µg/ml biotin, 1% glucose, 25 µg/ml of each proteinogenic amino acid with the addition of 0.4% BH broth) at 37° C. overnight, centrifuged off at 6000×g for 10 min and resuspended in 2 ml of phosphate-buffered physiological NaCl solution (about $2\times10^9$ microbes/ml). 100 µl of this cell suspension, and 1:10 and 1:100 dilutions, are plated out on predried agar plates (1.5% agar, 20% defibrinated horse blood, and 1.5% agar, 20% bovine serum in ⅒ Müller-Hinton medium diluted with PBS, respectively) which contain the compound of the invention to be tested in a concentration equivalent to 5×MIC and 10×MIC, respectively, and incubated at 37° C. for 48 h. The resulting colonies (cfu) are counted.

TABLE C

| | Example No. (concentration) | | |
|---|---|---|---|
| | 12 (5× MIC) | 42 (5× MIC) | Biphenomycin B (10× MIC) |
| S. aureus 133 | $1.3 \times 10^{-10}$ | $5.3 \times 10^{-10}$ | $1.7 \times 10^{-6}$ |

The spontaneous resistance rate for Example 42 is additionally determined as follows: the bacterial organisms undergo microaerophilic culture on Columbia blood agar plates at 37° C. overnight and are resuspended in phosphate-buffered physiological NaCl solution (approx. $1.5\times10^{10}$ microbes/ml). 50 µl of this cell suspension are plated out on predried agar plates (1.5% agar, 20% defibrinated horse blood) which contains the compound of the invention to be tested in a concentration corresponding to 10×MIC, and incubated at 37° C. for 48 h. The resulting colonies (cfu) are counted. A spontaneous resistance rate of $6.7\times10^{-11}$ for S. aureus 133 was found for Example 42.

Isolation of the Biphenomycin-resistant S. aureus Strains RN4220Bi$^R$ and T17

The S. aureus strain RN422OBi$^R$ is isolated in vitro. For this purpose, 100 µl portions of an S. aureus RN4220 cell suspension (about $1.2\times10^8$ cfu/ml) are plated out on an antibiotic-free agar plate (18.5 mM $Na_2HPO_4$, 5.7 mM $KH_2PO_4$, 9.3 mM $NH_4Cl$, 2.8 mM $MgSO_4$, 17.1 mM NaCl, 0.033 µg/ml thiamine hydrochloride, 1.2 µg/ml nicotinic acid, 0.003 µg/ml biotin, 1% glucose, 25 µg/ml of each proteinogenic amino acid with the addition of 0.4% BH broth and 1% agarose) and on an agar plate containing 2 µg/ml biphenomycin B (10×MIC), and incubated at 37° C. overnight. Whereas about $1\times10^7$ cells grow on the antibiotic-free plate, about 100 colonies grow on the antibiotic-containing plate, corresponding to a resistance rate of $1\times10^{-5}$. Some of the colonies grown on the antibiotic-containing plate are tested for the biphenomycin B MIC. One colony with an MIC of >50 µM is selected for further use, and the strain is referred to as RN4220Bi$^R$.

The S. aureus strain T17 is isolated in vivo. CFW1 mice are infected intraperitoneally with $4\times10^7$ S. aureus 133 cells per mouse. 0.5 h after the infection, the animals are treated intravenously with 50 mg/kg biphenomycin B. The kidneys are removed from the surviving animals on day 3 after the infection. After homogenization of the organs, the homogenates are plated out as described for RN4220Bi$^R$ on antibiotic-free and antibiotic-containing agar plates and incubated at 37° C. overnight. About half the colonies isolated from the kidney show growth on the antibiotic-containing plates ($2.2\times10^6$ colonies), demonstrating the accumulation of biphenomycin B-resistant S. aureus cells in the kidney of the treated animals. About 20 of these colonies are tested for the biphenomycin B MIC, and a colony with an MIC of >50 µM is selected for further cultivation, and the strain is referred to as T17.

C. Exemplary Embodiments of Pharmaceutical Compositions

The compounds of the invention can be converted into pharmaceutical preparations in the following way:

Solution which can be Administered Intravenously:

Composition:
1 mg of the compound of Example 1, 15 g of polyethylene glycol 400 and 250 g of water for injections.

Preparation:
The compound of the invention is dissolved together with polyethylene glycol 400 in the water with stirring. The solution is sterilized by filtration (pore diameter 0.22 µm) and dispensed infusion bottles. These are closed with infusion stoppers and crimped caps.

The invention claimed is:
1. A compound of formula

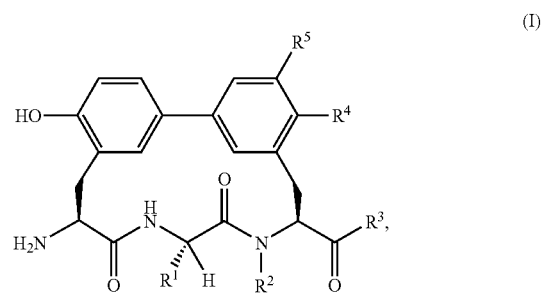

(I)

in which
R¹ is selected from the group consisting of aminomethyl, 2-aminoethyl, 3-aminoprop-1-yl, 4-aminobut-1-yl, hydroxymethyl, 2-hydroxy-ethyl, aminocarbonylmethyl, 2-aminocarbonylethyl, 2-hydroxycarbonylethyl, 3-guanidinoprop-1-yl, 3-amino-2-hydroxyprop-1-yl and 4-amino-3-hydroxybut-1-yl, R² is selected from the group consisting of hydrogen, methyl, ethyl and cyclopropyl, R³ is —NR⁶R⁷, R⁴ is selected from the group consisting of hydrogen, halogen, amino, hydroxy, hydroxycarbonyl, aminocarbonyl, nitro and methyl, R⁵ is selected from the group consisting of hydrogen, halogen, amino, hydroxy, aminocarbonyl, hydroxycarbonyl, nitro and methyl,
  whereby R⁵ is selected from the group consisting of halogen, amino, hydroxy, aminocarbonyl, hydroxycarbonyl, nitro and methyl, if R⁴ is hydroxy, R⁶ is selected from the group consisting of hydrogen, ($C_1$-$C_6$)-alkyl, ($C_5$-$C_6$)-cycloalkyl, 5- to 7-membered heterocyclyl and phenyl,
  whereby alkyl, cycloalkyl, heterocyclyl and phenyl may be substituted with 1 to 3 substituents, whereby said substituents are selected independently of one another from the group consisting of amino, hydroxy, aminocarbonyl, hydroxycarbonyl, ($C_1$-$C_4$)-alkyl, ($C_1$-$C_6$)-alkylamino, 5- to 7-membered heterocyclyl, phenyl, 5- or 6-membered heteroaryl, ($C_1$-$C_6$)-alkoxycarbonyl and ($C_1$-$C_6$)-alkylaminocarbonyl,
  in which alkyl, alkylamino, heterocyclyl, aryl, heteroaryl and alkylaminocarbonyl may be substituted with 1 to 3 substituents, whereby said substituents are selected independently of one another from the group consisting of amino, hydroxy, aminocarbonyl and hydroxycarbonyl, R⁷ is selected from the group consisting of hydrogen and ($C_1$-$C_4$)-alkyl,
  whereby alkyl may be substituted with 1 to 2 substituents, whereby said substituents are selected independently of one another from the group consisting of amino, hydroxy and ($C_1$-$C_6$)-alkylamino,
or
R⁶ and R⁷ together with the nitrogen atom to which they are bonded form a piperazinyl, whereby piperazinyl may be substituted with 1 to 3 substituents, whereby said substituents are selected independently of one another from the group consisting of amino, hydroxy, optionally amino substituted ($C_1$-$C_6$)-alkyl, and ($C_1$-$C_6$)-alkylamino;
or one of the salts thereof.

2. The compound of claim 1, whereby

R¹ is selected from the group consisting of 2-aminoethyl, 3-aminoprop-1-yl, 4-aminobut-1-yl and 3-amino-2-hydroxyprop-1-yl, R² is selected from the group consisting of hydrogen, methyl and ethyl, R³ is —NR⁶R⁷, R⁴ is selected from the group consisting of hydrogen, fluorine, chlorine, amino, hydroxy and methyl, R⁵ is selected from the group consisting of hydrogen, fluorine and hydroxy,
  whereby R⁵ is fluorine if R⁴ is hydroxy, R⁶ is a group of the formula

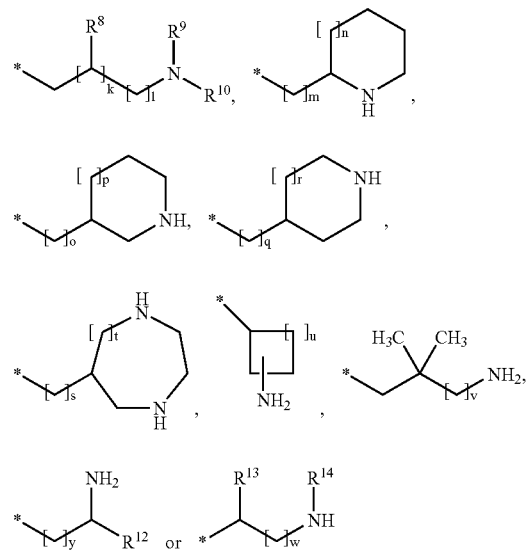

whereby
R⁸ is selected from the group consisting of hydrogen and hydroxy,

R⁹ and R¹⁴ are independently of one another selected from the group consisting of hydrogen, methyl and a group of the formula

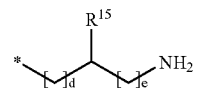

in which
* is the point of attachment to the nitrogen atom,

R¹⁵ is selected from the group consisting of hydrogen and *—(CH₂)_f—NH₂,
in which
f is a number 1, 2 or 3,
d is a number 0, 1, 2 or 3,
and
e is a number 1, 2 or 3, R¹⁰ is selected from the group consisting of hydrogen and aminoethyl,
or
R⁹ and R¹⁰ form together with the nitrogen atom to which they are bonded a piperazine ring, R¹² and R¹³ are independently of one another a group of the formula *—(CH₂)_{Z1}—OH or *—(CH₂)_{Z2}—NH₂,
in which
* is the point of attachment to the nitrogen atom,
Z1 and Z2 are independently of one another a number 1, 2, 3 or 4,
k and t are independently of one another a number 0 or 1,
l, w and y are independently of one another a number 1, 2, 3 or 4, m, r, s and v are independently of one another a number 1 or 2, n, o, p and q are independently of one another a number 0, 1 or 2, u is a number 0, 1, 2 or 3,

may independently of one another if w or y is 3 carry a hydroxy group on the middle carbon atom of the three-membered chain,

* is the point of attachment to the nitrogen atom, and $R^7$ is hydrogen.

3. The compound of claim 1, whereby $R^1$ is selected from the group consisting of 3-aminoprop-1-yl and 3-amino-2-hydroxyprop-1-yl, $R^2$ is selected from the group consisting of hydrogen and methyl, $R^3$ is —$NR^6R^7$, $R^4$ is selected from the group consisting of hydrogen, fluorine, chlorine and methyl, $R^5$ is hydrogen, $R^6$ is a group of the formula

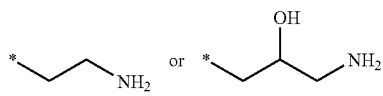

whereby

* is the point of attachment to the nitrogen atom, and $R^7$ is hydrogen.

4. A Process for preparing a compound of formula (I) according to claim 1, whereby a compound of formula (I) is a compound of formula (Ia), or one of the salts thereof, whereby a compound of formula

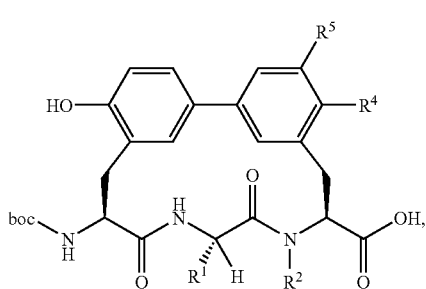

(II)

in which $R^1$, $R^2$, $R^4$ and $R^5$ have the meaning indicated in claim 1, and boc is tert-butoxycarbonyl, is reacted in a two-stage process first in the presence of one or more dehydrating reagents with a compound of formula

HNR⁶R⁷ (III), in which $R^6$ and $R^7$ have the meaning indicated above, and then with an acid to give a compound of formula

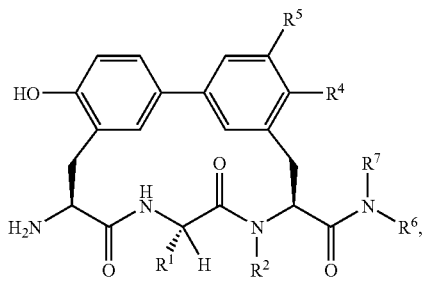

(Ia)

in which $R^1$, $R^2$, $R^3$, $R^4$, $R^5$, $R^6$ and $R^7$ have the meaning indicated above.

5. A Process for preparing a compound of formula (I) according to claim 1, whereby a compound of formula (I) is a compound of formula (Ia), or one of the salts thereof, whereby a compound of formula

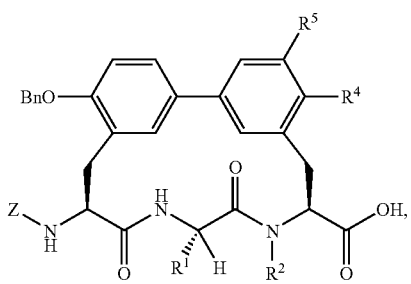

(IV)

in which $R^1$, $R^2$, $R^4$ and $R^5$ have the meaning indicated in claim 1, and Z is benzyloxycarbonyl, is reacted in a two-stage process first in the presence of one or more dehydrating reagents with compounds of the formula

HNR⁶R⁷ (III), in which R and R have the meaning indicated above, and then with an acid to give a compound of formula

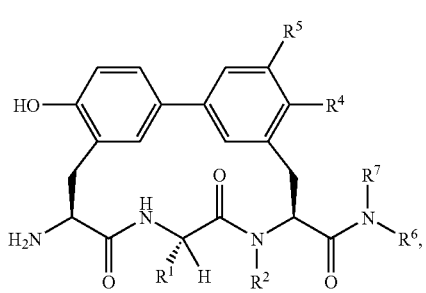

(Ia)

in which $R^1$, $R^2$, $R^4$, $R^5$, $R^6$ and $R^7$ have the meaning indicated above.

6. A Process for preparing a compound of formula (I) according to claim 1, whereby a compound of formula (I) is a compound of formula (Ia), whereby a compound of formula

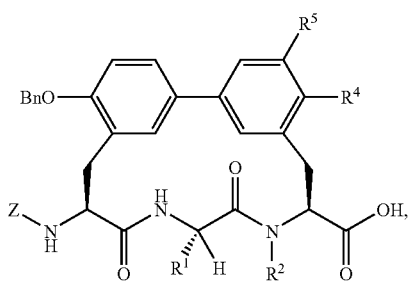

(IV)

in which $R^1$, $R^2$, $R^4$ and $R^5$ have the meaning indicated in claim 1, and Z is benzyloxycarbonyl, is reacted in a two-stage process first in the presence of one or more dehydrating reagents with compounds of the formula $HNR^6R^7$ (III), in which $R^6$ and $R^7$ have the meaning indicated above, and then by hydrogenolysis to give a compound of formula

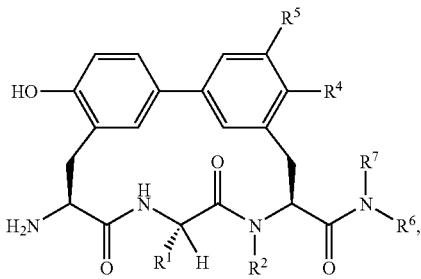

(Ia)

in which $R^1$, $R^2$, $R^4$, $R^5$, $R^6$ and $R^7$ have the meaning indicated above.

7. A Process for preparing a compound of formula (I) according to claim 1, whereby a salt of said compound of formula (I) is converted into said compound of formula (I) by chromatography with addition of a base.

8. A method for the production of a medicament comprising mixing using a compound of claim 1 with at least one inert, non-toxic pharmaceutically acceptable excipient.

9. A medicament comprising at least one compound of claim 1 in combination with at least one inert, nontoxic, pharmaceutically acceptable excipient.

10. A Method for controlling bacterial infections in humans and animals by administration of an antibacterially effective amount of at least one compound of claim 1.

11. A Method for controlling bacterial infections in humans and animals by administration of an antibacterially effective amount of at least one medicament of claim 9.

* * * * *